(12) United States Patent
Geneste et al.

(10) Patent No.: US 9,938,269 B2
(45) Date of Patent: Apr. 10, 2018

(54) INHIBITOR COMPOUNDS OF PHOSPHODIESTERASE TYPE 10A

(75) Inventors: Hervé Geneste, Ludwigshafen (DE); Michael Ochse, Ludwigshafen (DE); Karla Drescher, Ludwigshafen (DE); Berthold Behl, Ludwigshafen (DE); Loic Laplanche, Ludwigshafen (DE); Jürgen Dinges, North Chicago, IL (US); Clarissa Jakob, North Chicago, IL (US); Katja Jantos, Ludwigshafen (DE)

(73) Assignees: ABBVIE INC., North Chicago, IL (US); ABBVIE DEUTSCHLAND GMBH & CO KG, Wiesbaden (DE)

( * ) Notice: Subject to any disclaimer, the term of this patent is extended or adjusted under 35 U.S.C. 154(b) by 793 days.

(21) Appl. No.: 13/534,127

(22) Filed: Jun. 27, 2012

(65) Prior Publication Data

US 2013/0005705 A1 Jan. 3, 2013

Related U.S. Application Data

(60) Provisional application No. 61/503,040, filed on Jun. 30, 2011.

(51) Int. Cl.
| | |
|---|---|
| C07D 471/04 | (2006.01) |
| C07D 403/14 | (2006.01) |
| C07D 405/14 | (2006.01) |
| C07D 409/14 | (2006.01) |
| C07D 413/14 | (2006.01) |

(52) U.S. Cl.
CPC ......... C07D 471/04 (2013.01); C07D 403/14 (2013.01); C07D 405/14 (2013.01); C07D 409/14 (2013.01); C07D 413/14 (2013.01)

(58) Field of Classification Search
CPC ... C07D 401/14; C07D 413/14; C07D 495/04
USPC ......................................... 546/113, 176, 114
See application file for complete search history.

(56) References Cited

U.S. PATENT DOCUMENTS

| | | | |
|---|---|---|---|
| 6,933,295 B2 | 8/2005 | Straub et al. | |
| 7,495,112 B2 | 2/2009 | Muller et al. | |
| 8,536,164 B2 * | 9/2013 | Butler ................. | C07D 401/04 514/211.1 |
| 2006/0264457 A1 | 11/2006 | Devasthale et al. | |
| 2007/0155779 A1 | 7/2007 | Verhoest et al. | |
| 2013/0203756 A1 * | 8/2013 | Bunda ................... | A61K 31/44 514/234.8 |

FOREIGN PATENT DOCUMENTS

| | | | |
|---|---|---|---|
| CA | 1073461 | * | 3/1980 |
| EP | 1090917 | | 4/2001 |
| GB | 1560726 A | | 2/1980 |
| WO | 03093499 A2 | | 11/2003 |
| WO | 2004037814 A1 | | 5/2004 |
| WO | 2005012485 A2 | | 2/2005 |
| WO | 2005120514 A1 | | 12/2005 |
| WO | 2006028957 A1 | | 3/2006 |
| WO | 2007022280 A1 | | 2/2007 |
| WO | 2007082546 A1 | | 7/2007 |
| WO | 2007085954 A2 | | 8/2007 |
| WO | 2007096743 A1 | | 8/2007 |
| WO | 2007098169 A1 | | 8/2007 |
| WO | 2007098214 A1 | | 8/2007 |
| WO | 2007100880 A1 | | 9/2007 |
| WO | 2007103370 A2 | | 9/2007 |
| WO | 2007103554 A1 | | 9/2007 |
| WO | 2007137819 A1 | | 12/2007 |
| WO | 2007137820 A1 | | 12/2007 |
| WO | 2007139464 A1 | | 12/2007 |
| WO | 2008001182 A1 | | 1/2008 |
| WO | 2008004117 A1 | | 1/2008 |
| WO | 2008006372 A1 | | 1/2008 |
| WO | 2008020302 A2 | | 2/2008 |
| WO | 2009025823 A1 | | 2/2009 |
| WO | 2009025839 A2 | | 2/2009 |
| WO | 2009029214 A1 | | 3/2009 |
| WO | 2009036766 A1 | | 3/2009 |
| WO | 2009068246 A2 | | 6/2009 |
| WO | 2009068320 A1 | | 6/2009 |
| WO | 2009070583 A1 | | 6/2009 |
| WO | 2009070584 A1 | | 6/2009 |
| WO | 2010077686 A1 | | 7/2010 |
| WO | 2010138585 A1 | | 12/2010 |
| WO | 2012058133 A1 | | 5/2012 |
| WO | 2012085721 A1 | | 6/2012 |

OTHER PUBLICATIONS

ACS on STN resgistry 1241707-08-3/RN Chemical Library Sep. 16, 2010.*
Baggaley K.H., et al., "Synthesis of 2-Substituted Isothiazolopyridin-3-Ones," Journal of Heterocyclic Chemistry, 1982, vol. 19 (6), pp. 1393-1396.
Cantin L.D., et al., "PDE-10A Inhibitors as Insulin Secretagogues," Bioorganic and Medicinal Chemistry Letters, 2007, vol. 17 (10), pp. 2869-2873.
CAPLUS Accession No. 1991:185288, Retrieved on Nov. 1, 1990.
Chappie T., et al., "PDE10A Inhibitors: An Assessment of the Current CNS Drug Discovery Landscape," Current Opinion in Drug Discovery and Development, 2009, vol. 12 (4), pp. 458-467.

(Continued)

*Primary Examiner* — Shirley V Gembeh

(74) *Attorney, Agent, or Firm* — Neal, Gerber & Eisenberg LLP

(57) ABSTRACT

The present invention relates to novel carboxamide compounds, pharmaceutical compositions containing them, and their use in therapy. The compounds possess valuable therapeutic properties and are particularly suitable for treating or controlling medical disorders selected from neurological disorders and psychiatric disorders, for ameliorating the symptoms associated with such disorders and for reducing the risk of such disorders.

33 Claims, No Drawings

(56) References Cited

OTHER PUBLICATIONS

Database CA [Online] Chemical Abstracts Service, Columbus, Ohio, US; Hisashi T., et al., "Preparation of Diphenylpyridines for Treatment of Ischemia", Retrieved from STN Database Accession No. 1991:185288 Compounds rn 133300-81-9 and rn 133300-82-0.

Diaz G.J., et al., "The [3H]dofetilide Binding Assay is a Predictive Screening Tool for hERG Blockade and Proarrhythmia: Comparison of Intact Cell and Membrane Preparations and Effects of Altering [K+]o," Journal of Pharmacological and Toxicological Methods, 2004, vol. 50 (3), pp. 187-199.

Francis S.H., et al., "Mammalian Cyclic Nucleotide Phosphodiesterases: Molecular Mechanisms and Physiological Functions," Physiological Reviews, 2011, vol. 91 (2), pp. 651-690.

Grauer S.M., et al., "PDE10A Inhibitor Activity in Preclinical Models of the Positive, Cognitive and Negative Symptoms of Schizophrenia," Journal of Pharmacology and Experimental Therapeutics (155994), 2009, DOI:10.1124/jpet.109.155994, 66 pages.

International Search Report for Application No. PCT/EP2012/062544, dated Sep. 26, 2012, 4 pages.

Nishi A., et al., "Distinct Roles of PDE4 and PDE10A in the Regulation of cAMP/PKA Signaling in the Striatum," The Journal of Neuroscience, 2008, vol. 28 (42), pp. 10460-10471.

Rodefer J.S., et al., "PDE10A Inhibition Reverses Subchronic PCP-Induced Deficits in Attentional Set-Shifting in Rats," European Journal of Neuroscience, 2005, vol. 21 (4), pp. 1070-1076.

Schmidt C.J., et al., "Preclinical Characterization of Selective Phosphodiesterase 10A Inhibitors: A New Therapeutic Approach to the Treatment of Schizophrenia," Journal of Pharmacology and Experimental Therapeutics, 2008, 325 (2), pp. 681-690.

Seeger T.F., et al., "Immunohistochemical localization of PDE10A in the Rat Brain," Brain Research, 2003, vol. 985 (2), pp. 113-126.

Sotty F., et al., "Phosphodiesterase 10A Inhibition Modulates the Sensitivity of the Mesolimbic Dopaminergic System to D-amphetamine: Involvement of the D1-Regulated Feedback Control of Midbrain Dopamine Neurons," Journal of Neurochemistry, 2009, vol. 109 (3), pp. 766-775.

Lima, L.M. et al., "Bioisosterism: a useful strategy for molecular modification and drug design," Curr. Med. Chem. (2005) 12:23-49.

Silverman, R.B. et al., The Organic Chemistry of Drug Design and Drug Action, Third Edition, Academic Press, California (2014) Chapter 2, pp. 59-66.

\* cited by examiner

INHIBITOR COMPOUNDS OF PHOSPHODIESTERASE TYPE 10A

CROSS-REFERENCE TO RELATED APPLICATION

This claims priority to U.S. Provisional Patent Application No. 61/503,040, filed on Jun. 30, 2011, the contents of which are herein fully incorporated by reference.

The present invention relates to novel compounds which are inhibitors of phosphodiesterase type 10A and to their use for the manufacture of a medicament and which thus are suitable for treating or controlling of medical disorders selected from neurological disorders and psychiatric disorders, for ameliorating the symptoms associated with such disorders and for reducing the risk of such disorders.

BACKGROUND OF THE INVENTION

Phosphodiesterase type 10A (hereinafter PDE10A) is a dual-substrate phosphodiesterase that can convert both cAMP to AMP and cGMP to GMP. PDE10A is highly prominent in the mammalian brain. In the rat, as well as in other mammalian species, PDE10A and the mRNA of PDE10A are highly enriched in the GABAergic medium spiny projection neurons (MSNs) of the striatal complex (caudate nucleus, nucleus accumbens, and olfactory tubercle) where the output is regulated by the effect of PDE10A on cAMP and cGMP signalling cascades (see e.g. C. J. Schmidt et al, The Journal of Pharmacology and Experimental Therapeutics 325 (2008) 681-690, A. Nishi, The Journal of Neuroscience 2008, 28, 10450-10471).

MSNs express two functional classes of neurons: the $D_1$ class expressing $D_1$ dopamine receptors and the $D_2$ class expressing $D_2$ dopamine receptors. The $D_1$ class of neurons is part of the 'direct' striatal output pathway, which broadly functions to facilitate behavioral responses. The $D_2$ class of neurons is part of the 'indirect' striatal output pathway, which functions to suppress behavioral responses that compete with those being facilitated by the 'direct' pathway. PDE10A regulation of cAMP and/or cGMP signaling in the dendritic compartment of these neurons may be involved in filtering the cortico/thalamic input into the MSN. Furthermore, PDE10A may be involved in the regulation of GABA release in the substantia nigra and globus pallidus (Seeger, T. F. et al. Brain Research, 2003, 985, 1 13-126) Inhibition of PDE10A results in striatal activation and behavioral suppression such as dampened locomotion, inhibition of conditioned avoidance response (CAR), and activity in the rat auditory gating model, suggesting that inhibitors of phosphodiesterase type 10A represent a novel class of antipsychotic agents.

The hypotheses around the physiological role of PDE10A and the therapeutic utility of PDE10A inhibitors derive in part from studies with papaverine (J. A. Siuciak et al. loc. cit.), the first extensively profiled pharmacological tool compound for this target. The PDE10A inhibitor papaverine was shown to be active in several antipsychotic models. Papaverine potentiated the cataleptic effect of the $D_2$ receptor antagonist haloperidol in rats, but did not cause catalepsy on its own (WO 03/093499). Papaverine reduced hyperactivity in rats induced by PCP, while reduction of amphetamine-induced hyperactivity was insignificant (WO 03/093499). These models suggest that PDE10A inhibition has the classic antipsychotic potential that would be expected from theoretical considerations. Papaverine, however has significant limitations in this regard with relatively poor potency and selectivity and a very short exposure half-life after systemic administration. It was found that inhibition of PDE10A reverses subchronic PCP-induced deficits in attentional set-shifting in rats suggesting that PDE10A inhibitors might alleviate cognitive deficits associated with schizophrenia. (Rodefer et al., Eur. J. Neurosci., 4 (2005) 1070-1076).

The discovery of a new class of PDE10A inhibitors with improved potency, selectivity, and pharmacokinetic properties, provided an opportunity to further explore the physiology of PDE10A and the potential therapeutic utility of inhibiting this enzyme. The new class of inhibitors are exemplified by MP-10 (PF-2545920: 2-{-4-[1-methylpyridine-4-yl-1-H-pyrazol-3-3ly]phenoxymethyl}-quinoline) and TP-10, i.e. 2-{4-[pyridine-4-yl-1-(2,2,2-trifluoroethyl)-1-H-pyrazol-3-3ly]phenoxymethyl}-quinoline. The compounds offer a therapeutic approach to the treatment of schizophrenia (see C. J. Schmidt et al., loc cit.; S. M. Grauer et al., Journal of Pharmacology and Experimental Therapeutics, fast forward DOI 10.1124 JPET 109.155994). Positive signals in rodent models of schizophrenia include the: attenuation of conditioned avoidance response (CAR), inhibition of hyperactivity caused by amphetamine-induced dopamine release or phencyclidine (PCP) mediated NMDA receptor blockade, attenuation of pharmacologically impaired social or object recognition, and antagonism of apomorphine-induced climbing. Taken together, these data suggest a broad suppression of all 3 symptoms clusters (positive symptoms, negative symptoms & cognitive dysfunctions) linked to schizophrenia (see C. J. Schmidt et al., loc cit.; S. M. Grauer et al., loc. cit).

Beyond schizophrenia, selective PDE10 inhibitors may have the potential for the treatment of Huntington's disease (S. H. Francis et al., Physiol. Rev., 91 (2011) 651-690) and they may be an therapeutic option for substance abuse disorders (F. Sotty et al., J. Neurochem., 109 (2009) 766-775). Furthermore, it has been suggested that PDE10A inhibitors may be useful for treatment of obesity and non-insulin dependent diabetes (see e.g. WO 2005/120514, WO 2005/012485, Cantin et al, Bioorganic & Medicinal Chemistry Letters 17 (2007) 2869-2873).

In summary, inhibitors of PDE10A offer a promising therapeutic approach to the treatment or prevention of neurological and psychiatric disorders, in particular schizophrenia and related disorders, including symptoms linked to schizophrenia such as cognitive dysfunction.

Several classes of compounds which are inhibitors of PDE10A have been described in the art, the recent compound groups are:

Pyrido[3,2-e]pyridazines—see WO 2007/137819, WO 2007/137820, WO 2009/068246, WO 2009/068320, WO 2009/070583 and WO 2009/070584;

4-substituted phthalazines and quinazolines WO 2007/085954, WO 2007/022280, WO 2007/096743, WO 2007/103370, WO 2008/020302, WO 2008/006372 and WO 2009/036766;

4-substituted cinnazolines—see WO 2006/028957, WO 2007/098169, WO 2007/098214, WO 2007/103554, WO 2009/025823 and WO 2009/025839;

Isoquinolines and isoquinolinones—see WO 2007/100880 and WO 2009/029214

MP10 and MP10 like compounds: US 2007/0155779, WO 2008/001182 and WO 2008/004117; and Benzodiazepines—see WO 2007/082546.

For a further review see also T. Chappie et al. Current Opinion in Drug Discovery & Development 12(4), (2009) 458-467) and the literature cited therein.

Although some of the compounds of prior art are known to inhibit PDE10A effectively having $IC_{50}$ values of less than 50 nM, there is still an ongoing need for compounds which inhibit PDE10A. In particular, there is an ongoing need for compounds which have one of the following characteristics:

i. Selective inhibition of PDE10A, in particular vis-à-vis inhibition of other phosphodisesterases such as PDE3 or PDE4;
ii. metabolic stability, in particular microsomal stability, e.g. measured in vitro, in liver microsomes from various species (e.g. rat or human) in human cells, such as hepatocytes;
iii. no or only low inhibition of cytochrome P450 (CYP) enzymes: cytochrome P450 (CYP) is the name for a superfamily of heme proteins having enzymatic activity (oxidase). They are also particularly important for the degradation (metabolism) of foreign substances such as drugs or xenobiotics in mammalian organisms. The principal representatives of the types and subtypes of CYP in the human body are: CYP 1A2, CYP 2C9, CYP 2D6 and CYP 3A4. If CYP 3A4 inhibitors (e.g. grapefruit juice, cimetidine, erythromycin) are used at the same time as medicinal substances which are degraded by this enzyme system and thus compete for the same binding site on the enzyme, the degradation thereof may be slowed down and thus effects and side effects of the administered medicinal substance may be undesirably enhanced;
iv. a suitable solubility in water (in mg/ml);
v. suitable pharmacokinetics (time course of the concentration of the compound of the invention in plasma or in tissue, for example brain). The pharmacokinetics can be described by the following parameters: half-life, volume of distribution (in $l \cdot kg^{-1}$), plasma clearance (in $l \cdot h^{-1} \cdot kg^{-1}$), AUC (area under the curve, area under the concentration-time curve (in $ng \cdot h \cdot l^{-1}$), oral bioavailability, (the dose-normalized ratio of AUC after oral administration and AUC after intravenous administration), the so-called brain-plasma ratio (the ratio of AUC in brain tissue and AUC in plasma);
vi. no or only low blockade of the hERG channel: compounds which block the hERG channel may cause a prolongation of the QT interval and thus lead to serious disturbances of cardiac rhythm (for example so-called "torsade de pointes"). The potential of compounds to block the hERG channel can be determined by means of the displacement assay with radiolabelled dofetilide which is described in the literature (G. J. Diaz et al., Journal of Pharmacological and Toxicological Methods, 50 (2004), 187-199). A smaller IC50 in this dofetilide assay means a greater probability of potent hERG blockade. In addition, the blockade of the hERG channel can be measured by electrophysiological experiments on cells which have been transfected with the hERG channel, by so-called whole-cell patch clamping (G. J. Diaz et al., Journal of Pharmacological and Toxicological Methods, 50 (2004), 187-199).
vii. high free fraction in brain, i.e. the fraction of the compound bound to proteins should be low.
viii. low lipophilicity.

BRIEF DESCRIPTION OF THE INVENTION

The present invention is thus based on the object of providing compounds which inhibit PDE10A at low concentrations.

The compounds are further intended to display at least one of the properties i. to viii. mentioned above, in particular high selectivity with regard to inhibition of PDE10A, high selectivity vis-à-vis other phosphodiesterases such as, enhanced metabolic stability, in particular microsomal and/or cytosolic stability, low affinity to the HERG receptor, low inhibition of cytochrome P450 (CYP) enzymes, suitable solubility in water and suitable pharmacokinetics.

This object and further objects are achieved by the compounds of the general formula I described below, the N-oxides, the prodrugs, the hydrates and the tautomers thereof and the pharmaceutically suitable salts thereof:

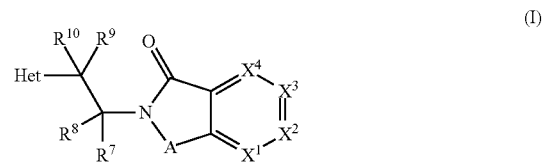

wherein
$X^1$ is N or C—$R^1$
$X^2$ is N or C—$R^2$
$X^3$ is N or C—$R^3$
$X^4$ is N or C—$R^4$
provided that 0, 1 or 2 of the moieties $X^1$, $X^2$, $X^3$ or $X^4$ is N;
A is selected from the group consisting of O, S, S(=O), S(=O)$_2$, NR$^{5a}$ and CR$^5$R$^6$;
Het is selected from
  i. monocyclic hetaryl having 1 or 2 nitrogen atoms and optionally a further heteroatom selected from O, S and N as ring members, which is unsubstituted or may carry 1, 2, 3 or 4 identical or different substituents R$^x$,
  ii. fused bicyclic hetaryl having 1 or 2 nitrogen atoms and optionally a further heteroatom selected from O, S and N as ring members, benzothienyl or benzofuryl, where bicyclic hetaryl, benzothienyl and benzofuryl are, independently of each other, unsubstituted or may carry 1, 2, 3 or 4 identical or different substituents R$^x$, and
  iii. phenyl, which carries a monocyclic hetaryl radical having 1 or 2 nitrogen atoms and optionally a further heteroatom selected from O, S and N as ring members, which in addition to monocyclic hetaryl, may carry 1, 2 or 3 identical or different substituents R$^x$,
where
  R$^x$ is selected from the group consisting of H, halogen, $C_1$-$C_4$-alkyl, $C_1$-$C_4$-alkoxy, $C_1$-$C_4$-fluoroalkyl, $C_1$-$C_4$-fluoroalkoxy, $C_3$-$C_6$-cycloalkyl, $C_1$-$C_4$-alkoxy-$C_1$-$C_4$-alkoxy, $C_1$-$C_4$-alkoxy-$C_1$-$C_4$-alkyl, OH, hydroxy-$C_1$-$C_4$-alkyl, O—$C_3$-$C_6$-cycloalkyl, benzyloxy, C(O)O—($C_1$-$C_4$-alkyl), O—($C_1$-$C_4$-alkyl)-CO$_2$H, N(R$^{x1}$)(R$^{x2}$), C(O)N(R$^{x1}$)(R$^{x2}$), $C_1$-$C_4$-alkyl-N(R$^{x1}$)(R$^{x2}$), —NR$^{x3}$—C(O)—N(R$^{x1}$)(R$^{x2}$), NR$^{x3}$—C(O)O—($C_1$-$C_4$-alkyl), —N(R$^{x3}$)—SO$_2$—R$^{x4}$, phenyl, CN, —SF$_5$, —OSF$_5$, —SO$_2$R$^{x4}$, —SR$^{x4}$ and trimethylsilyl, where R$^{x1}$, R$^{x2}$, R$^{x3}$ and R$^{x4}$, independently of each other are selected from the group consisting of hydrogen, $C_1$-$C_4$-alkyl, $C_1$-$C_4$-fluoroalkyl and $C_3$-$C_6$-cycloalkyl or R$^{x1}$ and R$^{x2}$ form together with the N atom to which they are attached a 3- to 7-membered, nitrogen heterocycle which may have 1, 2 or 3 further different or identical heteroatoms or heteroatom containing groups selected from the group of O, N, S, SO and $SO_2$ as ring members and which may carry 1, 2, 3, 4, 5 or 6 substituents selected from $C_1$-$C_4$-alkyl;

$R^1$, $R^4$ independently of each other, are selected from the group consisting of hydrogen, halogen, OH, $C_1$-$C_4$-alkyl, trimethylsilyl, $C_1$-$C_4$-alkylsulfanyl, $C_1$-$C_4$-alkoxy-$C_1$-$C_4$-alkyl, $C_1$-$C_4$-alkoxy, $C_1$-$C_4$-alkoxy-$C_1$-$C_4$-alkoxy, $C_1$-$C_4$-alkylsulfanyl-$C_1$-$C_4$-alkoxy, $C_2$-$C_4$-alkenyloxy, $C_1$-$C_4$-fluoroalkyl, $C_1$-$C_4$-fluoroalkoxy, cyclopropyl, optionally substituted by 1, 2 or 3 methyl groups, fluorinated cyclopropyl, CN, $NR^{x1}R^{x2}$, $NR^{x1}R^{x2}$—$C_1$-$C_4$-alkoxy and the moiety Y-Cyc;

$R^2$, $R^3$ independently of each other, are selected from the group consisting of hydrogen, halogen, OH, $C_1$-$C_4$-alkyl, trimethylsilyl, $C_1$-$C_4$-alkoxy-$C_1$-$C_4$-alkyl, $C_1$-$C_4$-alkoxy, $C_1$-$C_4$-alkoxy-$C_1$-$C_4$-alkoxy, $C_2$-$C_4$-alkenyloxy, $C_1$-$C_4$-fluoroalkyl, $C_1$-$C_4$-fluoroalkoxy, cyclopropyl, optionally substituted by 1, 2 or 3 methyl groups, fluorinated cyclopropyl, CN, $NR^{x1}R^{x2}$ and the moiety Y-Cyc;

provided that one or two or the radicals $R^1$, $R^2$, $R^3$, $R^4$ are a moiety Y-Cyc;

$R^5$, $R^6$ independently of each other are selected from the group consisting of hydrogen, OH, halogen, $C_1$-$C_4$-alkyl, trimethylsilyl, $C_1$-$C_4$-fluoroalkyl, $C_1$-$C_4$-fluoroalkoxy, $C_3$-$C_6$-cycloalkyl, optionally substituted by 1, 2 or 3 methyl groups, and fluorinated $C_3$-$C_6$-cycloalkyl or the radicals $R^5$, $R^6$ together with the carbon atom to which they are bound form a carbonyl group or a saturated 3- to 6-membered carbocycle or a saturated 3- to 6-membered heterocycle having 1 or 2 non-adjacent heteroatoms as ring members, where the carbocycle and the heterocycle are unsubstituted or may carry 1, 2, 3 or 4 substituents selected from fluorine and methyl;

$R^{5a}$ is selected from the group consisting of from $C_1$-$C_4$-alkyl, $C_1$-$C_4$-alkoxy, $C_1$-$C_4$-fluoroalkyl, $C_1$-$C_4$-fluoroalkoxy, $C_3$-$C_6$-cycloalkyl, optionally substituted by 1, 2 or 3 methyl groups, fluorinated $C_3$-$C_6$-cycloalkyl, phenyl, benzyl, 5- or 6-membered hetaryl having 1, 2 or 3 heteroatoms selected from O, S and N as ring members, and 5- or 6-membered hetarylmethyl having 1, 2 or 3 heteroatoms selected from O, S and N as ring members, where the rings in the last four mentioned radicals are unsubstituted or carry 1, 2, 3 or 4 substituents selected from fluorine, $C_1$-$C_4$-alkyl, $C_1$-$C_4$-fluoroalkyl, $C_1$-$C_4$-alkoxy and $C_1$-$C_4$-fluoroalkoxy;

$R^7$, $R^8$, $R^9$, $R^{10}$ independently of each other are selected from the group consisting of hydrogen, halogen, $C_1$-$C_4$-alkyl, trimethylsilyl, $C_1$-$C_4$-fluoroalkyl, $C_1$-$C_4$-fluoroalkoxy, $C_3$-$C_6$-cycloalkyl, or the radicals together with the carbon atoms to which they are bound form a saturated 3- to 6-membered carbocycle or a saturated 3- to 6-membered heterocycle having 1 or 2 non-adjacent heteroatoms as ring members, where the carbocycle and the heterocycle are unsubstituted or may carry 1, 2, 3 or 4 substituents selected from fluorine and methyl or either the radicals $R^7$, $R^8$ or the radicals $R^9$, $R^{10}$ together with the carbon atom to which they are bound form a saturated 3- to 6-membered carbocycle or a saturated 3- to 6-membered heterocycle having 1 or 2 non-adjacent heteroatoms as ring members, where the carbocycle and the heterocycle are unsubstituted or may carry 1, 2, 3 or 4 substituents selected from fluorine and methyl;

Y is a chemical bond, $CH_2$, O, O—$CH_2$, $NR^y$, $NR^y$—$CH_2$, $NR^y$—$S(O)_2$, S, S(O), $S(O)_2$, 1,2-ethandiyl, 1,2-ethendiyl or 1,2-ethyndiyl, where $R^y$ is selected from the group consisting of hydrogen, $C_1$-$C_4$-alkyl, $C_1$-$C_4$-alkylcarbonyl, $C_1$-$C_4$-alkylsulfonyl, $C_1$-$C_4$-fluoroalkylsulfonyl;

Cyc is a radical selected from the group consisting of phenyl, naphthyl, 4- to 8-membered saturated or partially unsaturated monocarbocyclic radicals, 7- to 10-membered saturated or partially unsaturated bicarbocyclic radicals, 4- to 8-membered saturated or partially unsaturated heteromonocyclic radicals, saturated or partially unsaturated 7- to 10 membered heterobicyclic radicals, 5- or 6-membered monocyclic hetaryl, and 8- to 10 membered bicyclic hetaryl, where the saturated or partially unsaturated heteromonocyclic and heterobicyclic radicals have 1, 2, 3 or 4 heteroatoms or heteroatom containing groups as ring members, which are selected from O, S, SO, $SO_2$ and N, and where the 5- or 6-membered monocyclic hetaryl and the 8- to 10-membered bicyclic hetaryl have 1, 2, 3 or 4 heteroatoms as ring members, which are selected from O, S and N, where phenyl, naphthyl, the saturated or partially unsaturated mono- and bicarbocyclic radicals, the heteromonocyclic and heterobicyclic radicals and the mono and bicyclic heteroaromatic radicals are unsubstituted or carry 1, 2, 3, 4 or 5 radicals $R^{C1}$ or one radical Y'—$R^{C2}$ and 0, 1, 2, 3 or 4 radicals $R^{C1}$; where $R^{C1}$ is selected from hydrogen, halogen, OH, CN, $NO_2$, $C_1$-$C_4$-alkyl, $C_1$-$C_4$-alkoxy, $C_1$-$C_4$-alkylsulfanyl, hydroxy-$C_1$-$C_4$-alkyl, $C_1$-$C_4$-alkoxy-$C_1$-$C_4$-alkyl, $C_1$-$C_4$-alkoxy-$C_1$-$C_4$-alkoxy, cyano-$C_1$-$C_4$-alkyl, $C_1$-$C_4$-fluoroalkyl, $C_1$-$C_4$-fluoroalkoxy, $C_1$-$C_4$-alkylsulfonyl, $C(O)R^a$, Z—$C(O)OR^b$, Z—$C(O)NR^cR^d$, $S(O)_2NR^cR^d$ and Z—$NR^eR^f$, where $R^a$ is selected from the group consisting of $C_1$-$C_4$-alkyl and $C_1$-$C_4$-fluoroalkyl, $R^b$ is selected from the group consisting of hydrogen, $C_1$-$C_4$-alkyl, $C_2$-$C_4$-alkenyl and $C_1$-$C_4$-fluoroalkyl, $R^c$, $R^d$ is selected from the group consisting of hydrogen, $C_1$-$C_4$-alkyl, $C_1$-$C_4$-fluoroalkyl, $C_1$-$C_4$-alkoxy and $C_1$-$C_4$-fluoroalkoxy, $R^e$, $R^f$ is selected from the group consisting of hydrogen, $C_1$-$C_4$-alkyl, $C_1$-$C_4$-fluoroalkyl, $C_1$-$C_4$-alkoxy and $C_1$-$C_4$-fluoroalkoxy, Z is a covalent bond or $C_1$-$C_4$-alkandiyl, or two radicals $R^{C1}$ which are bound at adjacent carbon atoms may form a fused 5- or 6-membered carbocyclic radical or a fused 5- or 6-membered heterocyclic radical having 1, 2 or 3 heteroatoms as ring members, which are selected from O, S and N;

or two radicals $R^{C1}$ which are bound at the same carbon atom may form a spiro 5- or 6-membered carbocyclic radical or a spiro 5- or 6-membered heterocyclic radical having 1 or 2 heteroatoms as ring members, which are selected from O, S and N, or two radicals $R^{C1}$ which are bound at the same carbon atom may form an oxygen atom, where the fused and the spiro radicals are unsubstituted or carry 1, 2, 3 or 4 radicals $R^{c3}$;

Y' is a chemical bond, $CH_2$, O, O—$CH_2$, $S(O)_2$, $NR^{y'}$, $NR^{y'}$—$CH_2$ or $NR^{y'}$—$S(O)_2$, where $R^{y'}$ is selected from the group consisting of hydrogen, $C_1$-$C_4$-alkyl, $C_1$-$C_4$-alkylcarbonyl, $C_1$-$C_4$-alkylsulfonyl, $C_1$-$C_4$-fluoroalkylsulfonyl;

$R^{C2}$ is a carbocyclic or heterocyclic radical selected from the group consisting of phenyl, 3- to 7-membered saturated or partially unsaturated monocarbocyclic radicals, 3- to 7-membered saturated or partially unsaturated heteromonocyclic radicals, having 1, 2 or 3 heteroatoms as ring members, which are selected from O, S and N, and 5- or 6-membered heteroaromatic radicals, having 1, 2 or 3 heteroatoms as ring members, which are selected from O, S and N, where the carbocyclic and the heterocyclic radical is unsubstituted or carries 1, 2, 3, 4 or 5 radicals $R^{c3}$;

$R^{C3}$ is selected from hydrogen, halogen, OH, CN, $C_1$-$C_4$-alkyl, $C_1$-$C_4$-alkoxy, hydroxy-$C_1$-$C_4$-alkyl, $C_1$-$C_4$-alkoxy-$C_1$-$C_4$-alkyl, cyano-$C_1$-$C_4$-alkyl, $C_1$-$C_4$-fluoroalkyl, $C_1$-$C_4$-fluoroalkoxy, $C_2$-$C_6$-alkenyl, C(O)$R^a$, Z—C(O)O$R^b$, Z—C(O)N$R^c R^d$, S(O)$_2$N$R^c R^d$ and Z—N$R^e R^f$, where, Z, $R^a$, $R^b$, $R^c$, $R^d$, $R^e$ and $R^f$ are as defined above or two radicals $R^{C3}$ which are bound at the same atom may form an oxygen atom.

The present invention therefore relates to the compounds of the general formula I, their tautomers, the hydrates thereof, the pharmaceutically suitable salts of the compounds of formula I, the prodrugs of the compounds of formula I and the pharmaceutically suitable salts of said prodrugs, tautomers or hydrates of the compounds of formula I.

The compounds of the formula I, their salts, their prodrugs, their hydrates and their tautomers effectively inhibit PDE10A even at low concentrations. They are additionally distinguished by a high selectivity in relation to the inhibition of the PDE10A vis-à-vis inhibition of other phosphodiesterase, such as PDE3 or PDE4. The compounds of the invention may additionally have one or more of the properties ii. to viii. mentioned above.

The compounds of the formula I, their salts, their prodrugs, their hydrates and their tautomers are therefore particularly suitable for treating disorders and conditions in creatures, especially human creatures, which can be treated or controlled by inhibition of phosphodiesterase type 10A.

The invention therefore also relates to the use of carboxamide compounds of the formula I, their tautomers, their hydrates and their pharmaceutically suitable salts for the manufacture of a medicament, in particular of a medicament which is suitable for the treatment of a disorder or a condition which can be treated by inhibition of phosphodiesterase type 10A.

The invention further relates to a medicament, in particular a medicament which is suitable for the treatment of a disorder or a condition which can be treated by inhibition of phosphodiesterase type 10A. The medicament comprises at least one compound of the formula I, as described herein, or a tautomer, or a hydrate or a prodrug of said compound I, or a pharmaceutically suitable salt of the compound of the formula I or a pharmaceutically suitable salt of the tautomer, the hydrate or the prodrug of compound of the formula I.

DETAILED DESCRIPTION OF THE INVENTION

The terms "compound of the formula I" and "compounds I" are used as synonyms.

The term "prodrugs" means compounds which are metabolized in vivo to the compounds I of the invention.

Typical examples of prodrugs are described in C. G. Wermuth (editor): The Practice of Medicinal Chemistry, Academic Press, San Diego, 1996, pages 671-715. These include for example phosphates, carbamates, amino acids, esters, amides, peptides, ureas and the like. Suitable prodrugs in the present case may be for example derivatives of those compounds I carrying an OH or $NH_2$-group, where the OH or $NH_2$-group forms an ester/amide/peptide linkage, i.e. where one of the hydrogen atoms of the OH or $NH_2$-group is substituted by a $C_1$-$C_4$-alkylcarbonyl group, e.g. by acetyl, propionyl, n-propylcarbonyl, isopropylcarbonyl, n-butylcarbonyl or tert-butylcarbonyl (pivaloyl), by benzoyl, or by an acyl group derived from an amino acid, e.g. glycine, alanine, serine, phenylalanine and the like, which is linked to the oxygen or nitrogen of the OH or $NH_2$-group via the carbonyl group of the amino acid. Further suitable prodrugs are alkylcarbonyloxyalkyl carbonates or carbamates of compounds I carrying an OH- or $NH_2$-group in which one of the hydrogen atoms of the OH- or $NH_2$-group has been replaced by a group of the formula —C(=O)—O—CHR$^p$—O—C(=O)—R$^q$ in which R$^p$ and R$^q$ are independently of one another $C_1$-$C_4$-alkyl. Such carbonates and carbamates are described for example in J. Alexander, R. Cargill, S. R. Michelson, H. Schwam, J. Medicinal Chem. 1988, 31(2), 318-322. These groups can then be eliminated under metabolic conditions and result in compounds I. Therefore, said prodrugs and their pharmaceutically acceptable salts are also part of the invention.

The term "pharmaceutically acceptable salts" refers to cationic or anionic salts compounds, wherein the counter ion is derived from pharmaceutically acceptable non-toxic bases or acids including inorganic or organic bases and inorganic or organic acids.

When the compound of formula I or its prodrug or N-oxide is acidic, salts may be prepared from pharmaceutically acceptable non-toxic bases, including inorganic and organic bases. Salts derived from inorganic bases include salts, wherein the counter ion is aluminium, ammonium, calcium, copper, ferric, ferrous, lithium, magnesium, manganic, manganous, potassium, sodium, zinc ion and the like. Particularly preferred are the ammonium, calcium, magnesium, potassium, and sodium ions. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, dibenzylethylene-diamine, diethylamine, 2-diethylamino-ethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of formula I or its prodrug or N-oxide is basic, salts may be prepared from pharmaceutically acceptable non-toxic acids, including inorganic and organic acids. Such acids include acetic, trifluoroacetic acid, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of formula I are meant to also include the pharmaceutically acceptable salts.

The compounds of the invention may be in the form of a mixture of diastereomers, or of a mixture of diastereomers in which one of the two diastereomers is enriched, or of essentially diastereomerically pure compounds (diastereomeric excess de>90%). The compounds are preferably in the form of essentially diastereomerically pure compounds (diastereomeric excess de>90%). The compounds I of the invention may furthermore be in the form of a mixture of enantiomers (for example as racemate), of a mixture of enantiomers in which one of the two enantiomers is enriched, or essentially in enantiomerically pure compounds (enantiomeric excess ee>90%). However, the compounds of the invention are frequently prone to racemization in relation to the stereochemistry of the carbon atom which carries the radical $R^1$, so that mixtures are frequently obtained in relation to this carbon atom, or compounds which exhibit a uniform stereochemistry in relation to this C atom form mixtures under physiological conditions. However, in relation to other stereocenters and the occurrence, associated therewith, of enantiomers and diastereomers, it is preferred to employ the compounds enantiomerically pure or diastereomerically pure.

The present invention moreover relates to compounds as defined herein, wherein one or more of the atoms depicted in formula I have been replaced by its stable, preferably non-radioactive isotope (e.g., hydrogen by deuterium, $^{12}C$ by $^{13}C$, $^{14}N$ by $^{15}N$, $^{16}O$ by $^{18}O$) and preferably wherein at least one hydrogen atom has been replaced by a deuterium atom. Of course, the compounds according to the invention contain more of the respective isotope than this naturally occurs and thus is anyway present in the compounds I.

The compounds of the formula I and their salts in the solid form may exist in more than one crystal structure (polymorphism), and may also be in the form of hydrates or other solvates. The present invention includes any polymorph of the compound I or its salt as well as any hydrate or other solvate.

In the context of the present description, unless stated otherwise, the terms "alkyl", "alkenyl", "alkoxy", "alkenyloxy", "fluoroalkyl", "fluoroalkoxy", "cycloalkyl", "fluorinated cycloalkyl", "alkylene", "alkandiyl", "hetaryl" and radicals derived therefrom, such as "alkylcarbonyl", "alkylsulfanyl", "alkylsulfonyl", "fluoroalkylsulfonyl", "hydroxylalkyl", "cyanoalkyl", "alkoxylalkyl", "alkoxyalkoxy", "alkylsulfanylalkyl", "alkylsulfanylalkoxy" and "hetarylmethyl" represent groups of individual radicals. The groups of noncyclic radicals "alkyl", "alkenyl", "alkoxy", "alkenyloxy", "fluoroalkyl", "fluoroalkoxy", "alkylene", "alkandiyl", and the groups of radicals derived therefrom always include both unbranched and branched "alkyl", "alkenyl", "alkoxy", "alkenyloxy", "fluoroalkyl", "fluoroalkoxy", "alkylene" and "alkandiyl", respectively.

The prefix $C_n$—$C_m$— indicates the respective number of carbons in the hydrocarbon unit. Unless indicated otherwise, fluorinated substituents preferably have one to five identical or different fluorine atoms.

The term "halogen" designates in each case, fluorine, bromine, chlorine or iodine, specifically fluorine, chlorine or bromine.

Examples of other meanings are:

Alkyl, and the alkyl moieties for example in alkylcarbonyl, alkylsulfanyl, alkylsulfonyl, alkylsulfanylalkyl and alkylsulfaylalkoxy: saturated, straight-chain or branched hydrocarbon radicals having one or more C atoms, e.g. 1 to 4 carbon atoms, e.g. $C_1$-$C_4$-alkyl such as methyl, ethyl, propyl, 1-methylethyl, n-butyl, 1-methylpropyl, 2-methylpropyl and 1,1-dimethylethyl.

Fluoroalkyl and the fluoroalkyl moieties for example in fluoroalkylsulfonyl: an alkyl radical having ordinarily 1 to 4 C atoms, in particular 1 or 2 C-atoms ($C_1$-$C_2$-fluoroalkyl) as mentioned above, whose hydrogen atoms are partly or completely replaced by fluorine atoms such as fluoromethyl, difluoromethyl, trifluoromethyl, 2-fluoroethyl, 2,2-difluoroethyl, 2,2,2-trifluoroethyl, pentafluoroethyl, 2-fluoro-1-methylethyl, 2,2-difluoro-1-methylethyl, 2,2-trifluoro-1-methylethyl, 2-fluoropropyl, 3-fluoropropyl, 2,2-difluoropropyl, 2,3-difluoropropyl, 3,3,3-trifluoropropyl, 2,3,3,3-pentafluoropropyl, heptafluoropropyl, 1-(fluoromethyl)-2-fluoroethyl, 4-fluorobutyl, and nonafluorobutyl.

Cycloalkyl, and the cycloalkyl moieties for example in cycloalkoxy or cycloalkyl-$C_1$-$C_4$-alkyl: monocyclic, saturated hydrocarbon groups having three or more C atoms, e.g. 3, 4, 5, 6 or 7 carbon ring members, such as cyclopropyl, cyclobutyl, cyclopentyl, cyclohexyl and cycloheptyl.

Fluorinated cycloalkyl: monocyclic, saturated hydrocarbon groups having three or more C atoms, e.g. 3, 4, 5, 6 or 7 carbon ring members, such as cyclopropyl, cyclobutyl, cyclopentyl, cyclohexyl and cycloheptyl, wherein at least one, e.g. 1, 2, 3, 4, 5 or 6 of the hydrogen atoms are replaced by fluorine atoms, examples including 1-fluorocyclopropyl, 2-fluorocyclopropyl, 2,2-difluorocyclopropyl, 1,2-difluorocyclopropyl, 2,3-difluorocyclopropyl, etc.

Cycloalkoxy: a cycloalkyl radical as defined above which is linked via an oxygen atom, e.g. cyclopropyloxy, cyclobutyloxy, cyclopentyloxy or cyclohexyloxy.

Cycloalkylalkyl: a cycloalkyl radical as defined above which is linked via an alkylene group, in particular via a methylene, 1,1-ethylene or 1,2-ethylene group, e.g. cyclopropylmethyl, cyclobutylmethyl, cyclopentylmethyl or cyclohexylmethyl.

Alkenyl, and alkenyl moieties for example in alkenyloxy: monounsaturated, straight-chain or branched hydrocarbon radicals having two or more C atoms, e.g. 2 to 4 carbon atoms and one C=C-double bond in any position, e.g. $C_2$-$C_4$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl and 2-methyl-2-propenyl.

Alkoxy or alkoxy moieties for example in alkoxyalkyl and alkoxyalkoxy:

an alkyl radical as defined above having preferably 1 to 4 C atoms, which is connected to the remainder of the molecule via an O atom: e.g. methoxy, ethoxy, n-propoxy, 1-methylethoxy, butoxy, 1-methylpropoxy, 2-methylpropoxy or 1,1-dimethylethoxy.

Fluoroalkoxy: alkoxy as described above, in which the hydrogen atoms of these groups are partly or completely replaced by fluorine atoms, i.e. for example $C_1$-$C_4$-fluoroalkoxy, in particular $C_1$-$C_2$-fluoroalkoxy, such as fluoromethoxy, difluoromethoxy, trifluoromethoxy, 2-fluoroethoxy, 2,2-difluoroethoxy, 2,2,2-trifluoroethoxy, pentafluoroethoxy, 2-fluoropropoxy, 3-fluoropropoxy, 2,2-difluoropropoxy, 2,3-difluoropropoxy, 3,3,3-trifluoropropoxy, 2,2,3,3,3-pentafluoropropoxy, heptafluoropropoxy, 1-(fluoromethyl)-2-fluoroethoxy, specifically fluoromethoxy, difluoromethoxy, trifluoromethoxy, 2-fluoroethoxy, or 2,2,2-trifluoroethoxy.

Hydroxyalkyl: an alkyl radical ordinarily having 1 to 4 C atoms, in which one hydrogen atom is replaced by an OH radical. Examples thereof are $CH_2$—OH, 1-hydroxyethyl, 2-hydroxyethyl, 1-hydroxypropyl, 2-hydroxypropyl, 1-methyl-1-hydroxyethyl, 1-methyl-2-hydroxyethyl, 3-hydroxypropyl, 2-hydroxybutyl, 3-hydroxybutyl, 4-hydroxybutyl, 1-methyl-2-hydroxypropyl, 1,1-dimethyl-2-hydroxyetyl, 1-methyl-1-hydroxypropyl etc.

Cyanoalkyl: an alkyl radical ordinarily having 1 to 4 C atoms, in which one hydrogen atom is replaced by a CN radical. Examples thereof are $CH_2$—CN, 1-cyanoethyl, 2-cyanoethyl, 1-cyanopropyl, 2-cyanopropyl, 1-methyl-1-cyanoethyl, 1-methyl-2-cyanoethyl, 3-cyanopropyl, 2-cyanobutyl, 3-cyanobutyl, 4-cyanobutyl, 1-methyl-2-cyanopropyl, 1,1-dimethyl-2-cyanoetyl, 1-methyl-1-cyanopropyl etc.

Alkoxyalkyl: an alkyl radical ordinarily having 1 to 4 C atoms, in which one hydrogen atom is replaced by an alkoxy radical ordinarily having 1 to 4 C atoms. Examples thereof are $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl, 4-(1,1-dimethylethoxy)butyl, etc.

Alkoxyalkoxy: an alkoxyalkyl radical as defined above ordinarily having 1 to 4 C atoms both in the alkoxy and the alkyl moiety which is connected to the remainder of the molecule via an O atom: Examples thereof are $OCH_2$—$OCH_3$, $OCH_2$—$OC_2H_5$, n-propoxymethoxy, $OCH_2$—$OCH(CH_3)_2$, n-butoxymethoxy, (1-methylpropoxy)methoxy, (2-methylpropoxy)methoxy, $OCH_2$—$OC(CH_3)_3$, 2-(methoxy)ethoxy, 2-(ethoxy)ethoxy, 2-(n-propoxy)ethoxy, 2-(1-methylethoxy)ethoxy, 2-(n-butoxy)ethoxy, 2-(1-methylpropoxy)ethoxy, 2-(2-methylpropoxy)ethoxy, 2-(1,1-dimethyl-ethoxy)ethoxy, etc.

Alkylcarbonyl: alkyl as defined above preferably having 1 to 4 C atoms, which is connected via a carbonyl group to the remainder of the molecule, e.g. acetyl, propionyl, butyryl, isobutyryl, pentanoyl, pivaloyl and the like.

Alkylsulfanyl and the alkylsulfanyl radicals in alkylsulfanylalkyl and alkylsulfanylalkoxy: alkyl as defined above preferably having 1 to 4 C atoms, which is connected via an S atom to the remainder of the molecule, e.g. methylsulfanyl, ethylsulfanyl, n-propylsulfanyl and the like.

Alkylsulfonyl: alkyl as defined above preferably having 1 to 4 C atoms, which is connected via an $SO_2$ group to the remainder of the molecule, e.g. methylsulfonyl, ethylsulfonyl, n-propylsulfonyl and the like.

Fluoroalkylsulfanyl: fluoroalkyl as defined above preferably having 1 to 4 C atoms, which is connected via an S atom to the remainder of the molecule, e.g. fluoromethylsulfanyl, difluoromethylsulfanyl, trifluoromethylsulfanyl, 2-fluoroethylsulfanyl, 2,2-difluoroethylsulfanyl, 2,2,2-trifluoroethylsulfanyl, pentafluoroethylsulfanyl, 2-fluoropropylsulfanyl, 3-fluoropropylsulfanyl, 2,2-difluoropropylsulfanyl, 2,3-difluoropropylsulfanyl, and heptafluoropropylsulfanyl.

Fluoroalkylsulfonyl: fluoroalkyl as defined above preferably having 1 to 4 C atoms, which is connected via an $SO_2$ group to the remainder of the molecule, e.g. fluoromethylsulfonyl, difluoromethylsulfonyl, trifluoromethylsulfonyl, 2-fluoroethylsulfonyl, 2,2-difluoroethylsulfonyl, 2,2,2-trifluoroethylsulfonyl, pentafluoroethylsulfonyl, 2-fluoropropylsulfonyl, 3-fluoropropylsulfonyl, 2,2-difluoropropylsulfonyl, 2,3-difluoropropylsulfonyl, and heptafluoropropylsulfonyl.

Alkylsulfanylalkyl: an alkyl radical ordinarily having 1 to 4 C atoms, in which one hydrogen atom is replaced by an alkylsulfanyl radical ordinarily having 1 to 4 C atoms. Examples thereof are $CH_2$—$SCH_3$, $CH_2$—$SC_2H_5$, n-propylsulfanylmethyl, $CH_2$—$SCH(CH_3)_2$, n-butylsulfanylmethyl, (1-methylpropsulfanyl)methyl, (2-methylpropsulfanyl)methyl, $CH_2$—$OC(CH_3)_3$, 2-(methylsulfanyl)ethyl, 2-(ethylsulfanyl)ethyl, 2-(n-propylsulfanyl)ethyl, 2-(1-methylethylsulfanyl)ethyl, 2-(n-butylsulfanyl)ethyl, 2-(1-methylpropylsulfanyl)ethyl, 2-(2-methylpropylsulfanyl)ethyl, 2-(1,1-dimethylethylsulfanyl)ethyl, 2-(methylsulfanyl)propyl, 2-(ethylsulfanyl)propyl, 2-(n-propylsulfanyl)propyl, 2-(1-methylethylsulfanyl)propyl, 2-(n-butylsulfanyl)propyl, 2-(1-methylpropylsulfanyl)propyl, 2-(2-methylpropylsulfanyl)propyl, 2-(1,1-dimethylethylsulfanyl)propyl, 3-(methylsulfanyl)propyl, 3-(ethylsulfanyl)propyl, 3-(n-propylsulfanyl)propyl, 3-(1-methylethylsulfanyl)propyl, 3-(n-butylsulfanyl)propyl, 3-(1-methylpropylsulfanyl)propyl, 3-(2-methylpropylsulfanyl)propyl, 3-(1,1-dimethylethylsulfanyl)propyl, 2-(methylsulfanyl)butyl, 2-(ethylsulfanyl)butyl, 2-(n-propylsulfanyl)butyl, 2-(1-methylethylsulfanyl)butyl, 2-(n-butylsulfanyl)butyl, 2-(1-methylpropylsulfanyl)butyl, 2-(2-methylpropylsulfanyl)butyl, 2-(1,1-dimethylethylsulfanyl)butyl, 3-(methylsulfanyl)butyl, 3-(ethylsulfanyl)butyl, 3-(n-propylsulfanyl)butyl, 3-(1-methylethylsulfanyl)butyl, 3-(n-butylsulfanyl)butyl, 3-(1-methylpropylsulfanyl)butyl, 3-(2-methylpropylsulfanyl)butyl, 3-(1,1-dimethyl-ethylsulfanyl)butyl, 4-(methylsulfanyl)butyl, 4-(ethylsulfanyl)butyl, 4-(n-propylsulfanyl)butyl, 4-(1-methylethylsulfanyl)butyl, 4-(n-butylsulfanyl)butyl, 4-(1-methylpropylsulfanyl)butyl, 4-(2-methylpropylsulfanyl)butyl, 4-(1,1-dimethylethylsulfanyl)butyl, etc.

"Alkylen" or "Alkandiyl": a saturated hydrocarbon chain having ordinarily from 1 to 4 carbon atoms, such as methylen (—$CH_2$—), 1,2-ethylen (—$CH_2CH_2$—), 1,1-ethandiyl (—$CH(CH_3)$—), 1,2-propandiyl, 1,3-propandiyl, 1,4-butandiyl, 1,2-butandiyl, 1,3-butandiyl, 1-methyl-1,2-propandiyl, 2-methyl-1,3-propandiyl, 1-methyl-1,1-ethandiyl, 1-methyl-1,2-propandiyl etc.

Saturated or partially unsaturated 4 to 7-membered monocarbocyclic radicals include cycloalkyl as defined above and cycloalkenyl having ordinarily from 4 to 7 carbon atoms as ring members, e.g. 1-cyclobuten-1-yl, 2-cyclobutenyl, 1-cyclopentenyl, 2-cyclopentenyl, 1-cyclohexenyl, 2-cyclohexenyl, 3-cyclohexenyl, 1-cycloheptenyl, 2-cycloheptenyl, 3-cycloheptenyl.

Saturated or partially unsaturated 7 to 10-membered bicarbocyclic radicals include bicyclic carbocyclic radicals which ordinarily have from 7 to 10 carbon atoms as ring members and which are saturated or which have one or more, e.g. one or two C=C double bonds, or which include a monounsaturated carbocycle where the double bond is part of a fused benzene ring, e.g. bicyclo[2,2,1]-1-heptyl, bicyclo[2,2,1]-2-heptyl, bicyclo[2,2,1]-7-heptyl, bicyclo[3,3,0]-1- octyl, bicyclo[3,3,0]-2-octyl, bicyclo[3,3,0]-3-octyl, bicyclo[2,2,2]-1-octyl, bicyclo[2,2,2]-2-octyl, bicyclo[3,2,1]-1-octyl, bicyclo[3,2,1]-2-octyl, bicyclo[3,2,1]-6-octyl, bicyclo[3,2,1]-8-octyl, bicyclo[4,3,0]-1-nonyl, bicyclo[4,3,0]-2-nonyl, bicyclo[4,3,0]-3-nonyl, bicyclo[4,3,0]-7-nonyl, bicyclo[4,3,0]-8-nonyl, bicyclo[4,4,0]-1-decyl, bicyclo[4,4,0]-2-decyl, bicyclo[4,4,0]-3-decyl, bicyclo[2,2,1]-hept-2-en-1-yl, bicyclo[2,2,1]-hept-2-en-2-yl, bicyclo[2,2,1]-hept-2-en-5-yl, bicyclo[2,2,1]-hept-2-en-7-yl, bicyclo[2,2,2]-oct-2-en-1-yl, bicyclo[2,2,2]-oct-2-en-2-yl, bicyclo[2,2,2]-oct-2-en-5-yl, bicyclo[2,2,2]-oct-2-en-7-yl, bicyclo[3,3,0]-2-octen-1-yl, bicyclo[3,3,0]-2-octen-2-yl, bicyclo[3,3,0]-2-octen-3-yl, bicyclo[3,3,0]-2-octen-4-yl, bicyclo[3,3,0]-2-octen-5-yl, bicyclo[3,3,0]-2-octen-6-yl, bicyclo[3,3,0]-2-octen-7-yl, bicyclo[3,3,0]-2-octen-8-yl, inden-1-yl, inden-2-yl, inden-4-yl, inden-6-yl, tetrahydro-1-naphthyl, tetrahydro-2-naphthyl, tetrahydro-5-naphthyl, tetrahydro-6-naphthyl, etc.

Heterocyclyl: a heterocyclic radical which may be saturated or partly unsaturated and which may be a monocyclic heterocyclic radical ordinarily having 3, 4, 5, 6, 7 or 8 ring atoms or a heterobicyclic radical ordinarily having 7, 8, 9 or 10 ring atoms, where ordinarily 1, 2, 3 or 4, in particular 1, 2 or 3, of the ring atoms are heteroatoms such as N, S or O, or heteroatom groups such as S(=O) or S(=O)$_2$ besides carbon atoms as ring members.

Examples of saturated heteromonocycles are in particular:
Saturated heteromonocyclic radical which ordinarily has 3, 4, 5, 6 or 7 ring atoms, where ordinarily 1, 2 or 3 of the ring atoms are heteroatoms such as N, S or O, besides carbon atoms as ring members. These include for example:
C-bonded, 3- or 4-membered saturated rings such as 2-oxiranyl, 2-oxetanyl, 3-oxetanyl, 2-aziridinyl, 3-thiethanyl, 1-azetidinyl, 2-azetidinyl.
C-bonded, 5-membered saturated rings such as tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl.
C-bonded, 6-membered saturated rings such as: tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl. N-bonded, 5-membered saturated rings such as:
tetrahydropyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl.
N-bonded, 6-membered saturated rings such as:
piperidin-1-yl, hexahydropyrimidin-1-yl, hexahydropyrazin-1-yl, hexahydro-pyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl.

Unsaturated heteromonocyclic radicals which ordinarily have 4, 5, 6 or 7 ring atoms, where ordinarily 1, 2 or 3 of the ring atoms are heteroatoms such as N, S or O, besides carbon atoms as ring members. These include for example:
C-bonded, 5-membered, partially unsaturated rings such as: 2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl.

C-bonded, 6-membered, partially unsaturated rings such as:
2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetra-hydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-6-tetrahydropyrimidin-2-yl, 3,4,5,6-tetrahydropyrimidin-4-yl, 3,4,5,6-tetra-hydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl.

N-bonded, 5-membered, partially unsaturated rings such as: 2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl.

N-bonded, 6-membered, partially unsaturated rings such as: 1,2,3,4-tetrahydropyridin-1-yl, 1,2,5,6-tetrahydropyridin-1-yl, 1,4-dihydropyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydro-pyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl.

Examples of saturated or partially unsaturated heterobicycles are in particular radicals corresponding to saturated or partially unsaturated bicarbocyclic radicals, wherein 1, 2 or 3 CH or $CH_2$ moieties have been replaced by N, NH, O, S, S(=O) or $S(=O)_2$, such as 2-oxa-6-azaspiro-[3,4]octyl, 2-azabicyclo[2.2.1]heptyl, 5-azabicyclo[2.2.1]heptyl, 2,5-diazabicyclo[2.2.1]heptyl, 3-azabicyclo[3.2.1]octyl, 8-azabicyclo[3.2.1]octyl, 3,8-diazabicyclo[3.2.1]octyl, dihydroindolyl, dihydroindolizynyl, dihydroisoindolyl, dihydroquinolinyl, dihydroisoquinolinyl, chromenyl and chromanyl.

Hetaryl: a 5- or 6-membered aromatic heteromonocyclic radical (also termed 5- or 6-membered monocyclic hetaryl) which ordinarily has 1, 2, 3 or 4 heteroatoms as ring members, which are selected from O, S and N, and which has in particular 1, 2, 3 or 4 nitrogen atoms or a heteroatom selected from oxygen and sulfur and, if appropriate, 1 or 2 nitrogen atoms as ring members besides carbon atoms as ring members and a 8- to 10-membered aromatic heterobicyclic radical (also termed 8- to 10-membered bicyclic hetaryl) which ordinarily has 1, 2, 3 or 4 heteroatoms as ring members, which are selected from O, S and N, and which has in particular 1, 2, 3 or 4 nitrogen atoms or a heteroatom selected from oxygen and sulfur and, if appropriate, 1 or 2 nitrogen atoms as ring members besides carbon atoms as ring members: for example C-bonded, 5-membered monocyclic hetaryl having 1, 2 or 3 or 4 nitrogen atoms or a heteroatom selected from oxygen and sulfur and, if appropriate, having 1, 2 or 3 nitrogen atoms as ring members, such as: 2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl.

C-bonded, 6-membered monocyclic hetaryl having 1, 2 or 3 nitrogen atoms as ring members, such as: pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl.

N-bonded, 5-membered heteroaromatic radicals having 1, 2, 3 or 4 nitrogen atoms as ring members, such as: pyrrol-1-yl, pyrazol-1-yl, imidazol-1-yl, 1,2,3-triazol-1-yl, 1,2,4-triazol-1-yl, tetrazol-1-yl.

bicyclic 8 to 10-membered hetaryl, hetaryl which has one of the aforementioned 5- or 6-membered heteroaromatic rings and a further aromatic carbocycle or 5- or 6-membered heterocycle fused thereto, for example a fused benzene, thiophene, furane, pyrrole, pyrazole, imidazole, pyridine or pyrimidine ring. These bicyclic hetaryl include for example quinolinyl, isoquinolinyl, cinnolinyl, indolyl, indolizynyl, isoindolyl, indazolyl, benzofuryl, benzothienyl, benzo[b]thiazolyl, benzoxazolyl, benzthiazolyl, benzimidazolyl, imidazo[1,2-a] pyridine-2-yl, thieno[3,2-b]pyridine-5-yl, imidazo-[2,1-b]-thiazol-6-yl and 1,2,4-triazolo[1,5-a]pyridine-2-yl.

Hetarylalkyl: a hetaryl radical as defined above which is linked via an alkylene group, in particular via a methylene, 1,1-ethylene or 1,2-ethylene group, to the remainder of the molecule.

The expression "optionally substituted" in the context of the present invention means that the respective moiety is unsubstituted or has 1, 2 or 3, in particular 1, substituents which are selected from halogen, $C_1$-$C_4$-alkyl, $C_1$-$C_4$-haloalkyl, OH, SH, CN, $CF_3$, O—$CF_3$, COOH, O—$CH_2$—COOH, $C_1$-$C_6$-alkoxy, $C_1$-$C_4$-haloalkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2$NH—$C_1$-$C_6$-alkyl, CON—($C_1$-$C_6$-alkyl)$_2$, $SO_2$N—($C_1$-$C_6$-alky)$_2$, NH—$SO_2$—$C_1$-$C_6$-alkyl, NH—CO—$C_1$-$C_6$-alkyl, $SO_2$—$C_1$-$C_6$-alkyl, O-phenyl, O—$CH_2$-phenyl, CONH-phenyl, $SO_2$NH-phenyl, CONH-hetaryl, $SO_2$NH-hetaryl, $SO_2$-phenyl, NH—$SO_2$-phenyl, NH—CO-phenyl, NH—$SO_2$-hetaryl and NH—CO-hetaryl, where phenyl and hetaryl in the last 11 radicals mentioned are unsubstituted or may have 1, 2 or 3 substituents which are selected from halogen, $C_1$-$C_4$-alkyl, $C_1$-$C_4$-haloalkyl, $C_1$-$C_4$-alkoxy and $C_1$-$C_4$-haloalkoxy.

In relation to their use as inhibitors of PDE10A, the variables Het, $X^1$, $X^2$, $X^3$, $X^4$, A, $R^1$, $R^2$, $R^3$, $R^4$, $R^5$, $R^{5a}$, $R^6$, $R^7$, $R^8$, $R^9$, $R^{10}$, Y, Cyc and Z preferably have the following meanings, where these represent, both considered on their own and in combination with at least one other or all, special configurations of the compounds of the formula I:

Het is preferably selected from the group consisting of C-bound 6-membered monocyclic hetaryl, which has 1 or 2 nitrogen atoms as ring members, benzofuryl and C-bound, fused bicyclic hetaryl, which has 1 or 2 nitrogen atoms as ring members and optionally a further heteroatom selected from O, S and N as ring member, where monocyclic hetaryl, benzofuryl and bicyclic hetaryl may be unsubstituted or may carry 1, 2, 3 or 4 substituents $R^x$, in particular 0, 1 or 2 substituents $R^x$. In this regard, $R^x$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, phenyl, $C_3$-$C_6$-cycloalkyl, optionally substituted by 1, 2 or 3 methyl groups, and fluorinated $C_3$-$C_6$-cycloalkyl. In this regard, $R^x$ is in particular selected from fluorine, chlorine, methyl, fluoromethyl, difluoromethyl, trifluoromethyl, methoxy, fluoromethoxy, difluoromethoxy, trifluoromethoxy, phenyl, cyclopropyl, optionally substituted by 1, 2 or 3 methyl groups, and fluorinated cyclopropyl.

In a particular embodiment of the invention, Het is selected from fused bicyclic hetaryl, which has 1 or 2 nitrogen atoms as ring members and optionally a further heteroatom selected from O, S and N as ring member and which may be unsubstituted or may carry 1, 2, 3 or 4 substituents $R^x$, in particular 0, 1 or 2 substituents $R^x$. In this regard, $R^x$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl, optionally substituted by 1, 2 or 3 methyl groups, and fluorinated $C_3$-$C_6$-cycloalkyl. In this regard, $R^x$ is in particular selected from fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl.

In another particular embodiment of the invention, Het is selected from 6-membered monocyclic hetaryl, which may be unsubstituted or may carry 1, 2, 3 or 4 substituents $R^x$, in particular 0, 1 or 2 substituents $R^x$. In this regard, $R^x$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, phenyl, $C_3$-$C_6$-cycloalkyl, optionally substituted by 1, 2 or 3 methyl groups, and fluorinated $C_3$-$C_6$-cycloalkyl. In this regard, $R^x$ is in particular selected from fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl or one $R^x$ may also be phenyl.

Particular preference is given to those Het radicals, which have at least one imino-nitrogen as ring member, which is located in the position adjacent to carbon atom bound to the group $CR^9R^{10}$. Particular preference is given to those Het radicals, which have at least one imino-nitrogen as ring member, which is located in the position adjacent to carbon atom bound to the group $CR^9R^{10}$ and which are selected from the group consisting of C-bound 6-membered monocyclic hetaryl, which has 1 or 2 nitrogen atoms as ring members, benzofuryl and C-bound, fused bicyclic hetaryl, which has 1 or 2 nitrogen atoms as ring members and optionally a further heteroatom selected from O, S and N as ring member, where monocyclic hetaryl, benzofuryl and bicyclic hetaryl may be unsubstituted or may carry 1, 2, 3 or 4 substituents $R^x$, in particular 0, 1 or 2 substituents $R^x$. In this regard, $R^x$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, phenyl, $C_3$-$C_6$-cycloalkyl, optionally substituted by 1, 2 or 3 methyl groups, and fluorinated $C_3$-$C_6$-cycloalkyl. In this regard, $R^x$ is in particular selected from fluorine, chlorine, methyl, fluoromethyl, difluoromethyl, trifluoromethyl, methoxy, fluoromethoxy, difluoromethoxy, trifluoromethoxy, phenyl, cyclopropyl, optionally substituted by 1, 2 or 3 methyl groups, and fluorinated cyclopropyl. Particular examples of Het are selected from the group consisting of 2-benzofuryl, 2-pyridyl, 3-pyridazinyl, 2-pyrimidinyl, 2-quinolinyl, 2-quinazolinyl, 2-quinoxalinyl, benzimidazol-2-yl, 1-methylbenzimidazol-2-yl, benzothiaozo-2-yl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl, where the aforementioned radicals are unsubstituted or may carry 1, 2 or 3 radicals $R^x$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl.

In a particular embodiment of the invention, Het has at least one imino-nitrogen as ring member, which is located in the position adjacent to carbon atom bound to the group $CR^9R^{10}$ and Het is selected from the group consisting of fused bicyclic hetaryl, which has 1 or 2 nitrogen atoms as ring members and optionally a further heteroatom selected from O, S and N as ring member, where bicyclic hetaryl may be unsubstituted or may carry 1, 2, 3 or 4 substituents $R^x$, in particular 0, 1 or 2 substituents $R^x$. In this regard, $R^x$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl, optionally substituted by 1, 2 or 3 methyl groups, and fluorinated $C_3$-$C_6$-cycloalkyl. In this regard, $R^x$ is in particular selected from fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl. Particular examples of Het of this embodiment are 2-quinolinyl, 2-quinazolinyl, 2-quinoxalinyl, benzimidazol-2-yl, 1-methylbenzimidazol-2-yl, benzothiaozo-2-yl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl, where the aforementioned radicals are unsubstituted or may carry 1, 2 or 3 radicals $R^x$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl.

Particular preference is given to compounds of the formula I, where Het is 2-quinolinyl or imidazo[1,2-a]pyridine-2-yl, where these radicals are unsubstituted or may carry 1, 2 or 3 radicals $R^x$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl.

Particular preference is given to compounds of the formula I, where Het is 1-methylbenzimidazol-2-yl or benzothiazol-2-yl, where these radicals are unsubstituted or may carry 1, 2 or 3 radicals $R^x$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl.

Particular preference is given to compounds of the formula I, where Het is 2-pyridyl, where 2-pyridyl unsubstituted or may carry 1, 2 or 3 radicals $R^x$ as defined above, which are in particular selected from the group consisting of halogen, $C_1$-$C_4$-alkyl, $C_1$-$C_4$-haloalkyl, $C_1$-$C_4$-alkoxy, $C_1$-$C_4$-haloalkyoxy, cyclopropyl, optionally substituted by 1, 2 or 3 methyl groups, and fluorinated cyclopropyl, such as fluorine, chlorine, methyl, ethyl, isopropyl, fluoromethyl, difluoromethyl, trifluoromethyl, methoxy, fluoromethoxy, difluoromethoxy, trifluoromethoxy, cyclopropyl, 1-methylcyclopropyl, 1-fluorocyclopropyl and 2-fluorocyclopropyl.

$X^1$ is preferably N or $CR^1$.
$X^2$ is preferably $CR^2$.
$X^3$ is preferably $CR^3$.
$X^4$ is preferably $CR^4$.

In this regard, those radicals $R^1$, $R^2$, $R^3$ and $R^4$, which are different from Y-Cyc, are in particular selected, independently of each other, from the group consisting of hydrogen, fluorine, $C_1$-$C_4$-alkyl, fluorinated $C_1$-$C_2$-alkyl, $C_1$-$C_4$-alkoxy, fluorinated $C_1$-$C_2$-alkoxy, cyclopropyl, optionally substituted by 1, 2 or 3 methyl groups, and fluorinated cyclopropyl. In particular $R^2$ and $R^3$ are both hydrogen.

In a particular group of embodiments of the invention, $X^1$ is N, $X^2$ is C—$R^2$, $X^3$ is C—$R^3$ and $X^4$ is C—$R^4$, where $R^2$, $R^3$ and $R^4$ are as defined above. In another particular group of embodiments of the invention, $X^1$ is C—$R^1$, $X^2$ is C—$R^2$, $X^3$ is C—$R^3$ and $X^4$ is C—$R^4$.

In preferred embodiments of the invention, either $R^1$ or $R^4$ is a radical Y-Cyc and $R^2$ and $R^3$, if present, have a meaning different from Y-Cyc. Amongst these, a particular embodiment relates to those compounds of the formula I, where $X^4$ is C—$R^4$ and $R^4$ is a radical Y-Cyc. Amongst these, another particular embodiment relates to those compounds of the formula I, where $X^1$ is C—$R^1$ and $R^1$ is a radical Y-Cyc.

In particular embodiments of the invention, $X^4$ is C—$R^4$ and $R^4$ is a radical Y-Cyc, while $X^1$ is N or C—$R^1$, $X^2$ is C—$R^2$ and $X^3$ is C—$R^3$, where $R^1$, if present, $R^2$ and $R^3$ have a meaning different from Y-Cyc. In this regard, $R^1$, $R^2$ and $R^3$ are as defined above and preferably selected, independently of each other, from the group consisting of hydrogen, fluorine, $C_1$-$C_4$-alkyl, fluorinated $C_1$-$C_2$-alkyl, $C_1$-$C_4$-alkoxy, fluorinated $C_1$-$C_2$-alkoxy, cyclopropyl, optionally substituted by 1, 2 or 3 methyl groups, and fluorinated cyclopropyl. In particular $R^2$ and $R^3$ are both hydrogen.

In other particular embodiments of the invention, $X^1$ is C—$R^1$ and $R^1$ is a radical Y-Cyc, while $X^4$ is N or C—$R^4$, $X^2$ is C—$R^2$ and $X^3$ is C—$R^3$, where $R^4$, if present, $R^2$ and $R^3$ have a meaning different from Y-Cyc. In this regard, $R^2$, $R^3$ and $R^4$, if present, are as defined above and preferably selected, independently of each other, from the group consisting of hydrogen, fluorine, $C_1$-$C_4$-alkyl, fluorinated $C_1$-$C_2$-alkyl, $C_1$-$C_4$-alkoxy, fluorinated $C_1$-$C_2$-alkoxy, cyclopropyl, optionally substituted by 1, 2 or 3 methyl groups, and fluorinated cyclopropyl. In particular $R^2$ and $R^3$ are both hydrogen.

In special embodiments of the invention, $X^4$ is C—$R^4$ and $R^4$ is a radical Y-Cyc, while $X^1$ is N, $X^2$ is C—$R^2$ and $X^3$ is C—$R^3$, where $R^2$ and $R^3$ have a meaning different from Y-Cyc.

In other special embodiment of the invention, $X^4$ is C—$R^4$ and $R^4$ is a radical Y-Cyc, while $X^1$ is C—$R^1$, $X^2$ is C—$R^2$ and $X^3$ is C—$R^3$, where $R^1$, $R^2$ and $R^3$ have a meaning different from Y-Cyc.

In further special embodiments of the invention, $X^1$ is C—$R^1$ and $R^1$ is a radical Y-Cyc, while $X^4$ is N, $X^2$ is C—$R^2$ and $X^3$ is C—$R^3$, where $R^2$ and $R^3$ have a meaning different from Y-Cyc.

In further special embodiments of the invention, $X^1$ is C—$R^1$ and $R^1$ is a radical Y-Cyc, while $X^4$ is C—$R^4$, $X^2$ is C—$R^2$ and $X^3$ is C—$R^3$, where $R^4$, $R^2$ and $R^3$ have a meaning different from Y-Cyc.

In the aforementioned special embodiments, those $R^1$, $R^2$, $R^3$ and $R^4$, if present, which are different from Y-Cyc are preferably selected, independently of each other, from the group consisting of hydrogen, fluorine, $C_1$-$C_4$-alkyl, fluorinated $C_1$-$C_2$-alkyl, $C_1$-$C_4$-alkoxy, fluorinated $C_1$-$C_2$-alkoxy, cyclopropyl, optionally substituted by 1, 2 or 3 methyl groups, and fluorinated cyclopropyl. In particular $R^2$ and $R^3$ are both hydrogen.

In the moieties Y-Cyc, Y is preferably selected from O, NH and a chemical bond. In particular embodiments of the invention Y is a chemical bond.

Preferably, Cyc is selected from the groups of
(i) saturated 4-, 5-, 6- or 7-membered heteromonocycles or a saturated 7-, 8-, 9- or 10-membered heterobicycle, where the heteromonocycle and the heterobicycle have one nitrogen or oxygen atom as ring member and may have one further heteroatom or heteroatom group as ring member, which is selected from the group consisting of O, S, S(=O), S(=O)$_2$ and N, where the saturated heteromonocycle and the saturated heterobicycle are unsubstituted or carry 1, 2, 3, 4 or 5, in particular 1, 2, or 3 radicals $R^{C1}$ or one radical Y'—$R^{C2}$ and 0, 1, 2, 3 or 4, in particular 0, 1 or 2 radicals $R^{C1}$, where $R^{C1}$, $R^{C2}$ and Y' are as defined herein and where Y', if present, is preferably a chemical bond or O; and
(ii) phenyl or a 5- or 6 membered hetaryl, which has one heteroatom, selected from O, S and N as ring member and optionally one or two further heteroatoms as ring members, and which is in particular selected from the group consisting of pyridyl, pyrimidinyl, furyl, thienyl, pyrrolyl, imidazolyl, pyrazolyl, oxazolyl and thiazolyl, where phenyl and the 5- or 6 membered hetaryl are unsubstituted or carry 1, 2, 3, 4 or 5, in particular 1, 2, or 3 radicals $R^{C1}$ or one radical Y'—$R^{C2}$ and 0, 1, 2, 3 or 4, in particular 0, 1 or 2 radicals $R^{C1}$, where $R^{C1}$, $R^{C2}$ and Y' are as defined herein and where Y', if present, is preferably a chemical bond or O.

In this regard, $R^{C1}$ is preferably selected from the group consisting of fluorine, chlorine, CN, methyl, difluoromethyl, trifluoromethyl, methoxy and $NH_2$, or, if Cyc is phenyl, two radicals $R^{C1}$ which are bound to adjacent carbon atoms, together with the phenyl ring to which they are bound, form a bicyclic heterocyclic radical, which is selected from 5- or 6-indolyl, 5- or 6-benzimidazolyl, 5- or 6-benzopyrazolyl, 5- or 6-benzotriazolyl, 5- or 6-benzofuranyl, 2,3-dihydrobenzofuran-5-yl, 2,3-dihydrobenzofuran-6-yl, 1,3-dihydroindol-2-on-5-yl, 1,3-dihydroindol-2-on-6-yl, 5- or 6-quinolinyl, 5- or 6-isoquinolinyl, 5- or 6-quinazolinyl, 2-amino-5-quinazolinyl, and 2-amino-6-quinazolinyl.

In this regard, $R^{C2}$ is preferably selected from the group consisting of phenyl, $C_3$-$C_6$-cycloalkyl, optionally substituted by 1, 2, or 3 methyl groups, fluorinated $C_3$-$C_6$-cycloalkyl, and 5- or 6-membered saturated heteromonocyclic radicals, having 1, 2 or 3 heteroatoms as ring members, which are selected from O, S and N, where phenyl the saturated heteromonocyclic radical is unsubstituted or carries 1, 2 or 3 radicals $R^{C3}$, which are preferably selected from fluorine, chlorine, CN, methyl, difluoromethyl, trifluoromethyl, methoxy and $NH_2$.

In particular, Cyc is selected from the groups of
(i) saturated 4-, 5-, 6- or 7-membered heteromonocycles, where the heteromonocycle has one nitrogen or oxygen atom as ring member and may have one further heteroatom or heteroatom group as ring member, which is selected from the group consisting of O, S, S(=O), S(=O)$_2$ and N, where the saturated heteromonocycle and the saturated heterobicycle are unsubstituted or carry 1, 2, or 3 radicals $R^C$, where $R^{C1}$ is as defined herein; and
(ii) phenyl or a 5- or 6 membered hetaryl, selected from pyridyl, pyrimidinyl, furyl, thienyl, pyrrolyl, imidazolyl, pyrazolyl, oxazolyl and thiazolyl, where phenyl and the 5- or 6 membered hetaryl are unsubstituted or carry 1, 2, 3, 4 or 5, in particular 1, 2, or 3 radicals $R^{C1}$ or one radical Y'—$R^{C2}$ and 0, 1, 2, 3 or 4, in particular 0, 1 or 2 radicals $R^{C1}$, where $R^{C1}$, $R^{C2}$ and Y' are as defined herein and where Y', if present, is preferably a chemical bond or O.

In particular embodiments of the invention, Cyc is selected from the group consisting of saturated 4-, 5-, 6- or 7-membered heteromonocycles or a saturated 7-, 8-, 9- or 10-membered heterobicycle, where the heteromonocycle and the heterobicycle have one nitrogen or oxygen atom as ring member and may have one further heteroatom or heteroatom group as ring member, which is selected from the group consisting of O, S, S(=O), S(=O)$_2$ and N, where the saturated heteromonocycle and the saturated heterobicycle are unsubstituted or carry 1, 2, 3, 4 or 5, in particular 1, 2, or 3 radicals $R^{C1}$ or one radical Y'—$R^{C2}$ and 0, 1, 2, 3 or 4, in particular 0, 1 or 2 radicals $R^{C1}$, where $R^{C1}$, $R^{C2}$ and Y' are as defined herein and where Y', if present, is preferably a chemical bond or O.

In special embodiments of the invention, Cyc is selected from the group consisting of saturated 4-, 5-, 6- or 7-membered heteromonocycles, where the heteromonocycle has one nitrogen or oxygen atom as ring member and may have one further heteroatom or heteroatom group as ring member, which is selected from the group consisting of O, S, S(=O), S(=O)$_2$ and N, where the saturated heteromonocycle and the saturated heterobicycle are unsubstituted or carry 1, 2, or 3 radicals $R^C$, where $R^{C1}$ is as defined herein.

In this particular and special embodiments Y is preferably selected from O, NH and a chemical bond, with particular preference given to Y being a chemical bond.

In this particular and special embodiments Y-Cyc is e.g. selected from the group consisting of 1-piperidinyl, 4,4- difluoro-1-piperidinyl, 4-piperidinyl, 1-methyl-4-piperidinyl, 1-piperazinyl, 4-methyl-1-piperazinyl, morpholin-4-yl, 2-oxa-6-azaspiro-[3,4]octyl, 2,5-diazabicyclo[2.2.1]heptan-2-yl, 3,8-diazabicyclo[3.2.1]octan-8-yl, thiomorpholin-4-yl, 1-oxothiomorpholin-4-yl, N-(oxetan-3-yl)amino, 1,1-dioxothiomorpholin-4-yl and oxetan-3-ylamino and especially from the group consisting of 1-piperidinyl, 4,4-difluoro-1-piperidinyl, 4-piperidinyl, 1-methyl-4-piperidinyl, 1-piperazinyl, 4-methyl-1-piperazinyl, morpholin-4-yl, thiomorpholin-4-yl, 1-oxothiomorpholin-4-yl, N-(oxetan-3-yl) amino, 1,1-dioxothiomorpholin-4-yl and oxetan-3-ylamino.

In other particular embodiments of the invention, Cyc is phenyl or a 5- or 6 membered heteroaromatic radical, which has one heteroatom, selected from O, S and N as ring member and optionally one or two further heteroatoms as ring members, and which is in particular selected from the group consisting of pyridyl, pyrimidinyl, furyl, thienyl, pyrrolyl, imidazolyl, pyrazolyl, oxazolyl and thiazolyl, where phenyl and the 5- or 6 membered heteroaromatic radical are unsubstituted or either carry, independently of each other, carry 1, 2, 3, 4 or 5, in particular 1, 2, or 3 radicals $R^{C1}$ or one radical $Y'$—$R^{C2}$ and 0, 1, 2, 3 or 4, in particular 0, 1 or 2 radicals $R^{C1}$, where $R^{C1}$, $R^{C2}$ and Y' are as defined herein and where Y', if present, is preferably a chemical bond or O.

In other special embodiments of the invention, Cyc is selected from the group consisting of phenyl or a 5- or 6 membered hetaryl, selected from pyridyl, pyrimidinyl, furyl, thienyl, pyrrolyl, imidazolyl, pyrazolyl, oxazolyl and thiazolyl, where phenyl and the 5- or 6 membered hetaryl are unsubstituted or carry 1, 2, 3, 4 or 5, in particular 1, 2, or 3 radicals $R^{C1}$ or one radical $Y'$—$R^{C2}$ and 0, 1, 2, 3 or 4, in particular 0, 1 or 2 radicals $R^{C1}$, where $R^{C1}$, $R^{C2}$ and Y' are as defined herein and where Y', if present, is preferably a chemical bond or O. In particular Cyc is selected from the group consisting of phenyl and 5- or 6-membered hetaryl selected from the group consisting of pyridyl, pyrimidinyl, furyl, thienyl, pyrrolyl, imidazolyl, pyrazolyl, oxazolyl and thiazolyl, where phenyl and hetaryl are unsubstituted or carry 1, 2 or 3 radicals $R^{C1}$ which are selected from the group consisting of fluorine, chlorine, CN, methyl, difluoromethyl, trifluoromethyl, methoxy and $NH_2$, or, if Cyc is phenyl, two radicals $R^{C1}$ which are bound to adjacent carbon atoms, together with the phenyl ring to which they are bound, form a bicyclic heterocyclic radical, which is selected from 5- or 6-indolyl, 5- or 6-benzimidazolyl, 5- or 6-benzopyrazolyl, 5- or 6-benzotriazolyl, 5- or 6-benzofuranyl, 2,3-dihydrobenzofuran-5-yl, 2,3-dihydrobenzofuran-6-yl, 1,3-dihydroindol-2-on-5-yl, 1,3-dihydroindol-2-on-6-yl, 5- or 6-quinolinyl, 5- or 6-isoquinolinyl, 5- or 6-quinazolinyl, 2-amino-5-quinazolinyl, and 2-amino-6-quinazolinyl. Amongst these, particular preference is given to compounds, where Y is a chemical bond. Amongst these, particular preference is given to compounds, where Cyc is selected from the group consisting of phenyl and 5- or 6-membered hetaryl selected from the group consisting of pyridyl, pyrimidinyl, furyl, thienyl, pyrrolyl, imidazolyl, pyrazolyl, oxazolyl and thiazolyl, where phenyl and hetaryl are unsubstituted or carry 1, 2 or 3 radicals $R^{C1}$ which are selected from the group consisting of fluorine, chlorine, CN, methyl, difluoromethyl, trifluoromethyl, methoxy and $NH_2$.

With regard to these particular or special embodiments, $R^{C1}$ is preferably selected from the group consisting of fluorine, chlorine, CN, methyl, difluoromethyl, trifluoromethyl, methoxy and $NH_2$, or, if Cyc is phenyl, two radicals $R^{C1}$ which are bound to adjacent carbon atoms, together with the phenyl ring to which they are bound, form a bicyclic heterocyclic radical, which is selected from 5- or 6-indolyl, 5- or 6-benzimidazolyl, 5- or 6-benzopyrazolyl, 5- or 6-benzotriazolyl, 5- or 6-benzofuranyl, 2,3-dihydrobenzofuran-5-yl, 2,3-dihydrobenzofuran-6-yl, 1,3-dihydroindol-2-on-5-yl, 1,3-dihydroindol-2-on-6-yl, 5- or 6-quinolinyl, 5- or 6-isoquinolinyl, 5- or 6-quinazolinyl, 2-amino-5-quinazolinyl, and 2-amino-6-quinazolinyl.

With regard to these particular or special embodiments, $R^{C2}$ is preferably selected from the group consisting of phenyl, $C_3$-$C_6$-cycloalkyl, optionally substituted by 1, 2, or 3 methyl groups, fluorinated $C_3$-$C_6$-cycloalkyl, and 5- or 6-membered saturated heteromonocyclic radicals, having 1, 2 or 3 heteroatoms as ring members, which are selected from O, S and N, where phenyl the saturated heteromonocyclic radical is unsubstituted or carries 1, 2 or 3 radicals $R^{C3}$, which are preferably selected from fluorine, chlorine, CN, methyl, difluoromethyl, trifluoromethyl, methoxy and $NH_2$.

In particular embodiments of the invention A is a radical $CR^5R^6$. In these particular embodiments, $R^5$ and $R^6$ are as defined above and in particular, independently of each other, selected from the group consisting of hydrogen, fluorine and $C_1$-$C_4$-alkyl, especially hydrogen, fluorine or methyl.

In other particular embodiments of the invention A is a radical O.

In further particular embodiments of the invention A is a radical N—$R^{5a}$. In these particular embodiments, $R^{5a}$ is as defined above and in particular selected from the group consisting of hydrogen, $C_1$-$C_4$-alkyl, $C_1$-$C_2$-fluoroalkyl, cyclopropyl, optionally substituted by 1, 2 or 3 methyl groups, fluorinated cyclopropyl, phenyl and benzyl, where the rings of phenyl and benzyl are unsubstituted or carry 1, 2 or 3 substituents selected from fluorine, methyl, $C_1$-fluoroalkyl, methoxy and $C_1$-fluoroalkoxy, especially from methyl.

In a group of embodiments, A is different from $CH_2$, if $X^1$ is C—$R^1$, $X^2$ is N or C—$R^2$, $X^3$ is C—$R^3$ and $X^4$C—$R^4$.

Preference is given to compounds of the formula I, where $R^7$, $R^8$ are selected from hydrogen and fluorine and in particular to those compounds, where both $R^7$ and $R^8$ are hydrogen.

Preference is given to compounds of the formula I, where $R^9$, $R^{10}$ are selected from hydrogen and fluorine and in particular to those compounds, where both $R^9$ and $R^{10}$ are hydrogen.

A particular preferred embodiment of the invention relates to the compounds of formula I-A, described below, to the N-oxides, the prodrugs, the hydrates and the tautomers thereof and to the pharmaceutically suitable salts thereof:

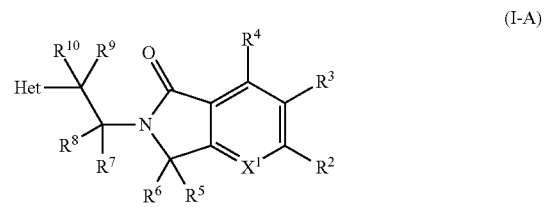

(I-A)

where Het, $X^1$, $R^2$, $R^3$, $R^4$, $R^5$, $R^6$, $R^7$, $R^8$, $R^9$ and $R^{10}$ are as defined here and in the claims.

In the compounds of formula I-A, $R^5$ and $R^6$ are as defined above and in particular, independently of each other, selected from the group consisting of hydrogen, fluorine and $C_1$-$C_4$-alkyl, especially hydrogen, fluorine or methyl. In another embodiment of the compounds of formula I-A, the radicals $R^5$ and $R^6$ together with the carbon atom to which they are bound form a carbonyl group.

Another particular preferred embodiment of the invention relates to the compounds of formula I-B, described below, to the N-oxides, the prodrugs, the hydrates and the tautomers thereof and to the pharmaceutically suitable salts thereof:

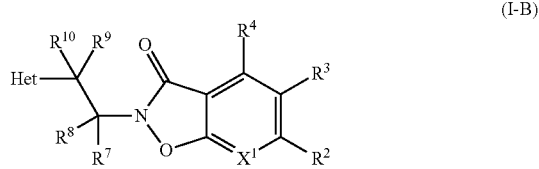

(I-B)

where Het, $X^1$, $R^2$, $R^3$, $R^4$, $R^7$, $R^8$, $R^9$ and $R^{10}$ are as defined here and in the claims.

Another particular preferred embodiment of the invention relates to the compounds of formula I-C, described below, to the N-oxides, the prodrugs, the hydrates and the tautomers thereof and to the pharmaceutically suitable salts thereof:

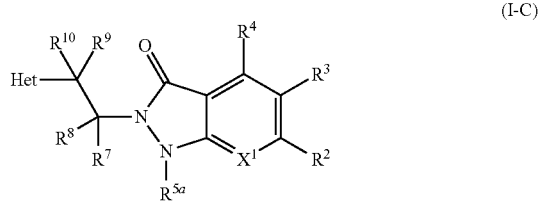

(I-C)

where Het, $X^1$, $R^2$, $R^3$, $R^4$, $R^{5a}$, $R^7$, $R^8$, $R^9$ and $R^{10}$ are as defined here and in the claims.

In the compounds of formula I-C, $R^{5a}$ is in particular selected from the group consisting of hydrogen, $C_1$-$C_4$-alkyl, $C_1$-$C_2$-fluoroalkyl, cyclopropyl, optionally substituted by 1, 2 or 3 methyl groups, fluorinated cyclopropyl, phenyl and benzyl, where the rings of phenyl and benzyl are unsubstituted or carry 1, 2 or 3 substituents selected from fluorine, methyl, $C_1$-fluoroalkyl, methoxy and $C_1$-fluoroalkoxy, especially from methyl.

In relation to their use as inhibitors of PDE10A, the variables Het, $X^1$, $R^1$, $R^2$, $R^3$, $R^4$, $R^7$, $R^8$, $R^9$, $R^{10}$, Y and Cyc in formulae I-A, I-B and I-C have the meanings given above, in particular the following meanings, where these represent, both considered on their own and in combination with at least one other or all, special configurations of the compounds of the formula I-A, I-B and I-C:

In formulae I-A, I-B and I-C, $R^4$ is preferably a radical Y-Cyc and $X^1$ is N or C—$R^1$, where $R^1$ is as defined above and preferably has a meaning different from Y-Cyc. In formulae I-A, I-B and I-C, $R^1$ is in particular selected from the group consisting of hydrogen, fluorine, $C_1$-$C_4$-alkyl, fluorinated $C_1$-$C_2$-alkyl, $C_1$-$C_4$-alkoxy, fluorinated $C_1$-$C_2$-alkoxy, cyclopropyl, optionally substituted by 1, 2 or 3 methyl groups, and fluorinated cyclopropyl.

In formulae I-A, I-B and I-C, the variables $R^2$ and $R^3$ preferably have a meaning different from Y-Cyc. In this regard, $R^2$ and $R^3$ are as defined above and preferably selected, independently of each other, from the group consisting of hydrogen, fluorine, $C_1$-$C_4$-alkyl, fluorinated $C_1$-$C_2$-alkyl, $C_1$-$C_4$-alkoxy, fluorinated $C_1$-$C_2$-alkoxy, cyclopropyl, optionally substituted by 1, 2 or 3 methyl groups, and fluorinated cyclopropyl. In particular $R^2$ and $R^3$ are both hydrogen.

Preference is given to compounds of the formulae I-A, I-B and I-C, where $R^7$, $R^8$ are selected from hydrogen and fluorine and in particular to those compounds, where both $R^7$ and $R^8$ are hydrogen.

Preference is given to compounds of the of the formulae I-A, I-B and I-C, where $R^9$, $R^{10}$ are selected from hydrogen and fluorine and in particular to those compounds, where both $R^9$ and $R^{10}$ are hydrogen.

In the compounds of formulae I-A, I-B and I-C, Het is preferably selected from the group consisting of C-bound 6-membered monocyclic hetaryl, which has 1 or 2 nitrogen atoms as ring members, benzofuryl and C-bound, fused bicyclic hetaryl, which has 1 or 2 nitrogen atoms as ring members and optionally a further heteroatom selected from O, S and N as ring member, where monocyclic hetaryl, benzofuryl and bicyclic hetaryl may be unsubstituted or may carry 1, 2, 3 or 4 substituents $R^x$, in particular 0, 1 or 2 substituents $R^x$. In this regard, $R^x$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, phenyl, $C_3$-$C_6$-cycloalkyl, optionally substituted by 1, 2 or 3 methyl groups, and fluorinated $C_3$-$C_6$-cycloalkyl. In this regard, $R^x$ is in particular selected from fluorine, chlorine, methyl, fluoromethyl, difluoromethyl, trifluoromethyl, methoxy, fluoromethoxy, difluoromethoxy, trifluoromethoxy, phenyl, cyclopropyl, optionally substituted by 1, 2 or 3 methyl groups, and fluorinated cyclopropyl.

In a particular embodiment of the compounds of the formulae I-A, I-B and I-C, Het is selected from fused bicyclic hetaryl, which has 1 or 2 nitrogen atoms as ring members and optionally a further heteroatom selected from O, S and N as ring member and which may be unsubstituted or may carry 1, 2, 3 or 4 substituents $R^x$, in particular 0, 1 or 2 substituents $R^x$. In this regard, $R^x$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl, optionally substituted by 1, 2 or 3 methyl groups, and fluorinated $C_3$-$C_6$-cycloalkyl. In this regard, $R^x$ is in particular selected from fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl.

In another particular embodiment of the compounds of the formulae I-A, I-B and I-C, Het is selected from 6-membered monocyclic hetaryl, which may be unsubstituted or may carry 1, 2, 3 or 4 substituents $R^x$, in particular 0, 1 or 2 substituents $R^x$. In this regard, $R^x$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, phenyl, $C_3$-$C_6$-cycloalkyl, optionally substituted by 1, 2 or 3 methyl groups, and fluorinated $C_3$-$C_6$-cycloalkyl. In this regard, $R^x$ is in particular selected from fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl or one $R^x$ may also be phenyl.

In the compounds of formulae I-A, I-B and I-C, particular preference is given to those Het radicals, which have at least one imino-nitrogen as ring member, which is located in the position adjacent to carbon atom bound to the group $CR^9R^{10}$. Particular preference is given to those Het radicals, which have at least one imino-nitrogen as ring member, which is located in the position adjacent to carbon atom bound to the group $CR^9R^{10}$ and which are selected from the group consisting of C-bound 6-membered monocyclic hetaryl, which has 1 or 2 nitrogen atoms as ring members, benzofuryl and C-bound, fused bicyclic hetaryl, which has 1 or 2 nitrogen atoms as ring members and optionally a further heteroatom selected from O, S and N as ring member, where monocyclic hetaryl, benzofuryl and bicyclic hetaryl may be unsubstituted or may carry 1, 2, 3 or 4 substituents $R^x$, in particular 0, 1 or 2 substituents $R^x$. In this regard, $R^x$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, phenyl, $C_3$-$C_6$-cycloalkyl, optionally substituted by 1, 2 or 3 methyl groups, and fluorinated $C_3$-$C_6$-cycloalkyl. In this regard, $R^x$ is in particular selected from fluorine, chlorine, methyl, fluoromethyl, difluoromethyl, trifluoromethyl, methoxy, fluoromethoxy, difluoromethoxy, trifluoromethoxy, phenyl, cyclopropyl, optionally substituted by 1, 2 or 3 methyl groups, and fluorinated cyclopropyl. Particular examples of Het are selected from the group consisting of 2-benzofuryl, 2-pyridyl, 3-pyridazinyl, 2-pyrimidinyl, 2-quinolinyl, 2-quinazolinyl, 2-quinoxalinyl, benzimidazol-2-yl, 1-methylbenzimidazol-2-yl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl, where the aforementioned radicals are unsubstituted or may carry 1, 2 or 3 radicals $R^x$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl.

In a particular embodiment of the compounds of the formulae I-A, I-B and I-C, Het has at least one imino-nitrogen as ring member, which is located in the position adjacent to carbon atom bound to the group $CR^9R^{10}$ and Het is selected from the group consisting of fused bicyclic hetaryl, which has 1 or 2 nitrogen atoms as ring members and optionally a further heteroatom selected from O, S and N as ring member, where bicyclic hetaryl may be unsubstituted or may carry 1, 2, 3 or 4 substituents $R^x$, in particular 0, 1 or 2 substituents $R^x$. In this regard, $R^x$ is preferably selected from halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl, optionally substituted by 1, 2 or 3 methyl groups, and fluorinated $C_3$-$C_6$-cycloalkyl. In this regard, $R^x$ is in particular selected from fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl. Particular examples of Het of this embodiment are 2-quinolinyl, 2-quinazolinyl, 2-quinoxalinyl, benzimidazol-2-yl, 1-methylbenzimidazol-2-yl, benzothiazol-2-yl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl, where the aforementioned radicals are unsubstituted or may carry 1, 2 or 3 radicals $R^x$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl.

Particular preference is given to compounds of the formulae I-A, I-B and I-C, where Het is 2-quinolinyl or imidazo[1,2-a]pyridine-2-yl, where these radicals are unsubstituted or may carry 1, 2 or 3 radicals $R^x$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl.

Particular preference is also given to compounds of the formulae I-A, I-B and I-C, where Het is 1-methylbenzimidazol-2-yl or benzothiazol-2-yl, where these radicals are unsubstituted or may carry 1, 2 or 3 radicals $R^x$ as defined above, which are in particular selected from the group consisting of fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl.

Particular preference is given to compounds of the formulae I-A, I-B and I-C, where Het is 2-pyridyl, where 2-pyridyl unsubstituted or preferably carries 1, 2 or 3 radicals $R^x$ as defined above, which are in particular selected from the group consisting of halogen, $C_1$-$C_4$-alkyl, $C_1$-$C_4$-haloalkyl, $C_1$-$C_4$-alkoxy, $C_1$-$C_4$-haloalkyoxy, cyclopropyl, optionally substituted by 1, 2 or 3 methyl groups, and fluorinated cyclopropyl, such as fluorine, chlorine, methyl, ethyl, isopropyl, fluoromethyl, difluoromethyl, trifluoromethyl, methoxy, fluoromethoxy, difluoromethoxy, trifluoromethoxy, cyclopropyl, 1-methylcyclopropyl, 1-fluorocyclopropyl and 2-fluorocyclopropyl.

An especially preferred embodiment of the invention relates to the compounds of formulae I-Aa, I-Ab, I-Ac and I-Ad, described below, to the N-oxides, the prodrugs, the hydrates and the tautomers thereof and to the pharmaceutically suitable salts thereof:

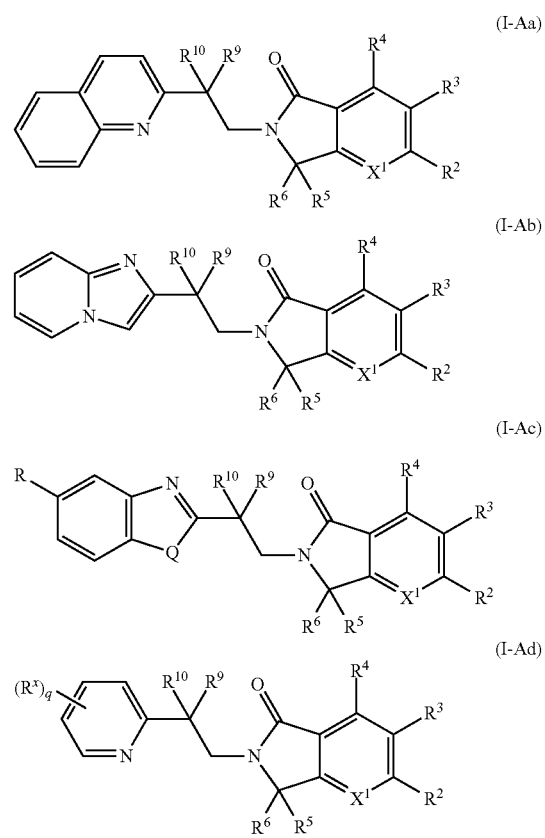

where $X^1$, $R^2$, $R^3$, $R^4$, $R^5$, $R^6$, $R^9$ and $R^{10}$ are as defined here and in the claims.

In formula I-Ac, R is H, F or $CH_3$ and Q is S, O or in particular N—$CH_3$.

In formula I-Ad, q is 0 or in particular 1 and $R^x$ is selected from the group consisting of $C_1$-$C_4$-alkyl, $C_1$-$C_4$-alkyl, $C_1$-$C_4$-alkoxy, $C_1$-$C_4$-fluoroalkyl, $C_1$-$C_4$-fluoroalkoxy, cyclopropyl, which is optionally substituted by 1, 2 or 3 methyl groups, and fluorinated cyclopropyl.

In the compounds of formulae I-Aa, I-Ab, I-Ac and I-Ad, $R^5$ and $R^6$ are as defined above and in particular, independently of each other, selected from the group consisting of hydrogen, fluorine and $C_1$-$C_4$-alkyl, especially hydrogen, fluorine or methyl. In another embodiment of the compounds of formulae I-Aa, I-Ab, I-Ac and I-Ad, the radicals $R^5$ and $R^6$ together with the carbon atom to which they are bound form a carbonyl group.

Another especially preferred embodiment of the invention relates to the compounds of formulae I-Ba, I-Bb, I-Bc and I-Bd, described below, to the N-oxides, the prodrugs, the hydrates and the tautomers thereof and to the pharmaceutically suitable salts thereof:

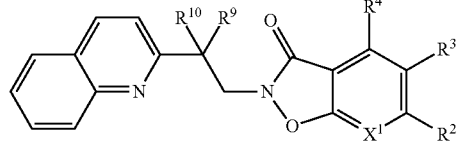
(I-Ba)

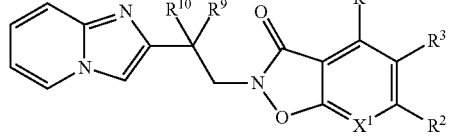
(I-Bb)

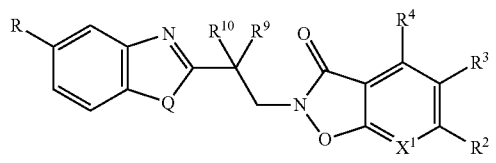
(I-Bc)

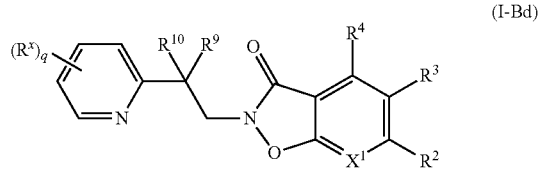
(I-Bd)

where $X^1$, $R^2$, $R^3$, $R^4$, $R^9$ and $R^{10}$ are as defined here and in the claims.

In formula I-Bc, R is H, F or $CH_3$ and Q is S, O or in particular N—$CH_3$.

In formula I-Bd, q is 0 or or in particular 1 and $R^x$ is selected from the group consisting of $C_1$-$C_4$-alkyl, $C_1$-$C_4$-alkyl, $C_1$-$C_4$-alkoxy, $C_1$-$C_4$-fluoroalkyl, $C_1$-$C_4$-fluoroalkoxy, cyclopropyl, which is optionally substituted by 1, 2 or 3 methyl groups, and fluorinated cyclopropyl.

Another especially preferred embodiment of the invention relates to the compounds of formulae I-Ca, I-Cb, I-Cc and I-Cd, described below, to the N-oxides, the prodrugs, the hydrates and the tautomers thereof and to the pharmaceutically suitable salts thereof:

(I-Ca)

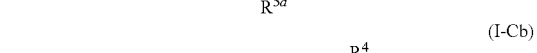
(I-Cb)

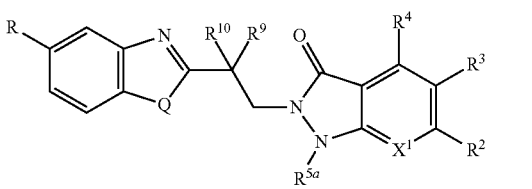
(I-Cc)

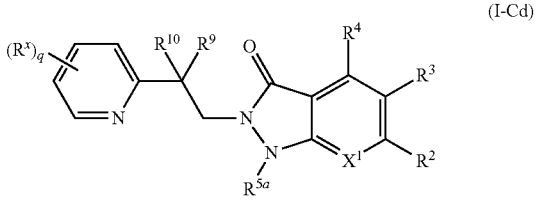
(I-Cd)

where $X^1$, $R^2$, $R^3$, $R^4$, $R^5$, $R^{5a}$, $R^6$, $R^9$ and $R^{10}$ are as defined here and in the claims.

In formula I-Cc, R is H, F or $CH_3$ and Q is S, O or in particular N—$CH_3$.

In formula I-Cd, q is 0 or or in particular 1 and $R^x$ is selected from the group consisting of $C_1$-$C_4$-alkyl, $C_1$-$C_4$-alkyl, $C_1$-$C_4$-alkoxy, $C_1$-$C_4$-fluoroalkyl, $C_1$-$C_4$-fluoroalkoxy, cyclopropyl, which is optionally substituted by 1, 2 or 3 methyl groups, and fluorinated cyclopropyl.

In the compounds of formulae I-Ca, I-Cb, I-Cc and I-Cd, $R^{5a}$ is in particular selected from the group consisting of hydrogen, $C_1$-$C_4$-alkyl, $C_1$-$C_2$-fluoroalkyl, cyclopropyl, optionally substituted by 1, 2 or 3 methyl groups, fluorinated cyclopropyl, phenyl and benzyl, where the rings of phenyl and benzyl are unsubstituted or carry 1, 2 or 3 substituents selected from fluorine, methyl, $C_1$-fluoroalkyl, methoxy and $C_1$-fluoroalkoxy, especially from methyl.

In relation to their use as inhibitors of PDE10A, the variables $X^1$, $R^1$, $R^2$, $R^3$, $R^4$, $R^9$, $R^{10}$, Y and Cyc in formulae I-Aa, I-Ab, I-Ac, I-Ad, I-Ba, I-Bb, I-Bc, I-Bd, I-Ca, I-Cb, I-Cc and I-Cd have the meanings given above, in particular the meanings given for formulae I-A, I-B and I-C and the meanings give below, where these represent, both considered on their own and in combination with at least one other or all, special configurations of the compounds of the formula I-Aa, I-Ab, I-Ac, I-Ad, I-B a, I-Bb, I-Bc, I-Bd, I-Ca, I-Cb, I-Cc and I-Cd.

In formulae I-Aa, I-Ab, I-Ac, I-Ad, I-Ba, I-Bb, I-Bc, I-Bd, I-Ca, I-Cb, I-Cc and I-Cd, $R^4$ is preferably a radical Y-Cyc and $X^1$ is N or C—$R^1$, where $R^1$ is as defined above and preferably has a meaning different from Y-Cyc. In formulae I-Aa, I-Ab, I-Ac, I-Ad, I-Ba, I-Bb, I-Bc, I-Bd, I-Ca, I-Cb, I-Cc and I-Cd, where $X^1$ is C—$R^1$, $R^1$ is in particular selected from the group consisting of hydrogen, fluorine, $C_1$-$C_4$-alkyl, fluorinated $C_1$-$C_2$-alkyl, $C_1$-$C_4$-alkoxy, fluorinated $C_1$-$C_2$-alkoxy, cyclopropyl, optionally substituted by 1, 2 or 3 methyl groups, and fluorinated cyclopropyl.

A particular group of embodiments relates to compounds of formulae I-A, I-B and I-C and likewise to compounds of the formulae I-Aa, I-Ab, I-Ac, I-Ad, I-Ba, I-Bb, I-Bc, I-Bd, I-Ca, I-Cb, I-Cc, as well as to the N-oxides, the prodrugs, the tautomers and the hydrates thereof, and to the pharmaceutically acceptable salts thereof, where $X^1$ is N.

In formulae I-Aa, I-Ab, I-Ac, I-Ad, I-Ba, I-Bb, I-Bc, I-Bd, I-Ca, I-Cb, I-Cc and I-Cd, the variables $R^2$ and $R^3$ preferably have a meaning different from Y-Cyc. In this regard, $R^2$ and $R^3$ are as defined above and preferably selected, independently of each other, from the group consisting of hydrogen, fluorine, $C_1$-$C_4$-alkyl, fluorinated $C_1$-$C_2$-alkyl, $C_1$-$C_4$-alkoxy, fluorinated $C_1$-$C_2$-alkoxy, cyclopropyl, optionally substituted by 1, 2 or 3 methyl groups, and fluorinated cyclopropyl. In particular $R^2$ and $R^3$ are both hydrogen.

Preference is given to compounds of the of the formulae I-Aa, I-Ab, I-Ac, I-Ad, I-Ba, I-Bb, I-Bc, I-Bd, I-Ca, I-Cb, I-Cc and I-Cd, where $R^9$, $R^{10}$ are selected from hydrogen and fluorine and in particular to those compounds, where both $R^9$ and $R^{10}$ are hydrogen.

In the compounds of formulae I-A, I-B and I-C, and likewise in the compounds of formulae I-Aa, I-Ab, I-Ac, I-Ac, I-Ad, I-Ba, I-Bb, I-Bc, I-Bd, I-Ca, I-Cb, I-Cc and I-Cd, Y in the moieties Y-Cyc is preferably selected from O, NH and a chemical bond. In particular embodiments of the compounds of formulae I-A, I-B and I-C, and likewise of the compounds of formulae I-Aa, I-Ab, I-Ac, I-Ac, I-Ad, I-Ba, I-Bb, I-Bc, I-Bd, I-Ca, I-Cb, I-Cc and I-Cd Y is a chemical bond.

In the compounds of formulae I-A, I-B and I-C, and likewise in the compounds of formulae I-Aa, I-Ab, I-Ac, I-Ac, I-Ad, I-Ba, I-Bb, I-Bc, I-Bd, I-Ca, I-Cb, I-Cc and I-Cd, Cyc is preferably selected from the groups of (i) saturated 4-, 5-, 6- or 7-membered heteromonocycles or a saturated 7-, 8-, 9- or 10-membered heterobicycle, where the heteromonocycle and the heterobicycle have one nitrogen or oxygen atom as ring member and may have one further heteroatom or heteroatom group as ring member, which is selected from the group consisting of O, S, S(=O), S(=O)$_2$ and N, where the saturated heteromonocycle and the saturated heterobicycle are unsubstituted or carry 1, 2, 3, 4 or 5, in particular 1, 2, or 3 radicals $R^{C1}$ or one radical Y'—$R^{C2}$ and 0, 1, 2, 3 or 4, in particular 0, 1 or 2 radicals $R^{C1}$, where $R^{C1}$, $R^{C2}$ and Y' are as defined herein and where Y', if present, is preferably a chemical bond or O; and (ii) phenyl or a 5- or 6 membered hetaryl, which has one heteroatom, selected from O, S and N as ring member and optionally one or two further heteroatoms as ring members, and which is in particular selected from the group consisting of pyridyl, pyrimidinyl, furyl, thienyl, pyrrolyl, imidazolyl, pyrazolyl, oxazolyl and thiazolyl, where phenyl and the 5- or 6 membered hetaryl are unsubstituted or carry 1, 2, 3, 4 or 5, in particular 1, 2, or 3 radicals $R^{C1}$ or one radical Y'—$R^{C2}$ and 0, 1, 2, 3 or 4, in particular 0, 1 or 2 radicals $R^{C1}$, where $R^{C1}$, $R^{C2}$ and Y' are as defined herein and where Y', if present, is preferably a chemical bond or O.

In this regard, $R^{C1}$ is preferably selected from the group consisting of fluorine, chlorine, CN, methyl, difluoromethyl, trifluoromethyl, methoxy and NH$_2$, or, if Cyc is phenyl, two radicals $R^{C1}$ which are bound to adjacent carbon atoms, together with the phenyl ring to which they are bound, form a bicyclic heterocyclic radical, which is selected from 5- or 6-indolyl, 5- or 6-benzimidazolyl, 5- or 6-benzopyrazolyl, 5- or 6-benzotriazolyl, 5- or 6-benzofuranyl, 2,3-dihydrobenzofuran-5-yl, 2,3-dihydrobenzofuran-6-yl, 1,3-dihydroindol-2-on-5-yl, 1,3-dihydroindol-2-on-6-yl, 5- or 6-quinolinyl, 5- or 6-isoquinolinyl, 5- or 6-quinazolinyl, 2-amino-5-quinazolinyl, and 2-amino-6-quinazolinyl.

In this regard, $R^{C2}$ is preferably selected from the group consisting of phenyl, $C_3$-$C_6$-cycloalkyl, optionally substituted by 1, 2, or 3 methyl groups, fluorinated $C_3$-$C_6$-cycloalkyl, and 5- or 6-membered saturated heteromonocyclic radicals, having 1, 2 or 3 heteroatoms as ring members, which are selected from O, S and N, where phenyl the saturated heteromonocyclic radical is unsubstituted or carries 1, 2 or 3 radicals $R^{c3}$, which are preferably selected from fluorine, chlorine, CN, methyl, difluoromethyl, trifluoromethyl, methoxy and NH$_2$.

In the compounds of formulae I-A, I-B and I-C, and likewise in the compounds of formulae I-Aa, I-Ab, I-Ac, I-Ac, I-Ad, I-Ba, I-Bb, I-Bc, I-Bd, I-Ca, I-Cb, I-Cc and I-Cd, Cyc is in particular selected from the groups of (i) saturated 4-, 5-, 6- or 7-membered heteromonocycles, where the heteromonocycle has one nitrogen or oxygen atom as ring member and may have one further heteroatom or heteroatom group as ring member, which is selected from the group consisting of O, S, S(=O), S(=O)$_2$ and N, where the saturated heteromonocycle and the saturated heterobicycle are unsubstituted or carry 1, 2, or 3 radicals $R^{C1}$, where $R^{C1}$ is as defined herein; and (ii) phenyl or a 5- or 6 membered hetaryl, selected from pyridyl, pyrimidinyl, furyl, thienyl, pyrrolyl, imidazolyl, pyrazolyl, oxazolyl and thiazolyl, where phenyl and the 5- or 6 membered hetaryl are unsubstituted or carry 1, 2, 3, 4 or 5, in particular 1, 2, or 3 radicals $R^{C1}$ or one radical Y'—$R^{C2}$ and 0, 1, 2, 3 or 4, in particular 0, 1 or 2 radicals $R^{C1}$, where $R^{C1}$, $R^{C2}$ and Y' are as defined herein and where Y', if present, is preferably a chemical bond or O.

In particular embodiments of the compounds of formulae I-A, I-B and I-C, and likewise of the compounds of formulae I-Aa, I-Ab, I-Ac, I-Ac, I-Ad, I-Ba, I-Bb, I-Bc, I-Bd, I-Ca, I-Cb, I-Cc and I-Cd, Cyc is selected from the group consisting of saturated 4-, 5-, 6- or 7-membered heteromonocycles or a saturated 7-, 8-, 9- or 10-membered heterobicycle, where the heteromonocycle and the heterobicycle have one nitrogen or oxygen atom as ring member and may have one further heteroatom or heteroatom group as ring member, which is selected from the group consisting of O, S, S(=O), S(=O)$_2$ and N, where the saturated heteromonocycle and the saturated heterobicycle are unsubstituted or carry 1, 2, 3, 4 or 5, in particular 1, 2, or 3 radicals $R^{C1}$ or one radical Y'—$R^{C2}$ and 0, 1, 2, 3 or 4, in particular 0, 1 or 2 radicals $R^{C1}$, where $R^{C1}$, $R^{C2}$ and Y' are as defined herein and where Y', if present, is preferably a chemical bond or O.

In special embodiments of the compounds of formulae I-A, I-B and I-C, and likewise of the compounds of formulae I-Aa, I-Ab, I-Ac, I-Ac, I-Ad, I-Ba, I-Bb, I-Bc, I-Bd, I-Ca, I-Cb, I-Cc and I-Cd, Cyc is selected from the group consisting of saturated 4-, 5-, 6- or 7-membered heteromonocycles, where the heteromonocycle has one nitrogen or oxygen atom as ring member and may have one further heteroatom or heteroatom group as ring member, which is selected from the group consisting of O, S, S(=O), S(=O)$_2$ and N, where the saturated heteromonocycle and the saturated heterobicycle are unsubstituted or carry 1, 2, or 3 radicals $R^{C1}$, where $R^{C1}$ is as defined herein.

In these particular and special embodiments Y is preferably selected from O, NH and a chemical bond, with particular preference given to Y being a chemical bond.

In these particular and special embodiments Y-Cyc is e.g. selected from the group consisting of 1-piperidinyl, 4,4-difluoro-1-piperidinyl, 4-piperidinyl, 1-methyl-4-piperidinyl, 1-piperazinyl, 4-methyl-1-piperazinyl, morpholin-4-yl, 2-oxa-6-azaspiro-[3,4]octyl, 2,5-diazabicyclo[2.2.1]heptan-2-yl, 3,8-diazabicyclo[3.2.1]octan-8-yl, thiomorpholin-4-yl, 1-oxothiomorpholin-4-yl, N-(oxetan-3-yl)amino, 1,1-dioxothiomorpholin-4-yl and oxetan-3-ylamino and especially from the group consisting of 1-piperidinyl, 4,4-difluoro-1-piperidinyl, 4-piperidinyl, 1-methyl-4-piperidinyl, 1-piperazinyl, 4-methyl-1-piperazinyl, morpholin-4-yl, thiomorpholin-4-yl, 1-oxothiomorpholin-4-yl, N-(oxetan-3-yl)amino, 1,1-dioxothiomorpholin-4-yl and oxetan-3-ylamino.

In other particular embodiments of the compounds of formulae I-A, I-B and I-C, and likewise of the compounds of formulae I-Aa, I-Ab, I-Ac, I-Ac, I-Ad, I-Ba, I-Bb, I-Bc, I-Bd, I-Ca, I-Cb, I-Cc and I-Cd, Cyc is phenyl or a 5- or 6 membered heteroaromatic radical, which has one heteroatom, selected from O, S and N as ring member and optionally one or two further heteroatoms as ring members, and which is in particular selected from the group consisting of pyridyl, pyrimidinyl, furyl, thienyl, pyrrolyl, imidazolyl, pyrazolyl, oxazolyl and thiazolyl, where phenyl and the 5- or 6 membered heteroaromatic radical are unsubstituted or either carry, independently of $R^{C2}$ each other, carry 1, 2, 3, 4 or 5, in particular 1, 2, or 3 radicals $R^{C1}$ or one radical Y'- and 0, 1, 2, 3 or 4, in particular 0, 1 or 2 radicals $R^{C1}$, where $R^{C1}$, $R^{C2}$ and Y' are as defined herein and where Y', if present, is preferably a chemical bond or O.

In other special embodiments of the compounds of formulae I-A, I-B and I-C, and likewise of the compounds of formulae I-Aa, I-Ab, I-Ac, I-Ac, I-Ad, I-Ba, I-Bb, I-Bc, I-Bd, I-Ca, I-Cb, I-Cc and I-Cd, Cyc is selected from the group consisting of phenyl or a 5- or 6 membered hetaryl, selected from pyridyl, pyrimidinyl, furyl, thienyl, pyrrolyl, imidazolyl, pyrazolyl, oxazolyl and thiazolyl, where phenyl and the 5- or 6 membered hetaryl are unsubstituted or carry 1, 2, 3, 4 or 5, in particular 1, 2, or 3 radicals $R^{C1}$ or one radical Y'—$R^{C2}$ and 0, 1, 2, 3 or 4, in particular 0, 1 or 2 radicals $R^{C1}$, where $R^{C1}$, $R^{C2}$ and Y' are as defined herein and where Y', if present, is preferably a chemical bond or O. In particular Cyc is selected from the group consisting of phenyl and 5- or 6-membered hetaryl selected from the group consisting of pyridyl, pyrimidinyl, furyl, thienyl, pyrrolyl, imidazolyl, pyrazolyl, oxazolyl and thiazolyl, where phenyl and hetaryl are unsubstituted or carry 1, 2 or 3 radicals $R^{C1}$ which are selected from the group consisting of fluorine, chlorine, CN, methyl, difluoromethyl, trifluoromethyl, methoxy and $NH_2$, or, if Cyc is phenyl, two radicals $R^{C1}$ which are bound to adjacent carbon atoms, together with the phenyl ring to which they are bound, form a bicyclic heterocyclic radical, which is selected from 5- or 6-indolyl, 5- or 6-benzimidazolyl, 5- or 6-benzopyrazolyl, 5- or 6-benzotriazolyl, 5- or 6-benzofuranyl, 2,3-dihydrobenzofuran-5-yl, 2,3-dihydrobenzofuran-6-yl, 1,3-dihydroindol-2-on-5-yl, 1,3-dihydroindol-2-on-6-yl, 5- or 6-quinolinyl, 5- or 6-isoquinolinyl, 5- or 6-quinazolinyl, 2-amino-5-quinazolinyl, and 2-amino-6-quinazolinyl. Amongst these, particular preference is given to compounds, where Y is a chemical bond. Amongst these, particular preference is given to compounds, where In particular Cyc is selected from the group consisting of phenyl and 5- or 6-membered hetaryl selected from the group consisting of pyridyl, pyrimidinyl, furyl, thienyl, pyrrolyl, imidazolyl, pyrazolyl, oxazolyl and thiazolyl, where phenyl and hetaryl are unsubstituted or carry 1, 2 or 3 radicals $R^{C1}$ which are selected from the group consisting of fluorine, chlorine, CN, methyl, difluoromethyl, trifluoromethyl, methoxy and $NH_2$.

With regard to these particular or special embodiments of the compounds of formulae I-A, I-B and I-C, and likewise of the compounds of formulae I-Aa, I-Ab, I-Ac, I-Ac, I-Ad, I-Ba, I-Bb, I-Bc, I-Bd, I-Ca, I-Cb, I-Cc and I-Cd, $R^{C1}$ is preferably selected from the group consisting of fluorine, chlorine, CN, methyl, difluoromethyl, trifluoromethyl, methoxy and $NH_2$, or, if Cyc is phenyl, two radicals $R^{C1}$ which are bound to adjacent carbon atoms, together with the phenyl ring to which they are bound, form a bicyclic heterocyclic radical, which is selected from 5- or 6-indolyl, 5- or 6-benzimidazolyl, 5- or 6-benzopyrazolyl, 5- or 6-benzotriazolyl, 5- or 6-benzofuranyl, 2,3-dihydrobenzofuran-5-yl, 2,3-dihydrobenzofuran-6-yl, 1,3-dihydroindol-2-on-5-yl, 1,3-dihydroindol-2-on-6-yl, 5- or 6-quinolinyl, 5- or 6-isoquinolinyl, 5- or 6-quinazolinyl, 2-amino-5-quinazolinyl, and 2-amino-6-quinazolinyl.

With regard to these particular or special embodiments of the compounds of formulae I-A, I-B and I-C, and likewise in the compounds of formulae I-Aa, I-Ab, I-Ac, I-Ac, I-Ad, I-Ba, I-Bb, I-Bc, I-Bd, I-Ca, I-Cb, I-Cc and I-Cd, $R^{C2}$ is preferably selected from the group consisting of phenyl, $C_3$-$C_6$-cycloalkyl, optionally substituted by 1, 2, or 3 methyl groups, fluorinated $C_3$-$C_6$-cycloalkyl, and 5- or 6-membered saturated heteromonocyclic radicals, having 1, 2 or 3 heteroatoms as ring members, which are selected from O, S and N, where phenyl the saturated heteromonocyclic radical is unsubstituted or carries 1, 2 or 3 radicals $R^{C3}$, which are preferably selected from fluorine, chlorine, CN, methyl, difluoromethyl, trifluoromethyl, methoxy and $NH_2$.

Particular embodiment of the invention relates to the compounds of formula I, to the N-oxides, the prodrugs, the hydrates and the tautomers thereof and to the pharmaceutically suitable salts thereof, where the compounds of the formula I are selected from the group consisting of:

4-Pyridin-4-yl-2-(2-quinolin-2-yl-ethyl)-1,2-dihydro-pyrrolo[3,4-c]pyridin-3-one, 7-Pyridin-4-yl-2-(2-quinolin-2-yl-ethyl)-2,3-dihydro-pyrrolo[3,4-c]pyridin-1-one, 4-Pyridin-4-yl-6-(2-quinolin-2-yl-ethyl)-6,7-dihydro-pyrrolo[3,4-b]pyridin-5-one, 3,3-Difluoro-7-pyridin-4-yl-2-(2-quinolin-2-yl-ethyl)-2,3-dihydro-isoindol-1-one, 7-Pyridin-4-yl-2-(2-quinolin-2-yl-ethyl)-2,3-dihydro-isoindol-1-one, 3,3-Dimethyl-7-pyridin-4-yl-2-(2-quinolin-2-yl-ethyl)-2,3-dihydro-isoindol-1-one, 6-[3-Oxo-2-(2-quinolin-2-yl-ethyl)-2,3-dihydro-1H-isoindol-4-yl]-1H-quinazolin-4-one, 7-(3-Methyl-3H-benzoimidazol-5-yl)-2-(2-quinolin-2-yl-ethyl)-2,3-dihydro-isoindol-1-one, 5-[3-oxo-2-(2-quinolin-2-yl-ethyl)-2,3-dihydro-1H-isoindol-4-yl]-1,3-dihydro-benzoimidazol-2-one, 7-(3H-Benzotriazol-5-yl)-2-(2-quinolin-2-yl-ethyl)-2,3-dihydro-isoindol-1-one, 7-(3H-Benzoimidazol-5-yl)-2-(2-quinolin-2-yl-ethyl)-2,3-dihydro-isoindol-1-one, 7-(2-Amino-quinazolin-6-yl)-2-(2-quinolin-2-yl-ethyl)-2,3-dihydro-isoindol-1-one, 2-(2,2-Difluoro-2-quinolin-2-yl-ethyl)-7-pyridin-4-yl-2,3-dihydro-isoindol-1-one, 6-Fluoro-7-pyridin-4-yl-2-(2-quinolin-2-yl-ethyl)-2,3-dihydro-isoindol-1-one, 5-Fluoro-7-pyridin-4-yl-2-(2-quinolin-2-yl-ethyl)-2,3-dihydro-isoindol-1-one, 4-Fluoro-7-pyridin-4-yl-2-(2-quinolin-2-yl-ethyl)-2,3-dihydro-isoindol-1-one,
1-Methyl-4-(pyridin-4-yl)-2-(2-(quinolin-2-yl)ethyl)-1,2-dihydroindazol-3-one,
4-Pyridin-4-yl-2-(2-quinolin-2-yl-ethyl)-benzo[d]isoxazol-3-one,
7-Pyridin-4-yl-2-(2-thieno[3,2-b]pyridin-5-yl-ethyl)-2,3-dihydro-isoindol-1-one,
2-(2-Imidazo[1,2-a]pyridin-2-yl-ethyl)-7-pyridin-4-yl-2,3-dihydro-isoindol-1-one,
7-Phenyl-2-(2-quinolin-2-yl-ethyl)-2,3-dihydro-isoindol-1-one,
7-(4-Fluoro-phenyl)-2-(2-quinolin-2-yl-ethyl)-2,3-dihydro-isoindol-1-one,
7-(4-Methoxy-phenyl)-2-(2-quinolin-2-yl-ethyl)-2,3-dihydro-isoindol-1-one,
2-(2-Quinolin-2-yl-ethyl)-7-thiophen-2-yl-2,3-dihydro-isoindol-1-one,
2-(2-Quinolin-2-yl-ethyl)-7-thiophen-3-yl-2,3-dihydro-isoindol-1-one,
7-(3-Methoxy-phenyl)-2-(2-quinolin-2-yl-ethyl)-2,3-dihydro-isoindol-1-one,
7-(3-Fluoro-phenyl)-2-(2-quinolin-2-yl-ethyl)-2,3-dihydro-isoindol-1-one,
7-(2-Methoxy-phenyl)-2-(2-quinolin-2-yl-ethyl)-2,3-dihydro-isoindol-1-one,
7-(2-Fluoro-phenyl)-2-(2-quinolin-2-yl-ethyl)-2,3-dihydro-isoindol-1-one,
7-Pyridin-3-yl-2-(2-quinolin-2-yl-ethyl)-2,3-dihydro-isoindol-1-one,
7-Furan-2-yl-2-(2-quinolin-2-yl-ethyl)-2,3-dihydro-isoindol-1-one,
7-(3-Fluoro-4-methoxy-phenyl)-2-(2-quinolin-2-yl-ethyl)-2,3-dihydro-isoindol-1-one,
7-(3,4-Difluoro-phenyl)-2-(2-quinolin-2-yl-ethyl)-2,3-dihydro-isoindol-1-one,
7-Benzo[1,3]dioxol-5-yl-2-(2-quinolin-2-yl-ethyl)-2,3-dihydro-isoindol-1-one,
7-(2,3-Dihydro-benzo[1,4]dioxin-6-yl)-2-(2-quinolin-2-yl-ethyl)-2,3-dihydro-isoindol-1-one,
7-(3,4-Dimethoxy-phenyl)-2-(2-quinolin-2-yl-ethyl)-2,3-dihydro-isoindol-1-one,
7-(2,4-Dimethoxy-phenyl)-2-(2-quinolin-2-yl-ethyl)-2,3-dihydro-isoindol-1-one,
7-(4-Dimethylamino-phenyl)-2-(2-quinolin-2-yl-ethyl)-2,3-dihydro-isoindol-1-one,
7-(4-Methoxy-pyridin-3-yl)-2-(2-quinolin-2-yl-ethyl)-2,3-dihydro-isoindol-1-one,
7-(3,5-Difluoro-phenyl)-2-(2-quinolin-2-yl-ethyl)-2,3-dihydro-isoindol-1-one,
7-(2,5-Dimethoxy-phenyl)-2-(2-quinolin-2-yl-ethyl)-2,3-dihydro-isoindol-1-one,
2-[3-Oxo-2-(2-quinolin-2-yl-ethyl)-2,3-dihydro-1H-isoindol-4-yl]-pyrrole-1-carboxylic acid tert-butyl ester,
7-(3-Dimethylamino-phenyl)-2-(2-quinolin-2-yl-ethyl)-2,3-dihydro-isoindol-1-one,
7-(2-Dimethylamino-phenyl)-2-(2-quinolin-2-yl-ethyl)-2,3-dihydro-isoindol-1-one,
7-(2,4-Difluoro-phenyl)-2-(2-quinolin-2-yl-ethyl)-2,3-dihydro-isoindol-1-one,
7-Furan-3-yl-2-(2-quinolin-2-yl-ethyl)-2,3-dihydro-isoindol-1-one,
7-(1H-Indol-5-yl)-2-(2-quinolin-2-yl-ethyl)-2,3-dihydro-isoindol-1-one,
7-(4-Methyl-thiophen-2-yl)-2-(2-quinolin-2-yl-ethyl)-2,3-dihydro-isoindol-1-one,
{4-[3-Oxo-2-(2-quinolin-2-yl-ethyl)-2,3-dihydro-1H-isoindol-4-yl]-phenyl}-acetonitrile,
7-(2,3-Difluoro-phenyl)-2-(2-quinolin-2-yl-ethyl)-2,3-dihydro-isoindol-1-one,
7-(2,5-Difluoro-phenyl)-2-(2-quinolin-2-yl-ethyl)-2,3-dihydro-isoindol-1-one,
7-(5-Fluoro-2-methoxy-phenyl)-2-(2-quinolin-2-yl-ethyl)-2,3-dihydro-isoindol-1-one,
7-(1H-Pyrazol-3-yl)-2-(2-quinolin-2-yl-ethyl)-2,3-dihydro-isoindol-1-one,
7-(6-Methoxy-pyridin-3-yl)-2-(2-quinolin-2-yl-ethyl)-2,3-dihydro-isoindol-1-one,
7-(2-Fluoro-3-methoxy-phenyl)-2-(2-quinolin-2-yl-ethyl)-2,3-dihydro-isoindol-1-one,
7-(2,3-Dihydro-benzofuran-5-yl)-2-(2-quinolin-2-yl-ethyl)-2,3-dihydro-isoindol-1-one,
7-(2,3-Dimethoxy-phenyl)-2-(2-quinolin-2-yl-ethyl)-2,3-dihydro-isoindol-1-one,
7-Pyrimidin-5-yl-2-(2-quinolin-2-yl-ethyl)-2,3-dihydro-isoindol-1-one,
7-(6-Morpholin-4-yl-pyridin-3-yl)-2-(2-quinolin-2-yl-ethyl)-2,3-dihydro-isoindol-1-one,
7-(3-Methanesulfonyl-phenyl)-2-(2-quinolin-2-yl-ethyl)-2,3-dihydro-isoindol-1-one,
7-(2-Methoxy-pyrimidin-5-yl)-2-(2-quinolin-2-yl-ethyl)-2,3-dihydro-isoindol-1-one,
7-Quinolin-5-yl-2-(2-quinolin-2-yl-ethyl)-2,3-dihydro-isoindol-1-one,
7-(1H-Indol-4-yl)-2-(2-quinolin-2-yl-ethyl)-2,3-dihydro-isoindol-1-one,
7-(1H-Indol-6-yl)-2-(2-quinolin-2-yl-ethyl)-2,3-dihydro-isoindol-1-one,
7-(2-Methyl-pyridin-4-yl)-2-(2-quinolin-2-yl-ethyl)-2,3-dihydro-isoindol-1-one,
7-(2-Methoxy-pyridin-3-yl)-2-(2-quinolin-2-yl-ethyl)-2,3-dihydro-isoindol-1-one,
7-(3-Methoxymethyl-phenyl)-2-(2-quinolin-2-yl-ethyl)-2,3-dihydro-isoindol-1-one,
7-Isoquinolin-4-yl-2-(2-quinolin-2-yl-ethyl)-2,3-dihydro-isoindol-1-one,
7-(5-Methoxy-pyridin-3-yl)-2-(2-quinolin-2-yl-ethyl)-2,3-dihydro-isoindol-1-one,
7-(1-Methyl-1H-pyrazol-4-yl)-2-(2-quinolin-2-yl-ethyl)-2,3-dihydro-isoindol-1-one,
7-Isoquinolin-5-yl-2-(2-quinolin-2-yl-ethyl)-2,3-dihydro-isoindol-1-one,
7-Benzofuran-5-yl-2-(2-quinolin-2-yl-ethyl)-2,3-dihydro-isoindol-1-one,
7-(4-Methyl-thiophen-3-yl)-2-(2-quinolin-2-yl-ethyl)-2,3-dihydro-isoindol-1-one,
7-(2-Methyl-2H-pyrazol-3-yl)-2-(2-quinolin-2-yl-ethyl)-2,3-dihydro-isoindol-1-one,
7-Quinolin-6-yl-2-(2-quinolin-2-yl-ethyl)-2,3-dihydro-isoindol-1-one,
7-(3-Fluoro-5-methoxy-phenyl)-2-(2-quinolin-2-yl-ethyl)-2,3-dihydro-isoindol-1-one,
7-(5-Fluoro-pyridin-3-yl)-2-(2-quinolin-2-yl-ethyl)-2,3-dihydro-isoindol-1-one,
7-(1H-Pyrazol-4-yl)-2-(2-quinolin-2-yl-ethyl)-2,3-dihydro-isoindol-1-one,
7-(5-Methanesulfonyl-pyridin-3-yl)-2-(2-quinolin-2-yl-ethyl)-2,3-dihydro-isoindol-1-one,
7-(3-Morpholin-4-yl-phenyl)-2-(2-quinolin-2-yl-ethyl)-2,3-dihydro-isoindol-1-one,
{3-[3-Oxo-2-(2-quinolin-2-yl-ethyl)-2,3-dihydro-1H-isoindol-4-yl]-phenyl}-acetonitrile, 2-(2-Quinolin-2-yl-ethyl)-7-thiazol-2-yl-2,3-dihydro-isoindol-1-one,
7-Pyrimidin-2-yl-2-(2-quinolin-2-yl-ethyl)-2,3-dihydro-isoindol-1-one,
7-(3H-Imidazol-4-yl)-2-(2-quinolin-2-yl-ethyl)-2,3-dihydro-isoindol-1-one,
2-(2-Quinolin-2-yl-ethyl)-7-(5-trifluoromethyl-pyridin-2-yl)-2,3-dihydro-isoindol-1-one,
7-(2-Methyl-pyridin-3-yl)-2-(2-quinolin-2-yl-ethyl)-2,3-dihydro-isoindol-1-one,
7-(5-Methyl-pyridin-2-yl)-2-(2-quinolin-2-yl-ethyl)-2,3-dihydro-isoindol-1-one,
7-(5-Fluoro-pyridin-2-yl)-2-(2-quinolin-2-yl-ethyl)-2,3-dihydro-isoindol-1-one,
7-(3-Methyl-pyridin-2-yl)-2-(2-quinolin-2-yl-ethyl)-2,3-dihydro-isoindol-1-one,
5-[3-oxo-2-(2-quinolin-2-yl-ethyl)-2,3-dihydro-1H-isoindol-4-yl]-1,3-dihydro-indol-2-one,
7-(6-Methyl-pyridin-3-yl)-2-(2-quinolin-2-yl-ethyl)-2,3-dihydro-isoindol-1-one,
7-(1H-Indol-7-yl)-2-(2-quinolin-2-yl-ethyl)-2,3-dihydro-isoindol-1-one,
7-(1H-Indazol-5-yl)-2-(2-quinolin-2-yl-ethyl)-2,3-dihydro-isoindol-1-one,
7-(3-Methyl-3H-imidazol-4-yl)-2-(2-quinolin-2-yl-ethyl)-2,3-dihydro-isoindol-1-one,
7-(1-Methyl-1H-imidazol-2-yl)-2-(2-quinolin-2-yl-ethyl)-2,3-dihydro-isoindol-1-one,
6-[3-Oxo-2-(2-quinolin-2-yl-ethyl)-2,3-dihydro-1H-isoindol-4-yl]-1,3-dihydro-indol-2-one,
7-(1H-Indazol-6-yl)-2-(2-quinolin-2-yl-ethyl)-2,3-dihydro-isoindol-1-one,
2-(2-Quinolin-2-yl-ethyl)-7-(6-trifluoromethyl-pyridin-3-yl)-2,3-dihydro-isoindol-1-one,
7-Morpholin-4-yl-2-(2-quinolin-2-yl-ethyl)-2,3-dihydro-isoindol-1-one,
7-[4-(4-Methyl-piperazin-1-yl)-piperidin-1-yl]-2-(2-quinolin-2-yl-ethyl)-2,3-dihydro-isoindol-1-one,
7-(1S,4S)-2,5-Diaza-bicyclo[2.2.1]hept-2-yl-2-(2-quinolin-2-yl-ethyl)-2,3-dihydro-isoindol-1-one,
7-piperazin-1-yl-2-(2-quinolin-2-yl-ethyl)-2,3-dihydro-isoindol-1-one,
7-(3,8-Diaza-bicyclo[3.2.1]oct-8-yl)-2-(2-quinolin-2-yl-ethyl)-2,3-dihydro-isoindol-1-one,
7-(1,1-Dioxo-1-thiomorpholin-4-yl)-2-(2-quinolin-2-yl-ethyl)-2,3-dihydro-isoindol-1-one,
7-[4-(1-Methyl-piperidin-4-yl)-piperazin-1-yl]-2-(2-quinolin-2-yl-ethyl)-2,3-dihydro-isoindol-1-one,
7-(4-Pyridin-4-yl-piperazin-1-yl)-2-(2-quinolin-2-yl-ethyl)-2,3-dihydro-isoindol-1-one,
7-(4-Methyl-piperazin-1-yl)-2-(2-quinolin-2-yl-ethyl)-2,3-dihydro-isoindol-1-one,
7-(3-Phenyl-piperidin-1-yl)-2-(2-quinolin-2-yl-ethyl)-2,3-dihydro-isoindol-1-one,
7-(3-Phenoxy-piperidin-1-yl)-2-(2-quinolin-2-yl-ethyl)-2,3-dihydro-isoindol-1-one,
7-[1,4]Oxazepan-4-yl-2-(2-quinolin-2-yl-ethyl)-2,3-dihydro-isoindol-1-one,
7-(7-nitro-3,4-dihydroisoquinolin-2(1H)-yl)-2-(2-(quinolin-2-yl)ethyl)isoindolin-1-one,
7-(7-amino-3,4-dihydroisoquinolin-2(1H)-yl)-2-(2-(quinolin-2-yl)ethyl)isoindolin-1-one,
4-Chloro-N-{2-[3-oxo-2-(2-quinolin-2-yl-ethyl)-2,3-dihydro-1H-isoindol-4-yl]-1,2,3,4-tetrahydro-isoquinolin-7-yl}-benzenesulfonamide,
4-Isopropyl-N-{2-[3-oxo-2-(2-quinolin-2-yl-ethyl)-2,3-dihydro-1H-isoindol-4-yl]-,2,3,4-tetrahydro-isoquinolin-7-yl}-benzenesulfonamide,
2-[2-(6-Fluoro-quinolin-2-yl)-ethyl]-7-morpholin-4-yl-2,3-dihydro-isoindol-1-one,
2-[2-(6-Methoxy-quinolin-2-yl)-ethyl]-7-morpholin-4-yl-2,3-dihydro-isoindol-1-one,
2-[2-(4-Chloro-quinolin-2-yl)-ethyl]-7-morpholin-4-yl-2,3-dihydro-isoindol-1-one,
2-[2-(8-Chloro-quinolin-2-yl)-ethyl]-7-morpholin-4-yl-2,3-dihydro-isoindol-1-one,
4-Morpholin-4-yl-6-(2-quinolin-2-yl-ethyl)-6,7-dihydro-pyrrolo[3,4-b]pyridin-5-one,
7-Morpholino-2-(3-(pyrimidin-2-yl)phenethyl)isoindolin-1-one,
7-(Pyridin-4-yl)-2-(3-(pyrimidin-2-yl)phenethyl)isoindolin-1-one,
(2-(2-Phenylpyrimidin-4-yl)ethyl)-7-(pyridin-4-yl)isoindolin-1-one,
Pyridine-3-sulfonic acid [3-oxo-2-(2-quinolin-2-yl-ethyl)-2,3-dihydro-1H-isoindol-4-yl]-amide,
7-[(Pyridin-2-ylmethyl)-amino]-2-(2-quinolin-2-yl-ethyl)-2,3-dihydro-isoindol-1-one,
7-[(Pyridin-4-ylmethyl)-amino]-2-(2-quinolin-2-yl-ethyl)-2,3-dihydro-isoindol-1-one,
7-[(Pyridin-3-ylmethyl)-amino]-2-(2-quinolin-2-yl-ethyl)-2,3-dihydro-isoindol-1-one,
7-(Pyridin-3-ylmethoxy)-2-(2-quinolin-2-yl-ethyl)-2,3-dihydro-isoindol-1-one,
7-(Pyridin-4-ylmethoxy)-2-(2-quinolin-2-yl-ethyl)-2,3-dihydro-isoindol-1-one,
7-(Pyridin-2-ylmethoxy)-2-(2-quinolin-2-yl-ethyl)-2,3-dihydro-isoindol-1-one,
4-Morpholin-4-yl-2-(2-quinolin-2-yl-ethyl)-2,3-dihydro-isoindol-1-one,
4-(1,1-Dioxo-1-thiomorpholin-4-yl)-2-(2-quinolin-2-yl-ethyl)-2,3-dihydro-isoindol-1-one,
7-[8-(4-Methyl-piperazine-1-sulfonyl)-3,4-dihydro-1H-isoquinolin-2-yl]-2-(2-quinolin-2-yl-ethyl)-2,3-dihydro-isoindol-1-one,
7-[8-(Morpholine-4-sulfonyl)-3,4-dihydro-1H-isoquinolin-2-yl]-2-(2-quinolin-2-yl-ethyl)-2,3-dihydro-isoindol-1-one,
7-(2-Oxa-6-aza-spiro[3.4]oct-6-yl)-2-(2-quinolin-2-yl-ethyl)-2,3-dihydro-isoindol-1-one,
7-(1-oxo-thiomorpholin-4-yl)-2-(2-quinolin-2-yl-ethyl)-2,3-dihydro-isoindol-1-one,
7-(2-Oxa-6-aza-spiro[3.5]non-6-yl)-2-(2-quinolin-2-yl-ethyl)-2,3-dihydro-isoindol-1-one,
4-(1,1-Dioxo-thiomorpholin-4-yl)-6-(2-quinolin-2-yl-ethyl)-6,7-dihydro-pyrrolo[3,4-b]pyridin-5-one,
4-(4-Methyl-piperazin-1-yl)-6-(2-quinolin-2-yl-ethyl)-6,7-dihydro-pyrrolo[3,4-b]pyridin-5-one,
7-(3-Amino-azetidin-1-yl)-2-(2-quinolin-2-yl-ethyl)-2,3-dihydro-isoindol-1-one,
7-[4-(4-Methoxy-benzyloxy)-phenyl]-2-(2-quinolin-2-yl-ethyl)-2,3-dihydro-isoindol-1-one,
4-piperazin-1-yl-2-(2-quinolin-2-yl-ethyl)-2,3-dihydro-isoindol-1-one,
7-(5,5-Difluoro-hexahydro-cyclopenta[c]pyrrol-2-yl)-2-(2-quinolin-2-yl-ethyl)-2,3-dihydro-isoindol-1-one,
7-(4,4-Difluoro-piperidin-1-yl)-2-(2-quinolin-2-yl-ethyl)-2,3-dihydro-isoindol-1-one,
4-(4-Methyl-piperazin-1-yl)-2-(2-quinolin-2-yl-ethyl)-2,3-dihydro-isoindol-1-one,
7-(Azetidin-3-ylamino)-2-(2-quinolin-2-yl-ethyl)-2,3-dihydro-isoindol-1-one, 7-[4-(4-Isopropenyl-phenoxy)-phenyl]-2-(2-quinolin-2-yl-ethyl)-2,3-dihydro-isoindol-1-one,
7-[(3S,4S)-4-(2-Fluoro-4-trifluoromethoxy-phenyl)-3-methyl-piperidin-1-yl]-2-(2-quinolin-2-yl-ethyl)-2,3-dihydro-isoindol-1-one,
7-[4-(2,6-Dimethyl-pyridin-3-yloxy)-3-fluoro-phenyl]-2-(2-quinolin-2-yl-ethyl)-2,3-dihydro-isoindol-1-one,
7-(1-Pyridin-4-ylmethyl-1H-indol-5-yl)-2-(2-quinolin-2-yl-ethyl)-2,3-dihydro-isoindol-1-one,
2-(2-Quinolin-2-yl-ethyl)-7-thiomorpholin-4-yl-2,3-dihydro-isoindol-1-one,
7-(8-Methyl-3,8-diaza-bicyclo[3.2.1]oct-3-yl)-2-(2-quinolin-2-yl-ethyl)-2,3-dihydro-isoindol-1-one,
7-(3-Methyl-3,8-diaza-bicyclo[3.2.1]oct-8-yl)-2-(2-quinolin-2-yl-ethyl)-2,3-dihydro-isoindol-1-one,
2-[2-(1-Methyl-1H-benzoimidazol-2-yl)-ethyl]-7-morpholin-4-yl-2,3-dihydro-isoindol-1-one,
7-(5-Methyl-hexahydro-pyrrolo[3,4-c]pyrrol-2-yl)-2-(2-quinolin-2-yl-ethyl)-2,3-dihydro-isoindol-1-one,
7-[3-Chloro-4-(4-hydroxy-4-methyl-cyclohexylamino)-phenyl]-2-(2-quinolin-2-yl-ethyl)-2,3-dihydro-isoindol-1-one,
4-(1H-Pyrazol-4-yl)-6-(2-quinolin-2-yl-ethyl)-6,7-dihydro-pyrrolo[3,4-b]pyridin-5-one,
7-[4-(4-Ethyl-piperazin-1-yl)-piperidin-1-yl]-2-(2-quinolin-2-yl-ethyl)-2,3-dihydro-isoindol-1-one,
2-(2-Quinolin-2-yl-ethyl)-7-(3,4,5,6-tetrahydro-2H-[4,4']bipyridinyl-1-yl)-2,3-dihydro-isoindol-1-one,
7-(4-Pyridin-3-yl-piperazin-1-yl)-2-(2-quinolin-2-yl-ethyl)-2,3-dihydro-isoindol-1-one,
4-(4-Fluoro-phenyl)-6-(2-quinolin-2-yl-ethyl)-6,7-dihydro-pyrrolo[3,4-b]pyridin-5-one,
4-(4-Methoxy-phenyl)-6-(2-quinolin-2-yl-ethyl)-6,7-dihydro-pyrrolo[3,4-b]pyridin-5-one,
4-(2-Methyl-2H-pyrazol-3-yl)-6-(2-quinolin-2-yl-ethyl)-6,7-dihydro-pyrrolo[3,4-b]pyridin-5-one,
4-piperazin-1-yl-6-(2-quinolin-2-yl-ethyl)-6,7-dihydro-pyrrolo[3,4-b]pyridin-5-one,
4-(2-oxo-2,3-dihydro-1H-indol-6-yl)-6-(2-quinolin-2-yl-ethyl)-6,7-dihydro-pyrrolo[3,4-b]pyridin-5-one,
4-Pyrimidin-5-yl-6-(2-quinolin-2-yl-ethyl)-6,7-dihydro-pyrrolo[3,4-b]pyridin-5-one,
7-[4-(4-Methyl-piperazin-1-ylmethyl)-phenyl]-2-(2-quinolin-2-yl-ethyl)-2,3-dihydro-isoindol-1-one,
7-(4-Morpholin-4-ylmethyl-phenyl)-2-(2-quinolin-2-yl-ethyl)-2,3-dihydro-isoindol-1-one,
7-(3-Methoxy-pyridin-4-yl)-2-(2-quinolin-2-yl-ethyl)-2,3-dihydro-isoindol-1-one,
7-(3-Chloro-pyridin-4-yl)-2-(2-quinolin-2-yl-ethyl)-2,3-dihydro-isoindol-1-one,
7-(2-Chloro-pyridin-4-yl)-2-(2-quinolin-2-yl-ethyl)-2,3-dihydro-isoindol-1-one,
7-(6-Methyl-pyridin-3-ylmethoxy)-2-(2-quinolin-2-yl-ethyl)-2,3-dihydro-isoindol-1-one,
7-(3-Fluoro-pyridin-4-yl)-2-(2-quinolin-2-yl-ethyl)-2,3-dihydro-isoindol-1-one,
7-(3-Amino-4-methyl-piperidin-1-yl)-2-(2-quinolin-2-yl-ethyl)-2,3-dihydro-isoindol-1-one,
2-[2-(1H-Benzoimidazol-2-yl)-ethyl]-7-(1,1-dioxothiomorpholin-4-yl)-2,3-dihydro-isoindol-1-one,
7-[(1S,4S)-5-(4-Chloro-phenyl)-2,5-diaza-bicyclo[2.2.1]hept-2-yl]-2-(2-quinolin-2-yl-ethyl)-2,3-dihydro-isoindol-1-one,
7-(4-Methyl-piperazin-1-ylmethyl)-2-(2-quinolin-2-yl-ethyl)-2,3-dihydro-isoindol-1-one,
7-Morpholin-4-ylmethyl-2-(2-quinolin-2-yl-ethyl)-2,3-dihydro-isoindol-1-one,
7-(2-Methyl-pyridin-3-ylmethoxy)-2-(2-quinolin-2-yl-ethyl)-2,3-dihydro-isoindol-1-one,
4-Methoxy-7-(1H-pyrazol-4-yl)-2-(2-quinolin-2-yl-ethyl)-2,3-dihydro-isoindol-1-one,
4-Pyridin-4-yl-2-(2-quinolin-2-yl-ethyl)-2,3-dihydro-isoindol-1-one,
7-(2-Methoxy-pyridin-4-yl)-2-(2-quinolin-2-yl-ethyl)-2,3-dihydro-isoindol-1-one,
4-Methoxy-7-pyrimidin-5-yl-2-(2-quinolin-2-yl-ethyl)-2,3-dihydro-isoindol-1-one,
7-(1,1-Dioxo-thiomorpholin-4-yl)-2-[2-(1-methyl-1H-benzoimidazol-2-yl)-ethyl]-2,3-dihydro-isoindol-1-one,
4-Methoxy-7-pyridin-3-yl-2-(2-quinolin-2-yl-ethyl)-2,3-dihydro-isoindol-1-one,
4-Methoxy-7-(4-methoxy-phenyl)-2-(2-quinolin-2-yl-ethyl)-2,3-dihydro-isoindol-1-one,
7-(4-Fluoro-phenyl)-4-methoxy-2-(2-quinolin-2-yl-ethyl)-2,3-dihydro-isoindol-1-one,
7-(4-Dimethylaminomethyl-phenyl)-2-(2-quinolin-2-yl-ethyl)-2,3-dihydro-isoindol-1-one,
7-(1,1-Dioxo-thiomorpholin-4-yl)-4-methoxy-2-(2-quinolin-2-yl-ethyl)-2,3-dihydro-isoindol-1-one,
7-(1,1-Dioxo-tetrahydrothiophen-3-ylamino)-2-(2-quinolin-2-yl-ethyl)-2,3-dihydro-isoindol-1-one,
7-(6-Fluoro-pyridin-3-ylmethoxy)-2-(2-quinolin-2-yl-ethyl)-2,3-dihydro-isoindol-1-one,
7-(Hexahydro-pyrrolo[3,4-c]pyrrol-2-yl)-2-(2-quinolin-2-yl-ethyl)-2,3-dihydro-isoindol-1-one,
7-(4-Aminomethyl-phenyl)-2-(2-quinolin-2-yl-ethyl)-2,3-dihydro-isoindol-1-one,
7-(4-Methylaminomethyl-phenyl)-2-(2-quinolin-2-yl-ethyl)-2,3-dihydro-isoindol-1-one,
2-[2-(1-Methyl-1H-benzoimidazol-2-yl)-ethyl]-7-pyridin-4-yl-2,3-dihydro-isoindol-1-one,
2-[2-(1-Methyl-1H-benzoimidazol-2-yl)-ethyl]-7-pyridin-3-yl-2,3-dihydro-isoindol-1-one,
2-[2-(1-Methyl-1H-benzoimidazol-2-yl)-ethyl]-7-pyrimidin-5-yl-2,3-dihydro-isoindol-1-one,
4-Hydroxy-7-pyridin-4-yl-2-(2-quinolin-2-yl-ethyl)-2,3-dihydro-isoindol-1-one,
4-Ethoxy-7-pyridin-4-yl-2-(2-quinolin-2-yl-ethyl)-2,3-dihydro-isoindol-1-one,
4-(1H-Pyrazol-3-yl)-2-(2-quinolin-2-yl-ethyl)-2,3-dihydro-isoindol-1-one,
4-Pyridin-3-yl-2-(2-quinolin-2-yl-ethyl)-2,3-dihydro-isoindol-1-one,
4-(2-Methyl-2H-pyrazol-3-yl)-2-(2-quinolin-2-yl-ethyl)-2,3-dihydro-isoindol-1-one,
4-(4-Methoxy-phenyl)-2-(2-quinolin-2-yl-ethyl)-2,3-dihydro-isoindol-1-one,
4-(3-Methoxy-propoxy)-7-pyridin-4-yl-2-(2-quinolin-2-yl-ethyl)-2,3-dihydro-isoindol-1-one,
4-Isopropoxy-7-pyridin-4-yl-2-(2-quinolin-2-yl-ethyl)-2,3-dihydro-isoindol-1-one,
7-(4-Pyrrolidin-1-yl-piperidin-1-yl)-2-(2-quinolin-2-yl-ethyl)-2,3-dihydro-isoindol-1-one,
7-[1,4']Bipiperidinyl-1'-yl-2-(2-quinolin-2-yl-ethyl)-2,3-dihydro-isoindol-1-one,
4-Pyrimidin-5-yl-2-(2-quinolin-2-yl-ethyl)-2,3-dihydro-isoindol-1-one,
7-(4-Methoxy-phenyl)-2-[2-(1-methyl-1H-benzoimidazol-2-yl)-ethyl]-2,3-dihydro-isoindol-1-one,
4-Methoxy-7-(2-methyl-2H-pyrazol-3-yl)-2-(2-quinolin-2-yl-ethyl)-2,3-dihydro-isoindol-1-one,
7-(4-Fluoro-phenyl)-2-[2-(1-methyl-1H-benzoimidazol-2-yl)-ethyl]-2,3-dihydro-isoindol-1-one, 4-(4-Fluoro-phenyl)-2-(2-quinolin-2-yl-ethyl)-2,3-dihydro-isoindol-1-one,
4-(2-Methyl-2H-pyrazol-3-yl)-6-(2-[1,2,4]triazolo[1,5-a]pyridin-2-yl-ethyl)-6,7-dihydro-pyrrolo[3,4-b]pyridin-5-one,
6-[2-(1-Methyl-1H-benzoimidazol-2-yl)-ethyl]-4-(2-methyl-2H-pyrazol-3-yl)-6,7-dihydro-pyrrolo[3,4-b]pyridin-5-one,
4-Pyrimidin-5-yl-6-(2-[1,2,4]triazolo[1,5-a]pyridin-2-yl-ethyl)-6,7-dihydro-pyrrolo[3,4-b]pyridin-5-one,
6-[2-(1-Methyl-1H-benzoimidazol-2-yl)-ethyl]-4-morpholin-4-yl-6,7-dihydro-pyrrolo[3,4-b]pyridin-5-one,
2-(2-Imidazo[1,2-a]pyridin-2-yl-ethyl)-4-methoxy-7-pyrimidin-5-yl-2,3-dihydro-isoindol-1-one,
2-(2-Imidazo[1,2-a]pyridin-2-yl-ethyl)-4-methoxy-7-pyridin-3-yl-2,3-dihydro-isoindol-1-one,
7-(1S,5S)-3,6-Diaza-bicyclo[3.2.0]hept-3-yl-2-(2-quinolin-2-yl-ethyl)-2,3-dihydro-isoindol-1-one,
7-(3aR,7aS)-Octahydro-pyrrolo[3,2-c]pyridin-5-yl-2-(2-quinolin-2-yl-ethyl)-2,3-dihydro-isoindol-1-one,
2-[2-(5-Fluoro-1-methyl-1H-benzoimidazol-2-yl)-ethyl]-7-pyridin-4-yl-2,3-dihydro-isoindol-1-one,
2-[2-(1-Ethyl-1H-benzoimidazol-2-yl)-ethyl]-7-pyridin-4-yl-2,3-dihydro-isoindol-1-one,
2-(2-Benzothiazol-2-yl-ethyl)-7-pyridin-4-yl-2,3-dihydro-isoindol-1-one,
7-((R)-3-Amino-pyrrolidin-1-yl)-2-(2-quinolin-2-yl-ethyl)-2,3-dihydro-isoindol-1-one,
4-(1H-Pyrazol-4-yl)-2-(2-quinolin-2-yl-ethyl)-2,3-dihydro-isoindol-1-one,
6-[2-(1-Methyl-1H-benzoimidazol-2-yl)-ethyl]-4-(4-methyl-piperazin-1-yl)-6,7-dihydro-pyrrolo[3,4-b]pyridin-5-one,
4-Morpholin-4-yl-6-(2-[1,2,4]triazolo[1,5-a]pyridin-2-yl-ethyl)-6,7-dihydro-pyrrolo[3,4-b]pyridin-5-one,
7-(2-Methyl-morpholin-4-yl)-2-(2-quinolin-2-yl-ethyl)-2,3-dihydro-isoindol-1-one,
7-(2-Dimethylaminomethyl-morpholin-4-yl)-2-(2-quinolin-2-yl-ethyl)-2,3-dihydro-isoindol-1-one,
7-Pyridin-4-yl-2-(2-[1,2,4]triazolo[1,5-a]pyridin-2-yl-ethyl)-2,3-dihydro-isoindol-1-one,
7-Morpholin-4-yl-2-(2-[1,2,4]triazolo[1,5-a]pyridin-2-yl-ethyl)-2,3-dihydro-isoindol-1-one,
7-(1,1-Dioxo-thiomorpholin-4-yl)-2-(2-[1,2,4]triazolo[1,5-a]pyridin-2-yl-ethyl)-2,3-dihydro-isoindol-1-one,
7-(4-Methyl-piperazin-1-yl)-2-(2-[1,2,4]triazolo[1,5-a]pyridin-2-yl-ethyl)-2,3-dihydro-isoindol-1-one,
7-(1,1-Dioxo-thiomorpholin-4-yl)-2-(2-imidazo[1,2-a]pyridin-2-yl-ethyl)-2,3-dihydro-isoindol-1-one,
2-(2-Imidazo[1,2-a]pyridin-2-yl-ethyl)-7-pyridin-3-yl-2,3-dihydro-isoindol-1-one,
7-(4-Fluoro-phenyl)-2-(2-imidazo[1,2-a]pyridin-2-yl-ethyl)-2,3-dihydro-isoindol-1-one,
2-(2-Imidazo[1,2-a]pyridin-2-yl-ethyl)-7-(4-methoxy-phenyl)-2,3-dihydro-isoindol-1-one,
2-(2-Imidazo[1,2-a]pyridin-2-yl-ethyl)-7-pyrimidin-5-yl-2,3-dihydro-isoindol-1-one,
2-(2-Imidazo[1,2-a]pyridin-2-yl-ethyl)-7-(2-methyl-2H-pyrazol-3-yl)-2,3-dihydro-isoindol-1-one,
2-(2-Imidazo[1,2-a]pyridin-2-yl-ethyl)-7-(2-methyl-pyridin-3-yl)-2,3-dihydro-isoindol-1-one,
6-[2-(2-Imidazo[1,2-a]pyridin-2-yl-ethyl)-3-oxo-2,3-dihydro-1H-isoindol-4-yl]-1,3-dihydro-indol-2-one,
2-(2-Imidazo[1,2-a]pyridin-2-yl-ethyl)-7-(1H-pyrazol-4-yl)-2,3-dihydro-isoindol-1-one,
2-(2-Imidazo[1,2-a]pyridin-2-yl-ethyl)-7-(1H-indazol-6-yl)-2,3-dihydro-isoindol-1-one,
7-(3H-Benzoimidazol-5-yl)-2-(2-imidazo[1,2-a]pyridin-2-yl-ethyl)-2,3-dihydro-isoindol-1-one,
5-[2-(2-Imidazo[1,2-a]pyridin-2-yl-ethyl)-3-oxo-2,3-dihydro-1H-isoindol-4-yl]-1,3-dihydro-benzoimidazol-2-one,
4-(Pyridin-3-ylmethoxy)-2-(2-quinolin-2-yl-ethyl)-isoindole-1,3-dione,
4-(Pyridin-4-ylmethoxy)-2-(2-quinolin-2-yl-ethyl)-isoindole-1,3-dione,
4-Methoxy-7-morpholin-4-yl-2-(2-quinolin-2-yl-ethyl)-2,3-dihydro-isoindol-1-one,
4-Pyridin-4-yl-2-(2-quinolin-2-yl-ethyl)-isoindole-1,3-dione
4-(1,1-Dioxothiomorpholin-4-yl)-2-(2-quinolin-2-yl-ethyl)-isoindole-1,3-dione
7-(2-Methoxy-pyridin-4-yl)-2-(2-quinolin-2-yl-ethyl)-2,3-dihydro-isoindol-1-one,
7-(2-Ethyl-morpholin-4-yl)-2-(2-quinolin-2-yl-ethyl)-2,3-dihydro-isoindol-1-one,
2-[2-(1H-Imidazo[4,5-b]pyridin-2-yl)-ethyl]-7-pyridin-3-yl-2,3-dihydro-isoindol-1-one,
2-[2-(1-Methyl-1H-benzoimidazol-2-yl)-ethyl]-7-(4-methyl-piperazin-1-yl)-2,3-dihydro-isoindol-1-one,
6-(2-Imidazo[1,2-a]pyridin-2-yl-ethyl)-4-(2-methyl-2H-pyrazol-3-yl)-6,7-dihydro-pyrrolo[3,4-b]pyridin-5-one,
6-(2-Imidazo[1,2-a]pyridin-2-yl-ethyl)-4-pyrimidin-5-yl-6,7-dihydro-pyrrolo[3,4-b]pyridin-5-one,
4-(2-Oxa-6-aza-spiro[3.4]oct-6-yl)-6-(2-quinolin-2-yl-ethyl)-6,7-dihydro-pyrrolo[3,4-b]pyridin-5-one,
4-(4,4-Difluoro-piperidin-1-yl)-6-(2-quinolin-2-yl-ethyl)-6,7-dihydro-pyrrolo[3,4-b]pyridin-5-one,
7-(2,6-Dimethyl-morpholin-4-yl)-2-(2-quinolin-2-yl-ethyl)-2,3-dihydro-isoindol-1-one,
6-(2-Quinolin-2-yl-ethyl)-4-(tetrahydro-furo[3,4-c]pyrrol-5-yl)-6,7-dihydro-pyrrolo[3,4-b]pyridin-5-one,
4-Methoxy-7-(4-methyl-piperazin-1-yl)-2-(2-quinolin-2-yl-ethyl)-2,3-dihydro-isoindol-1-one,
2-[2-(5-Fluoro-1-methyl-1H-benzoimidazol-2-yl)-ethyl]-7-morpholin-4-yl-2,3-dihydro-isoindol-1-one,
2-(2-Benzothiazol-2-yl-ethyl)-7-morpholin-4-yl-2,3-dihydro-isoindol-1-one,
2-(2-Imidazo[1,2-a]pyridin-2-yl-ethyl)-4-methoxy-7-morpholin-4-yl-2,3-dihydro-isoindol-1-one,
4-(3,6-Dihydro-2H-pyran-4-yl)-6-(2-quinolin-2-yl-ethyl)-6,7-dihydro-pyrrolo[3,4-b]pyridin-5-one,
4-(4,5-Dihydro-furan-3-yl)-6-(2-quinolin-2-yl-ethyl)-6,7-dihydro-pyrrolo[3,4-b]pyridin-5-one,
4-Methylsulfanylmethoxy-7-pyridin-4-yl-2-(2-quinolin-2-yl-ethyl)-2,3-dihydro-isoindol-1-one,
4-Difluoromethoxy-7-pyridin-4-yl-2-(2-quinolin-2-yl-ethyl)-2,3-dihydro-isoindol-1-one,
4-Methoxy-7-[4-(1-methyl-piperidin-4-yl)-piperazin-1-yl]-2-(2-quinolin-2-yl-ethyl)-2,3-dihydro-isoindol-1-one,
6-(2-Imidazo[1,2-a]pyridin-2-yl-ethyl)-4-morpholin-4-yl-6,7-dihydro-pyrrolo[3,4-b]pyridin-5-one,
4-Pyridin-3-yl-2-(2-quinolin-2-yl-ethyl)-isoindole-1,3-dione,
4-Morpholin-4-yl-2-(2-quinolin-2-yl-ethyl)-isoindole-1,3-dione,
6-(2-Imidazo[1,2-a]pyridin-2-yl-ethyl)-4-(4-methyl-piperazin-1-yl)-6,7-dihydro-pyrrolo[3,4-b]pyridin-5-one,
7-(Oxetan-3-ylamino)-2-(2-quinolin-2-yl-ethyl)-2,3-dihydro-isoindol-1-one,
4-(Oxetan-3-ylamino)-6-(2-quinolin-2-yl-ethyl)-6,7-dihydro-pyrrolo[3,4-b]pyridin-5-one,
4-Methylaminomethoxy-7-pyridin-4-yl-2-(2-quinolin-2-yl-ethyl)-2,3-dihydro-isoindol-1-one, 7-(2-Ethyl-6-methyl-morpholin-4-yl)-2-(2-quinolin-2-yl-ethyl)-2,3-dihydro-isoindol-1-one,
2-[2-(1-Ethyl-1H-benzoimidazol-2-yl)-ethyl]-7-morpholin-4-yl-2,3-dihydro-isoindol-1-one,
7-(Octahydro-[1,5]naphthyridin-1-yl)-2-(2-quinolin-2-yl-ethyl)-2,3-dihydro-isoindol-1-one,
4-Fluoro-2-(2-imidazo[1,2-a]pyridin-2-yl-ethyl)-7-pyridin-4-yl-2,3-dihydro-isoindol-1-one,
5-[3-oxo-2-(2-quinolin-2-yl-ethyl)-2,3-dihydro-1H-isoindol-4-yl]-thiophene-2-carbonitrile,
7-[2-(4-Methyl-piperazin-1-yl)-pyrimidin-5-yl]-2-(2-quinolin-2-yl-ethyl)-2,3-dihydro-isoindol-1-one,
7-(2-Ethoxy-pyrimidin-5-yl)-2-(2-quinolin-2-yl-ethyl)-2,3-dihydro-isoindol-1-one,
7-(5-Pyrrolidin-1-ylmethyl-thiophen-2-yl)-2-(2-quinolin-2-yl-ethyl)-2,3-dihydro-isoindol-1-one,
7-(2-Dimethylamino-pyrimidin-5-yl)-2-(2-quinolin-2-yl-ethyl)-2,3-dihydro-isoindol-1-one,
7-(5-Piperidin-1-ylmethyl-thiophen-2-yl)-2-(2-quinolin-2-yl-ethyl)-2,3-dihydro-isoindol-1-one,
7-(3-Chloro-thiophen-2-yl)-2-(2-quinolin-2-yl-ethyl)-2,3-dihydro-isoindol-1-one,
3-Methyl-5-[3-oxo-2-(2-quinolin-2-yl-ethyl)-2,3-dihydro-1H-isoindol-4-yl]-thiophene-2-carbonitrile,
7-(2-Chloro-thiophen-3-yl)-2-(2-quinolin-2-yl-ethyl)-2,3-dihydro-isoindol-1-one,
7-(2-Cyclopropyl-pyridin-4-yl)-2-(2-quinolin-2-yl-ethyl)-2,3-dihydro-isoindol-1-one,
7-(3,6-Dimethoxy-pyridazin-4-yl)-2-(2-quinolin-2-yl-ethyl)-2,3-dihydro-isoindol-1-one,
2-{2-[1-(2-Morpholin-4-yl-ethyl)-1H-benzoimidazol-2-yl]-ethyl}-7-pyridin-4-yl-2,3-dihydro-isoindol-1-one,
2-{2-[1-(2-Dimethylamino-ethyl)-1H-benzoimidazol-2-yl]-ethyl}-7-pyridin-4-yl-2,3-dihydro-isoindol-1-one,
2-{2-[1-(3-Dimethylamino-propyl)-1H-benzoimidazol-2-yl]-ethyl}-7-pyridin-4-yl-2,3-dihydro-isoindol-1-one,
4-Fluoro-2-(2-imidazo[1,2-a]pyridin-2-yl-ethyl)-7-morpholin-4-yl-2,3-dihydro-isoindol-1-one,
1-Oxy-4-pyrimidin-5-yl-6-(2-quinolin-2-yl-ethyl)-6,7-dihydro-pyrrolo[3,4-b]pyridin-5-one,
6-(2-Quinolin-2-yl-ethyl)-4-(tetrahydro-pyran-4-yl)-6,7-dihydro-pyrrolo[3,4-b]pyridin-5-one,
7-(2-Methoxymethyl-morpholin-4-yl)-2-(2-quinolin-2-yl-ethyl)-2,3-dihydro-isoindol-1-one,
4-Fluoromethoxy-7-pyridin-4-yl-2-(2-quinolin-2-yl-ethyl)-2,3-dihydro-isoindol-1-one,
2-[2-(4-Fluoro-1-methyl-1H-benzoimidazol-2-yl)-ethyl]-7-pyridin-4-yl-2,3-dihydro-isoindol-1-one,
2-[2-(1,5-Dimethyl-1H-benzoimidazol-2-yl)-ethyl]-7-pyridin-4-yl-2,3-dihydro-isoindol-1-one,
2-[2-(1-Propyl-1H-benzoimidazol-2-yl)-ethyl]-7-pyridin-4-yl-2,3-dihydro-isoindol-1-one,
2-[2-(1-Isopropyl-1H-benzoimidazol-2-yl)-ethyl]-7-pyridin-4-yl-2,3-dihydro-isoindol-1-one,
2-[2-(1-Isopropyl-1H-benzoimidazol-2-yl)-ethyl]-7-morpholin-4-yl-2,3-dihydro-isoindol-1-one,
7-Morpholin-4-yl-2-[2-(1-propyl-1H-benzoimidazol-2-yl)-ethyl]-2,3-dihydro-isoindol-1-one,
2-[2-(1,5-Dimethyl-1H-benzoimidazol-2-yl)-ethyl]-7-morpholin-4-yl-2,3-dihydro-isoindol-1-one,
2-[2-(4-Fluoro-1-methyl-1H-benzoimidazol-2-yl)-ethyl]-7-morpholin-4-yl-2,3-dihydro-isoindol-1-one,
2-(2-Imidazo[1,2-a]pyridin-2-yl-ethyl)-4-morpholin-4-yl-2,3-dihydro-isoindol-1-one,
6-(2-Quinolin-2-yl-ethyl)-4-(tetrahydro-furan-3-yl)-6,7-dihydro-pyrrolo[3,4-b]pyridin-5-one,
2-(2-Imidazo[1,2-a]pyridin-2-yl-ethyl)-7-morpholin-4-yl-2,3-dihydro-isoindol-1-one,
2-[2-(1H-Benzoimidazol-2-yl)-ethyl]-7-(4-fluoro-phenyl)-2,3-dihydro-isoindol-1-one,
2-[2-(1H-Benzoimidazol-2-yl)-ethyl]-7-pyrimidin-5-yl-2,3-dihydro-isoindol-1-one,
2-[2-(1H-Benzoimidazol-2-yl)-ethyl]-7-(2-methyl-2H-pyrazol-3-yl)-2,3-dihydro-isoindol-1-one,
2-(2-Imidazo[1,2-a]pyridin-2-yl-ethyl)-4-(1H-pyrazol-3-yl)-2,3-dihydro-isoindol-1-one,
6-[2-(5,7-Dimethyl-[1,2,4]triazolo[1,5-a]pyrimidin-2-yl)-ethyl]-4-pyridin-4-yl-6,7-dihydro-pyrrolo[3,4-b]pyridin-5-one,
2-(2-Imidazo[1,2-a]pyridin-2-yl-ethyl)-4-pyridin-4-yl-2,3-dihydro-isoindol-1-one,
7-(3aS,8aR)-Octahydro-pyrrolo[3,4-c]azepin-2-yl-2-(2-quinolin-2-yl-ethyl)-2,3-dihydro-isoindol-1-one,
7-(3aS,8aS)-Octahydro-pyrrolo[3,4-c]azepin-2-yl-2-(2-quinolin-2-yl-ethyl)-2,3-dihydro-isoindol-1-one,
1-[5-oxo-6-(2-quinolin-2-yl-ethyl)-6,7-dihydro-5H-pyrrolo[3,4-b]pyridin-4-yl]-piperidine-4-carboxylic acid ethyl ester,
4-[8-(Morpholine-4-sulfonyl)-3,4-dihydro-1H-isoquinolin-2-yl]-2-(2-quinolin-2-yl-ethyl)-2,3-dihydro-isoindol-1-one,
4-[8-(4-Methyl-piperazine-1-sulfonyl)-3,4-dihydro-1H-isoquinolin-2-yl]-2-(2-quinolin-2-yl-ethyl)-2,3-dihydro-isoindol-1-one,
4-(3-Methyl-pyridin-4-yl)-6-(2-quinolin-2-yl-ethyl)-6,7-dihydro-pyrrolo[3,4-b]pyridin-5-one,
4-(1H-Pyrazol-3-yl)-6-(2-quinolin-2-yl-ethyl)-6,7-dihydro-pyrrolo[3,4-b]pyridin-5-one,
4-(3,6-dimethoxypyridazin-4-yl)-6-(2-(quinolin-2-yl)ethyl)-6,7-dihydro-5H-pyrrolo[3,4-b]pyridin-5-one,
4-(2-Dimethylamino-pyrimidin-5-yl)-6-(2-quinolin-2-yl-ethyl)-6,7-dihydro-pyrrolo[3,4-b]pyridin-5-one,
4-(2-Methyl-thiazol-5-yl)-6-(2-quinolin-2-yl-ethyl)-6,7-dihydro-pyrrolo[3,4-b]pyridin-5-one,
4-(2-Ethoxy-pyrimidin-5-yl)-6-(2-quinolin-2-yl-ethyl)-6,7-dihydro-pyrrolo[3,4-b]pyridin-5-one,
4-(2-Methoxy-pyridin-4-yl)-6-(2-quinolin-2-yl-ethyl)-6,7-dihydro-pyrrolo[3,4-b]pyridin-5-one,
4-Pyridin-3-yl-6-(2-quinolin-2-yl-ethyl)-6,7-dihydro-pyrrolo[3,4-b]pyridin-5-one,
6-(2-Quinolin-2-yl-ethyl)-4-thiophen-3-yl-6,7-dihydro-pyrrolo[3,4-b]pyridin-5-one,
4-Furan-3-yl-6-(2-quinolin-2-yl-ethyl)-6,7-dihydro-pyrrolo[3,4-b]pyridin-5-one,
4-(1,5-Dimethyl-1H-pyrazol-4-yl)-6-(2-quinolin-2-yl-ethyl)-6,7-dihydro-pyrrolo[3,4-b]pyridin-5-one,
4-(1-Ethyl-1H-pyrazol-4-yl)-6-(2-quinolin-2-yl-ethyl)-6,7-dihydro-pyrrolo[3,4-b]pyridin-5-one,
4-(2,5-Dimethyl-2H-pyrazol-3-yl)-6-(2-quinolin-2-yl-ethyl)-6,7-dihydro-pyrrolo[3,4-b]pyridin-5-one,
4-(3,5-Dimethyl-isoxazol-4-yl)-6-(2-quinolin-2-yl-ethyl)-6,7-dihydro-pyrrolo[3,4-b]pyridin-5-one,
4-(3-Methyl-thiophen-2-yl)-6-(2-quinolin-2-yl-ethyl)-6,7-dihydro-pyrrolo[3,4-b]pyridin-5-one,
4-(1-Methyl-1H-pyrrol-3-yl)-6-(2-quinolin-2-yl-ethyl)-6,7-dihydro-pyrrolo[3,4-b]pyridin-5-one,
4-Pyridazin-4-yl-6-(2-quinolin-2-yl-ethyl)-6,7-dihydro-pyrrolo[3,4-b]pyridin-5-one,
4-Cyclopropyl-pyridin-4-yl)-6-(2-quinolin-2-yl-ethyl)-6,7-dihydro-pyrrolo[3,4-b]pyridin-5-one,
6-(2-Quinolin-2-yl-ethyl)-4-thiazol-4-yl-6,7-dihydro-pyrrolo[3,4-b]pyridin-5-one, 4-(2-Dimethylamino-pyrimidin-5-yl)-2-(2-quinolin-2-yl-ethyl)-2,3-dihydro-isoindol-1-one,
4-(2-Methyl-thiazol-5-yl)-2-(2-quinolin-2-yl-ethyl)-2,3-dihydro-isoindol-1-one,
4-(2-Ethoxy-pyrimidin-5-yl)-2-(2-quinolin-2-yl-ethyl)-2,3-dihydro-isoindol-1-one,
4-(2-Methoxy-pyridin-4-yl)-2-(2-quinolin-2-yl-ethyl)-2,3-dihydro-isoindol-1-one,
2-(2-Quinolin-2-yl-ethyl)-4-thiophen-3-yl-2,3-dihydro-isoindol-1-one,
4-Furan-3-yl-2-(2-quinolin-2-yl-ethyl)-2,3-dihydro-isoindol-1-one,
4-(1-Ethyl-1H-pyrazol-4-yl)-2-(2-quinolin-2-yl-ethyl)-2,3-dihydro-isoindol-1-one,
4-(2,5-Dimethyl-2H-pyrazol-3-yl)-2-(2-quinolin-2-yl-ethyl)-2,3-dihydro-isoindol-1-one,
4-(3,5-Dimethyl-isoxazol-4-yl)-2-(2-quinolin-2-yl-ethyl)-2,3-dihydro-isoindol-1-one,
4-(5-Methyl-pyrazin-2-yl)-2-(2-quinolin-2-yl-ethyl)-2,3-dihydro-isoindol-1-one,
4-(3-Methyl-thiophen-2-yl)-2-(2-quinolin-2-yl-ethyl)-2,3-dihydro-isoindol-1-one,
4-(1-Methyl-1H-pyrrol-3-yl)-2-(2-quinolin-2-yl-ethyl)-2,3-dihydro-isoindol-1-one,
4-Pyridazin-4-yl-2-(2-quinolin-2-yl-ethyl)-2,3-dihydro-isoindol-1-one,
4-(2-Cyclopropyl-pyridin-4-yl)-2-(2-quinolin-2-yl-ethyl)-2,3-dihydro-isoindol-1-one,
2-(2-Quinolin-2-yl-ethyl)-4-thiazol-4-yl-2,3-dihydro-isoindol-1-one,
4-(6-Methoxy-pyrazin-2-yl)-2-(2-quinolin-2-yl-ethyl)-2,3-dihydro-isoindol-1-one,
4-(3-Phenyl-piperidin-1-yl)-2-(2-quinolin-2-yl-ethyl)-2,3-dihydro-isoindol-1-one,
6-(2-Imidazo[1,2-a]pyridin-2-yl-ethyl)-4-pyridin-3-yl-6,7-dihydro-pyrrolo[3,4-b]pyridin-5-one,
6-[2-(1-Methyl-1H-benzoimidazol-2-yl)-ethyl]-4-(oxetan-3-ylamino)-6,7-dihydro-pyrrolo[3,4-b]pyridin-5-one,
6-(2-Imidazo[1,2-a]pyridin-2-yl-ethyl)-4-(oxetan-3-ylamino)-6,7-dihydro-pyrrolo[3,4-b]pyridin-5-one,
4-(3-Phenoxy-piperidin-1-yl)-2-(2-quinolin-2-yl-ethyl)-2,3-dihydro-isoindol-1-one,
2-(2-Imidazo[1,2-a]pyridin-2-yl-ethyl)-4-methoxy-7-(oxetan-3-ylamino)-2,3-dihydro-isoindol-1-one,
4-(4-Dimethylamino-piperidin-1-yl)-6-(2-quinolin-2-yl-ethyl)-6,7-dihydro-pyrrolo[3,4-b]pyridin-5-one,
6-[2-(1-Methyl-1H-benzoimidazol-2-yl)-ethyl]-4-pyrimidin-5-yl-6,7-dihydro-pyrrolo[3,4-b]pyridin-5-one,
6-(2-Imidazo[1,2-a]pyridin-2-yl-ethyl)-4-(1H-pyrazol-4-yl)-6,7-dihydro-pyrrolo[3,4-b]pyridin-5-one,
1-[5-oxo-6-(2-quinolin-2-yl-ethyl)-6,7-dihydro-5H-pyrrolo[3,4-b]pyridin-4-yl]-piperidine-4-carboxylic acid,
6-[2-(1-Methyl-1H-benzoimidazol-2-yl)-ethyl]-4-pyridin-4-yl-6,7-dihydro-pyrrolo[3,4-b]pyridin-5-one,
6-[2-(1-Methyl-1H-benzoimidazol-2-yl)-ethyl]-4-pyridin-3-yl-6,7-dihydro-pyrrolo[3,4-b]pyridin-5-one,
6-(2-Imidazo[1,2-a]pyridin-2-yl-ethyl)-4-pyridin-4-yl-6,7-dihydro-pyrrolo[3,4-b]pyridin-5-one,
4-Methoxy-2-[2-(1-methyl-1H-benzoimidazol-2-yl)-ethyl]-7-pyridin-4-yl-2,3-dihydro-isoindol-1-one,
4-Methoxy-2-[2-(1-methyl-1H-benzoimidazol-2-yl)-ethyl]-7-morpholin-4-yl-2,3-dihydro-isoindol-1-one,
2-(2-Imidazo[1,2-a]pyridin-2-yl-ethyl)-4-methoxy-7-(1H-pyrazol-4-yl)-2,3-dihydro-isoindol-1-one,
2-(2-Imidazo[1,2-a]pyridin-2-yl-ethyl)-4-methoxy-7-(2-methyl-2H-pyrazol-3-yl)-2,3-dihydro-isoindol-1-one,
2-(2-Imidazo[1,2-a]pyridin-2-yl-ethyl)-4-methoxy-7-pyridin-4-yl-2,3-dihydro-isoindol-1-one,
6-(2-Benzothiazol-2-yl-ethyl)-4-pyridin-4-yl-6,7-dihydro-pyrrolo[3,4-b]pyridin-5-one,
6-(2-Benzothiazol-2-yl-ethyl)-4-(oxetan-3-ylamino)-6,7-dihydro-pyrrolo[3,4-b]pyridin-5-one,
6-(2-Benzothiazol-2-yl-ethyl)-4-morpholin-4-yl-6,7-dihydro-pyrrolo[3,4-b]pyridin-5-one,
4-Fluoro-2-(2-imidazo[1,2-a]pyridin-2-yl-ethyl)-7-pyridin-3-yl-2,3-dihydro-isoindol-1-one,
4-Fluoro-7-(4-fluoro-phenyl)-2-(2-imidazo[1,2-a]pyridin-2-yl-ethyl)-2,3-dihydro-isoindol-1-one,
4-Fluoro-2-(2-imidazo[1,2-a]pyridin-2-yl-ethyl)-7-(4-methoxy-phenyl)-2,3-dihydro-isoindol-1-one,
4-Fluoro-2-(2-imidazo[1,2-a]pyridin-2-yl-ethyl)-7-pyrimidin-5-yl-2,3-dihydro-isoindol-1-one,
4-Fluoro-2-(2-imidazo[1,2-a]pyridin-2-yl-ethyl)-7-(2-methyl-2H-pyrazol-3-yl)-2,3-dihydro-isoindol-1-one,
4-Fluoro-2-(2-imidazo[1,2-a]pyridin-2-yl-ethyl)-7-(1H-pyrazol-4-yl)-2,3-dihydro-isoindol-1-one,
4-[3-(Fluoromethyl)pyrrolidin-1-yl]-6-(2-imidazo[1,2-a]pyridin-2-ylethyl)-7H-pyrrolo[3,4-b]pyridin-5-one,
6-[2-(1,3-Benzothiazol-2-yl)ethyl]-4-[3-(difluoromethyl)pyrrolidin-1-yl]-7H-pyrrolo[3,4-b]pyridin-5-one,
4-[3-(Difluoromethyl)pyrrolidin-1-yl]-6-(2-imidazo[1,2-a]pyridin-2-ylethyl)-7H-pyrrolo[3,4-b]pyridin-5-one,
6-[2-(1,3-Benzothiazol-2-yl)ethyl]-4-[3-(fluoromethyl)pyrrolidin-1-yl]-7H-pyrrolo[3,4-b]pyridin-5-one,
4-(3-Methoxy-4-pyridyl)-2-[2-(2-quinolyl)ethyl]isoindolin-1-one,
4-(3-Methoxy-4-pyridyl)-6-[2-(2-quinolyl)ethyl]-7H-pyrrolo[3,4-b]pyridin-5-one,
6-[2-(1,3-Benzothiazol-2-yl)ethyl]-4-(1,1-dioxo-1,4-thiazinan-4-yl)-7H-pyrrolo[3,4-b]pyridin-5-one trifluoroacetate,
6-[2-(Benzofuran-2-yl)ethyl]-4-(4-pyridyl)-7H-pyrrolo[3,4-b]pyridin-5-one,
6-[2-(7-Methyl-2-quinolyl)ethyl]-4-morpholino-7H-pyrrolo[3,4-b]pyridin-5-one,
6-[2-(Benzothiophen-2-yl)ethyl]-4-(4-pyridyl)-7H-pyrrolo[3,4-b]pyridin-5-one,
6-[2-(7-Methyl-2-quinolyl)ethyl]-4-(4-pyridyl)-7H-pyrrolo[3,4-b]pyridin-5-one trifluoroacetate,
6-[2-(Benzothiophen-2-yl)ethyl]-4-morpholino-7H-pyrrolo[3,4-b]pyridin-5-one trifluoroacetate,
2-[2-(1,3-Benzothiazol-2-yl)ethyl]-7-methoxy-4-(4-pyridyl)isoindolin-1-one,
6-[2-(Benzofuran-2-yl)ethyl]-4-morpholino-7H-pyrrolo[3,4-b]pyridin-5-one,
6-[2-(5-Isopropyl-2-pyridyl)ethyl]-4-(4-pyridyl)-7H-pyrrolo[3,4-b]pyridin-5-one,
2-[2-(1,3-Benzothiazol-2-yl)ethyl]-7-methoxy-4-(2-methyl-pyrazol-3-yl)isoindolin-1-one,
2-[2-(1,3-Benzothiazol-2-yl)ethyl]-7-methoxy-4-(1H-pyrazol-3-yl)isoindolin-1-one,
6-[2-(5-Isopropyl-2-pyridyl)ethyl]-4-morpholino-7H-pyrrolo[3,4-b]pyridin-5-one,
6-[2-(6-Fluoro-1,3-benzothiazol-2-yl)ethyl]-4-(4-pyridyl)-7H-pyrrolo[3,4-b]pyridin-5-one,
6-[2-(6-Chloro-1,3-benzothiazol-2-yl)ethyl]-4-(4-pyridyl)-7H-pyrrolo[3,4-b]pyridin-5-one,
6-[2-(6-Chloro-1,3-benzothiazol-2-yl)ethyl]-4-morpholino-7H-pyrrolo[3,4-b]pyridin-5-one,
6-[2-(6-Fluoro-1,3-benzothiazol-2-yl)ethyl]-4-morpholino-7H-pyrrolo[3,4-b]pyridin-5-one,
6-[2-(6-Methyl-2-quinolyl)ethyl]-4-(4-pyridyl)-7H-pyrrolo[3,4-b]pyridin-5-one, 6-[2-(4-Ethylthiazol-2-yl)ethyl]-4-(4-pyridyl)-7H-pyrrolo[3,4-b]pyridin-5-one,
6-[2-(4,5-Dimethylthiazol-2-yl)ethyl]-4-(4-pyridyl)-7H-pyrrolo[3,4-b]pyridin-5-one,
6-[2-(3-Methyl-2-pyridyl)ethyl]-4-(4-pyridyl)-7H-pyrrolo[3,4-b]pyridin-5-one,
6-[2-(4-Methyl-2-pyridyl)ethyl]-4-(4-pyridyl)-7H-pyrrolo[3,4-b]pyridin-5-one,
4-Methoxy-2-[2-(1-methyl-1H-benzoimidazol-2-yl)-ethyl]-7-(oxetan-3-ylamino)-2,3-dihydro-isoindol-1-one,
4-(3-Fluoro-pyridin-4-yl)-6-(2-quinolin-2-yl-ethyl)-6,7-dihydro-pyrrolo[3,4-b]pyridin-5-one,
6-(2-Imidazo[1,2-a]pyridin-2-yl-ethyl)-4-(1H-pyrazol-3-yl)-6,7-dihydro-pyrrolo[3,4-b]pyridin-5-one,
4-Furan-3-yl-6-(2-imidazo[1,2-a]pyridin-2-yl-ethyl)-6,7-dihydro-pyrrolo[3,4-b]pyridin-5-one,
6-[2-(1,5-Dimethyl-1H-benzoimidazol-2-yl)-ethyl]-4-morpholin-4-yl-6,7-dihydro-pyrrolo[3,4-b]pyridin-5-one,
6-[2-(1,5-Dimethyl-1H-benzoimidazol-2-yl)-ethyl]-4-(oxetan-3-ylamino)-6,7-dihydro-pyrrolo[3,4-b]pyridin-5-one,
6-[2-(1,3-Benzoxazol-2-yl)ethyl]-4-morpholino-7H-pyrrolo[3,4-b]pyridin-5-one,
6-[2-(1,3-Benzoxazol-2-yl)ethyl]-4-(4-pyridyl)-7H-pyrrolo[3,4-b]pyridin-5-one,
6-[2-(1,3-Benzothiazol-2-yl)ethyl]-4-(4-methylpiperazin-1-yl)-7H-pyrrolo[3,4-b]pyridin-5-one,
6-[2-(1,3-Benzothiazol-2-yl)ethyl]-4-(2,3-dihydrofuran-4-yl)-7H-pyrrolo[3,4-b]pyridin-5-one trifluoroacetate,
6-[2-(1,3-Benzothiazol-2-yl)ethyl]-4-(2-fluoro-4-pyridyl)-7H-pyrrolo[3,4-b]pyridin-5-one trifluoroacetate,
6-[2-(1,3-Benzothiazol-2-yl)ethyl]-4-(3-furyl)-7H-pyrrolo[3,4-b]pyridin-5-one trifluoroacetate,
6-(2-Imidazo[2,1-b]thiazol-6-ylethyl)-4-(4-pyridyl)-7H-pyrrolo[3,4-b]pyridin-5-one trifluoroacetate,
6-[2-(1,3-Benzothiazol-2-yl)ethyl]-4-(2-oxa-7-azaspiro[3.4]octan-7-yl)-7H-pyrrolo[3,4-b]pyridin-5-one,
6-(2-Imidazo[2,1-b]thiazol-6-ylethyl)-4-morpholino-7H-pyrrolo[3,4-b]pyridin-5-one,
4-(1,3,3a,4,6,6a-Hexahydrofuro[3,4-c]pyrrol-5-yl)-6-[2-(1,3-benzothiazol-2-yl)ethyl]-7H-pyrrolo[3,4-b]pyridin-5-one,
6-[2-(1,3-Benzothiazol-2-yl)ethyl]-4-(4-piperidyloxy)-7H-pyrrolo[3,4-b]pyridin-5-one trifluoroacetate,
2-[2-(1,3-Benzothiazol-2-yl)ethyl]-4-(1H-pyrazol-3-yl)isoindolin-1-one,
6-[2-(1,3-Benzothiazol-2-yl)ethyl]-4-(1H-pyrazol-3-yl)-7H-pyrrolo[3,4-b]pyridin-5-one,
6-[2-(1,3-Benzothiazol-2-yl)ethyl]-4-(3-pyridyl)-7H-pyrrolo[3,4-b]pyridin-5-one trifluoroacetate,
2-[2-(1,3-Benzothiazol-2-yl)ethyl]-4-(4-pyridyl)isoindolin-1-one,
6-[2-(1,3-Benzothiazol-2-yl)ethyl]-4-(2-methylpyrazol-3-yl)-7H-pyrrolo[3,4-b]pyridin-5-one trifluoroacetate,
2-[2-(1,3-Benzothiazol-2-yl)ethyl]-4-morpholino-isoindolin-1-one,
4-[3-(Difluoromethyl)pyrrolidin-1-yl]-6-[2-(2-quinolyl)ethyl]-7H-pyrrolo[3,4-b]pyridin-5-one,
4-[3-(Fluoromethyl)pyrrolidin-1-yl]-6-[2-(2-quinolyl-ethyl]-7H-pyrrolo[3,4-b]pyridin-5-one,
6-[2-(1,3-Benzothiazol-2-yl)ethyl]-4-thiazol-4-yl-7H-pyrrolo[3,4-b]pyridin-5-one,
4-Fluoro-7-(oxetan-3-ylamino)-2-[2-(2-quinolyl)ethyl]isoindolin-1-one,
4-fluoro-7-(3-pyridyl)-2-[2-(2-quinolyl)ethyl]isoindolin-1-one,
4-Fluoro-7-(2-methylpyrazol-3-yl)-2-[2-(2-quinolyl)ethyl]isoindolin-1-one,
4-Fluoro-7-morpholino-2-[2-(2-quinolyl)ethyl]isoindolin-1-one,
4-Fluoro-7-(4-methoxyphenyl)-2-[2-(2-quinolyl)ethyl]isoindolin-1-one,
4-Fluoro-7-(1H-pyrazol-4-yl)-2-[2-(2-quinolyl)ethyl]isoindolin-1-one trifluoroacetate,
4-Fluoro-7-pyrimidin-5-yl-2-[2-(2-quinolyl)ethyl]isoindolin-1-one trifluoroacetate,
4-Fluoro-7-(4-fluorophenyl)-2-[2-(2-quinolyl)ethyl]isoindolin-1-one,
6-[2-(1,3-Benzothiazol-2-yl)ethyl]-4-(2-methylpyrimidin-5-yl)-7H-pyrrolo[3,4-b]pyridin-5-one,
1-[5-oxo-6-[2-(2-quinolyl)ethyl]-7H-pyrrolo[3,4-b]pyridin-4-yl]azetidine-3-carboxylic acid
4-(oxetan-3-yloxy)-6-[2-(2-quinolyl)ethyl]-7H-pyrrolo[3,4-b]pyridin-5-one,
2-(2-Imidazo[1,2-a]pyridin-2-yl-ethyl)-7-methoxy-4-pyridin-4-yl-2,3-dihydro-isoindol-1-one trifluoroacetate,
2-[2-(1-Difluoromethyl-1H-benzoimidazol-2-yl)-ethyl]-7-morpholin-4-yl-2,3-dihydro-isoindol-1-one trifluoroacetate,
2-[2-(1-Difluoromethyl-1H-benzoimidazol-2-yl)-ethyl]-7-pyridin-4-yl-2,3-dihydro-isoindol-1-one trifluoroacetate,
4-Pyridin-4-yl-6-(2-quinolin-2-yl-ethyl)-5,6-dihydro-pyrrolo[3,4-b]pyridin-7-one
6-(2-Imidazo[1,2-a]pyridin-2-yl-ethyl)-4-pyridin-4-yl-5,6-dihydro-pyrrolo[3,4-b]pyridin-7-one
6-(2-Quinolin-2-yl-ethyl)-6,7-dihydro-pyrrolo[3,4-b]pyridin-5-one trifluoroacetate,
2-(2-Imidazo[1,2-a]pyridin-2-yl-ethyl)-7-methoxy-4-(1H-pyrazol-3-yl)-2,3-dihydro-isoindol-1-one,
2-[2-(1H-Imidazo[4,5-b]pyridin-2-yl)-ethyl]-7-pyridin-4-yl-2,3-dihydro-isoindol-1-one,
2-(2-Imidazo[1,2-a]pyridin-2-yl-ethyl)-7-methoxy-4-pyridin-3-yl-2,3-dihydro-isoindol-1-one trifluoroacetate,
2-(2-Imidazo[1,2-a]pyridin-2-yl-ethyl)-7-methoxy-4-(4-methoxy-phenyl)-2,3-dihydro-isoindol-1-one trifluoroacetate,
4-(4-Methoxy-phenyl)-6-(2-quinolin-2-yl-ethyl)-5,6-dihydro-pyrrolo[3,4-b]pyridin-7-one trifluoroacetate,
4-(2-Methyl-2H-pyrazol-3-yl)-6-(2-quinolin-2-yl-ethyl)-5,6-dihydro-pyrrolo[3,4-b]pyridin-7-one trifluoroacetate,
6-(2-Imidazo[1,2-a]pyridin-2-yl-ethyl)-4-pyridin-3-yl-5,6-dihydro-pyrrolo[3,4-b]pyridin-7-one trifluoroacetate,
6-(2-Imidazo[1,2-a]pyridin-2-yl-ethyl)-4-(4-methoxy-phenyl)-5,6-dihydro-pyrrolo[3,4-b]pyridin-7-one trifluoroacetate,
6-(2-Imidazo[1,2-a]pyridin-2-yl-ethyl)-4-(2-methyl-2H-pyrazol-3-yl)-5,6-dihydro-pyrrolo[3,4-b]pyridin-7-one trifluoroacetate,
4-Pyridin-3-yl-6-(2-quinolin-2-yl-ethyl)-5,6-dihydro-pyrrolo[3,4-b]pyridin-7-one trifluoroacetate,
2-(2-Imidazo[1,2-a]pyridin-2-yl-ethyl)-7-methoxy-4-(2-methyl-2H-pyrazol-3-yl)-2,3-dihydro-isoindol-1-one trifluoroacetate,
4-(4-Pyridyl)-6-(2-quinoxalin-2-ylethyl)-7H-pyrrolo[3,4-b]pyridin-5-one,
6-[2-(6-Methyl-2-pyridyl)ethyl]-4-morpholino-7H-pyrrolo[3,4-b]pyridin-5-one,
4-Pyrimidin-5-yl-6-[2-(2-quinolyl)ethyl]-5H-pyrrolo[3,4-b]pyridin-7-one
6-[2-(5-Methyl-2-pyridyl)ethyl]-4-morpholino-7H-pyrrolo[3,4-b]pyridin-5-one, hydrochloride
6-[2-(1-Methylimidazol-2-yl)ethyl]-4-(4-pyridyl)-7H-pyrrolo[3,4-b]pyridin-5-one trifluoroacetate, 6-[2-(6-Methyl-2-pyridyl)ethyl]-4-(4-pyridyl)-7H-pyrrolo[3,4-b]pyridin-5-one trifluoroacetate,
4-(4-Pyridyl)-6-[2-(2-pyridyl)ethyl]-7H-pyrrolo[3,4-b]pyridin-5-one trifluoroacetate,
4-(4-Pyridyl)-6-(2-thieno[3,2-b]pyridin-5-ylethyl)-7H-pyrrolo[3,4-b]pyridin-5-one,
6-[2-(3,5-Dimethyl-2-pyridyl)ethyl]-4-(4-pyridyl)-7H-pyrrolo[3,4-b]pyridin-5-one,
6-[2-(5,6-Dimethyl-2-pyridyl)ethyl]-4-(4-pyridyl)-7H-pyrrolo[3,4-b]pyridin-5-one trifluoroacetate,
2-[2-[4-(3-Pyridyl)-5,7-dihydropyrrolo[3,4-b]pyridin-6-yl]ethyl]imidazo[1,2-a]pyridine trifluoroacetate,
6-[2-(5-Methyl-2-pyridyl)ethyl]-4-(3-pyridyl)-7H-pyrrolo[3,4-b]pyridin-5-one trifluoroacetate,
2-[2-[4-(2-Methylpyrazol-3-yl)-5,7-dihydropyrrolo[3,4-b]pyridin-6-yl]ethyl]imidazo[1,2-a]pyridine trifluoroacetate,
2-[2-[4-(4-Methoxyphenyl)-5,7-dihydropyrrolo[3,4-b]pyridin-6-yl]ethyl]imidazo[1,2-a]pyridine trifluoroacetate,
4-(1,1-Dioxo-1,4-thiazinan-4-yl)-6-[2-(5-methyl-2-pyridyl)ethyl]-7H-pyrrolo[3,4-b]pyridin-5-one trifluoroacetate,
6-[2-(5-Methyl-2-pyridyl)ethyl]-4-pyrimidin-5-yl-7H-pyrrolo[3,4-b]pyridin-5-one trifluoroacetate,
6-[2-(5-Methyl-2-pyridyl)ethyl]-4-(4-pyridyl)-7H-pyrrolo[3,4-b]pyridin-5-one trifluoroacetate,
7-Morpholino-2-(2-quinoxalin-2-ylethyl)isoindolin-1-one,
6-[2-(6-Methoxy-2-pyridyl)ethyl]-4-morpholino-7H-pyrrolo[3,4-b]pyridin-5-one,
4-(4-Pyridyl)-6-[2-[4-(4-pyridyl)-2-quinolyl]ethyl]-7H-pyrrolo[3,4-b]pyridin-5-one,
4-(2,2,3,3,5,5,6,6-Octadeuteriomorpholin-4-yl)-6-[2-(2-quinolyl)ethyl]-7H-pyrrolo[3,4-b]pyridin-5-one,
4-Morpholino-6-[2-(5-phenyl-2-pyridyl)ethyl]-7H-pyrrolo[3,4-b]pyridin-5-one,
6-[2-(1-Methylimidazol-4-yl)ethyl]-4-(4-pyridyl)-7H-pyrrolo[3,4-b]pyridin-5-one trifluoroacetate,
6-[2-(5-Phenyl-2-pyridyl)ethyl]-4-(4-pyridyl)-7H-pyrrolo[3,4-b]pyridin-5-one trifluoroacetate,
6-[2-(3,5-Dimethyl-2-pyridyl)ethyl]-4-morpholino-7H-pyrrolo[3,4-b]pyridin-5-one,
6-[2-(5-Methyl-2-pyridyl)ethyl]-4-(oxetan-3-ylamino)-7H-pyrrolo[3,4-b]pyridin-5-one,
4-Morpholino-6-(2-thieno[3,2-b]pyridin-5-ylethyl)-7H-pyrrolo[3,4-b]pyridin-5-one,
6-[2-(6-Fluoroimidazo[1,2-a]pyridin-2-yl)ethyl]-4-morpholino-7H-pyrrolo[3,4-b]pyridin-5-one, hydrochloride
6-[2-(6-Fluoroimidazo[1,2-a]pyridin-2-yl)ethyl]-4-morpholino-7H-pyrrolo[3,4-b]pyridin-5-one trifluoroacetate,
6-[2-(6-Fluoroimidazo[1,2-a]pyridin-2-yl)ethyl]-4-(4-pyridyl)-7H-pyrrolo[3,4-b]pyridin-5-one trifluoroacetate,
4-Morpholino-6-(2-quinoxalin-2-ylethyl)-7H-pyrrolo[3,4-b]pyridin-5-one trifluoroacetate,
6-[2-(8-Methylimidazo[1,2-a]pyridin-2-yl)ethyl]-4-(4-pyridyl)-7H-pyrrolo[3,4-b]pyridin-5-one trifluoroacetate,
6-[2-(5-Fluoro-2-pyridyl)ethyl]-4-(4-pyridyl)-7H-pyrrolo[3,4-b]pyridin-5-one trifluoroacetate,
6-[2-(5-Fluoro-2-pyridyl)ethyl]-4-morpholino-7H-pyrrolo[3,4-b]pyridin-5-one trifluoroacetate,
6-[2-(5-Ethyl-2-pyridyl)ethyl]-4-morpholino-7H-pyrrolo[3,4-b]pyridin-5-one trifluoroacetate,
4-Morpholino-6-[2-[5-(trifluoromethyl)-2-pyridyl]ethyl]-7H-pyrrolo[3,4-b]pyridin-5-one trifluoroacetate,
6-[2-(5-Ethyl-2-pyridyl)ethyl]-4-(4-pyridyl)-7H-pyrrolo[3,4-b]pyridin-5-one trifluoroacetate,
6-[2-(5-Chloro-2-pyridyl)ethyl]-4-(4-pyridyl)-7H-pyrrolo[3,4-b]pyridin-5-one trifluoroacetate,
6-[2-(6-Methoxy-2-pyridyl)ethyl]-4-(3-pyridyl)-7H-pyrrolo[3,4-b]pyridin-5-one trifluoroacetate,
6-[2-(5,6-Dimethyl-2-pyridyl)ethyl]-4-(oxetan-3-ylamino)-7H-pyrrolo[3,4-b]pyridin-5-one trifluoroacetate,
6-[2-(5-Chloro-2-pyridyl)ethyl]-4-morpholino-7H-pyrrolo[3,4-b]pyridin-5-one,
4-(4-Pyridyl)-6-[2-[5-(trifluoromethyl)-2-pyridyl]ethyl]-7H-pyrrolo[3,4-b]pyridin-5-one trifluoroacetate,
6-[2-(4,5-Dimethyl-2-pyridyl)ethyl]-4-(4-pyridyl)-7H-pyrrolo[3,4-b]pyridin-5-one trifluoroacetate,
4-Fluoro-2-(2-imidazo[1,2-a]pyridin-2-ylethyl)-7-(oxetan-3-ylamino)isoindolin-1-one trifluoroacetate,
6-[2-(6-Methoxy-2-pyridyl)ethyl]-4-(oxetan-3-ylamino)-7H-pyrrolo[3,4-b]pyridin-5-one,
2,3,7,7-Tetradeuterio-6-[1,1-dideuterio-2-(3,4,5,6,7,8-hexadeuterio-2-quinolyl)ethyl]-4-(2,2,3,3,5,5,6,6-octadeuteriomorpholin-4-yl)pyrrolo[3,4-b]pyridin-5-one,
6-(2-Imidazo[1,2-a]pyridin-2-yl-1-methyl-ethyl)-4-morpholino-7H-pyrrolo[3,4-b]pyridin-5-one trifluoroacetate,
6-[2-(1,5-Naphthyridin-2-yl)ethyl]-4-(4-pyridyl)-7H-pyrrolo[3,4-b]pyridin-5-one,
2,3,7,7-Tetradeuterio-6-[2,2-dideuterio-2-(3,4,5,6,7,8-hexadeuterio-2-quinolyl)ethyl]-4-morpholino-pyrrolo[3,4-b]pyridin-5-one,
4-Morpholino-6-[2-(1,5-naphthyridin-2-yl)ethyl]-7H-pyrrolo[3,4-b]pyridin-5-one,
6-[2-(3-Methoxy-2-pyridyl)ethyl]-4-[2-(3-methoxy-2-pyridyl)ethylamino]-7H-pyrrolo[3,4-b]pyridin-5-one,
6-[2-(4-Ethylthiazol-2-yl)ethyl]-4-morpholino-7H-pyrrolo[3,4-b]pyridin-5-one,
6-[2-(4-Cyclopropylthiazol-2-yl)ethyl]-4-(4-pyridyl)-7H-pyrrolo[3,4-b]pyridin-5-one,
6-[2-(4-Cyclopropylthiazol-2-yl)ethyl]-4-morpholino-7H-pyrrolo[3,4-b]pyridin-5-one,
6-[2-(4,5-Dimethylthiazol-2-yl)ethyl]-4-morpholino-7H-pyrrolo[3,4-b]pyridin-5-one,
6-[2-(4,5-Dimethyl-2-pyridyl)ethyl]-4-morpholino-7H-pyrrolo[3,4-b]pyridin-5-one,
6-[2-(4-Methyl-2-pyridyl)ethyl]-4-morpholino-7H-pyrrolo[3,4-b]pyridin-5-one,
6-[2-(3-Methyl-2-pyridyl)ethyl]-4-morpholino-7H-pyrrolo[3,4-b]pyridin-5-one,
6-(2-Imidazo[1,2-a]pyridin-2-ylethyl)-4-(3-thienyl)-7H-pyrrolo[3,4-b]pyridin-5-one,
6-(2-Imidazo[1,2-a]pyridin-2-ylethyl)-4-(2-methyl-3-furyl)-7H-pyrrolo[3,4-b]pyridin-5-one,
6-(2-Imidazo[1,2-a]pyridin-2-ylethyl)-4-(5-methyl-2-furyl)-7H-pyrrolo[3,4-b]pyridin-5-one,
6-[2-(6-Fluoroimidazo[1,2-a]pyridin-2-yl)ethyl]-4-(3-furyl)-7H-pyrrolo[3,4-b]pyridin-5-one,
6-[2-(1,3-Benzothiazol-2-yl)ethyl]-4-(4,4-difluoro-1-piperidyl)-7H-pyrrolo[3,4-b]pyridin-5-one trifluoroacetate,
4-Methoxy-6-(2-quinolin-2-yl-ethyl)-6,7-dihydro-pyrrolo[3,4-b]pyridin-5-one,
4-(2-Dimethylamino-ethoxy)-7-pyridin-4-yl-2-(2-quinolin-2-yl-ethyl)-2,3-dihydro-isoindol-1-one,
4-(4-Hydroxy-piperidin-1-yl)-6-(2-quinolin-2-yl-ethyl)-6,7-dihydro-pyrrolo[3,4-b]pyridin-5-one trifluoroacetate,
1-[3-oxo-2-(2-quinolin-2-yl-ethyl)-2,3-dihydro-1H-isoindol-4-ylmethyl]-azetidine-3-carboxylic acid methyl ester
4-(2-Fluoro-ethoxy)-7-pyridin-4-yl-2-(2-quinolin-2-yl-ethyl)-isoindole-1,3-dione
4-(2-Fluoro-ethoxy)-7-pyridin-4-yl-2-(2-quinolin-2-yl-ethyl)-2,3-dihydro-isoindol-1-one,
4-(3-Fluoro-pyridin-4-yl)-6-(2-imidazo[1,2-a]pyridin-2-yl-ethyl)-6,7-dihydro-pyrrolo[3,4-b]pyridin-5-one, 6-[2-(1,5-Dimethyl-1H-benzoimidazol-2-yl)-ethyl]-4-pyrimidin-5-yl-6,7-dihydro-pyrrolo[3,4-b]pyridin-5-one,
6-[2-(1,5-Dimethyl-1H-benzoimidazol-2-yl)-ethyl]-4-pyridin-4-yl-6,7-dihydro-pyrrolo[3,4-b]pyridin-5-one,
2-(2-Imidazo[1,2-a]pyridin-2-ylethyl)-4-thiazol-4-yl-isoindolin-1-one,
6-[2-(1,3-Benzothiazol-2-yl)ethyl]-4-(1H-pyrazol-4-yl)-7H-pyrrolo[3,4-b]pyridin-5-one trifluoroacetate,
6-[2-(1,5-Dimethylbenzimidazol-2-yl)ethyl]-4-(3-pyridyl)-7H-pyrrolo[3,4-b]pyridin-5-one,
6-[2-(1,5-Dimethylbenzimidazol-2-yl)ethyl]-4-(2-methylpyrazol-3-yl)-7H-pyrrolo[3,4-b]pyridin-5-one
6-[2-(1,3-Benzothiazol-2-yl)ethyl]-4-(4-methoxyphenyl)-7H-pyrrolo[3,4-b]pyridin-5-one trifluoroacetate,
6-[2-(1,3-Benzothiazol-2-yl)ethyl]-4-(4-fluorophenyl)-7H-pyrrolo[3,4-b]pyridin-5-one trifluoroacetate,
6-[2-(1,3-Benzothiazol-2-yl)ethyl]-4-(3,6-dihydro-2H-pyran-4-yl)-7H-pyrrolo[3,4-b]pyridin-5-one
6-[2-(1,3-Benzothiazol-2-yl)ethyl]-4-pyrimidin-5-yl-7H-pyrrolo[3,4-b]pyridin-5-one,
4-(Fluoromethoxy)-2-(2-imidazo[1,2-a]pyridin-2-ylethyl)-7-pyrimidin-5-yl-isoindoline-1,3-dione
4-(6-Fluoro-1,4-diazepan-1-yl)-6-[2-(2-quinolyl)ethyl]-7H-pyrrolo[3,4-b]pyridin-5-one,
4-(4-Pyridyl)-6-[2-(4-quinolyl)ethyl]-7H-pyrrolo[3,4-b]pyridin-5-one trifluoroacetate,
4-Morpholino-6-[2-(4-quinolyl)ethyl]-7H-pyrrolo[3,4-b]pyridin-5-one,
7-(4-Fluorophenyl)-2-(2-thieno[3,2-b]pyridin-5-ylethyl)isoindolin-1-one,
7-Pyrimidin-5-yl-2-(2-thieno[3,2-b]pyridin-5-ylethyl)isoindolin-1-one,
7-(4-Methoxyphenyl)-2-(2-thieno[3,2-b]pyridin-5-ylethyl)isoindolin-1-one,
7-(1H-Pyrazol-5-yl)-2-(2-thieno[3,2-b]pyridin-5-ylethyl)isoindolin-1-one,
7-Morpholino-2-(2-thieno[3,2-b]pyridin-5-ylethyl)isoindolin-1-one,
7-(1H-Pyrazol-4-yl)-2-(2-thieno[3,2-b]pyridin-5-ylethyl)isoindolin-1-one,
2-(2-Imidazo[1,2-a]pyridin-2-yl-ethyl)-7-methoxy-4-pyrimidin-5-yl-2,3-dihydro-isoindol-1-one trifluoroacetate,
4-Morpholino-6-[2-(2-pyridyl)ethyl]-7H-pyrrolo[3,4-b]pyridin-5-one,
6-[2-(5-Methyl-2-pyridyl)ethyl]-4-morpholino-7H-pyrrolo[3,4-b]pyridin-5-one,
6-[2-(7-Ethylimidazo[1,2-a]pyridin-2-yl)ethyl]-4-(4-pyridyl)-7H-pyrrolo[3,4-b]pyridin-5-one,
6-[2-(6-Methoxy-2-pyridyl)ethyl]-4-(4-pyridyl)-7H-pyrrolo[3,4-b]pyridin-5-one,
6-[2-(5,6-Dimethyl-2-pyridyl)ethyl]-4-morpholino-7H-pyrrolo[3,4-b]pyridin-5-one, and
6-[2-(7-Ethylimidazo[1,2-a]pyridin-2-yl)ethyl]-4-morpholino-7H-pyrrolo[3,4-b]pyridin-5-one.

The compounds of the invention of the general formula I and the starting materials used to prepare them can be prepared in analogy to known processes of organic chemistry as are described in standard works of organic chemistry, e.g. Houben-Weyl, "Methoden der Organischen Chemie", Thieme-Verlag, Stuttgart, Jerry March "Advanced Organic Chemistry", 5$^{th}$ edition, Wiley & Sons and the literature cited therein, and R. Larock, "Comprehensive Organic Transformations", 2$^{nd}$ edition, Weinheim, 1999 and the literature cited therein. The compounds of the invention of the general formula I are advantageously prepared by the methods described below and/or in the experimental section.

Compounds of the formula I can be prepared e.g. by reacting a compound of the formula II

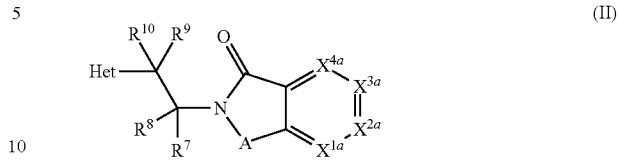

wherein
X$^{1a}$ is N or C—R$^{1a}$
X$^{2a}$ is N or C—R$^{2a}$
X$^{3a}$ is N or C—R$^{3a}$
X$^{4a}$ is N or C—R$^{4a}$
provided that 0, 1 or 2 of the moieties X$^{1a}$, X$^{2a}$; X$^{3a}$ or X$^{4a}$ is N;
Het, A, R$^7$, R$^8$, R$^9$ and R$^{10}$ are as defined for formulae I, I-A, I-B or I-C;
R$^{1a}$, R$^{4a}$ independently of each other, are selected from the group consisting of hydrogen, halogen, C$_1$-C$_4$-alkyl, trimethylsilyl, C$_1$-C$_4$-alkylsulfanyl, C$_1$-C$_4$-alkoxy-C$_1$-C$_4$-alkyl, C$_1$-C$_4$-alkoxy, C$_1$-C$_4$-alkoxy-C$_1$-C$_4$-alkoxy, C$_1$-C$_4$-alkylsulfanyl-C$_1$-C$_4$-alkoxy, C$_2$-C$_4$-alkenyloxy, C$_1$-C$_4$-fluoroalkyl, C$_1$-C$_4$-fluoroalkoxy, CN, NR$^{x1}$R$^{x2}$, NR$^{x1}$R$^{x2}$—C$_1$-C$_4$-alkoxy;
R$^{2a}$, R$^{3a}$ independently of each other, are selected from the group consisting of hydrogen, halogen, C$_1$-C$_4$-alkyl, trimethylsilyl, C$_1$-C$_4$-alkoxy-C$_1$-C$_4$-alkyl, C$_1$-C$_4$-alkoxy, C$_1$-C$_4$-alkoxy-C$_1$-C$_4$-alkoxy, C$_2$-C$_4$-alkenyloxy, C$_1$-C$_4$-fluoroalkyl, C$_1$-C$_4$-fluoroalkoxy, CN and NR$^{x1}$R$^{x2}$;
provided that 1 or 2 of the radicals R$^{1a}$, R$^{2a}$, R$^{3a}$ and R$^{4a}$, in particular exactly one of these radicals is bromine or iodine, while the others are different from bromine or iodine;
with a compound of formula III,

M-Y-Cyc (III)

where Y and Cyc are as defined herein and wherein
M is a Li, B(OR$^{B1}$)(OR$^{B2}$) radical or an Sn(R$^{Sn}$)$_3$ radical, where R$^{B1}$ and R$^{B2}$ are, independently of each other, hydrogen or C$_1$-C$_4$-alkyl or R$^{B1}$ and R$^{B2}$ together form a C$_2$-C$_6$-alkandiyl moietyl, e.g. ethan-1,2-diyl, propan-1,3-diyl or 1,1,2,2-tetramethylethan-1,2-diyl, and wherein R$^{s11}$ is C$_1$-C$_6$-alkyl or C$_3$-C$_6$-cycloalkyl or phenyl.

Amongst the compounds of formula III, where Y is a chemical bond, particular preference is given to the compounds of formula IIIa and, if R$^{B1}$ and R$^{B2}$ are hydrogen, the trimers thereof.

The reaction of the compound II with the compound III can be performed by analogy to known coupling reactions in the presence of suitable transition metal catalysts, in particular palladium catalysts. Typical reactions conditions are those of Stille coupling (see e.g. Stille et al. Angew. Chem. Int. Ed. Engl. 1986, 25, 508; J. Eluguero et al.; Synthesis 1997, 5, 563-566) or Suzuki coupling (see e.g. A. Suzuki et al, Chem. Rev. 1995, 95, 2457-2483, N. Zhe et al.; J. Med. Chem. 2005, 48 (5), 1569-1609; Young et al.; J. Med. Chem. 2004, 47 (6), 1547-1552; C. Slee et al.; Bioorg. Med. Chem. Lett. 2001, 9, 3243-3253).

Compounds of the formula I can also be prepared e.g. by reacting a compound of the formula II

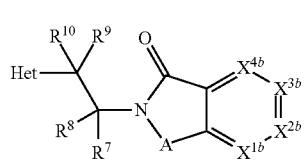
(IIa)

wherein
$X^{1b}$ is N or C—$R^{1b}$
$X^{2b}$ is N or C—$R^{2b}$
$X^{3b}$ is N or C—$R^{3b}$
$X^{4b}$ is N or C—$R^{4b}$
provided that 0, 1 or 2 of the moieties $X^{1b}$, $X^{2b}$, $X^{3b}$, or $X^{4b}$ is N;
Het, A, $R^7$, $R^8$, $R^9$ and $R^{10}$ are as defined for formulae I, I-A, I-B or I-C;
$R^{1b}$, $R^{4b}$ independently of each other, are selected from the group consisting of hydrogen, $C_1$-$C_4$-alkyl, trimethylsilyl, $C_1$-$C_4$-alkylsulfanyl, $C_1$-$C_4$-alkoxy-$C_1$-$C_4$-alkyl, $C_1$-$C_4$-alkoxy, $C_1$-$C_4$-alkoxy-$C_1$-$C_4$-alkoxy, $C_1$-$C_4$-alkylsulfanyl-$C_1$-$C_4$-alkoxy, $C_2$-$C_4$-alkenyloxy, $C_1$-$C_4$-fluoroalkyl, $C_1$-$C_4$-fluoroalkoxy, CN, $NR^{x1}R^{x2}$, $NR^{x1}R^{x2}$—$C_1$-$C_4$-alkoxy or a moiety M;
$R^{2b}$, $R^{3b}$ independently of each other, are selected from the group consisting of hydrogen, $C_1$-$C_4$-alkyl, trimethylsilyl, $C_1$-$C_4$-alkoxy-$C_1$-$C_4$-alkyl, $C_1$-$C_4$-alkoxy, $C_1$-$C_4$-alkoxy-$C_1$-$C_4$-alkoxy, $C_2$-$C_4$-alkenyloxy, $C_1$-$C_4$-fluoroalkyl, $C_1$-$C_4$-fluoroalkoxy, CN and $NR^{x1}R^{x2}$, or a moiety M;
provided that 1 or 2 of the radicals $R^{1b}$, $R^{2b}$, $R^{3b}$, and $R^{4b}$, in particular exactly one of these radicals is moiety M, while the others are different from M, where M is as defined for formula III and in particular a B(OR$^{B1}$)(OR$^{B2}$) radical;
with a compound of formula IIIb, Hal-Y-Cyc (IIIb)

where Y and Cyc are as defined herein and wherein Hal is bromine or iodine.

The reaction of the compound IIa with the compound IIIa can be performed by analogy tot the reaction of compound II with compound III.

The compounds II, IIa, III, IIIa and IIIb are known or can be prepared by standard methods of organic chemistry.

Compounds of the formula I, where Y-Cyc is a N-bound radical can be obtained by a coupling reaction between the compound II and the corresponding amine in the presence of a palladium catalyst in terms of a Buchwald-Hartwig reaction. Suitable palladium catalyst are for example tris-(dibenzylideneacetone)dipalladium(0) (Pd$_2$(dba)$_3$), [1,1-bis(diphenylphosphino)ferrocene]dichloropalladium(II) (PdCl$_2$(dppf)) or palladium acetate (Pd(OAc)$_2$). The reaction is usually carried out in the presence of a tri(substituted) phosphine, e.g. a triarylphosphine such as triphenylphosphine, tritolylphosphine or 2,2'-bis(diphenylphosphino)-1,1'-binaphthalene (BINAP), tri(cyclo)alkylphosphine such as tris-n-butylphosphine, tris(tert-butyl)phosphine or tris(cyclohexylphosphine), or dicyclohexyl-(2',4',6'-tri-iso-propyl-biphenyl-2-yl)-phosphane (X-Phos). Usually, the reaction is performed in the presence of a base such as an alkaline alkoxide, earth alkine alkoxide, alkaline carbonate or earth alkaline carbonate such as or sodium tert-butoxide or cesium carbonate.

E.g. compounds of the formula I (or likewise the compounds II), where A is $CR^5R^6$ can be prepared according to the following reaction schemes 1 and 2:

Scheme 1:

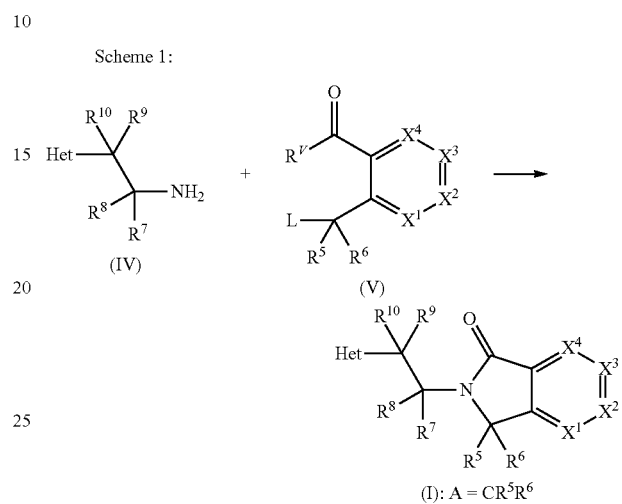

Scheme 2:

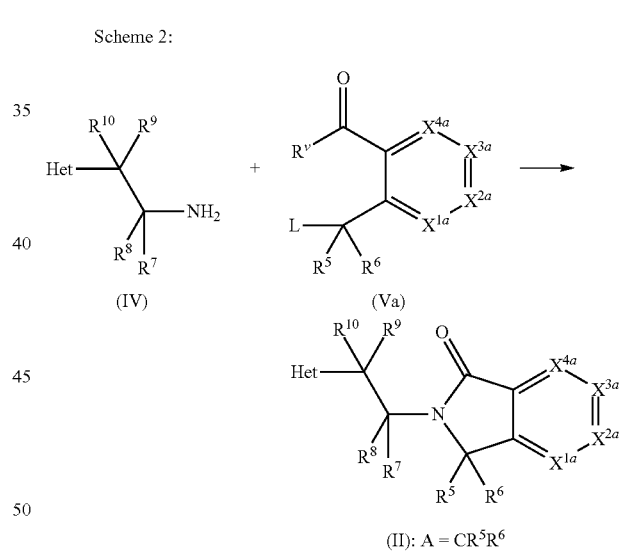

In schemes 1 and 2, $X^1$, $X^2$, $X^3$, $X^4$, $X^{1a}$, $X^{2a}$, $X^{3a}$, $X^{4a}$, $R^5$, $R^6$, $R^7$, $R^8$, $R^9$, $R^{10}$ and Het are as defined above, $R^V$ is $C_1$-$C_4$-alkoxy, e.g. methoxy or ethoxy, and L is a suitable leaving group, e.g. chlorine, bromine, alkylsulfonyloxy such as methan-sulfonyloxy or arylsulfonyloxy such as phenylsulfonyloxy or p-tolylsulfonyloxy. L may also be OH or $C_1$-$C_4$-alkoxy, if $CR^5R^6$ represents a carbonyl group.

Compounds of the formula I (or likewise the compounds II), where A is O can be prepared according to the following reaction schemes 3 and 4 by reacting a compound of the formulae VII or VIIa, respectively, with a suitable hydroxylamine compound VI, to give an amide compound VIII and VIIIa, respectively, and subsequent cyclisation (J. Med. Chem., 51(12), 3357-9 (2008).

Scheme 3:

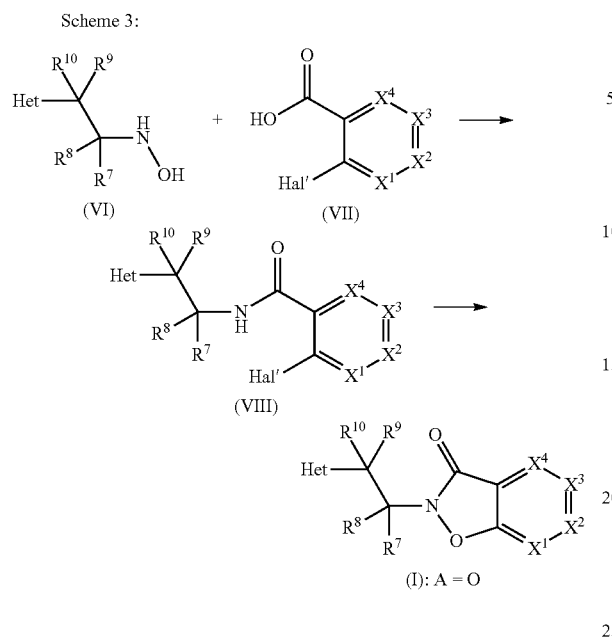

(I): A = O

Scheme 4:

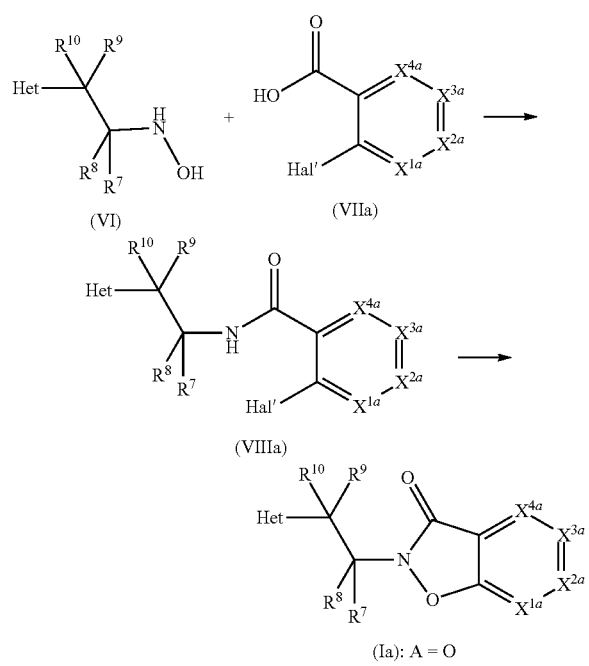

(Ia): A = O

In schemes 3 and 4, $X^1$, $X^2$, $X^3$, $X^4$, $X^{1a}$, $X^{2a}$, $X^{3a}$, $X^{4a}$, $R^7$, $R^8$, $R^9$, $R^{10}$ and Het are as defined above, and Hal' is a suitable leaving group, e.g. fluorine. The reaction of the carboxylic acid VII and VIIa, respectively, with a hydroxylamine compound VI is usually carried out in the presence of an activating agent of carboxylic acids, e.g. carbodiimides such as dicyclohexylcarbodiimide or diisopropylcarbodiimide or triazoles such as 1-hydroxybenzotriazole, 1-hydroxy-7-aza-benzotriazole, benzotriazol-1-yl-oxytripyrrolidino-phosphonium hexafluorophosphate or benzotriazole-1-yl-oxy-tris-(dimethylamino)-phosphonium hexafluorophosphate.

Compounds of the formula I (or likewise the compounds II), where A is $NR^{5a}$ can be prepared according to the following reaction schemes 5 and 6 by successively reacting compounds of the formulae X or Xa, respectively with a suitable hydroxy compound IX, in terms of a Mitsunobu reaction.

Scheme 5:

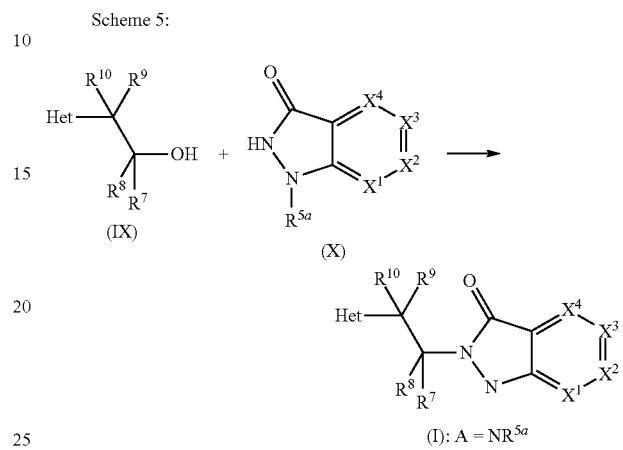

(I): A = $NR^{5a}$

Scheme 6:

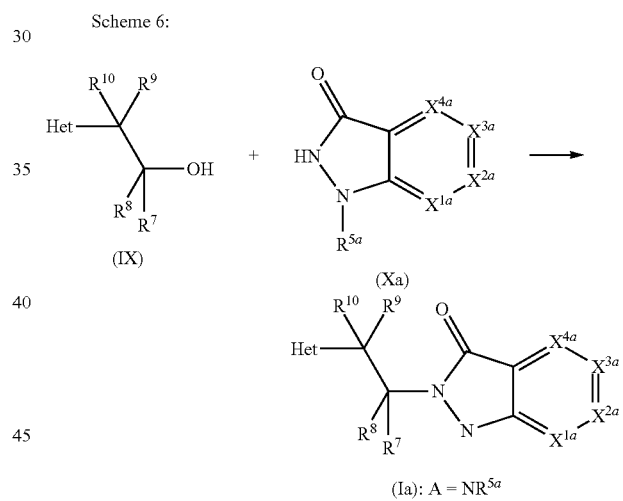

(Ia): A = $NR^{5a}$

In schemes 5 and 6, $X^1$, $X^2$, $X^3$, $X^4$, $X^{1a}$, $X^{2a}$, $X^{3a}$, $X^{4a}$, $R^{5a}$, $R^6$, $R^7$, $R^8$, $R^9$, $R^{10}$, and Het are as defined above. Compounds of the formulae X and Xa, respectively, can be prepared in analogy to known methods, e.g. as described in J. Heterocycl. Chem. 26, 257-64 (1989), WO 2004/037814 or WO 2006/056873

Apart from that, compounds of the formula I and likewise compounds of the formula II, where A is $CF_2$ can be prepared by successively reacting compounds of the formulae I and II, where A is C=O with a suitable sulfurizing agent, such as Lawenson's reagent or $P_2S_5$, obtain a compound of the formula I and then reacting the obtained thio-compound with a suitable fluorinating agent, e.g. HF or HF adduct of tetraalkyl-amonium fluoride in the presence of N-bromosuccinimid [Tet. Lett. 35(23), 3983-4 (1994)].

The N-oxides of compound I may be prepared from the compounds of formula I according to conventional oxidation methods, for example by treating said compounds with an organic peracid; such as metachloroperbenzoic acid or 3-chloroperbenzoic acid [Journal of Medicinal Chemistry 38(11), 1892-1903 (1995), WO 03/64572]; or with inorganic oxidizing agents; such as hydrogen peroxide [cf. Journal of Heterocyclic Chemistry 18 (7), 1305-1308 (1981)] or oxone [cf. Journal of the American Chemical Society 123(25), 5962-5973 (2001)]. The oxidation may lead to pure mono-N-oxides or to a mixture of different N-oxides, which can be separated by conventional methods; such as chromatography.

Compounds of the formula IIa can be prepared from compounds of the formula II by suitable metal-halogen exchange reactions.

The compounds of the formulae III, IV, VI and VIII as well as the compounds of the formulae V, Va, VII, VIIa, X and Xa are well known in the art or can be prepared by anology to well established reactions of organic synthetic chemistry or by analogy to the methods as described in standard works of organic chemistry, e.g. Houben-Weyl, "Methoden der Organischen Chemie", Thieme-Verlag, Stuttgart, Jerry March "Advanced Organic Chemistry", $5^{th}$ edition, Wiley & Sons and the literature cited therein, and R. Larock, "Comprehensive Organic Transformations", $2^{11d}$ edition, Weinheim, 1999 and the literature cited therein.

The reactions are usually performed in an organic solvent, including aprotic organic solvent, e.g. substituted amides, lactames and ureas; such as dimethylformamide, dimethylacetamide, N-methylpyrrolidone, tetramethyl urea, cyclic ethers; such as dioxane, tetrahydrofurane, halogenated hydrocarbons; such as dichloromethane, and mixtures thereof as well as mixtures thereof with $C_1$-$C_6$-alkanols and/or water.

The reactions described above will be usually performed at temperatures ranging from −10° C. to 100° C., depending on the reactivity of the used compounds.

The reaction mixtures are worked up in a conventional way, e.g. by mixing with water, separating the phases and, where appropriate, purifying the crude products by chromatography. The intermediates and final products in some cases result in the form of colorless or pale brownish, viscous oils which are freed of volatiles or purified under reduced pressure and at moderately elevated temperature. If the intermediates and final products are obtained as solids, the purification can also take place by recrystallization or digestion.

Due to their capability of inhibiting PDE10A at low concentrations, the compounds of the formula I, their N-oxides, their hydrates, their tautomers and their prodrugs and the pharmaceutically acceptable salts thereof, are particularly suitable for treating disorders or conditions, which can be treated by inhibition of phosphodiesterase type 10A. The terms "treating" and "treatment" in terms of the present invention have to be understood to include both curative treatment of the cause of a disease or disorder, the treatment of the symptoms associated with a disease or disorder, i.e. controlling the disease or disorder or ameliorating the conditions or symptoms associated with a disease or disorder, and prophylactic treatment, i.e. a treatment for reducing the risk of a disease or disorder.

Neurological and psychiatric disorders or conditions which can be treated by inhibition of PDE10A, including curative treatment, control or amelioration and prophylaxis, include CNS disorders, in particular schizophrenia, depression, bipolar disorders, cognitive dysfunctions associated with schizophrenia, cognitive dysfunctions associated with Alzheimer's disease, Huntington's disease (Huntington chorea), anxiety and substance-related disorders, especially substance use disorder, substance tolerance conditions associated with substance withdrawal. Disorders or conditions which can be treated by inhibition of PDE10A, including curative treatment, control or amelioration and prophylaxis, also include treatment of diet induced obesity.

Thus, the invention relates to the use of compounds of formula I, their N-oxides, their hydrates, their tautomers and their prodrugs and the pharmaceutically acceptable salts thereof, for treatment of disorders or conditions, which can be treated by inhibition of phosphodiesterase type 10A, i.e. the invention relates to the use of such compounds for curative treatment of such a disease or disorder, controlling such a disease or disorder, ameliorating the symptoms associated with such a disease or disorder and reducing the risk for such a disease or disorder.

The present invention also relates to a method for the treatment of a medical disorder, selected from neurological and psychiatric disorders which can be treated by inhibition of phosphodiesterase type 10A, said method comprising administering an effective amount of at least one compound, selected from the group of compounds of formula I, their N-oxides, their hydrates, their tautomers, their prodrugs and the pharmaceutically acceptable salts thereof, to a mammal in need thereof.

The present invention in particular relates to:
a method for treating, controlling, ameliorating or reducing the risk of schizophrenia in a mammalian;
a method for treating, controlling, ameliorating or reducing the risk of cognitive disturbances associated with schizophrenia in a mammalian;
a method for treating, controlling, ameliorating or reducing the risk of depression in a mammalian;
a method for treating, controlling, ameliorating or reducing the risk of bipolar disorders in a mammalian;
a method for treating or ameliorating the symptoms associated with substance use disorders in a mammalian;
a method for treating or ameliorating the symptoms associated with diet-induced obesity in a mammalian;
a method for treating, controlling, ameliorating or reducing the risk of cognitive disturbances associated with Alzheimer's disease in a mammalian;
a method for treating, controlling, ameliorating or reducing the risk of behavioral symptoms in Alzheimer's disease;
a method for treating, controlling, ameliorating or reducing the risk of anxiety in a mammalian;
a method for treating, controlling, ameliorating or reducing the risk of Huntington's disease in a mammalian;
which methods comprising administering an effective amount of at least one compound, selected from the group of compounds of formula I, their N-oxides, their hydrates, their tautomers, their prodrugs and the pharmaceutically acceptable salts thereof, to a mammal in need thereof.

The subject treated in the present methods is generally a mammal, preferably a human being, male or female, in whom inhibition of PDE10A is desired. The terms "effective amount" and "therapeutically effective amount" mean the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes, wherein there may be a slowing, interrupting, arresting, controlling, or stopping of the progression of the disorders described herein, but does not necessarily indicate a total elimination of all disorder symptoms, as well as the prophylactic therapy of the mentioned conditions, particularly in a patient who is predisposed to such disease or disorder. The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

A preferred embodiment of the present invention provides a method for treating schizophrenia, comprising: administering to a patient in need thereof an effective amount of at least one compound, selected from the group of compounds of formula I, their N-oxides, their hydrates, their tautomers, their prodrugs and the pharmaceutically acceptable salts thereof.

In another preferred embodiment, the present invention provides a method for treating cognitive disturbances associated with schizophrenia, comprising: administering to a patient in need thereof an effective amount of at least one compound, selected from the group of compounds of formula I, their N-oxides, their hydrates, their tautomers, their prodrugs and the pharmaceutically acceptable salts thereof.

At present, the fourth edition of the Diagnostic and Statistical Manual of Mental Disorders (DSM-IV) (1994, American Psychiatric Association, Washington, D.C.), provides a diagnostic tool including schizophrenia and other psychotic disorders. These include: disorders having psychotic symptoms as the defining feature. The term psychotic refers to delusions, prominent hallucinations, disorganized speech, disorganized or catatonic behavior. The disorder includes: paranoid, disorganized, catatonic, undifferentiated, and residual schizophrenia, schizophreniform disorder, schizoaffective disorder, delusional disorder, brief psychotic disorder, shared psychotic disorder, psychotic disorder due to a general medical condition, substance-induced psychotic disorder, and psychotic disorder not otherwise specified. The skilled artisan will recognize that there are alternative nomenclatures, nosologies, and classification systems for neurological and psychiatric disorders, and particular schizophrenia, and that these systems evolve with medical scientific progress. Thus, the term "schizophrenia" is intended to include like disorders that are described in other diagnostic sources.

In another preferred embodiment, the present invention provides a method for treating substance-related disorders, comprising: administering to a patient in need thereof an effective amount of at least one compound, selected from the group of compounds of formula I, their N-oxides, their hydrates, their tautomers, their prodrugs and the pharmaceutically acceptable salts thereof.

In another preferred embodiment, the present invention provides a method for treating anxiety, comprising: administering to a patient in need thereof an effective amount of at least one compound, selected from the group of compounds of formula I, their N-oxides, their hydrates, their tautomers, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein the term "anxiety" includes treatment of those anxiety disorders and related disorder as described in the DSM-IV. The skilled artisan will recognize that there are alternative nomenclatures, nosologies, and classification systems for neurological and psychiatric disorders, and particular anxiety, and that these systems evolve with medical scientific progress. Thus, the term "anxiety" is intended to include like disorders that are described in other diagnostic sources.

In another preferred embodiment, the present invention provides a method for treating depression, comprising: administering to a patient in need thereof an effective amount of at least one compound, selected from the group of compounds of formula I, their N-oxides, their hydrates, their tautomers, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including depression and related disorders. Depressive disorders include, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder. As used herein the term "depression" includes treatment of those depression disorders and related disorder as described in the DSM-1V.

In another preferred embodiment, the present invention provides a method for treating substance-related disorders, especially substance dependence, substance abuse, substance tolerance, and substance withdrawal, comprising: administering to a patient in need thereof an effective amount at least one compound, selected from the group of compounds of formula I, their N-oxides, their hydrates, their tautomers, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including disorders related to taking a drug of abuse (including alcohol), to the side effects of a medication, and to toxin exposure. Substances include alcohol, amphetamine and similarly acting sympathomimetics, caffeine, cannabis, cocaine, hallucinogens, inhalants, nicotine, opioids, phencyclidine (PCP) or similarly acting arylcyclohexylamines, and sedatives, hypnotics, or anxiolytics. Also, polysubstance dependence and other unknown substance-related disorders are included. The skilled artisan will recognize that there are alternative nomenclatures, nosologies, and classification systems for neurological and psychiatric disorders, and particular substance-related disorders, and that these systems evolve with medical scientific progress. Thus, the term "substance-related disorder" is intended to include like disorders that are described in other diagnostic sources.

In the treatment, prevention, control, amelioration, or reduction of risk of conditions which require inhibition of PDE10A an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day. When treating, preventing, controlling, ameliorating, or reducing the risk of neurological and psychiatric disorders or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligram to about 50 milligrams, in the case of a 70 kg adult human, the total daily dose will generally be from about 7 milligrams to about 350 milligrams. This dosage regimen may be adjusted to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present invention may be administered by conventional routes of administration, including parenteral (e.g., intramuscular, intrapentoneal, intravenous, ICV, intracisternal injection or infusion, subcutaneous injection, or implant), oral, by inhalation spray, nasal, vaginal, rectal, sublingual, or topical routes of administration.

The compounds according to the present invention are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefore, contemporaneously or sequentially with a compound of Formula I. When a compound of formula I is used contemporaneously with one or more other drugs, a pharmaceutical composition in unit dosage form containing such other drugs and the compound of formula I is preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of formula I. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The present invention also relates to pharmaceutical compositions (i.e. medicaments) which comprise at least one compound of the present invention and, where appropriate, one or more suitable excipients.

These excipients/drug carriers are chosen according to the pharmaceutical form and the desired mode of administration.

The compounds of the present invention can be used to manufacture pharmaceutical compositions for parenteral (e.g., intramuscular, intrapentoneal, intravenous, ICV, intracisternal injection or infusion, subcutaneous injection, or implant), oral, sublingual, intratracheal, intranasal, topical, transdermal, vaginal or rectal administration, and be administered to animals or humans in unit dose forms, mixed with conventional pharmaceutical carriers, for the prophylaxis or treatment of the above impairments or diseases.

In the pharmaceutical compositions, the at least one compound of the present invention may be formulated alone or together with further active compounds, in suitable dosage unit formulations containing conventional excipients, which generally are non-toxic and/or pharmaceutically acceptable. Carriers or excipients can be solid, semisolid or liquid materials which serve as vehicles, carriers or medium for the active compound. Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], 4$^{th}$ edition, Aulendorf: ECV-Editio-Kantor-Verlag, 1996.

Suitable unit dose forms include forms for oral administration, such as tablets, gelatin capsules, powders, granules and solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

If a solid composition is prepared in the form of tablets, the main ingredient is mixed with a pharmaceutical carrier such as gelatin, starch, lactose, magnesium stearate, talc, silicon dioxide or the like.

The tablets may be coated with sucrose, a cellulose derivative or another suitable substance or be treated otherwise in order to display a prolonged or delayed activity and in order to release a predetermined amount of the active basic ingredient continuously.

A preparation in the form of gelatin capsules is obtained by mixing the active ingredient with an extender and taking up the resulting mixture in soft or hard gelatin capsules.

A preparation in the form of a syrup or elixir or for administration in the form of drops may comprise active ingredients together with a sweetener, which is preferably calorie-free, methylparaben or propylparaben as antiseptics, a flavoring and a suitable coloring.

The water-dispersible powders or granules may comprise the active ingredients mixed with dispersants, wetting agents or suspending agents such as polyvinylpyrrolidones, and sweeteners or taste improvers.

Rectal administration is achieved by the use of suppositories which are prepared with binders which melt at the rectal temperature, for example cocobutter or polyethylene glycols. Parenteral administration is effected by using aqueous suspensions, isotonic salt solutions or sterile and injectable solutions which comprise pharmacologically suitable dispersants and/or wetting agents, for example propylene glycol or polyethylene glycol.

The active basic ingredient may also be formulated as microcapsules or liposomes/centrosomes, if suitable with one or more carriers or additives.

In addition to the compounds of the general formula I, their prodrugs, their N-oxides, their tautomers, their hydrates or their pharmaceutically suitable salts, the compositions of the invention may comprise further active basic ingredients which may be beneficial for the treatment of the impairments or diseases indicated above.

The present invention thus further relates to pharmaceutical compositions in which a plurality of active basic ingredients are present together, where at least one thereof is a compound of the invention.

When producing the pharmaceutical compositions, the compounds according to the invention are optionally mixed or diluted with one or more carriers.

The following examples are intended for further illustration of the present invention.

Abbreviations which have been used in the descriptions of the schemes and the Examples that follow are:

AIBN for azobisisobutyronitrile; BINAP for 2,2'-bis(diphenylphosphino)-1,1'-binaphthyl; BOC for tert-butyloxycarbonyl; DCM for dichloromethane; DEAD for diethyl azodicarboxylate; DIAD for diisopropyl azodicarboxylate; DIPEA for N,N-diisopropylethylamine; DMF for dimethylformamide; DMSO for dimethyl sulfoxide; EA or EtOAc for ethyl acetate (ethyl ethanoate); Et for ethyl; EtOH for ethanol; HOAc or AcOH for acetic acid; LDA for lithium diisopropylamide; LiHMDS for lithium bis (trimethylsilyl) amide; Me for methyl; MeOD or MeOD-d$_4$ for deuterated methanol; MeOH for methanol; NBS for N-bromosuccinimde; n-Bu for n-butyl; NIS for N-iodosuccinimide; OAc for acetate; Pd$_2$(dba)$_3$ for tris (dibenzylideneacetone)dipalladium(0): PdCl$_2$(dppf) for 1,1'-bis (diphenylphosphino)ferrocene-palladium (II)-dichloride; PE for petroleum ether; PyBOP for benzotriazol-1-yl-oxytripyrrolidinophosphonium hexafluorophosphate; Raney-Ni for Raney nickel; R$_t$ for retension time; TBAI for tetrabutylammonium iodide; TFA for trifluoroacetic acid; THF for tetrahydrofuran; TMSCl for trimethylsilyl chloride; X-PHOS for 2-dicyclohexylphosphino-2',4',6'-triisopropylbiphenyl.

LC-MS was recorded on Agilent 1200 HPLC/6110 SQ system.

The compounds I of the invention were purified in some cases by preparative HPLC. The compounds I then result as the salts.

PREPARATION EXAMPLES

I. Preparation of Intermediates
The starting materials used in the examples are either commercially available or can be synthesized by the average skilled person trained in organic chemistry following routine laboratory practice as outlined, for example in the examples below.
a) Preparation of compounds of the general formula IV (compounds Het-CR$^9$R$^{10}$—CR$^7$R$^8$—NH$_2$)
a1) 2-Quinolin-2-yl-ethylamine (also referred to as 2-(quinolin-2-yl)ethanamine)

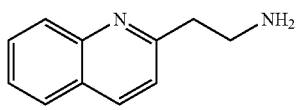 [SMILES: NCCc1ccc2ccccc2n1]

Route a)

a1.1a) Quinolin-2-yl-acetic acid ethyl ester

To a suspension of vacuum dried Zn dust (6.0 g, 93.8 mmol) in dry THF (100 mL) was added TMSCl (0.5 mL) dropwise over 5 min. under $N_2$ atmosphere and under stiffing. The mixture was stirred for 30 min. and warmed to 45° C. Ethyl bromoacetate (5.2 mL, 46.9 mmol) was added dropwise via a syringe. After addition, the mixture was stirred at the same temperature for 1 h. After sedation at room temperature for 2 h, a clear orange solution was formed. The orange solution (50 mL) was carefully sucked into a syringe through a long needle and added to a mixture of 2-bromoquinoline (2.0 g, 9.6 mmol) and $PdCl_2(dppf)$ (200 mg, 0.27 mmol) in a three-neck flask. The mixture was refluxed under $N_2$ for 3 h. The reaction was monitored with LCMS. Ethyl acetate (200 mL) was added to dilute the mixture and water (50 mL) was added to quench the reaction. The mixture was filtered through a celite pad. The filtration was partitioned between brine and ethyl acetate. The organic layer was separated, washed with brine (100 mL), dried over sodium sulfate and concentrated. The residue was purified with silica column (PE/EA=3:1) to give the title compound as orange oil (1.0 g, 48%). LCMS (ESI+): m/z 216 (M+H)$^+$, $R_t$: 0.62 min.

a1.2a) 2-Quinolin-2-yl-ethanol

To a cold (0° C.) solution of the compound from Example a1.1a (10 g, 45 mmol) in THF (200 mL) was added LiAlH$_4$ (2.65 mg, 70 mmol) in small portions over a period of 5 min. The resulting mixture was stirred for 1 h. Water was added dropwise very slowly. Then more water and EA were added. The organic phase was collected, dried and concentrated. The residue was purified by silica gel chromatography (PE/EA=2:1) to give the title compound as a yellow solid (2.5 g, 30%). LCMS (ESI+): m/z 174 (M+H)$^+$, $R_t$: 0.75 min.

a1.3a) 1-(2-Quinolin-2-yl-ethyl)pyrrolidine-2,5-dione

2-Quinolin-2-yl from Example a1.2a (2.5 g, 15 mmol), pyrrolidine-2,5-dione (2 g, 20 mmol) and triphenylphosphine (5.25 g, 20 mmol) were dissolved in THF (50 mL). DEAD (6.1 g, 35 mmol) was then added. The resultant mixture was stirred at room temperature overnight. The solvent was evaporated and the residue was purified by silica gel chromatography (PE/EA=2/1) to give the title compound as a yellow oil (2.5 g, 66%). LCMS (ESI+): m/z 255 (M+H)$^+$, $R_t$: 1.15 min.

a1.4a) 2-Quinolin-2-yl-ethylamine

A flask was charged with 1-(2-quinolin-2-yl-ethyl)pyrrolidine-2,5-dione from Example a1.3a (2.5 g, 20 mmol) and methanol (50 mL). Aqueous $NH_2NH_2$ (85%, 25 mL) was added. The solution was stirred at reflux overnight. The solvent was evaporated and the residue was purified by silica gel chromatography (DCM/MeOH=10/1) to give the title compound as a yellow solid (1.5 g, 43%). LCMS (ESI+): m/z 173 (M+H)$^+$, $R_t$: 1.42 min.

Route b)

a1.1b) 2-(Chloromethyl)quinoline

To a suspension of 2-(chloromethyl)quinoline hydrochloride (30 g, 0.14 mol) in EtOAc/H$_2$O (400 mL: 200 mL) was added NaHCO$_3$ powder portionwise until no gas evolved. The organic layer was collected, washed with brine (3*50 mL), dried over sodium sulfate and concentrated. The residue was used in next step without further purification (25 g, 100%).

a1.2b) Quinolin-2-yl-acetonitrile 2-(Chloromethyl)quinoline (25 g, 0.14 mol) was dissolved in a mixture of EtOH/H$_2$O (200 mL: 100 mL). Sodium cyanide (7.5 g, 0.15 mol) was added. The mixture was heated to 50° C. and stirred overnight. Ethanol was removed under reduced pressure. The residue was extracted with EtOAc (3*200 mL). The remaining aqueous phase was treated with 1M FeSO$_4$ solution (200 mL). The combined organic layer was washed with water (3*50 mL), dried over sodium sulfate and concentrated. The residue was purified with silica column (PE/EA=5:1). The waste water phase was treated with 1M FeSO$_4$ solution (50 mL).

a1.3b) 2-Quinolin-2-yl-ethylamine

To a solution of quinolin-2-yl-acetonitrile (19 g, 0.11 mol) in EtOH (400 mL) was added Raney-Ni (1.0 g) and NH$_3$—H$_2$O (conc., 100 mL). The mixture was hydrogenated with H$_2$ (2 atm) overnight. The mixture was filtered and concentrated. The residue was dissolved in water (200 mL). HCl (3 M, 20 mL) was added. The aqueous solution was washed with EtOAc (3*100 mL) and adjusted to pH=6 with NaHCO$_3$. The resulting aqueous solution was washed with DCM (2*100 mL). The aqueous phase was freeze-dried to give a yellow solid. DCM (300 mL) was added to the solid. The mixture was stirred at room temperature for half an hour. The filtrate was concentrated in vacuo to give the title compound as a yellow solid (7.3 g, 36.5%).

a2) 2-(8-Chloro-quinolin-2-yl)-ethylamine

According to route a) starting from 2-bromo-8-chloro-quinoline a3) 2-(7-Fluoro-quinolin-2-yl)-ethylamine According to route a) starting from 2-bromo-7-fluoro-quinoline a4) 2-(6-Methoxy-quinolin-2-yl)-ethylamine According to route b) starting from 2-chloromethyl-6-methoxy-quinoline a5) 2-(6-Fluoro-quinolin-2-yl)-ethylamine according to route b) starting from 2-chloromethyl-6-fluoro-quinoline a6) 2-(4-Chloro-quinolin-2-yl)-ethylamine According to route b) starting from 4-chloro-2-chloromethyl-quinoline a7) 2-(3-Fluoro-quinolin-2-yl)-ethylamine According to route b) starting from 3-fluoro-2-chloromethyl-quinoline They were used in the next step without purification.

b1) 2,2-Difluoro-2-quinolin-2-yl-ethylamine

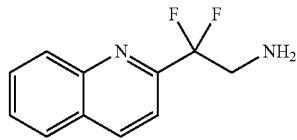 [SMILES: NCC(F)(F)c1ccc2ccccc2n1]

b1.1) Difluoroquinolin-2-yl acetic acid ethyl ester

2-Bromoquinoline (5.0 g, 24.0 mmol), ethyl 2-bromodifluoroacetate (5.8 g, 28.8 mmol) and copper powder (3.5 g, 55.2 mmol) in DMSO (20 mL) were stirred at 55° C. for 5 hours. The solid was filtered off, water (100 mL) and EA (150 mL) were added. The organic layer was separated, dried over sodium sulfate and concentrated to give the title compound as a yellow oil (4.2 g, 70%), which was used in the next step without further purification. LCMS (ESI+): m/z 252 (M+H)$^+$, R$_t$: 0.934 min.

b1.2) 2,2-Difluoro-2-quinolin-2-ylethanol

To a solution of difluoroquinolin-2-yl acetic acid ethyl ester (2 g, 7.9 mmol) in ethanol (20 mL) was added NaBH$_4$ (317 mg, 1.0 mmol) at 0° C. under N$_2$. The mixture was stirred for 1 hour and then at room temperature for 1.5 hours. The solution was quenched with dilute HCl (0.1 N, 20 mL). The mixture was neutralized with saturated NaHCO$_3$ solution and extracted with EtOAc (3*100 mL). The combined organic layer was dried over sodium sulfate. The solvent was evaporated and the residue was purified by column chromatography on silica gel (PE: EA=10:1) to give the title compound as a yellow solid (0.7 g, 44%). LCMS (ESI+): m/z 210 (M+H)$^+$, R$_t$: 0.747 min.

b1.3) Trifluoromethanesulfonic acid 2,2-difluoro-2-quinolin-2-yl ethyl ester

To a solution of 2,2-difluoro-2-quinolin-2-ylethanol (300 mg, 1.4 mmol) and triethylamine (217 mg, 2.1 mmol) in anhydrous DCM (5 mL) was added dropwise trifluoromethanesulphonic anhydride (606 mg, 2.1 mmol) at −70° C. The reaction mixture was stirred for 1 hour. The resulting solution was warmed slowly to room temperature and stirred for 1 hour. The solid was removed by filtration. Water (5 mL) and DCM (30 mL) were added, the organic layer was separated, dried over sodium sulfate and evaporated to give the crude title compound as an orange oil (450 mg, 92%), which was used in the next step without further purification. LCMS (ESI+): m/z 342 (M+H)$^+$, R$_t$: 1.006 min.

b1.4) 2,2-Difluoro-2-quinolin-2-yl-ethyl azide

A mixture of trifluoromethanesulfonic acid 2,2-difluoro-2-quinolin-2-yl ethyl ester (500 mg, 1.7 mmol) and sodium azide (450 mg, 6.9 mmol) in DMF (5 mL) was stirred at 60° C. for 12 hours. Water (20 mL) and EA (100 mL) were added. The organic layer was separated, dried over sodium sulfate and concentrated to give the crude title compound as a yellow oil (300 mg, 74%), which was used in the next step without further purification. LCMS (ESI+): m/z 235 (M+H)$^+$, R$_t$: 0.943 min.

b1.5) 2,2-Difluoro-2-quinolin-2-yl-ethylamine

A mixture of 2,2-difluoro-2-quinolin-2-yl-ethyl azide (300 mg, 1.2 mmol) and Pd/C (100 mg) in EA (10 mL) was stirred at room temperature for 2 hours under H$_2$ (1.5 atm). The catalyst Pd/C was filtered off, the filtrate was concentrated to give the crude title compound as white solid (240 mg, 90%), which was used in the next step without further purification. LCMS (ESI+): m/z 209 (M+H)$^+$, R$_t$: 0.610 min.

c1) 2-Thieno[3,2-b]pyridin-5-yl-ethylamine

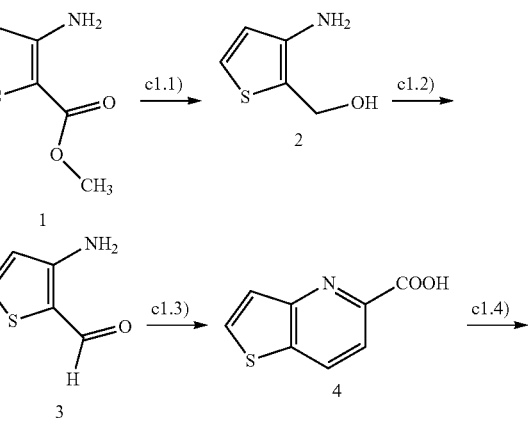

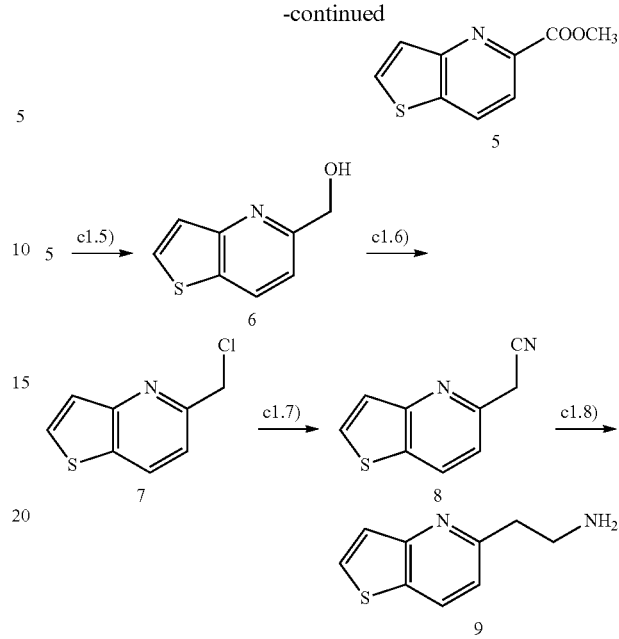

c1.1) Compound (2)

To a suspension of LiAlH$_4$ (1.39 g, 36.58 mmol) in anhydrous THF (30 mL) was added a solution of methyl 3-aminothiophene 2-carboxylate (compound 1, 5.00 g, 31.81 mmol) dropwise at 0° C. The reaction mixture was stirred at room temperature overnight. Water (4 mL) was added dropwise to quench the reaction. The mixture was stirred for 30 min. and then more water was added (10 mL). The solid was filtered off and then washed with NaOH solution (50 mL, 5 N). The filtrate was concentrated in vacuo and the residue was dissolved in EtOAc (200 mL). The solution was dried over Na$_2$SO$_4$, filtered and concentrated in vacuo. The crude solid was used in the next step without further purification (2.71 g, yield 66%). LCMS (ESI+): m/z 130 (M+H)$^+$, R$_t$: 1.57 min.

c1.2) Compound (3)

A mixture of compound 2 (8.14 g, 63.00 mmol) and MnO$_2$ (32.8 g, 0.378 mol) in EtOAc (100 mL) was stirred at 30° C. for 48 h. The mixture was filtered and the filtrate was concentrated in vacuo. The residue was used in the next step without further purification (6.82 g, yield 85%). LCMS (ESI+): m/z 128 (M+H)$^+$, R$_t$: 1.55 min.

c1.3) Compound (4)

To a solution of compound 3 (6.82 g, 53.62 mmol) in EtOH (70 mL) was added a mixture of pyruvic acid (9.44 g, 0.107 mol) and NaOH (10.7 g, 0.268 mol) in H$_2$O (70 mL) in one portion. The mixture was heated at 60° C. for 2 h, then cooled and extracted with Et$_2$O/EtOAc (1:1, 30 mL). The aqueous layer was acidified with HCl (2 N) to pH=3 at 0° C. and the water was removed under reduced pressure. The residue was co-evaporated with toluene (50 mL×3) and then used in the next step without further purification. LCMS (ESI+): m/z 180 (M+H)$^+$, R$_t$: 1.50 min.

c1.4) Compound (5)

To a mixture of crude compound 4 (7 g, 39 mmol) in methanol (60 mL) was added thionyl chloride (10 mL) dropwise at 0° C. The reaction mixture was then heated at 65° C. for 3 h. The excess of solvent was removed under reduced pressure. The residue was diluted with EtOAc (100 mL) and washed with saturated NaHCO$_3$ aqueous solution (30 mL×4) and brine (30 mL). The organic layer was dried over Na$_2$SO$_4$, filtered and concentrated in vacuo. The residue was purified on a silica column (PE/EtOAc=5:1, v/v) to afford the title product as an off-white solid (715 mg, total yield 9.5%). LCMS (ESI+): m/z 194 (M+H)$^+$, R$_t$: 1.78 min.

c1.5) Compound (6)

To a solution of compound 5 (100 mg, 0.52 mmol) in THF (2 mL) was added LiBH$_4$ (11 mg) in one portion. The mixture was allowed to stir at room temperature overnight. The reaction was quenched with saturated NH$_4$Cl solution, then extracted with EtOAc (20 mL). The organic layer was washed with brine (10 mL), dried over Na$_2$SO$_4$, filtered and concentrated in vacuo. The yellow residue was used in the next step without further purification. LCMS (ESI+): m/z 166 (M+H)$^+$, R$_t$: 1.44 min.

c1.6) Compound (7)

A mixture of compound 6 (100 mg, crude) and thionyl chloride (1 mL) in DCM (3 mL) was stirred at room temperature for 3 h. The mixture was concentrated in vacuo. The residue was diluted with EtOAc (20 mL) and washed with saturated NaHCO$_3$ solution (6 mL×4) and brine (6 mL). The organic layer was dried over Na$_2$SO$_4$, filtered and concentrated in vacuo. The red residue was used in the next step without further purification. LCMS (ESI+): m/z 184 (M+H)$^+$, R$_t$: 1.88 min.

c1.7) Compound (8)

A mixture of compound 7 (580 mg, 3.157 mmol) and NaCN (170 mg, 3.473 mmol) in EtOH (12 mL) and H$_2$O (4 mL) was stirred at 50° C. for 60 h. The mixture was diluted with EtOAc (50 mL) and washed with brine (15 mL×4). The organic layer was dried over Na$_2$SO$_4$, filtered and concentrated in vacuo. The residue was purified on a silica column (PE/EtOAc=10:1, v/v) to afford the title product as an off-white solid (280 mg, yield 51%). LCMS (ESI+): m/z 175 (M+H)$^+$, R$_t$: 1.89 min.

c1.8) 2-Thieno[3,2-b]pyridin-5-yl-ethylamine (9)

A mixture of compound 8 (283 mg, 1.624 mmol) and Raney-Ni in MeOH (12 mL) and ammonium hydroxide (2 mL) was stirred at room temperature under hydrogen atmosphere (1.5 atm) overnight. The mixture was then filtered and the filtrate was concentrated in vacuo. The yellow residue was used in the next step without further purification (183 mg, yield 63%). LCMS (ESI+): m/z 179 (M+H)$^+$, R$_t$: 1.47 min.

c2) Methyl 2-bromo-6-methylbenzoate (10)

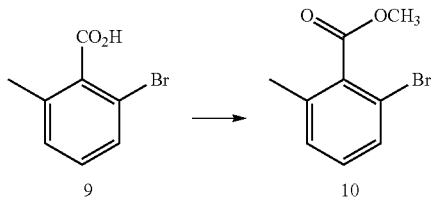

The compound 9 (40 g, 186 mmol) was dissolved in SOCl$_2$ (54.3 ml, 744 mmol), stirred and heated to about 80° C. for about 3 h in a 500 mL pear flask. The MeOH (200 ml) was added dropwise via dropping funnel to the solution in an ice bath. The resulting solution was stirred at about 80° C. for about 30 min. The reaction mixture was diluted with ethyl acetate. Washed with sat NaHCO$_3$, water, and sat NaCl. The combined organic layers were dried with Na$_2$SO$_4$, filtered and concentrated to give it asmethyl 2-bromo-6-methylbenzoate (40 g, 175 mmol, 94% yield).

LC-MS: m/z 229 (M+H)RT=2.05 min./3 min.

c3) Methyl 2-bromo-6-(bromomethyl)benzoate (11)

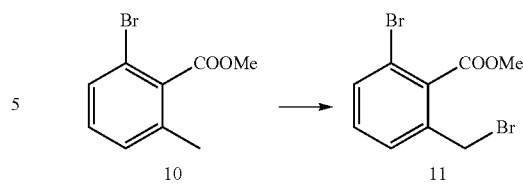

A mixture of compound 10 (2.50 g, 9.05 mmol), N-bromosuccinimide (1.93 g, 10.86 mmol) and azobisisbutyronitrile (0.669 g, 4.07 mmol) in tetrachloromethane (20 mL) was stirred at reflux overnight. The mixture was concentrated in vacuo. The residue was purified on a silica column (PE/EtOAc=200:1, v/v) to afford the title product as a white solid as a white solid (1.62 g, yield 50%).

LC-MS: m/z 355 (M+H)RT=2.33 min./3 min.

c4) 7-Bromo-2-(2-(thieno[3,2-b]pyridin-5-yl)ethyl)isoindolin-1-one

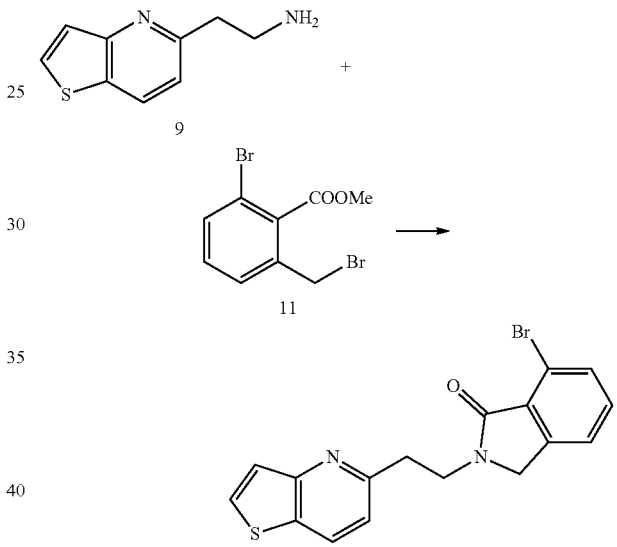

A mixture of compound 9 (183 mg, 1.06 mmol) and 11 (364 mg, 1.06 mmol) in ethanol (5 mL) was stirred at reflux overnight. The mixture was concentrated in vacuo and purified on a silica column (pet. ether/EtOAc=1:1, v/v) to afford the title product as a white solid (178 mg, yield 41%).

LC-MS: m/z 421 (M+H) RT=1.91 min./3 min.

$^1$H NMR (400 MHz, CDCl$_3$): δ=8.11 (d, J=8.4 Hz, 1H), 7.75 (d, J=5.6 Hz, 1H), 7.58-7.56 (m, 1H), 7.51 (d, J=5.6 Hz, 1H), 7.33 (t, J=3.0 Hz, 1H), 7.25 (t, J=6.4 Hz, 1 H), 4.26 (s, 2H), 4.09 (t, J=7.2 Hz, 2H), 3.33 (t, J=7.2 Hz, 2H).

d1) 2-(Imidazo[1,2-a]pyridin-2-yl)ethylamine

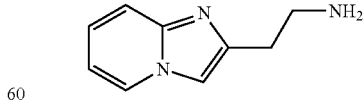

Route a)

d1.1a) Imidazo[1,2-a]pyridin-2-yl-acetic acid ethyl ester

A mixture of 2-aminopyridine (15 g, 159 mmol) and ethyl 4-chloro-3-oxobutanoate (compound 1, 26.2 g, 159 mmol) in THF (100 mL) was heated to reflux for 16 h. The mixture was concentrated and the residue was purified by silica gel chromatography (PE: EA=1:1) to afford the title compound as a yellow oil (5.0 g, 15%). LCMS (ESI+): m/z 205 (M+H)+, $R_t$: 1.61 min.

d1.2a) Imidazo[1,2-a]pyridin-2-yl-acetamide

A mixture of the compound from Example d1.1a) (600 mg, 2.94 mmol) in ammonium hydroxide (15 mL, 385 mmol) was heated to 90° C. for 3 h. The solvent was removed under reduced pressure. The residue was purified by plate-TLC (DCM: MeOH=10:1) to give the title compound as a yellow solid (230 mg, 45% yield). LCMS (ESI+): m/z 176 (M+H)+, $R_t$: 1.03 min.

d1.3a) 2-Imidazo[1,2-a]pyridin-2-ylethylamine (4)

Borane tetrahydrofuran complex BH$_3$.THF (10 mL, 10.0 mmol) was added to a mixture of the compound from Example d1.2a (200 mg, 1.142 mmol) in THF (3 mL) at 0° C. The mixture was stirred at 35° C. for 16 h. After cooling to room temperature, MeOH (2 mL) and HCl (6N, 2 mL) were added. The mixture was stirred at room temperature for 2 h. The mixture was adjusted to pH=9 by NaOH (10%). The solvent was removed under reduced pressure. The residue was dissolved in MeOH (10 mL). The solid was removed by filtration. The filtrate was concentrated to give the crude title compound as a yellow solid (120 mg, 65%), which was directly taken to the next step without purification. LCMS (ESI+): m/z 162 (M+H)+, $R_t$: 0.36 min.

Route b)

d1.1b) 2-(Chloromethyl)imidazo[1,2-a]pyridine

To a solution of 1,3-dichloro-2-propanone (67.45 g, 531.3 mmol) in 1,2-dimethoxyethane (200 mL) was added 2-aminopyridine (50 g, 531.3 mmol) and the mixture was stirred at room temperature for 2 hours. During this time a thick precipitate was formed, which was collected by filtration. The precipitate was refluxed in absolute ethanol for 2 hours after which volatiles were removed by evaporation. The residue was dissolved in water (150 mL) and solid NaHCO$_3$ was added to neutralize the mixture. A white precipitate formed, and this was collected by filtration, washed with water and vacuum dried to yield the title compound pure as a cream white solid (60 g, 67.8%). LC-MS: m/z 167 (M+H); $R_t$=0.28 min.

d1.2b) 2-(Imidazo[1,2-a]pyridin-2-yl)acetonitrile

A mixture of 2-(chloromethyl)imidazo[1,2-a]pyridine (30 g, 180 mmol) and sodium cyanide (8 g, 163 mmol) in water (100 mL) and ethanol (100 mL) was heated and stirred for one night at 60° C. After cooling, the mixture was extracted with DCM (3×150 mL). The organic layers was washed with water, dried and evaporated under reduced pressure. The residue was purified by chromatography column on silica gel (eluted with PE/EA, 1:1) to give the title compound (16 g, yield: 50.4%) as a yellow solid. LC-MS: m/z 158.2 (M+H); $R_t$=0.62 min.

d1.3b) 2-(Imidazo[1,2-a]pyridin-2-yl)ethylamine

To a solution of 2-(imidazo[1,2-a]pyridin-2-yl)acetonitrile (13 g, 82.7 mmol) in THF (100 mL), BH$_3$.THF (450 mL, 450 mmol) was added dropwise at 0° C. After 30 min., the mixture was allowed to stir at 60° C. for one night. The reaction was quenched with MeOH (150 mL) and 6N aq. HCl (100 mL). The resulting mixture was refluxed for 2 hours. The solvent was distilled under reduced pressure. Aq. Na$_2$CO$_3$ was added to neutralize the mixture and the mixture was evaporated. The residue was purified by chromatography column (eluted with DCM/MeOH from 20:1 to 10:1) to give the title compound (10 g, yield: 75%) as a white solid. LC-MS: m/z 162.1 (M+H); $R_t$=0.73 min.

e1) 2-(3-(Pyrimidin-2-yl)phenyl)ethylamine

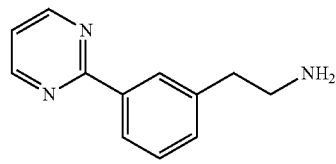 [SMILES: NCCc1cccc(-c2ncccn2)c1]

e1.1) 2-m-Tolylpyrimidine

A mixture of 3-methylboronic acid (2 g, 14.71 mmol), 2-bromopyrimidine (2.13 g, 13.37 mmol), K$_2$CO$_3$ (5.54 g, 40.1 mmol) and PdCl$_2$(dppf) (0.98 g, 1.34 mmol) in dioxane (30 mL) and H$_2$O (10 mL) was stirred at 100° C. under nitrogen for 2 h. The mixture was concentrated and the residue was purified by silica gel column chromatography, eluting with PE/EA (10:1) to give the title compound as a white solid (1.9 g, 82%). LCMS (ESI+): m/z 171 (M+H)+, $R_t$: 0.86 min.

e1.2) 2-(3-(Bromomethyl)phenyl)pyrimidine

A mixture of 2-m-tolylpyrimidine (1.00 g, 5.88 mmol), NBS (1.26 g, 7.05 mmol) and AIBN (0.43 g, 2.64 mmol) in CCl$_4$ (30 mL) was stirred at 90° C. overnight. The mixture was concentrated and the residue was purified by silica gel column, eluting with PE:EA (50:1) to give the title compound as a white solid (1.2 g, 81%). LCMS (ESI+): m/z 249 (M+H)+, $R_t$: 0.89 min.

e1.3) 2-(3-(Pyrimidin-2-yl)phenyl)acetonitrile

A mixture of 2-(3-(bromomethyl)phenyl)pyrimidine (100 mg, 0.4 mmol), NaCN (20 mg, 0.4 mmol) and TBAI (148 mg, 0.4 mmol) in toluene/H$_2$O (10 mL: 3 mL) was stirred at 60° C. overnight. Then the mixture was poured into a mixture of 0.5 g FeSO$_4$ in 2 mL water and extracted with EA (50 mL). The organic layer was dried over sodium sulfate, concentrated and the residue was purified by silica gel column (PE: EA=2:1) to give the title compound as a white solid (70 mg, 89%). LCMS (ESI+): m/z 196 (M+H)+, $R_t$: 0.75 min.

e1.4) 2-(3-(Pyrimidin-2-yl)phenyl)ethylamine

A mixture of 2-(3-(pyrimidin-2-yl)phenyl)acetonitrile (1.15 g, 5.89 mmol) and Raney-Ni (0.6 g) in NH$_3$—H$_2$O (3 mL) and MeOH (30 mL) was stirred at room temperature under H$_2$ (1.5 atm) overnight. The mixture was filtered. The filtrate was concentrated to afford the title compound as a yellow oil (0.95 g, 65%). LCMS (ESI+): m/z 200 (M+H)+, $R_t$: 0.57 min.

f1) 2-(2-Phenylpyrimidin-4-yl)ethylamine

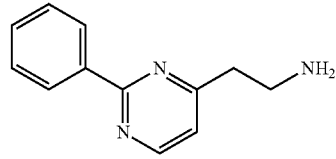 [SMILES: NCCc1ccnc(-c2ccccc2)n1]

f1.1) (E)-N'-Hydroxybenzimidamide

Benzonitrile (5.0 g, 48.5 mmol) was dissolved in 50 mL of methanol, potassium carbonate (13.4 g, 97.1 mmol) was added and hydroxylamine hydrochloride (5.1 g, 72.8 mmol) dissolved in 100 mL of methanol was added subsequently in small portions. The reaction mixture was refluxed for 5 h, then the solvent was evaporated and the residue was taken up in a 1:4 mixture of water (100 mL) and DCM (500 mL). The organic layer was separated, washed twice with water (100 mL), dried with magnesium sulfate, filtered and evaporated to afford the title compound as a white solid (4.9 g, 74.3%), which was used without further purification. LCMS (ESI+): m/z 137 (M+H)+, $R_t$: 0.29 min.

f1.2) 6-Methyl-2-phenylpyrimidine 1-oxide

To a solution of (E)-N'-hydroxybenzimidamide (5.0 g, 36.8 mmol) and 4,4-dimethoxybutan-2-one (5.3 g, 40.4 mmol) in iso-propanol (100 mL) was added TFA (4.6 g, 40.4 mmol) dropwise. The mixture was stirred at 100° C. overnight, concentrated to give the title compound as a yellow solid (5.3 g, 77.4%). LCMS (ESI+): m/z 187 (M+H)+, $R_t$: 0.639 min.

f1.3) 4-(Chloromethyl)-2-phenylpyrimidine

To a solution of 6-methyl-2-phenylpyrimidine 1-oxide (5.3 g, 28.5 mmol) in 1,4-dioxane (100 mL) was added POCl$_3$ (44 g, 285 mmol) dropwise at room temperature. The mixture stirred at 100° C. for 2 h, then cooled to room temperature and poured into ice water, extracted with EA (200 mL×2), concentrated and the residue was purified by silica gel column (PE: EA=50:1) to obtain the title compound as a yellow solid (2 g, 34.3%). LCMS (ESI+): m/z 205 (M+H)+, $R_t$: 0.93 min.

f1.4) 2-(2-Phenylpyrimidin-4-yl)acetonitrile

A mixture of 4-(chloromethyl)-2-phenylpyrimidine (3.7 g, 18.1 mmol) and NaCN (1.0 g, 19.9 mmol) in EtOH/H$_2$O (150 mL/50 mL) was stirred at 50° C. overnight. Then the mixture was poured into FeSO$_4$/H$_2$O and extracted with EA (300 mL), concentrated and the residue was purified by silica gel column (PE: EA=10:1) to give the title compound as a yellow solid (0.78 g, 22%). LCMS (ESI+): m/z 196 (M+H)+, $R_t$: 0.82 min.

f1.5) 2-(2-Phenylpyrimidin-4-yl)ethylamine

A mixture of the compound from Example f1.4) (0.78 g, 4 mmol) and Raney-Ni (0.50 g) in NH$_3$—H$_2$O (3 mL) and MeOH (30 mL) was stirred at room temperature under H$_2$ (1.5 atm) overnight. The mixture was filtered and concentrated to afford the title compound as a yellow oil (0.61 g, 76.6%). LCMS (ESI+): m/z 200 (M+H)+, $R_t$: 0.61 min. $^1$H NMR (400 MHz, MeOD): δ 2.99-3.00 (m, 2H), 3.12-3.17 (m, 2H), 4.1 (s, 2H), 7.36 (d, J=4.4 Hz, 1H), 7.53 (s, 3H), 8.41 (s, 2H), 8.79 (d, J=4.4 Hz, 1H).

g1) 2-[1,2,4]-Triazolo[1,5-a]pyridin-2-yl-ethylamine

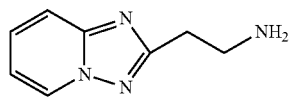 [SMILES: NCCc1nc2ccccn2n1]

g1.1) 2-Iminopyridin-1(2H)-amine hydroiodide

A solution of aminooxysulfonic acid (84 g, 0.744 mol) and potassium hydroxide (41.7 g, 0.744 mol) in 150 mL of H$_2$O (prepared at 0° C.) was added dropwise to a solution at 40° C. of 2-aminopyridine (70 g, 0.744 mol) in 100 mL H$_2$O within 15 min. The reaction mixture was stirred at 55° C. for 2 h. To this solution was added dropwise a solution of potassium carbonate (51.4 g, 0.372 mol) in 150 mL of H$_2$O and then, about half of the volume was evaporated in vacuo. The reaction mixture was diluted with 2-3-fold (v) of EtOH. The precipitate was filtered and the mother liquor evaporated to about 20% of its volume. Hydrogen iodide (95 g, 744 mmol) was added to the suspension. The reaction mixture was evaporated in vacuo. The residue was triturated with EtOH and the solid was filtrated to give the title compound (40 g, yield: 22.7%) as a white solid. LC-MS: m/z 110 (M+H)$R_t$=1.44 min. $^1$H NMR (400 MHz, DMSO-d$_6$): δ=8.28 (s, 2H), 8.04 (d, J=6 Hz, 1H), 7.84-7.80 (m, 1H), 7.09-7.06 (m, 1H), 6.87-6.83 (m, 1H).

g1.2) 2-([1,2,4]-Triazolo[1,5-a]pyridin-2-yl)acetonitrile

To a mixture of 2-iminopyridin-1(2H)-amine hydroiodide e (40 g, 169 mmol) and ethyl 2-cyanoacetate (38.2 g, 337 mmol) in ethanol (40 mL) sodium hydroxide (6.75 g, 169 mmol) was added. The reaction mixture was stirred at reflux overnight. Upon cooling a precipitate formed. The solid was filtered off, washed with a small amount of cool ethanol, dried and purified by column chromatography on silica gel (eluted with PE/EA from 3:1 to 1:1) to give the title compound (13 g, yield: 46.6%) as a white solid.

LC-MS: m/z 159 (M+H)$R_t$=1.15 min. $^1$H NMR (400 MHz, d6-DMSO): δ=8.94 (d, J=6.8 Hz, 1H), 7.81 (d, J=7.2 Hz, 1H), 7.70 (t, J=8.0 Hz, 1H), 7.23 (t, J=6.8 Hz, 1H), 4.40 (s, 2H).

g1.3) 2-([1,2,4]-Triazolo[1,5-a]pyridin-2-yl)ethylamine

To a solution of 2-([1,2,4]triazolo[1,5-a]pyridin-2-yl)acetonitrile (7 g, 44.3 mmol) in THF (100 mL) was added BH$_3$.THF (221 mL, 221 mmol) dropwise at 0° C. After 30 min., the mixture was allowed to stir at refluxed for 3 hours. The reaction was monitored by LCMS. The reaction was quenched with MeOH (150 mL) and the resulting mixture was refluxed for 2 hours. The solvent was distilled off under reduced pressure. The residue was purified by chromatography column (eluted with DCM/MeOH from 20:1 to 10:1) to give a crude product, which was recrystallized from PE/EA (10:1) to give the title compound (2.8 g, yield: 39%) as a light yellow solid. LC-MS: m/z 163 (M+H)$R_t$=0.57 min. $^1$H NMR (400 MHz, CDCl$_3$): δ=8.53 (d, J=6.8 Hz, 1H), 7.69 (d, J=9.2 Hz, 1H), 7.52-7.48 (m, 1H), 7.01-6.97 (m, 1H), 3.24 (t, J=6.4 Hz, 2H), 3.09 (t, J=6.4 Hz, 2H).

The compounds of the following Preparation Examples can be prepared using the standard operation procedures described above.

Preparation Example 1

6-[2-(Benzofuran-2-yl)ethyl]-4-bromo-7H-pyrrolo[3,4-b]pyridin-5-one

ESI-MS: [M+Na+]=379.00, [M+H+]=357.95

Preparation Example 2

6-[2-(Benzothiophen-2-yl)ethyl]-4-bromo-7H-pyrrolo[3,4-b]pyridin-5-one

Preparation Example 3

4-Bromo-6-[2-(7-methyl-2-quinolyl)ethyl]-7H-pyrrolo[3,4-b]pyridin-5-one

ESI-MS: 384.00, [M+H+]=383.05

Preparation Example 4

4-Bromo-6-[2-(5-isopropyl-2-pyridyl)ethyl]-7H-pyrrolo[3,4-b]pyridin-5-one

ESI-MS: 362.10, [M+H+]=361.05

Preparation Example 5

2-[2-(1,3-Benzothiazol-2-yl)ethyl]-4-bromo-7-methoxy-isoindolin-1-one

ESI-MS: 405.00, [M+H+]=404.00

Preparation Example 6

4-Bromo-6-[2-(6-chloro-1,3-benzothiazol-2-yl)ethyl]-7H-pyrrolo[3,4-b]pyridin-5-one ESI-MS: [M+Na+]=431.90, [M+H+]=409.90

Preparation Example 7

4-Bromo-6-[2-(6-fluoro-1,3-benzothiazol-2-yl)ethyl]-7H-pyrrolo[3,4-b]pyridin-5-one ESI-MS: [M+Na+]=415.85, [M+H+]=392.95

Preparation Example 8

4-Bromo-6-[2-(6-methyl-2-quinolyl)ethyl]-7H-pyrrolo[3,4-b]pyridin-5-one

ESI-MS: 384.00, [M+]=382.00

Preparation Example 9

4-Bromo-6-[2-(4,5-dimethylthiazol-2-yl)ethyl]-7H-pyrrolo[3,4-b]pyridin-5-one

ESI-MS: [M+Na+]=375.95, 355.00, [M+H+]=353.00

Preparation Example 10

4-Bromo-6-[2-(4-methyl-2-pyridyl)ethyl]-7H-pyrrolo[3,4-b]pyridin-5-one

ESI-MS: [2M+Na+]=688.10, 335.00, [M+H+]=333.05

Preparation Example 11

4-Bromo-6-[2-(3-methyl-2-pyridyl)ethyl]-7H-pyrrolo[3,4-b]pyridin-5-one

ESI-MS: [M+H+]=333.00

Preparation Example 12

4-Bromo-6-[2-(4-ethylthiazol-2-yl)ethyl]-7H-pyrrolo[3,4-b]pyridin-5-one

ESI-MS: [M+Na+]=376.00, 355.00, [M+H+]=353.00

Preparation Example 13

2-[2-(1,3-Benzothiazol-2-yl)ethyl]-4-bromo-isoindolin-1-one

ESI-MS: [M+]=373.00

Preparation Example 14

4-[(Z)-2-(Diisopropylamino)vinyl]-6-[2-(2-quinolyl)ethyl]-7H-pyrrolo[3,4-b]pyridin-5-one

ESI-MS: 416.20, [M+H+]=415.20

Preparation Example 15

4-Chloro-6-(2-quinolin-2-yl-ethyl)-5,6-dihydro-pyrrolo[3,4-b]pyridin-7-one

ESI-MS: [M+H+]=324.10

Preparation Example 16

4-Chloro-6-(2-imidazo[1,2-a]pyridin-2-yl-ethyl)-5,6-dihydro-pyrrolo[3,4-b]pyridin-7-one

ESI-MS: [M+H+]=313.10

Preparation Example 17

4-Bromo-6-[2-(5-methyl-pyridin-2-yl)-ethyl]-6,7-dihydro-pyrrolo[3,4-b]pyridin-5-one

ESI-MS: [M+H+]=333.00

Preparation Example 18

4-Bromo-6-(2-pyridin-2-yl-ethyl)-6,7-dihydro-pyrrolo[3,4-b]pyridin-5-one

ESI-MS: [M+Na+]=341.95, [M+H+]=319.00

Preparation Example 19

4-Bromo-6-[2-(5-phenyl-pyridin-2-yl)-ethyl]-6,7-dihydro-pyrrolo[3,4-b]pyridin-5-one

ESI-MS: [M+H+]=395.00

Preparation Example 20

4-Bromo-6-[2-(6-methyl-pyridin-2-yl)-ethyl]-6,7-dihydro-pyrrolo[3,4-b]pyridin-5-one

ESI-MS: [M+H+]=333.00

Preparation Example 21

4-Bromo-6-[2-(1-methyl-1H-imidazol-2-yl)-ethyl]-6,7-dihydro-pyrrolo[3,4-b]pyridin-5-one

ESI-MS: [M+H+]=322.05

Preparation Example 22

4-Bromo-6-[2-(1-methyl-1H-imidazol-4-yl)-ethyl]-6,7-dihydro-pyrrolo[3,4-b]pyridin-5-one

ESI-MS: [M+H+]=322.00

Preparation Example 23

7-Bromo-2-(2-quinoxalin-2-ylethyl)isoindolin-1-one

ESI-MS: [M+H+]=369.00

Preparation Example 24

4-Bromo-6-[2-(5,6-dimethyl-2-pyridyl)ethyl]-7H-pyrrolo[3,4-b]pyridin-5-one

ESI-MS: [M+H+]=347.10

Preparation Example 25

4-Bromo-6-[2-(7-ethylimidazo[1,2-a]pyridin-2-yl)ethyl]-7H-pyrrolo[3,4-b]pyridin-5-one

ESI-MS: [M+H+]=386.10

Preparation Example 26

4-Bromo-6-[2-(6-methoxy-2-pyridyl)ethyl]-7H-pyrrolo[3,4-b]pyridin-5-one

ESI-MS: [M+]=348.10

Preparation Example 27

4-Bromo-6-[2-(3,5-dimethyl-2-pyridyl)ethyl]-7H-pyrrolo[3,4-b]pyridin-5-one

ESI-MS: [M+H+]=347.00

Preparation Example 28

4-Bromo-6-[2-(6-fluoroimidazo[1,2-a]pyridin-2-yl)ethyl]-7H-pyrrolo[3,4-b]pyridin-5-one

ESI-MS: 377.00 (M+H+), [M+H+]=376.00

Preparation Example 29

4-Bromo-6-[2-(4-cyclopropylthiazol-2-yl)ethyl]-7H-pyrrolo[3,4-b]pyridin-5-one

ESI-MS: [M+H+]=365.00

II. Preparation of Compounds of the Formula I
II.1 Preparation of Compounds of the Formula I in which $X^3$ is N

Example 1

4-Pyridin-4-yl-2-(2-quinolin-2-yl-ethyl)-1,2-dihydro-pyrrolo[3,4-c]pyridin-3-one; compound with trifluoro-acetic acid 1.1 2-Cyano-3-methyl-but-2-enoic acid methyl ester A suspension of cyanoacetic acid methyl ester (56.60 g, 0.57 mol), acetone (39.80 g, 0.68 mol), HOAc (6.0 g, 0.10 mol) and NH$_4$OAc (4.0 g, 0.05 mol) in toluene (500 mL) was heated at reflux overnight with removal of water in a Dean-Stark trap. After cooling, the solvent was removed under reduced pressure and the residue was purified by column chromatography on silica using PE: EA=3:1 to give the title compound (40.30 g, 50.8%). $^1$H-NMR (400 MHz, CDCl$_3$): δ 3.82 (s, 3H), 2.42 (s, 3H), 2.32 (s, 3H), LCMS (ESI+): m/z 140 (M+H)$^+$, R$_t$: 0.72 min.

1.2 2-Cyano-5-dimethylamino-3-methyl-penta-2,4-dienoic acid methyl ester

N,N-Dimethylformamide dimethyl acetal (34.85 g, 0.29 mol) was added dropwise to a solution of 2-cyano-3-methyl-but-2-enoic acid methyl ester (40.30 g, 0.29 mol) in absolute EtOH (200 mL). After the addition, the solution was heated at reflux overnight and then concentrated to yield the crude title compound (36.80 g, 65.3%) which was used in the next step without further purification. LCMS (ESI+): m/z 195 (M+H)$^+$, R$_t$: 1.64 min.

1.3 2-Bromo-4-methyl-nicotinic acid methyl ester

The compound from example 1.2 (36.80 g, 0.19 mol) was dissolved in AcOH (150 mL) and the mixture was heated to 40° C. A solution of 30% HBr—AcOH (250 mL) was added dropwise and then the mixture was heated to 55° C. with stirring. After heating for 3 hours, the solution was concentrated, poured into water (200 mL), neutralized with solid Na$_2$CO$_3$, extracted with DCM (3×300 mL) and dried over Na$_2$SO$_4$. The organic phase was concentrated to dryness and the residue was purified by column chromatography on silica using PE: EA=5:1 to give the title compound as an off-white solid (34.68 g, 79.3%). $^1$H-NMR (400 MHz, CDCl$_3$): δ 8.26-8.25 (m, 1H), 7.15-7.14 (m, 1H), 3.98 (s, 3H), 2.34 (s, 3H). LCMS (ESI+): m/z 232 (M+2)$^+$, R$_t$: 1.97 min.

1.4 4-Methyl-[2,4]bipyridinyl-3-carboxylic acid methyl ester

Dioxane (70 mL) and 2N aqueous Cs$_2$CO$_3$ (38 mL, 0.076 mol) were added to a flask containing the compound from Example 1.3 (4.35 g, 0.019 mol), pyridine-4-boronic acid (2.80 g, 0.023 mol) and PdCl$_2$(dppf).CH$_2$Cl$_2$ (1.55 g, 0.0019 mol) under N$_2$ atmosphere. The reaction mixture was then heated to 95° C. and stirred overnight. The reaction mixture was cooled to room temperature and then filtered through Celite, the solvent was removed and the crude was purified with silica gel column chromatography (PE: EA=3/1 to 1/5) to give the crude title compound as an off-white solid (2.89 g, 66.7%). $^1$H-NMR (400 MHz, CDCl$_3$): δ 8.71-8.69 (m, 2H), 8.63-8.61 (m, 1H), 7.50-7.51 (m, 2H), 7.27-7.24 (m, 1H), 3.69 (s, 3H), 2.45 (s, 3H). LCMS (ESI+): m/z 229 (M+H)$^+$, R$_t$: 1.65 min.

1.5 4-Pyridin-4-yl-2-(2-quinolin-2-yl-ethyl)-1,2-dihydro-pyrrolo[3,4-c]pyridin-3-one To a solution of diisopropylamine (7.4 mL, 52.8 mmol) in THF (20 mL) was added dropwise n-BuLi (2.5 M solution in hexane, 20 mL, 52.8 mmol) at −78° C. The mixture was allowed to warm to 0° C. in 30 minutes. The compound from Example 1.4 (0.50 g, 2.2 mmol) was added dropwise to the above prepared LDA solution (5 mL) at −30° C., then the mixture was warmed to 0° C. slowly and stirred at this temperature for 30 minutes. A solution of BrCCl$_2$CCl$_2$Br (1.72 g, 5.28 mmol) in THF (5 mL) was added dropwise to the reaction mixture at −30° C., and the mixture was stirred at 0° C. for 2 h. After that, a suspension of 2-quinolin-2-yl-ethylamine from Example a1 (0.50 g, 3.0 mmol) in THF (20 mL) was added to the mixture and the reaction was stirred at room temperature overnight. The crude product was purified by Prep-HPLC to get the title compound (53 mg, 13.3%) as a white solid. $^1$H-NMR (400 MHz, MeOD): δ 9.00 (d, J=8.4 Hz, 1H), 8.91 (dm, J=5.2 Hz, 1H), 8.81 (dm, J=5.6 Hz, 2H), 8.39 (d, J=6.0 Hz, 2H), 8.24 (m, 2H), 8.00 (m, 2H), 7.89-7.83 (m, 2H), 4.85 (s, 2H), 4.23 (t, J=6.8 Hz, 2H), 3.72 (t, J=6.8 Hz, 2H); LCMS (ESI+): m/z 367 (M+H)$^+$, R$_t$: 1.46 min.

II.2 Preparation of Compounds of the Formula I in which $X^2$ is N

Example 2

7-Pyridin-4-yl-2-(2-quinolin-2-yl-ethyl)-2,3-dihydro-pyrrolo[3,4-c]pyridin-1-one 2.1 3-Bromo-5-methyl-pyridin-4-ylamine To a solution of 4-amino-3-picoline (10 g, 0.092 mmol) and HBr (50 mL) heated to 70° C. was added 15% H$_2$O$_2$ (16 mL) over one h. The reaction mixture was stirred for an additional hour and poured into ice (100 g). The pH of the solution was adjusted to about 5 with 50% NaOH and the resulting red precipitate was filtered. The pH was raised to about 9 and the resulting white precipitate was collected by filtration to afford the title compound (13.5 g, 78%).

2.2 5-Methyl-[3,4']bipyridinyl-4-ylamine

A mixture of 3-bromo-5-methyl-pyridin-4-ylamine (1.00 g, 5.347 mmol), pyridin-4-yl boronic acid (0.65 g, 5.347 mmol), $K_2CO_3$ (2.22 g, 16.04 mmol) and Pd(dppf)Cl$_2$ (436 mg, 0.5347 mmol) in water (3 mL) and 1,4-dioxane (15 mL) was stirred at 105° C. overnight. The mixture was diluted with EtOAc (100 mL) and washed with brine (30 mL×4). The organic layer was dried over $Na_2SO_4$, filtered and concentrated in vacuo. The residue was purified on a silica column (EtOAc) to afford the title product as a white solid (554 mg, yield 56%). LCMS (ESI+): m/z 186 (M+H)$^+$, R$_t$: 1.16 min.

2.3 4-Bromo-5-methyl-[3,4']bipyridinyl

To a cooled (0° C.) suspension of the compound from Example 2.2 (270 mg, 1.458 mmol) and CuBr (839 mg, 5.832 mmol) in 75% $H_2SO_4$ (5 mL) was added dropwise a solution of $NaNO_2$ (332 mg, 4.811 mmol) in water (2 mL). The mixture was stirred at 0° C. for 3 h and then neutralized with NaOH (2 N) at 0° C. The precipitates were filtered off, and the filtrate was extracted with EtOAc (50 mL×3). The organic layer was dried over $Na_2SO_4$, filtered and concentrated in vacuo. The residue was purified on a silica column (EtOAc) to afford the title product as an off-white solid (230 mg, yield 63%). $^1$H NMR (CDCl$_3$/TMS, 400 MHz) δ: 8.73 (s, 2H), 8.46 (s, 1H), 8.29 (s, 1H), 7.35-7.40 (m, 2H), 2.49 (s, 3H); LCMS (ESI+): m/z 249 (M+H)$^+$, R$_t$: 1.70 min.

2.4 5-Methyl-[3,4']bipyridinyl-4-carboxylic acid methyl ester

A mixture of 4-bromo-5-methyl-[3,4']bipyridinyl (3 g, 12.04 mmol), PdCl$_2$(dppf) (8.81 g, 12.04 mmol) and triethylamine (1.219 g, 12.04 mmol) in methanol (50 mL) was heated under CO atmosphere (10 atm) to 100° C. for about 8 h in a 100 mL pressure reaction vessel. The solution was concentrated to dryness to give a brown oil. The residue was purified by silica column (5:1=PE: EA). Collected fractions were concentrated to afford the title compound as an off-white solid (1.5 g, 42.6%). LCMS (ESI+): m/z 229 (M+H)$^+$, R$_t$: 0.52 min.

2.5 7-Pyridin-4-yl-2-(2-quinolin-2-yl-ethyl)-2,3-dihydro-pyrrolo[3,4-c]pyridin-1-one To a solution of diisopropylamine (7.4 mL, 52.8 mmol) in THF (20 mL) was added dropwise n-BuLi (2.5 M solution in hexane, 20 mL, 52.8 mmol) in THF (5 mL) at −78° C. The mixture was allowed to warm to 0° C. in 30 minutes. The compound from Example 2.4 (0.10 g, 0.44 mmol) was added dropwise to the above prepared LDA solution (1 mL) at −78° C., then the mixture was warmed to −30° C. slowly and stirred at this temperature for 30 minutes. A solution of Freon 113 (0.23 g, 1.05 mmol) in THF (5 mL) was added dropwise to the reaction mixture at −30° C., and the mixture was stirred at 0° C. for 2 h. After that, a suspension of 2-(quinolin-2-yl)ethylamine from Example a1 (0.07 g, 0.45 mmol) in dry THF (2 mL) was added to the mixture. TBAI (10 mg, 0.04 mmol) was added. The reaction mixture was stirred at room temperature overnight. The crude product was purified by plate-TLC using CH$_2$Cl$_2$: MeOH=10:1 and then by prep-HPLC to get the title compound (27 mg, 12.5%) as a yellow oil. LCMS (ESI+): m/z 367 (M+H)$^+$, R$_t$: 1.16 min. $^1$H-NMR (400 MHz, MeOD): δ 3.70 (t, J=6.4 Hz, 2H), 4.24 (t, J=6.4 Hz, 2H), 4.88 (s, 2H), 7.93 (t, J=7.6 Hz, 1H), 8.02-8.05 (dm, J=8.0 Hz, 1H), 8.10-8.13 (m, 3H), 8.21 (d, J=8.8 Hz, 1H), 8.28 (d, J=6.4 Hz, 1H), 8.83 (br, 3H), 8.99 (d, J=8.8 Hz, 1H), 9.09 (br, 1H).

II.3 Preparation of Compounds of the Formula I in which X$^1$ is N

Example 3

4-Pyridin-4-yl-6-(2-quinolin-2-yl-ethyl)-6,7-di-hydro-pyrrolo[3,4-b]pyridin-5-one 3.1 3-(2-Ethoxycarbonyl-ethylamino)-but-2-enoic acid ethyl ester A mixture of 3-aminopropionic acid ethyl ester hydrochloride (53.12 g, 0.35 mmol), 3-oxobutyric acid ethyl ester (43.70 mL, 0.35 mol) and anhydrous potassium carbonate (116.10 g, 0.84 mol) in 600 mL of toluene was refluxed in an equipment with a Dean-Stark trap overnight. The reaction mixture was cooled and diluted with EtOAc (300 mL) and CH$_2$Cl$_2$ (200 mL), filtered, and the obtained solution was concentrated under reduced pressure, yielding the crude title compound (76.2 g, 94.3%) which was used in the next step without further purification. LCMS (ESI+): m/z 230 (M+H)$^+$, R$_t$: 1.80 min.

3.2 2-Methyl-4-oxo-1,4,5,6-tetrahydropyridine-3-carboxylic acid ethyl ester

A solution of the compound from Example 3.1 (76.2 g, 0.33 mol) in 600 mL of toluene was supplied with sodium hydride (24 g of a 50% dispersion in oil, 0.50 mol) and the resulting yellow suspension was stirred and heated at reflux overnight. After the mixture had been cooled to room temperature, the reaction was quenched with water (300 mL) and the organic solvent was removed in vacuum. The obtained alkaline, aqueous solution was treated with 15% hydrochloric acid (200 mL), and then washed with Et$_2$O (3×300 mL). The aqueous phase was basified with NaHCO$_3$ and extracted with CH$_2$Cl$_2$ solution (3×300 mL). The combined organic layer was dried over Na$_2$SO$_4$, and concentrated to give the crude title compound (20.0 g, 33.3%) as a pale yellow solid which was used in the next step without further purification. LCMS (ESI+): m/z 184 (M+H)$^+$, R$_t$: 1.34 min.

3.3 2-Methyl-4-oxo-1,4-dihydro-pyridine-3-carboxylic acid ethyl ester

A mixture of the compound from Example 3.2 (20.0 g, 0.11 mol) and lead tetraacetate (146.2 g, 0.33 mol) in 250 mL of acetic acid was heated under reflux with stirring overnight. Next, the solvent was removed under diminished pressure and the dark yellow, oily residue was dissolved in EtOH/CH$_2$Cl$_2$ (1:10, 500 mL). The resulting suspension was filtered through a pad of silica gel (200 g), and the filtrate was concentrated to afford the crude title compound (16.8 g, 84.0%). $^1$H-NMR (400 MHz, DMSO-d$_6$): δ 11.57 (s, 1H), 7.56 (s, 1H), 6.07 (s, 1H), 4.22-4.16 (m, 2H), 3.34 (s, 3H), 2.18 (s, 3H), 1.25-1.22 (m, 3H). LCMS (ESI+): m/z 182 (M+H)$^+$, R$_t$: 1.24 min.

3.4 4-Chloro-2-methyl-nicotinic acid ethyl ester

The compound from Example 3.3 (16.8 g, 0.092 mol) in 150 mL of POCl$_3$ was stirred at reflux overnight. The reaction mixture was poured into ice, adjusted to pH=7~8 with solid NaOH, and then extracted with EtOAc (3×300 mL). The organic phase was washed with sat. NaHCO$_3$ and sat. NaCl solution, then the solvent was removed under reduced pressure and the residue was purified by column chromatography on silica gel using PE: EA=5:1 to get the title compound (4.2 g, 26.0%). $^1$H-NMR (400 MHz, DMSO-d$_6$): δ 8.53-8.52 (m, 1H), 7.54-7.52 (m, 1H), 6.07 (s, 1H), 4.43-4.41 (m, 2H), 2.52-2.44 (m, 3H), 1.36-1.32 (m, 3H). LCMS (ESI+): m/z 200 (M+H)$^+$, R$_t$: 1.83 min.

3.5 2-Methyl-[4,4']bipyridinyl-3-carboxylic acid ethyl ester

Dioxane (50 mL) and 2N aqueous Cs$_2$CO$_3$ (42 mL, 0.084 mol) were added to a flask containing the compound from Example 3.4 (4.20 g, 0.021 mol), pyridin-4-ylboronic acid (3.10 g, 0.025 mol) and PdCl$_2$(dppf).CH$_2$Cl$_2$ (1.71 g, 0.0021 mol) under N$_2$ atmosphere. The reaction mixture was then heated to 95° C. and stirred overnight. After the reaction mixture was cooled to room temperature and filtered over Celite, the solvent was removed and the crude compound was purified by silica gel column chromatography (PE: EA=3/1 to 1/5) to give the title compound (3.46 g, 68.1%). $^1$H-NMR (400 MHz, CDCl$_3$) δ: 8.69-8.63 (m, 3H), 8.63-8.61 (m, 1H), 7.31-7.26 (m, 2H), 7.15-7.14 (m, 1H), 4.15-4.13 (m, 2H), 2.67 (s, 3H), 1.06-1.02 (m, 3H). LCMS (ESI+): m/z 243 (M+H)$^+$, R$_t$: 1.70 min.

3.6 4-Pyridin-4-yl-6-(2-quinolin-2-yl-ethyl)-6,7-dihydro-pyrrolo[3,4-b]pyridin-5-one To a solution of diisopropylamine (7.4 mL, 52.8 mmol) in THF (20 mL) was added dropwise n-BuLi (2.5 M solution in hexane, 20 mL, 52.8 mmol) at −78° C. The mixture was allowed to warm to 0° C. in 30 minutes. The compound from Example 3.5 (0.50 g, 2.0 mmol) was added dropwise to the above prepared LDA solution (5 mL) at −30° C., then the mixture was warmed to 0° C. slowly and stirred at this temperature for 30 minutes. A solution of Freon 113 (562 mg, 3.0 mmol) in THF (5 mL) was added dropwise to the reaction mixture at −30° C., and the mixture was stirred at 0° C. for 2 h. After that, a suspension of 2-(quinolin-2-yl) ethylamine from Example a1 (0.50 g, 3.0 mmol) in DMF (2 mL) was added to the mixture and then TBAI (50 mg, 0.2 mmol). The reaction mixture was heated to 40° C. for 2 h. The crude product was first purified by plate-TLC using CH$_2$Cl$_2$: MeOH=10:1 to get the crude title compound (20 mg, 2.7%) which was then further purified by prep-HPLC. $^1$H-NMR (400 MHz, MeOD): δ 8.79 (d, J=5.2 Hz, 1H), 8.57-8.55 (m, 2H), 8.29 (d, J=8.4 Hz, 1H), 7.93 (d, J=8.0 Hz, 1H), 7.85 (d, J=8.8 Hz, 1H), 7.73-7.69 (m, 1H), 7.60-7.47 (m, 5H), 4.62 (s, 2H), 4.13 (t, J=6.8 Hz, 2H), 3.40-3.37 (t, J=6.8 Hz, 2H). LCMS (ESI+): m/z 367 (M+H)$^+$, R$_t$: 1.75 min.

II.4 Preparation of Compounds of the Formula I in which A is CR5R6

Example 4

3,3-Difluoro-7-pyridin-4-yl-2-(2-quinolin-2-yl-ethyl)-2,3-dihydro-isoindol-1-one 4.1 3-Bromophthalic acid KOH (1 g, 0.019 mol) was added to a solution of 1-bromo-2,3-dimethylbenzene (5 g, 0.027 mol) in water (200 mL). Then a solution of KMnO$_4$ (20 g, 0.13 mol) in water (100 mL) was added dropwise. After addition, the mixture was heated at reflux for 16 h. EtOH was added to reduce excessive KMnO$_4$ and the mixture was filtered. The filtrate was acidified with conc. HCl to pH=3, concentrated to 50 mL and then extracted with EA (200 mL). The organic layer was washed with water (50 mL) and dried over Na$_2$SO$_4$, and evaporated to afford the title compound as a white solid (4.5 g, 68%). LCMS (ESI+): m/z 245 (M+H)$^+$, R$_t$: 0.31 min.

4.2 4-Bromo-2-(2-quinolin-2-yl-ethyl)-isoindole-1,3-dione

A mixture of 3-bromophthalic acid (0.8 g, 3.3 mmol), 2-(quinolin-2-yl)ethanamine from Example a1 (1.1 g, 6.6 mmol) and AcONa (406 mg, 5.0 mmol) in AcOH (15 mL) was heated at reflux for 2 h. The solvent was evaporated under reduced pressure. The residue was dissolved in EA (15 mL) and washed with saturated Na$_2$CO$_3$ solution (10 mL) and water (10 mL) in sequence. The organic layer was dried over Na$_2$SO$_4$ and concentrated. The residue solid was washed with CH$_3$OH to give the title compound as a brown solid (400 mg, 32%). LCMS (ESI+): m/z 381 (M+H)$^+$, R$_t$: 1.58 min.

4.3 7-Bromo-2-(2-quinolin-2-yl-ethyl)-3-thioxo-2,3-dihydroisoindol-1-one

A mixture of the compound from Example 4.2 (0.35 g, 0.92 mmol) and Lawenson's reagent (409 mg, 1.01 mmol) in toluene (15 mL) was heated to reflux for 16 h. The solvent was removed under reduced pressure. The residue was purified by plate-TLC (DCM: PE=2:1) to give the title compound as a yellow solid (200 mg, 55%). LCMS (ESI+): m/z 397 (M+H)$^+$, R$_t$: 2.39 min.

4.4 7-Bromo-3,3-difluoro-2-(2-quinolin-2-yl-ethyl)-2,3-dihydro-isoindol-1-one

NBS (99 mg, 0.56 mmol) was added to a solution of the compound from Example 4.3 (100 mg, 0.25 mmol) and n-Bu$_4$NH$_2$F$_3$ (226 mg, 0.75 mmol) in DCM (10 mL) at 0° C. The reaction mixture was stirred at room temperature for 1 h. The mixture was poured into aqueous NaHSO$_3$—NaHCO$_3$ solution (0.1 M-0.1 M, 20 mL). The organic layer was dried over Na$_2$SO$_4$ and evaporated under reduced pressure. The residue was purified by plate-TLC (PE: EA=3:1) to give the title compound as a brown solid (50 mg, 50%). LCMS (ESI+): m/z 403 (M+H)$^+$, R$_t$: 2.29 min.

4.5 3,3-Difluoro-7-pyridin-4-yl-2-(2-quinolin-2-yl-ethyl)-2,3-dihydro-isoindol-1-one A mixture of the compound from Example 4.4 (50 mg, 0.12 mmol), PdCl$_2$(dppf)-CH$_2$Cl$_2$ adduct (13 mg, 0.016 mmol), pyridin-4-boronic acid (17 mg, 0.14 mmol) and K$_2$CO$_3$ (50 mg, 0.36 mmol) in dioxane/water (3:1, 20 mL) was heated to 100° C. for 30 min. The solvent was removed under reduced pressure. The residue was dissolved in DCM (10 mL), washed with water (5 mL*2). The organic layer was dried over Na$_2$SO$_4$ and concentrated. The residue oil was purified by silica gel chromatography (PE: EA=2: 1) to give the title compound as a white solid (40 mg, 80%). LCMS (ESI+): m/z 402 (M+H)$^+$, R$_t$: 2.12 min. $^1$H NMR (CDCl$_3$, 400 MHz): δ 3.41 (t, J=7.8 Hz, 2 H), 4.10 (t, J=8 Hz, 2 H), 7.35 (d, J=8.4 Hz, 1 H), 7.42 (d, J=5.2 Hz, 2 H), 7.52-7.513 (m, 2 H), 7.702-7.805 (m, 4 H), 8.047-8.102 (m, 2 H), 8.69 (s, 2 H).

Example 5

7-Pyridin-4-yl-2-(2-quinolin-2-yl-ethyl)-2,3-dihydro-isoindol-1-one 5.1 2-Bromo-6-methylbenzoic acid A solution of CuBr (45 g, 316 mmol) in HBr (80 mL) and H$_2$O (80 mL) was stirred at room temperature (the solution 1).

2-Amino-6-methylbenzoic acid (20 g, 132 mmol) was dissolved in HBr (80 mL) and H$_2$O (80 mL). The solution was cooled to 0° C. Aq. NaNO$_2$ (11 g, 160 mmol, in 20 mL water) was added dropwise while the temperature was maintained at 0-10° C. The mixture was stirred for 20 min. (the solution 2).

The solution 1 was added dropwise to the solution 2. Then the mixture was stirred at room temperature for 2 h. The solid was filtered to give the title compound as a yellow solid (16 g, 56%). LCMS (ESI+): m/z 215 (M+H)$^+$, R$_t$: 0.759 min.

5.2 2-Bromo-6-methylbenzoic acid methyl ester

2-Bromo-6-methylbenzoic acid (16 g, 74 mmol) was dissolved in $SOCl_2$ (30 mL). The mixture was stirred at reflux for 4 h. The solvent was evaporated. The residue was dissolved in methanol (40 mL) and the resulting solution was stirred at reflux overnight. Then the solvent was evaporated and the residue was purified by column chromatography on silica gel (PE: EA=50:1) to give the title compound as yellow oil (16 g, 93%). LCMS (ESI+): m/z 229 (M+H)$^+$, $R_t$: 0.868 min.

5.3 2-Bromo-6-bromomethylbenzoic acid methyl ester

To a solution of 2-bromo-6-methylbenzoic acid methyl ester (6 g, 26 mmol) in $CCl_4$ (40 mL) was added NBS (4.7 g, 26 mmol) and AIBN (215 mg, 1.3 mmol) under $N_2$. The mixture was heated to reflux overnight. The solution was cooled and filtered. The filtrate was concentrated and purified by column chromatography on silica gel (PE: EA=100:1) to give the compound as an off-white solid (6.2 g, 76%). LCMS (ESI+): m/z 307 (M+H)$^+$, $R_t$: 0.879 min.

5.4 7-Bromo-2-(2-quinolin-2-yl-ethyl)-2,3-dihydro-isoindol-1-one

A solution of 2-bromo-6-bromomethylbenzoic acid methyl ester (300 mg, 0.97 mmol) and 2-quinolin-2-ylethylamine from Example a1 (184 mg, 1.0 mmol) in anhydrous EtOH (10 mL) was stirred at reflux under $N_2$ overnight. The solvent was evaporated. The residue was purified by column chromatography on silica gel (DCM: $CH_3OH$=20:1) to give the title compound as a white solid (150 mg, 42%). LCMS (ESI+): m/z 367 (M+H)$^+$, $R_t$: 0.693 min.

5.5 7-Pyridin-4-yl-2-(2-quinolin-2-yl-ethyl)-2,3-dihydro-isoindol-1-one

A mixture of 7-bromo-2-(2-quinolin-2-yl-ethyl)-2,3-dihydro-isoindol-1-one (300 mg, 0.8 mmol), pyridine-4-ylboronic acid (151 mg, 1.2 mmol), Pd(dppf)$Cl_2$ (66 mg) and $Cs_2CO_3$ (666 mg, 2.0 mmol) in DME/EtOH/$H_2O$ (1/1/1, 15 mL) was stirred at 100° C. for 15 min. in a microwave. The solution was concentrated and purified by plate-TLC (PE/EA=1:2) to give the title compound as white solid (170 mg, 56%). LCMS (ESI+): m/z 366 (M+H)$^+$, $R_t$: 1.853 min. $^1$H NMR (DMSO-$d_6$, 400 MHz): δ 8.56 (dd, J=4.4 Hz, 1.6 Hz, 2H), 8.29 (d, J=8.4 Hz, 1H), 7.94 (d, J=7.2 Hz, 1H), 7.89 (d, J=8.8 Hz, 1H), 7.72-7.65 (m, 3H), 7.56-7.54 (m, 1H), 7.48 (d, J=8.8 Hz, 1H), 7.40 (dd, J=4.4 Hz, 1.6 Hz, 3H), 4.54 (s, 2H), 3.99 (t, J=7.2 Hz, 2H), 3.27 (t, J=7.4 Hz, 2H)

Example 6

3,3-Dimethyl-7-pyridin-4-yl-2-(2-quinolin-2-yl-ethyl)-2,3-dihydro-isoindol-1-one To a solution of the compound from Example 5 (150 mg, 0.4 mmol) in anhydrous THF (15 mL) was added dropwise LiHMDS (1.2 mL, 1.2 mmol) at −70° C. and stirred for 30 min. Then iodomethane (174 mg, 1.2 mmol) was added dropwise. The resulting solution was warmed slowly to room temperature and stirred for 1 hour. Water (2 mL) was added and the solvent was evaporated. The residue was purified by column chromatography on silica gel (DCM: $CH_3OH$=20:1) to give compound the title compound as a white solid (16 mg, 10%). LCMS (ESI+): m/z 394 (M+H)$^+$, $R_t$: 1.419 min. $^1$H-NMR (400 MHz, $CD_3OD$): δ 8.56 (d, J=5.2 Hz, 2H), 8.29 (d, J=8.4 Hz, 1H), 8.01 (d, J=8.4 Hz, 1H), 7.92 (d, J=8.4 Hz, 1H), 7.65-7.79 (m, 7H), 7.44 (d, J=8.0 Hz, 1H), 3.91 (t, J=7.2 Hz, 2H), 3.40 (t, J=7.6 Hz, 2H), 1.51 (s, 6H).

Examples 7 to 12 were prepared analogously to the method for Example 5.

Example 7

6-[3-oxo-2-(2-quinolin-2-yl-ethyl)-2,3-dihydro-1H-isoindol-4-yl]-1H-quinazolin-4-one trifluoroacetate ESI-MS: [M+Na$^+$]=456.20, [M+H$^+$]=433.10.

Example 8

7-(3-Methyl-3H-benzoimidazol-5-yl)-2-(2-quinolin-2-yl-ethyl)-2,3-dihydro-isoindol-1-one trifluoroacetate

ESI-MS: [M+H$^+$]=419.20.

Example 9

5-[3-oxo-2-(2-quinolin-2-yl-ethyl)-2,3-dihydro-1H-isoindol-4-yl]-1,3-dihydro-benzoimidazol-2-one trifluoroacetate

ESI-MS: [M+H]$^+$=421.10.

Example 10

7-(3H-Benzotriazol-5-yl)-2-(2-quinolin-2-yl-ethyl)-2,3-dihydro-isoindol-1-one trifluoroacetate

ESI-MS: [M+H]$^+$=406.10.

Example 11

7-(3H-Benzoimidazol-5-yl)-2-(2-quinolin-2-yl-ethyl)-2,3-dihydro-isoindol-1-one trifluoroacetate

ESI-MS: [M+H]$^+$=405.10.

Example 12

7-(2-Amino-quinazolin-6-yl)-2-(2-quinolin-2-yl-ethyl)-2,3-dihydro-isoindol-1-one

ESI-MS: [M+H]$^+$=432.10.

II.5 Preparation of Compounds I, where $R^9$ and $R^{10}$ are Different from H

Example 13

2-(2,2-Difluoro-2-quinolin-2-yl-ethyl)-7-pyridin-4-yl-2,3-dihydro-isoindol-1-one 13.1. 7-Bromo-2-(2,2-difluoro-2-quinolin-2-yl-ethyl)-2,3-dihydro-isoindol-1-one A solution of 2,2-difluoro-2-quinolin-2-yl-ethylamine from Example b1 (250 mg, 1.2 mmol) and 2-bromo-6-bromomethyl-benzoic acid methyl ester from Example 5.3 (554 mg, 1.8 mmol) in anhydrous EtOH (8 mL) was stirred at reflux under $N_2$ overnight. The solvent was evaporated. The residue was purified by column chromatography on silica gel (PE: EA=3:1) to give the title compound as white solid (150 mg, 31%). LCMS (ESI+): m/z 403 (M+H)$^+$, $R_t$: 0.937 min.

13.2 2-(2,2-Difluoro-2-quinolin-2-yl-ethyl)-7-pyridin-4-yl-2,3-dihydro-isoindol-1-one A mixture of 7-bromo-2-(2,2-difluoro-2-quinolin-2-yl-ethyl)-2,3-dihydro-isoindol-1-one (150 mg, 0.4 mmol), pyridine-4-ylboronic acid (69 mg, 1.5 mmol), Pd(dppf)Cl$_2$ (30 mg) and Cs$_2$CO$_3$ (303 mg, 2.5 mmol) in DME/EtOH/H$_2$O (1/1/1, 5 mL) was stirred at 100° C. for 15 min. in a microwave. The solution was concentrated and purified by plate-TLC (PE: EA=3:1) to give the title product as white solid (65 mg, 44%). LCMS (ESI+): m/z 402 (M+H)$^+$, R$_t$: 2.045 min.

$^1$H-NMR (400 MHz, DMSO): δ 8.62 (d, J=8.8 Hz, 1H), 8.5 (d, J=6.0 Hz, 2H), 8.12 (d, J=8.0 Hz, 1H), 8.06 (d, J=8.4 Hz, 1H), 7.89-7.86 (m, 2H), 7.76-7.72 (m, 3H), 7.46-7.42 (m, 2H), 7.3 (d, J=5.6 Hz, 1 H), 4.70 (s, 2H), 4.52 (t, J=7.2 Hz, 2H).

II.6 Preparation of Compounds of the Formula I in which One of the Radicals R$^1$, R$^2$ or R$^3$ is Different from H

Example 14

6-Fluoro-7-pyridin-4-yl-2-(2-quinolin-2-yl-ethyl)-2,3-dihydro-isoindol-1-one 14.1 3-Fluoro-2-iodo-6-methylbenzoic acid 5-Fluoro-2-methyl-benzoic acid (3.0 g, 19.5 mmol), NIS (4.8 g, 21.4 mmol), Pd(OAc)$_2$ (448 mg, 2 mmol) in 100 mL of DMF were stirred at 110° C. for 2 h. After completion of the reaction, the mixture was cooled to room temperature and poured into water, the product was extracted with EA, the organic layer was collected and dried with Na$_2$SO$_4$, concentrated and purified by silica-gel (PE/EA=6/1) to afford the title compound as an off-white solid (4.9 g, 89.7%). LCMS (ESI+): m/z (M+H)$^+$281.7, R$_t$: 1.786 min.

14.2 3-Fluoro-2-iodo-6-methylbenzoic acid ethyl ester

3-Fluoro-2-iodo-6-methylbenzoic acid (4.2 g, 15 mmol), K$_2$CO$_3$ (6.7 g, 30 mmol) in 50 mL of DMF were stirred at room temperature for 20 min. Ethyl iodide (3.04 g, 19.5 mmol) was added portionwise. The temperature was increased to 50° C. for 1 h. After the reaction was completed (monitored by TLC), solvent was evaporated. The residue was washed with water (3*50 mL) and extracted with EA. The organic layers were combined, dried over Na$_2$SO$_4$ and concentrated to afford the title product as an orange oil (4.1 g, 88.7%). LCMS (ESI+): m/z (M+H)$^+$309.7, R$_t$: 2.306 min.

14.3 6-Bromomethyl-3-fluoro-2-iodobenzoic acid ethyl ester

3-Fluoro-2-iodo-6-methylbenzoic acid ethyl ester (2.8 g, 9.1 mmol), NBS (2.43 g, 13.6 mmol), AIBN (89 mg, 0.55 mmol) and 50 mL of anhydrous CCl$_4$ were mixed and refluxed under N$_2$ atmosphere overnight. The reaction mixture was cooled, concentrated and the residue was purified by plate-TLC (PE/EA=12/1) to give the title compound as a white solid (2.0 g, 57.1%). LCMS (ESI+): m/z (M+H)$^+$ 387.7, R$_t$: 2.310 min.

14.4 6-Fluoro-7-iodo-2-(2-quinolin-2-yl-ethyl)-2,3-dihydro-isoindol-1-one

6-Bromomethyl-3-fluoro-2-iodobenzoic acid ethyl ester (0.5 g, 1.3 mmol), 2-quinolin-2-yl-ethylamine from Example a1 (0.22 g, 1.3 mmol), K$_2$CO$_3$ (0.36 g, 2.6 mmol) and 15 mL of EtOH were mixed and refluxed for 5 h. The reaction mixture was cooled, concentrated and the residue was purified by plate-TLC (PE/EA=2/1) to give the title compound as an off-white solid (0.35 g, 62.5%). LCMS (ESI+): m/z (M+H)$^+$433.7, R$_t$: 1.615 min.

14.5 6-Fluoro-7-pyridin-4-yl-2-(2-quinolin-2-yl-ethyl)-2,3-dihydro-isoindol-1-one The compound from Example 14.4 (300 mg, 0.69 mmol), pyridine-4-ylboronic acid (85 mg, 0.69 mmol), Pd(dppf)Cl$_2$ (30 mg) and K$_2$CO$_3$ (192 mg, 1.39 mmol) were dissolved in dioxane/H$_2$O (3/1, 6 mL) then the mixture was stirred in nitrogen atmosphere at 120° C. for 1 h in a microwave tube. The solution was concentrated and the residue was purified by plat-TLC (DCM/MeOH=12/1). The crude product was recrystallized from MeOH to give the title compound as a white solid (71 mg, 26.7%). LCMS (ESI+): m/z (M+H)$^+$ 384.7, R$_t$: 1.273 min. $^1$H NMR (DMSO-d$_6$, 400 MHz): δ 8.58 (dd, J=4.4 Hz, 1.6 Hz, 2H), 8.27 (d, J=8.4 Hz, 1H), 7.94 (d, J=7.6 Hz, 1H), 7.88 (d, J=8.0 Hz, 1H), 7.73-7.68 (m, 2H), 7.58-7.54 (m, 2H), 7.45 (d, J=8.8 Hz, 1H), 7.30 (d, J=4.8 Hz, 2H), 4.52 (s, 2H), 3.94 (t, J=7.4 Hz, 2H), 3.25 (t, J=7.2 Hz, 2H).

Example 15

5-Fluoro-7-pyridin-4-yl-2-(2-quinolin-2-yl-ethyl)-2,3-dihydro-isoindol-1-one 15.1 4-Fluoro-2-iodo-6-methylbenzoic acid The title compound was prepared in analogy to the process described in Example 14.1 starting from 4-fluoro-2-methyl benzoic acid. Yield: 69.4%; LCMS (ESI+): m/z (M+H)$^+$281.7, R$_t$: 1.952 min.

15.2 4-Fluoro-2-iodo-6-methylbenzoic acid ethyl ester

The title compound was prepared in analogy to the process described in Example 14.2 starting from the compound from Eample 15.1. Yield: 91%. LCMS (ESI+): m/z (M+H)$^+$309.7, R$_t$: 2.158 min.

15.3 2-Bromomethyl-4-fluoro-6-iodo-benzoic acid ethyl ester

The title compound was prepared in analogy to the process described in Example 14.3 starting from the compound from Example 15.2. Yield: 42%; LCMS (ESI+): m/z (M+H)$^+$387.7, R$_t$: 2.183 min.

15.4 5-Fluoro-7-iodo-2-(2-quinolin-2-yl-ethyl)-2,3-dihydro-isoindol-1-one

The title compound was prepared in analogy to the process described in Example 14.4 starting from the compound from Example 15.3. Yield: 55%; LCMS (ESI+): m/z (M+H)$^+$433.7, R$_t$: 1.721 min.

15.5 5-Fluoro-7-pyridin-4-yl-2-(2-quinolin-2-yl-ethyl)-2,3-dihydro-isoindol-1-one The title compound was prepared in analogy to the process described in Example 14.5 starting from the compound from Example 15.4. Yield: 27%; LCMS (ESI+): m/z (M+H)$^+$384.7, R$_t$: 1.290 min.; $^1$H NMR (DMSO-d$_6$, 400 MHz): δ 8.57 (dd, J=4.8 Hz, 2.0 Hz, 2H), 8.28 (d, J=8.0 Hz, 1H), 7.94 (d, J=7.2 Hz, 1H), 7.88 (d, J=8.4 Hz, 1H), 7.73-7.69 (m, 1H), 7.58-7.53 (m, 2H), 7.48 (d, J=8.0 Hz, 1H), 7.42 (dd, J=4.4 Hz, 1.2 Hz, 2H), 7.31 (dd, J=10 Hz, 2.4 Hz, 1H), 4.55 (s, 2H), 3.96 (t, J=7.2 Hz, 2H), 3.28 (t, J=7.2 Hz, 2H).

Example 16

4-Fluoro-7-pyridin-4-yl-2-(2-quinolin-2-yl-ethyl)-2,3-dihydro-isoindol-1-one 16.1 3-Fluoro-6-iodo-2-methylbenzoic acid The title compound was prepared in analogy to the process described in Example 14.1 starting from 3-fluoro-2-methyl benzoic acid. Yield: 74%; LCMS (ESI+): m/z (M+H)$^+$281.7, R$_t$: 1.738 min.

16.2 3-Fluoro-6-iodo-2-methylbenzoic acid ethyl ester

The title compound was prepared in analogy to the process described in Example 14.2 starting from 3-fluoro-6-iodo-2-methyl benzoic acid. Yield: 91%. LCMS (ESI+): m/z (M+H)+309.7, $R_t$: 2.358 min.

16.3 2-Bromomethyl-3-fluoro-6-iodo-benzoic acid ethyl ester

The title compound was prepared in analogy to the process described in Example 14.3 starting from the compound of Example 16.2. Yield: 40%; LCMS (ESI+): m/z (M+H)+387.7, $R_t$: 2.358 min.

16.4 4-Fluoro-7-iodo-2-(2-quinolin-2-yl-ethyl)-2,3-dihydro-isoindol-1-one

The title compound was prepared in analogy to the process described in Example 14.4 starting from the compound from Example 16.3. Yield: 39%; LCMS (ESI+): m/z (M+H)+433.7, $R_t$: 1.615 min.

16.5 4-Fluoro-7-pyridin-4-yl-2-(2-quinolin-2-yl-ethyl)-2,3-dihydro-isoindol-1-one The title compound was prepared in analogy to the process described in Example 14.5 starting from the compound of Example 16.4. Yield: 27%; LCMS (ESI+): m/z (M+H)+384.7, $R_t$: 1.299 min.; $^1$H NMR (DMSO-$d_6$, 400 MHz): δ 8.55 (dd, J=4.8 Hz, 1.6 Hz, 2H), 8.28 (d, J=8.4 Hz, 1H), 7.95 (d, J=8.4 Hz, 1H), 7.87 (d, J=8.4 Hz, 1H), 7.73-7.69 (m, 1H), 7.57-7.53 (m, 2H), 7.50 (t, J=4.2 Hz, 2H), 7.38-7.36 (dd, J=4.4 Hz, 1.6 Hz, 2H), 4.67 (s, 2H), 3.97 (t, J=7.2 Hz, 2H), 3.29 (t, J=7.2 Hz, 2H).

II.7 Preparation of Compounds of the Formula I in which A is $NR^{5a}$

Example 17

1-Methyl-4-(pyridin-4-yl)-2-(2-(quinolin-2-yl)ethyl)-1,2-dihydroindazol-3-one 17.1 Ethyl 2-bromo-6-fluorobenzoate To a solution of 2-bromo-6-fluoro-benzoic acid (5 g, 22.83 mmol) and $Cs_2CO_3$ (14.9 g, 45.7 mmol) in $CH_3CN$ (100 mL) was added $CH_3CH_2I$ (7.12 g, 45.7 mmol) dropwise. The mixture was stirred at 30° C. overnight. The mixture was filtered and the filtrate was concentrated. The residue was purified by silica gel column chromatography, eluting with PE/EA (10:1) to give the title compound as a colorless oil (2 g, 25%). LCMS (ESI+): m/z 247.249. (M+H)+, $R_t$: 0.93 min.

17.2 4-Bromo-1-methyl-1,2-dihydroindazol-3-one

A mixture of the compound from Example 17.1 (1.0 g, 4.0 mmol), acetic acid (290 mg, 4.8 mmol) and methylhydrazine (370 mg, 8.1 mmol) in ethanol (50 mL) was heated to about 80° C. overnight. The mixture was concentrated and the residue was purified by silica gel column chromatography, eluting with PE/EA (5:1) to give the title compound as colorless oil (0.4 g, 44%). LCMS (ESI+): m/z 227.229. (M+H)+, $R_t$: 0.73 min.

17.3 1-Methyl-4-(pyridin-4-yl)-1,2-dihydroindazol-3-one

A mixture of the compound from Example 17.2 (120 mg, 0.528 mmol), pyridin-4-ylboronic acid (65 mg, 0.528 mmol), $K_2CO_3$ (219 mg, 1.584 mmol) and $PdCl_2(dppf)$ (39 mg, 0.053 mmol) in 1,4-dioxane (12 mL) and water (4 mL) was heated to about 100° C. for about 2 h. The reaction mixture was concentrated and the residue was purified by silica gel column chromatography, eluting with PE/EA (1:1) to give the title compound as a yellow solid (80 mg, 54%). LCMS (ESI+): m/z 226. (M+H)+, $R_t$: 0.55 min.

17.4 1-Methyl-4-(pyridin-4-yl)-2-(2-(quinolin-2-yl)ethyl)-1,2-dihydroindazol-3-one A mixture of the compound from Example 17.3 (500 mg, 2.22 mmol), 2-quinolin-2-yl-ethanol from Example a1.2a (384 mg, 2.22 mmol), triphenylphosphine (1747 mg, 6.66 mmol) and DIAD (0.863 mL, 4.44 mmol) in $CH_2Cl_2$ (10 mL) was stirred at 25° C. over night. The mixture was concentrated and the residue was purified by silica gel column, eluting with DCM/MeOH (50:1) to give the title compound as colorless oil (200 mg, 23%). LCMS (ESI+): m/z 381. (M+H)+, $R_t$: 1.37 min.; $^1$H NMR (400 MHz, MeOD): δ 3.16 (t, J=6.0 Hz, 2H), 3.69 (s, 3H), 4.59 (t, J=6.0 Hz, 2H), 6.74 (dd, J=5.8, 2.0 Hz, 1H), 6.98 (d, J=8.4 Hz, 1H), 7.12-7.14 (m, 2H), 7.17-7.19 (m, 2H), 7.34-7.38 (m, 1H), 7.52-7.56 (m, 1H), 7.68 (d, J=8.0 Hz, 1H), 7.78 (d, J=8.4 Hz, 1H), 7.93 (d, J=8.8 Hz, 1H), 8.02-8.04 (m, 2H).

II.8 Preparation of Compounds of the Formula I in which A is O

Example 18

4-Pyridin-4-yl-2-(2-quinolin-2-yl-ethyl)-benzo[d]isoxazol-3-one 18.1 Vinylboronic acid To a rapidly stirred cold (−20° C.) solution of trimethyl borate (10.4 g, 0.1 mol) in anhydrous THF (100 mL) was added dropwise vinylmagnesium bromide (100 mL, 1 M in THF solution). When the addition was completed, the mixture was stirred at −20° C. for further 30 min. The reaction was then quenched with HCl (2 N), the mixture was extracted with EtOAc (200 mL) and washed with HCl (2 N) (50 mL×2) and brine (50 mL). The organic layer was dried over $Na_2SO_4$, filtered and concentrated in vacuo. The crude solid was used in the next step without further purification (6.8 g, yield 96%).

18.2 2-Vinylquinoline

A mixture of 2-bromoquinoline (5.00 g, 24.03 mmol), vinylboronic acid (2.07 g, 28.83 mmol), $K_2CO_3$ (9.96 g, 72.08 mmol) and $Pd(dppf)Cl_2$ (1.96 g, 2.403 mmol) in water (10 mL) and 1,4-dioxane (30 mL) was stirred at 105° C. overnight. The mixture was diluted with EtOAc (100 mL) and washed with brine (30 mL×4). The organic layer was dried over $Na_2SO_4$, filtered and concentrated in vacuo. The residue was purified on a silica column (PE/EtOAc=20:1, v/v) to afford the title product as a light orange oil (2.25 g, yield 60%). LCMS (ESI+): m/z 156 (M+H)+, $R_t$: 1.89 min.

18.3 N-(2-Quinolin-2-yl-ethyl)-hydroxylamine

A mixture of 2-vinylquinoline (2.25 g, 14.50 mmol) and hydroxylamine hydrochloride (10.1 g, 145.0 mmol) in MeOH (30 mL) was stirred at reflux overnight. The mixture was concentrated in vacuo. The residue was dissolved in EtOAc (100 mL) and washed with aqueous saturated $NaHCO_3$ solution (30 mL×5). The organic layer was dried over $Na_2SO_4$, filtered and concentrated in vacuo. The residue was then purified on a silica column (DCM/MeOH=50:1, v/v) to afford the title product as a yellow solid (2.18 g, yield 80%). LCMS (ESI+): m/z 189 (M+H)+, $R_t$: 1.59 min.

18.4 2-Bromo-6-fluoro-N-hydroxy-N-(2-quinolin-2-yl-ethyl)-benzamide

A mixture of N-(2-quinolin-2-yl-ethyl)-hydroxylamine (500 mg, 2.657 mmol), 2-bromo-6-fluorobenzoic acid (582 mg, 2.657 mmol), PyIBOP (1.66 g, 3.188 mmol) and DIPEA (412 mg, 3.188 mmol) in DMF (10 mL) was stirred at room temperature overnight. The mixture was diluted with EtOAc (50 mL) and washed with brine (15 mL×3). The organic layer was dried over $Na_2SO_4$, filtered and concentrated in vacuo. The residue was then purified on a silica column (pet.

ether/EtOAc=1:1, v/v) to afford the title product as a dark oil (crude, 1.01 g, yield 98%). LCMS (ESI+): m/z 389 (M+H)+, R$_t$: 1.86 min.

18.5 4-Bromo-2-(2-quinolin-2-yl-ethyl)-benzo[d]isoxazol-3-one

A mixture of the compound from Example 18.4 (1.01 g, 2.593 mmol) and Cs$_2$CO$_3$ (1.69 g, 5.187 mmol) in DMF (20 mL) was stirred at 80° C. overnight. The mixture was diluted with EtOAc (100 mL) and washed with brine (30 mL×3). The organic layer was dried over Na$_2$SO$_4$, filtered and concentrated in vacuo. The residue was purified on a silica column (PE/EtOAc=4:1, v/v) to afford the title product as a white solid (110 mg, yield 11%). LCMS (ESI+): m/z 369 (M+H)+, R$_t$: 1.90 min.

18.6 4-Pyridin-4-yl-2-(2-quinolin-2-yl-ethyl)-benzo[d]isoxazol-3-one

A mixture of the compound from Example 18.5 (110 mg, 0.2979 mmol), pyridine-4-ylboronic acid (44 mg, 0.3575 mmol), K$_2$CO$_3$ (124 mg, 0.8938 mmol) and Pd(dppf)Cl$_2$ (24 mg, 0.02979 mmol) in water (1 mL) and 1,4-dioxane (5 mL) was stirred at 105° C. overnight. The mixture was diluted with EtOAc (30 mL) and washed with brine (10 mL×4). The organic layer was dried over Na$_2$SO$_4$, filtered and concentrated in vacuo. The residue was purified by pre-TLC (eluent: EtOAc) to afford the title product as a white solid (68 mg, yield 62%). LCMS (ESI+): m/z 368 (M+H)+, R$_t$: 1.94 min.; $^1$H NMR (CDCl$_3$/TMS, 400 MHz) δ: 8.65 (d, J=5.2 Hz, 2H), 8.09 (d, J=8.0 Hz, 1H), 7.88 (d, J=8.4 Hz, 1H), 7.78 (d, J=8.4 Hz, 1H), 7.63-7.69 (m, 2H), 7.46-7.52 (m, 3H), 7.33 (d, J=8.8 Hz, 1H), 7.29 (d, J=8.0 Hz, 1H), 7.25-7.27 (m, 1H), 4.57 (t, J=7.2 Hz, 2H), 3.49 (t, J=7.0 Hz, 2H).

II.9 Preparation of Compounds of the Formula I in which Het is Different from 2-quinolin-2-yl Example 19

7-Pyridin-4-yl-2-(2-thieno[3,2-b]pyridin-5-yl-ethyl)-2,3-dihydro-isoindol-1-one 19.1 2-Iodo-6-methylbenzoic acid To a solution of 2-methylbenzoic acid (50 g, 0.36 mol) in DMF (800 mL) was added Pd(OAc)$_2$ (8 g, 0.036 mmol) and NIS (80 g, 0.36 mol). Then the reaction mixture was heated to 100° C. for 1.5 h. The reaction was monitored by TLC. When the starting material was consumed, the reaction mixture was cooled, concentrated in vacuo to remove the excess solvent. The residue was dissolved in DCM (500 mL), washed with brine (2*200 mL), dried by Na$_2$SO$_4$, filtered, concentrated and purified by silica gel chromatography, eluting with PE/EA=5:1 to give the title compound (92 g, 95%) as a white solid. LCMS (ESI+): m/z 263 (M+H)+, R$_t$: 1.90 min.

19.2 Methyl 2-iodo-6-methylbenzoate

To a solution of 2-iodo-6-methylbenzoic acid (80 g, 0.31 mol) in DCM (700 mL) was added SOCl$_2$ (55 g, 0.46 mol) dropwise at 0° C. After addition, the reaction mixture was stirred at reflux for 2 hours. The solvent was removed in vacco. The residue was added dropwise to MeOH (100 mL) at 0° C. The mixture was then refluxed overnight. The solvent was evaporated under reduce pressure. The residue was purified by silica gel chromatography eluting PE/EA=70:1 to give the title compound (43 g, 50%) as a white solid. LCMS (ESI+): m/z 277 (M+H)+, R$_t$: 2.17 min.

19.3 2-Bromomethyl-6-iodo-benzoic acid methyl ester

A mixture of 2-iodo-6-methyl-benzoic acid methyl ester (2.50 g, 9.055 mmol), N-bromosuccinimide (1.93 g, 10.86 mmol) and azobisisbutyronitrile (0.669 g, 4.075 mmol) in tetrachloromethane (20 mL) was stirred at reflux overnight. The mixture was concentrated in vacuo and the residue was purified on a silica column (PE/EtOAc=200:1, v/v) to afford the title product as a white solid as a white solid (1.62 g, yield 50%). LCMS (ESI+): m/z 355 (M+H)+, R$_t$: 2.33 min.

19.4 7-Iodo-2-(2-thieno[3,2-b]pyridin-5-yl-ethyl)-2,3-dihydro-isoindol-1-one

A mixture of 2-thieno[3,2-b]pyridin-5-yl-ethylamine from Example c1 (183 mg, 1.062 mmol) and the compound from Example 19.3 (364 mg, 1.062 mmol) in ethanol (5 mL) was stirred at reflux overnight. The mixture was concentrated in vacuo and purified on a silica column (pet. ether/EtOAc=1:1, v/v) to afford the title product as a white solid (178 mg, yield 41%). LCMS (ESI+): m/z 421 (M+H)+, R$_t$: 1.91 min.

19.5 7-Pyridin-4-yl-2-(2-thieno[3,2-b]pyridin-5-yl-ethyl)-2,3-dihydro-isoindol-1-one A mixture of the compound from Example 19.4 (178 mg, 0.4235 mmol), pyridine-4-ylboronic acid (63 mg, 0.5082 mmol), K$_2$CO$_3$ (176 mg, 1.271 mmol) and Pd(dppf)Cl$_2$ (35 mg, 0.04235 mmol) in 1,4-dioxane (5 mL) and water (1 mL) was stirred at 105° C. overnight. The mixture was diluted with EtOAc (30 mL) and washed with brine (10 mL×4). The organic layer was dried over Na$_2$SO$_4$, filtered and concentrated in vacuo. The residue was purified on a silica column (eluent: EtOAc) to afford the title product as a white solid (113 mg, yield 72%). LCMS (ESI+): m/z 372 (M+H)+, R$_t$: 1.86 min.; $^1$H NMR (CDCl$_3$/TMS, 400 MHz) δ 8.67 (d, J=4.8 Hz, 2H), 8.12 (d, J=8.0 Hz, 1H), 7.76 (d, J=5.6 Hz, 1H), 7.59 (t, J=7.4 Hz, 1H), 7.46-7.51 (m, 4H), 7.36 (d, J=7.6 Hz, 1H), 7.22 (d, J=8.0 Hz, 1H), 4.40 (s, 2H), 4.07 (t, J=7.2 Hz, 2H), 3.31 (t, J=7.2 Hz, 2H).

Example 20

2-(2-Imidazo[1,2-a]pyridin-2-yl-ethyl)-7-pyridin-4-yl-2,3-dihydro-isoindol-1-one 20.1 7-Bromo-2-(2-imidazo[1,2-a]pyridin-2-yl-ethyl)-2,3-dihydro-isoindol-1-one A mixture of 2-imidazo[1,2-a]pyridin-2-ylethylamine from Example d1 (120 mg, 0.744 mmol), methyl 2-bromo-6-(bromomethyl)benzoate from Example 5.3 (367 mg, 0.893 mmol) and DIPEA (0.260 mL, 1.489 mmol) in 2-propanol (15 mL) was heated to 85° C. for 2 h. The solvent was evaporated. The residue was purified by plate-TLC (DCM: MeOH=10:1) to give the title compound as a white solid (200 mg, 75%). LCMS (ESI+): m/z 356 (M+H)+, R$_t$: 1.77 min.

20.2 2-(2-Imidazo[1,2-a]pyridin-2-yl-ethyl)-7-pyridin-4-yl-2,3-dihydro-isoindol-1-one A mixture of 7-bromo-2-(2-imidazo[1,2-a]pyridin-2-yl-ethyl)-2,3-dihydro-isoindol-1-one (200 mg, 0.561 mmol), pyridine-4-ylboronic acid (83 mg, 0.674 mmol), PdCl$_2$(dppf)-CH$_2$Cl$_2$ (59.6 mg, 0.073 mmol) and K$_2$CO$_3$ (233 mg, 1.684 mmol) in 1,4-dioxane (8 mL) and water (4.00 mL) was heated to 100° C. for 30 min. The solvent was evaporated and the residue was dissolved in DCM (10 mL) and washed with water (10 mL). The organic layer was dried over Na$_2$SO$_4$, filtered and concentrated. The residue was purified by plate-TLC (DCM: MeOH=10:1) to give 220 mg of a black solid, which was further purified by reverse phase flash column (C18, MeOH—0.1% NH$_3$HCO$_3$/H$_2$O=20%~95%) to give the title compound as an off-white solid (150 mg, 0.423 mmol, 75%). LCMS (ESI+): m/z 355 (M+H)+, R$_t$: 1.69 min. $^1$H NMR (DMSO-d$_6$, TMS, 400

MHz): δ 3.02 (t, J=7.4 Hz, 2 H), 3.85 (t, J=7.2 Hz, 2 H), 4.50 (s, 2 H), 6.80-6.84 (m, 1 H), 7.15-7.19 (m, 1 H), 7.41-7.49 (m, 4 H), 7.64-7.69 (m, 2 H), 7.75 (s, 1H), 8.46 (d, J=7.2 Hz, 1H), 8.6 (d, J=4 Hz, 2H).

II.10 Preparation of Compounds of the Formula I in which A is CH$_2$
Route a)

Step C: 3-Oxo-2-(2-(quinolin-2-yl)ethyl)isoindolin-4-ylboronic acid (5)

Compound 3 (1.0 g, 2.4 mmol) and trimethyl borate (0.3 g, 2.9 mmol) were dissolved in dry THF (20 mL) at −78° C. n-BuLi (1.1 mL, 2.5 M in hexanes, 2.8 mmol) was added dropwise at −78° C. The mixture was warmed to 0° C. and stirred for 1 h. Aqueous NaOH (1M, 10 mL) was added. The

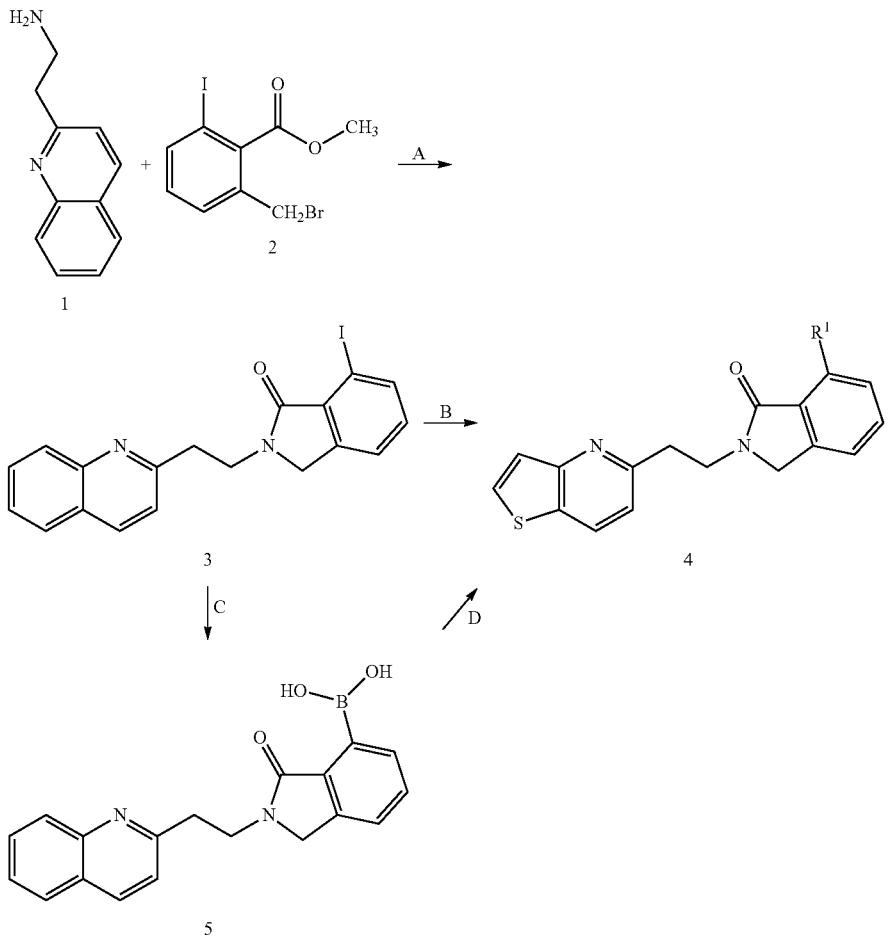

Step A: 7-Iodo-2-(2-(quinolin-2-yl)ethyl)isoindolin-1-one (3)

A mixture of 2-(quinolin-2-yl)ethylamine from Example a1 (compound 1, 7.3 g, 0.042 mol), methyl 2-(bromomethyl)-6-iodobenzoate from Example 19.3 (compound 2, g, 0.042 mol), and Et$_3$N (4.2 g, 0.042 mol) in dry isopropanol (100 mL) was refluxed under N$_2$ overnight. The reaction mixture was cooled to room temperature, filtered, and concentrated. The residue was purified with a silica column (PE/EA=3:1) to give the compound 3 (8.9 g, 50%) as a yellow solid. LCMS (ESI+): m/z 415 (M+H)$^+$, R$_t$: 1.94 min.

Step B: Compound (4)

A suspension of compound 3 (60 mg, 0.15 mmol), the corresponding boronic acid R$^1$—B(OH)$_2$ (0.17 mmol) and Pd(dppf)Cl$_2$ (6 mg) in dioxane (1.5 mL) and H$_2$O (1.5 mL) was stirred at room temperature for 2 min. and then heated by microwave irradiation at 100° C. for 20 min. Upon completion, the mixture was concentrated and purified by prep-HPLC to give compound 4.

organic solvent was removed under reduced pressure. The residue was extracted with DCM (2*50 mL). The water phase was adjusted to pH=2 by aqueous HCl (1M). The mixture was condensed under reduced pressure. The residue was dissolved in DCM/MeOH (10:1, 50 mL). The solid was removed by filtration. The filtrate was concentrated to give title compound as off-white solid (0.17 g, 21%). LCMS (ESI+): m/z 333 (M+H)$^+$, R$_t$: 1.68 min.

Step D: Compound (4)

A suspension of compound 5 (60 mg, 0.15 mmol), the corresponding bromide R$^1$—Br (0.17 mmol), Pd(dppf)Cl$_2$ (6 mg) in dioxane (1.5 mL) and H$_2$O (1.5 mL) was stirred at room temperature for 2 min. and then heated with microwave irradiation at 100° C. for 20 min. Upon completion, the mixture was concentrated and the residue was purified by prep-HPLC to give compound 4.

The following compounds of the Examples 21 to 98 listed below were prepared in an analogous manner.

| Ex. | IUPAC-Name | physico-chemical data |
|---|---|---|
| 21 | 7-Phenyl-2-(2-quinolin-2-yl-ethyl)-2,3-dihydro-isoindol-1-one | $^1$H NMR (DMSO-d$_6$): δ 8.29 (d, J = 8.4 Hz, 1H), 7.94 (d, J = 6.4 Hz, 1H), 7.90 (d, J = 5.2 Hz, 1H), 7.61 (d, J = 7.2 Hz, 1H), 7.56 (s, 1H), 7.54 (s, 1H), 7.48 (d, J = 8 Hz, 1H), 7.4 (m, 2H), 7.36 (m, 4H), 4.5 (s, 2H), 3.96 (t, J = 8 Hz, 1H), 3.29 (s, 2H); LCMS (ESI+): m/z 365 (M + H)$^+$, R$_t$: 1.72 min. |
| 22 | 7-(4-Fluoro-phenyl)-2-(2-quinolin-2-yl-ethyl)-2,3-dihydro-isoindol-1-one | $^1$H NMR (DMSO-d$_6$): δ 8.61 (m, 1H), 8.10 (d, J = 8 Hz, 1H), 8.0 (d, J = 8.4 Hz, 1H), 7.89 (t, J = 7.2 Hz, 1H), 7.74 (t, J = 7.2 Hz, 2H), 7.63 (d, J = 8 Hz, 1H), 7.59 (d, J = 2.8 Hz, 1H), 7.35 (t, J = 9.2 Hz, 3H), 7.1 (t, J = 8.8 Hz, 2H), 4.5 (s, 2H), 3.9 (t, J = 7.2 Hz, 2H), 3.38 (t, J = 8.8 Hz, 2H); LCMS (ESI+): m/z 383 (M + H)$^+$, R$_t$: 1.74 min. |
| 23 | 7-(4-Methoxy-phenyl)-2-(2-quinolin-2-yl-ethyl)-2,3-dihydro-isoindol-1-one | $^1$H NMR (DMSO-d$_6$): δ 8.59 (d, J = 4 Hz, 1H), 8.08 (d, J = 8 Hz, 1H), 8.00 (d, J = 8 Hz, 1H), 7.85 (t, J = 7.2 Hz, 1H), 7.68 (m, 2H), 7.58 (t, J = 8 Hz, 1H), 7.56 (d, J = 13.2 Hz, 1H), 7.28 (m, 3H), 6.85 (m, 2H), 4.52 (s, 2H), 3.98 (t, J = 7.2 Hz, 2H), 3.77 (s, 3H), 3.63 (t, J = 6.8 Hz, 2H); LCMS (ESI+): m/z 395 (M + H)$^+$, R$_t$: 1.72 min. |
| 24 | 2-(2-Quinolin-2-yl-ethyl)-7-thiophen-2-yl-2,3-dihydro-isoindol-1-one | $^1$H NMR (MeOD-d$_4$): δ 8.17 (d, J = 8.4 Hz, 1H), 7.83 (d, J = 8.8 Hz, 1H), 7.81 (d, J = 10.8 Hz, 1H), 7.61 (t, J = 6.8 Hz, 1H), 7.43 (m, 3H), 7.35 (m, 4H), 6.99 (d, J = 4 Hz, 1H), 4.35 (s, 2H), 3.98 (t, J = 7.2 Hz, 2H), 3.25 (t, J = 7.2 Hz, 2H); LCMS (ESI+): m/z 371 (M + H)$^+$, R$_t$: 1.70 min. |
| 25 | 2-(2-Quinolin-2-yl-ethyl)-7-thiophen-3-yl-2,3-dihydro-isoindol-1-one | $^1$H NMR (DMSO-d$_6$): δ 8.30 (d, J = 6.8 Hz, 1H), 7.92 (m, 2H), 7.82 (d, J = 1.6 Hz, 1H), 7.71 (t, J = 2 Hz, 1H), 7.59 (d, J = 7.2 Hz, 1H), 7.56 (d, J = 3.6 Hz, 1H), 7.51 (m, 4H), 7.39 (d, J = 1.2 Hz, 1H), 4.49 (s, 2H), 3.98 (t, J = 7.2 Hz, 2H), 3.28 (t, J = 8.8 Hz, 2H); LCMS (ESI+): m/z 371 (M + H)$^+$, R$_t$: 1.70 min. |
| 26 | 7-(3-Methoxy-phenyl)-2-(2-quinolin-2-yl-ethyl)-2,3-dihydro-isoindol-1-one | $^1$H NMR (DMSO-d$_6$): δ 8.30 (d, J = 4.8 Hz, 1H), 7.93 (d, J = 8.4 Hz, 1H), 7.90 (d, J = 8.8 Hz, 2H), 7.71 (d, J = 1.6 Hz, 1H), 7.56 (m, 3H), 7.48 (d, J = 8.4 Hz, 1H), 7.35 (d, J = 0.8 Hz, 1H), 7.34 (d, J = 1.2 Hz, 1H), 7.26 (t, J = 8.4 Hz, 1H), 6.97 (m, 2H), 6.91 (d, J = 1.2 Hz, 1H), 4.51 (s, 2H), 3.96 (d, J = 6.8 Hz, 2H), 3.72 (s, 3H), 3.26 (t, J = 7.2 Hz, 2H); LCMS (ESI+): m/z 395 (M + H)$^+$, R$_t$: 1.71 min. |
| 27 | 7-(3-Fluoro-phenyl)-2-(2-quinolin-2-yl-ethyl)-2,3-dihydro-isoindol-1-one | $^1$H NMR (DMSO-d$_6$): δ 8.28 (d, J = 8.4 Hz, 1H), 7.94 (d, J = 7.6 Hz, 1H), 7.89 (d, J = 8.4 Hz, 1H), 7.70 (t, J = 6.8 Hz, 1H), 7.60 (m, 2H), 7.54 (t, J = 6.8 Hz, 1H), 7.48 (d, J = 8.8 Hz, 1H), 7.41 (d, J = 7.6 Hz, 1H), 7.37 (t, J = 6.8 Hz, 1H), 7.24 (s, 1H), 7.22 (d, J = 2.8 Hz, 1H), 7.19 (d, J = 10.8 Hz, 1H), 4.52 (s, 2H), 3.97 (t, J = 6.8 Hz, 2H), 3.27 (t, J = 7.2 Hz, 2H); LCMS (ESI+): m/z 383 (M + H)$^+$, R$_t$: 1.74 min. |
| 28 | 7-(2-Methoxy-phenyl)-2-(2-quinolin-2-yl-ethyl)-2,3-dihydro-isoindol-1-one | $^1$H NMR (DMSO-d$_6$): δ 8.28 (d, J = 8.4 Hz, 1H), 7.93 (d, J = 3.6 Hz, 1H), 7.91 (d, J = 3.6 Hz, 1H), 7.71 (t, J = 7.2 Hz, 1H), 7.56 (d, J = 6.8 Hz, 1H), 7.51 (t, J = 7.2 Hz, 2H), 7.47 (d, J = 8.4 Hz, 1H), 7.31 (t, J = 4.8 Hz, 1H), 7.21 (d, J = 6.4 Hz, 1H), 7.05 (d, J = 7.2 Hz, 1H), 7.01 (d, J = 8 Hz, 1H), 6.92 (d, J = 6.8 Hz, 1H), 4.47 (s, 2H), 3.92 (t, J = 6.8 Hz, 2H), 3.55 (s, 3H), 3.24 (t, J = 7.2 Hz, 2H); LCMS (ESI+): m/z 395 (M + H)$^+$, R$_t$: 1.75 min. |
| 29 | 7-(2-Fluoro-phenyl)-2-(2-quinolin-2-yl-ethyl)-2,3-dihydro-isoindol-1-one | $^1$H NMR (DMSO-d$_6$): δ 8.28 (d, J = 8.0 Hz, 1H), 7.92 (t, J = 8 Hz, 2H), 7.71 (t, J = 7.2 Hz, 1H), 7.63 (m, 2H), 7.55 (t, J = 8 Hz, 1H), 7.47 (d, J = 8.8 Hz, 1H), 7.39 (m, 1H), 7.32 (d, J = 6.4 Hz, 1H), 7.31 (d, J = 5.6 Hz, 1H), 7.22 (d, J = 2.8 Hz, 1H), 7.21 (d, J = 6.4 Hz, 1H), 4.52 (s, 2H), 3.94 (t, J = 7.2 Hz, 2H), 3.25 (t, J = 7.2 Hz, 2H); LCMS (ESI+): m/z 383 (M + H)$^+$, R$_t$: 1.69 min. |
| 30 | 7-Pyridin-3-yl-2-(2-quinolin-2-yl-ethyl)-2,3-dihydro-isoindol-1-one | $^1$H NMR (DMSO-d$_6$): δ 8.60 (d, J = 2 Hz, 1H), 8.54 (d, J = 5.2 Hz, 1H), 8.29 (d, J = 9.2 Hz, 1H), 7.94 (d, J = 6.8 Hz, 1H), 7.89 (d, J = 8.4 Hz, 1H), 7.82 (d, J = 7.2 Hz, 1H), 7.72 (d, J = 6.8 Hz, 1H), 7.68 (d, J = 3.2 Hz, 1H), 7.66 (d, J = 7.2 Hz, 1H), 7.64 (t, J = 4.8 Hz, 1H), 7.54 (t, J = 7.2 Hz, 1H), 7.52 (d, J = 160 Hz, 1H), 7.40 (d, J = 5.2 Hz, 1H), 7.39 (d, J = 5.2 Hz, 1H), 4.52 (s, 2H), 3.94 (t, J = 7.2 Hz, 2H), 3.25 (t, J = 7.2 Hz, 2H); LCMS (ESI+): m/z 366 (M + H)$^+$, R$_t$: 1.263 min. |
| 31 | 7-Furan-2-yl-2-(2-quinolin-2-yl-ethyl)-2,3-dihydro-isoindol-1-one | $^1$H NMR (DMSO-d$_6$): δ 8.30 (d, J = 8.4 Hz, 1H), 7.95 (d, J = 3.6 Hz, 1H), 7.94 (s, 1H), 7.92 (s, 1H), 7.84 (d, J = 8.4 Hz, 1H), 7.78 (s, 1H), 7.72 (t, J = 7.6 Hz, 1H), 7.61 (t, J = 7.6 Hz, 1H), 7.56 (d, J = 8.0 Hz, 1H), 7.53 (d, J = 5.2 Hz, 1H), 7.49 (s, 1H), 7.47 (s, 1H), 7.45 (s, |

| Ex. | IUPAC-Name | physico-chemical data |
|---|---|---|
| | | 1H), 4.50 (s, 2H), 4.02 (t, J = 7.2 Hz, 2H), 3.29 (t, J = 7.2 Hz, 2H); LCMS (ESI+): m/z 355 (M + H)+, R$_t$: 1.68 min. |
| 32 | 7-(3-Fluoro-4-methoxy-phenyl)-2-(2-quinolin-2-yl-ethyl)-2,3-dihydro-isoindol-1-one | $^1$H NMR (DMSO-d$_6$): δ 8.29 (d, J = 8.4 Hz, 1H), 7.94 (d, J = 7.6 Hz, 1H), 7.89 (d, J = 8.8 Hz, 1H), 7.70 (t, J = 6.8 Hz, 1H), 7.61 (d, J = 7.2 Hz, 1H), 7.57 (d, J = 3.6 Hz, 1H), 7.54 (d, J = 6 Hz, 1H), 7.54 (d, J = 8.4 Hz, 1H), 7.48 (d, J = 8.0 Hz, 1H), 7.34 (d, J = 6.8 Hz, 1H), 7.29 (d, J = 13.2 Hz, 1H), 7.21 (d, J = 9.2 Hz, 1H), 7.15 (t, J = 8.4 Hz, 1H), 4.50 (s, 2H), 3.97 (t, J = 6.8 Hz, 2H), 3.87 (s, 3H), 3.28 (t, J = 8.8 Hz, 2H); LCMS (ESI+): m/z 413 (M + H)+, R$_t$: 1.74 min. |
| 33 | 7-(3,4-Difluoro-phenyl)-2-(2-quinolin-2-yl-ethyl)-2,3-dihydro-isoindol-1-one | $^1$H NMR (DMSO-d$_6$): δ 8.29 (d, J = 8.4 Hz, 1H), 7.94 (d, J = 8.0 Hz, 1H), 7.88 (d, J = 8.0 Hz, 1H), 7.70 (t, J = 7.2 Hz, 1H), 7.62 (t, J = 7.6 Hz, 1H), 7.60 (s, 1H), 7.54 (t, J = 7.6 Hz, 1H), 7.48 (t, J = 8.4 Hz, 1H), 7.47 (d, J = 8.0 Hz, 1H), 7.43 (d, J = 8.4 Hz, 1H), 7.37 (d, J = 7.2 Hz, 1H), 7.24 (m, 1H), 4.52 (s, 2H), 3.97 (t, J = 7.2 Hz, 2H), 3.27 (t, J = 7.2 Hz, 2H); LCMS (ESI+): m/z 401 (M + H)+, R$_t$: 1.77 min. |
| 34 | 7-Benzo[1,3]dioxol-5-yl-2-(2-quinolin-2-yl-ethyl)-2,3-dihydro-isoindol-1-one | $^1$H NMR (DMSO-d$_6$): δ 8.29 (d, J = 8.4 Hz, 1H), 7.94 (d, J = 7.2 Hz, 1H), 7.90 (d, J = 4.8 Hz, 1H), 7.70 (t, J = 7.2 Hz, 1H), 7.58 (t, J = 7.6 Hz, 1H), 7.55 (d, J = 2.4, 1H), 7.52 (d, J = 7.2 Hz, 1H), 7.48 (d, J = 8.4 Hz, 1H), 7.31 (d, J = 6.8 Hz, 1H), 6.97 (d, J = 1.2 Hz, 1H), 6.92 (d, J = 7.6 Hz, 1H), 6.89 (d, J = 1.2 Hz, 1H), 6.87 (d, J = 1.6 Hz, 1H), 4.49 (s, 2H), 3.96 (t, J = 7.2 Hz, 2H), 3.26 (t, J = 7.2 Hz, 2H); LCMS (ESI+): m/z 409 (M + H)+, R$_t$: 1.71 min. |
| 35 | 7-(2,3-Dihydro-benzo-[1,4]dioxin-6-yl)-2-(2-quinolin-2-yl-ethyl)-2,3-dihydro-isoindol-1-one | $^1$H NMR (DMSO-d$_6$): δ 8.62-8.60 (m, 1H), 8.10 (d, J = 8.4 Hz, 1H), 8.02 (d, J = 8.8 Hz, 1H), 7.88 (t, J = 4.8 Hz, 1H), 7.73-7.69 (m, 2H), 7.57 (t, J = 7.6 Hz, 1H), 7.52 (t, J = 7.6 Hz, 1H), 7.29 (d, J = 7.2 Hz, 1H), 6.87 (d, J = 1.2 Hz, 1H), 6.74 (s, 1H), 4.52 (s, 2H), 3.99 (t, J = 7.2 Hz, 2H), 3.38 (t, J = 7.2 Hz, 2H); LCMS (ESI+): m/z 423 (M + H)+, R$_t$: 1.70 min. |
| 36 | 7-(3,4-Dimethoxy-phenyl)-2-(2-quinolin-2-yl-ethyl)-2,3-dihydro-isoindol-1-one | $^1$H NMR (DMSO-d$_6$): δ 8.28 (d, J = 8.4 Hz, 1H), 7.93 (d, J = 8.0 Hz, 1H), 7.89 (d, J = 8.8 Hz, 1H), 7.70 (t, J = 8.4 Hz, 1H), 7.57 (t, J = 7.6 Hz, 1H), 7.52 (t, J = 7.6 Hz 2H), 7.48 (d, J = 8.4 Hz, 1H), 7.36 (d, J = 7.6 Hz, 1H), 7.03 (s, 1H), 6.95 (d, J = 2 Hz, 1H), 6.94 (s, 1H), 4.50 (s, 2H), 3.97 (t, J = 7.2 Hz, 2H), 3.78 (s, 3H), 3.67 (s, 3H), 3.26 (t, J = 7.2 Hz, 2H); LCMS (ESI+): m/z 425 (M + H)+, R$_t$: 1.66 min. |
| 37 | 7-(2,4-Dimethoxy-phenyl)-2-(2-quinolin-2-yl-ethyl)-2,3-dihydro-isoindol-1-one | $^1$H NMR (DMSO-d$_6$): δ 8.28 (d, J = 8.4 Hz, 1H), 7.93 (d, J = 8.0 Hz, 1H), 7.71 (t, J = 7.2 Hz, 1H), 7.54 (d, J = 8.0 Hz, 1H), 7.52 (d, J = 7.6 Hz, 1H), 7.47 (s, 1H), 7.45 (s, 1H), 7.18 (d, J = 7.2 Hz, 1H), 6.98 (d, J = 8.4 Hz, 1H), 6.56 (d, J = 2 Hz, 1H), 6.51 (d, J = 8.4 Hz, 1H), 4.45 (s, 2H), 3.92 (t, J = 7.2 Hz, 2H), 3.79 (s, 3H), 3.54 (s, 3H), 3.24 (t, J = 7.2 Hz, 2H); LCMS (ESI+): m/z 425 (M + H)+, R$_t$: 1.73 min. |
| 38 | 7-(4-Dimethylamino-phenyl)-2-(2-quinolin-2-yl-ethyl)-2,3-dihydro-isoindol-1-one | $^1$H NMR (DMSO-d$_6$): δ 8.29 (d, J = 8.8 Hz, 1H), 7.92 (d, J = 8.0 Hz, 1H), 7.71 (t, J = 8.4 Hz, 1H), 7.56-7.51 (m, 2H), 7.48 (d, J = 8.4 Hz, 1H), 7.44 (d, J = 8.0 Hz, 1H), 7.31-7.27 (m, 3H), 6.71 (d, J = 8.8 Hz, 1H), 4.47 (s, 2H), 3.96 (t, J = 7.2 Hz, 2H), 3.26 (t, J = 7.2 Hz, 2H), 2.96 (s, 3H); LCMS (ESI+): m/z 408 (M + H)+, R$_t$: 1.4 min. |
| 39 | 7-(4-Methoxy-pyridin-3-yl)-2-(2-quinolin-2-yl-ethyl)-2,3-dihydro-isoindol-1-one | $^1$H NMR (MeOD-d$_4$): δ 8.30 (d, J = 4.4 Hz, 1H), 8.14 (d, J = 8.4 Hz, 1H), 7.99 (s, 1H), 7.82 (d, J = 8.4 Hz, 1H), 7.78 (d, J = 7.6 Hz, 1H), 7.61 (t, J = 6.8 Hz,, H), 7.50 (t, J = 7.6 Hz, 1H), 7.44 (d, J = 8.0 Hz, 1H), 7.37 (d, J = 8.0 Hz, 1H), 7.18 (d, J = 7.2 Hz, 1H), 6.97 (d, J = 7.2 Hz, 1H), 4.37 (s, 2H), 3.93 (t, J = 7.2 Hz, 2H), 3.55 (s, 3H), 3.21 (t, J = 7.2 Hz, 2H); LCMS (ESI+): m/z 396 (M + H)+, R$_t$: 1.3 min. |
| 40 | 7-(3,5-Difluoro-phenyl)-2-(2-quinolin-2-yl-ethyl)-2,3-dihydro-isoindol-1-one | $^1$H NMR (DMSO-d$_6$): δ 8.29 (d, J = 8.4 Hz, 1H), 7.93 (d, J = 7.6 Hz, 1H), 7.87 (d, J = 8.0 Hz, 1H), 7.69 (t, J = 7.2 Hz, 1H), 7.64 (d, J = 2 Hz, 1H), 7.62 (s, 1H), 7.54 (t, J = 6.8 Hz, 1H), 7.48 (d, J = 8.4 Hz, 1H), 7.41 (m, 1H), 7.22 (d, J = 9.6 Hz, 1H), 7.12 (d, J = 2 Hz, 1H), 7.10 (d, J = 2 Hz, 1H), 4.53 (s, 2H), 3.97 (t, J = 7.2 Hz, 2H), 3.27 (t, J = 7.2 Hz, 2H); LCMS (ESI+): m/z 401 (M + H)+, R$_t$: 1.79 min. |
| 41 | 7-(2,5-Dimethoxy-phenyl)-2-(2-quinolin- | $^1$H NMR (MeOD-d$_4$): δ 8.18 (d, J = 2.2 Hz, 1H), 7.89 (d, J = 8.4 Hz, 1H), 7.82 (d, J = 8.0 Hz, 1H), 7.66 (t, J = 7.2 Hz, |

| Ex. | IUPAC-Name | physico-chemical data |
|---|---|---|
| | 2-yl-ethyl)-2,3-dihydro-isoindol-1-one | 1H), 7.48 (t, J = 7.6 Hz, 1H), 7.39 (t, J = 8.8 Hz, 1H), 7.18 (d, J = 7.2 Hz, 1H), 6.82 (s, 2H), 6.61 (s, 1H), 7.43 (d, J = 8.4 Hz, 1H), 7.37 (d, J = 7.2 Hz, 1H), 7.24 (m, 2H), 4.37 (s, 2H), 3.97 (t, J = 7.2 Hz, 2H), 3.65 (s, 3H), 3.44 (s, 3H), 3.28 (d, J = 11.2 Hz, 2H); LCMS (ESI+): m/z 425 (M + H)+, $R_t$: 1.71 min. |
| 42 | 2-[3-Oxo-2-(2-quinolin-2-yl-ethyl)-2,3-dihydro-1H-isoindol-4-yl]-pyrrole-1-carboxylic acid tert-butyl ester | $^1$H NMR (DMSO-$d_6$): δ 8.29 (d, J = 8.4 Hz, 1H), 7.94 (s, 1H), 7.92 (s, 1H), 7.72 (t, J = 8.4 Hz, 1H), 7.57-7.51 (m, 3H), 7.51 (d, J = 6 Hz, 1H), 7.35 (s, 1H), 7.31 (d, J = 6 Hz, 1H), 6.23 (t, J = 3.2 Hz, 1H), 6.16-6.15 (m, 1H), 4.49 (s, 2H), 3.94 (t, J = 7.2 Hz, 2H), 3.25 (t, J = 7.2 Hz, 2H), 1.07 (s, 9H); LCMS (ESI+): m/z 454 (M + H)+, $R_t$: 1.86 min. |
| 43 | 7-(3-Dimethylamino-phenyl)-2-(2-quinolin-2-yl-ethyl)-2,3-dihydro-isoindol-1-one | $^1$H NMR (DMSO-$d_6$): δ 8.27 (d, J = 8.4 Hz, 1H), 7.93 (d, J = 8.0 Hz, 1H), 7.90 (d, J = 8.8 Hz, 1H), 7.70 (t, J = 10 Hz, 1H), 7.59 (d, J = 7.2 Hz, 1H), 7.53 (d, J = 6.8 Hz 1H), 7.47 (d, J = 7.6 Hz, 1H), 7.33 (d, J = 6.4 Hz, 1H), 7.15 (t, J = 7.6 Hz, 1H), 6.74 (br, 1H), 6.72 (d, J = 2.8 Hz, 1H), 6.69 (d, J = 7.6 Hz, 1H), 4.50 (s, 2H), 3.96 (t, J = 7.2 Hz, 2H), 3.26 (t, J = 7.2 Hz, 2H), 2.85 (br, 6H); LCMS (ESI+): m/z 408 (M + H)+, $R_t$: 1.4 min. |
| 44 | 7-(2-Dimethylamino-phenyl)-2-(2-quinolin-2-yl-ethyl)-2,3-dihydro-isoindol-1-one | $^1$H NMR (DMSO-$d_6$): δ 8.88 (d, J = 8.4 Hz, 1H), 8.22 (d, J = 8.4 Hz, 1H), 8.10-8.07 (m, 2H), 7.94 (d, J = 8.8 Hz, 1H), 7.89 (t, J = 6 Hz, 1H), 7.80 (t, J = 2.8 Hz 3H), 7.62 (t, J = 8.0 Hz, 1H), 7.47 (t, J = 7.6 Hz, 1H), 7.43 (t, J = 6 Hz, 1H), 7.13 (d, J = 8.0 Hz, 1H), 4.26 (d, J = 8.0 Hz 1H), 4.06 (d, J = 7.2 Hz 1H), 3.60 (t, J = 6 Hz, 2H), 3.07 (br, 6H); LCMS (ESI+): m/z 408 (M + H)+, $R_t$: 1.37 min. |
| 45 | 7-(2,4-Difluoro-phenyl)-2-(2-quinolin-2-yl-ethyl)-2,3-dihydro-isoindol-1-one | $^1$H NMR (DMSO-$d_6$): δ 8.28 (d, J = 8.4 Hz, 1H), 7.91 (t, J = 8.4 Hz, 2H), 7.71 (t, J = 7.2 Hz, 1H), 7.64 (d, J = 6 Hz, 1H), 7.62 (d, J = 6 Hz, 1H), 7.54 (t, J = 7.6 Hz, 1H), 7.47 (d, J = 8.0 Hz, 1H), 7.33 (d, J = 6.4 Hz, 2H), 7.24 (t, J = 10 Hz, 1H), 7.10 (t, J = 9.2 Hz, 1H), 4.52 (s, 2H), 3.94 (t, J = 7.2 Hz, 2H), 3.25 (t, J = 7.2 Hz, 2H); LCMS (ESI+): m/z 401 (M + H)+, $R_t$: 1.74 min. |
| 46 | 7-Furan-3-yl-2-(2-quinolin-2-yl-ethyl)-2,3-dihydro-isoindol-1-one | $^1$H NMR (DMSO-$d_6$): δ 8.14 (d, J = 8.4 Hz, 1H), 8.01 (br, 1H), 7.82 (d, J = 8.8 Hz, 1H), 7.77 (d, J = 8.4 Hz, 1H), 7.59 (t, J = 6 Hz, 1H), 7.44-7.37 (br, 5H), 7.26 (d, J = 6.8 Hz 1H), 6.68 (br, 1H), 4.29 (br, 2H), 3.95 (d, J = 7.2 Hz, 2H), 3.23 (t, J = 6.8 Hz, 2H); LCMS (ESI+): m/z 355 (M + H)+, $R_t$: 1.65 min. |
| 47 | 7-(1H-Indol-5-yl)-2-(2-quinolin-2-yl-ethyl)-2,3-dihydro-isoindol-1-one | $^1$H NMR (DMSO-$d_6$): δ 8.29 (d, J = 8.4 Hz, 1H), 7.94 (d, J = 8.0 Hz, 1H), 7.88 (d, J = 8.0 Hz, 1H), 7.70 (t, J = 7.2 Hz, 1H), 7.62 (t, J = 7.6 Hz, 1H), 7.60 (s, 1H), 7.54 (t, J = 7.6 Hz, 1H), 7.48 (d, J = 8.4. Hz, 1H), 7.47 (d, J = 8.0 Hz, 1H), 7.43 (d, J = 8.4 Hz, 1H), 7.37 (d, J = 7.2 Hz, 1H), 7.24 (m 4.50 (s, 2H), 3.96 (t, J = 7.2 Hz, 2H), 3.26 (t, J = 7.2 Hz, 2H); LCMS (ESI+): m/z 404 (M + H)+, $R_t$: 1.68 min. |
| 48 | 7-(4-Methyl-thiophen-2-yl)-2-(2-quinolin-2-yl-ethyl)-2,3-dihydro-isoindol-1-one | $^1$H NMR (DMSO-$d_6$): δ 11.08 (br, 1H), 8.29 (d, J = 8.4 Hz, 1H), 7.94 (d, J = 8.4 Hz, 1H), 7.91 (d, J = 8.4 Hz, 1H), 7.71 (t, J = 6.4 Hz, 1H), 7.59-7.53 (br, 3H), 7.48 (t, J = 6.8 Hz, 2H), 7.35-7.33 (br, 3H), 7.16 (d, J = 8.0 Hz, 1H), 6.41 (br, 1H), 4.50 (s, 2H), 3.96 (t, J = 7.2 Hz, 2H), 3.29 (br, 3H), 3.26 (t, J = 7.2 Hz, 2H); LCMS (ESI+): m/z 385 (M + H)+, $R_t$: 1.78 min. |
| 49 | {4-[3-Oxo-2-(2-quinolin-2-yl-ethyl)-2,3-dihydro-1H-isoindol-4-yl]-phenyl}-acetonitrile | $^1$H NMR (DMSO-$d_6$): δ 8.66 (d, J = 7.2 Hz, 1H), 8.13 (d, J = 8.0 Hz, 1H), 8.03 (d, J = 8.0 Hz, 1H), 7.90 (t, J = 7.2 Hz, 1H), 7.66 (d, J = 3.6 Hz, 1H), 7.73 (d, J = 8.0 Hz, 1H), 7.64-7.58 (br, 2H), 7.31 (t, J = 6.8 Hz, 3H), 7.25 (d, J = 8.4 Hz, 1H), 7.43 (d, J = 8.4 Hz, 1H), 7.37 (d, J = 7.2 Hz, 1H), 7.24 (m, 2H), 4.56 (s, 2H), 4.09 (br, 2H), 3.99 (t, J = 7.2 Hz, 2H), 3.4 (t, J = 7.2 Hz, 2H); LCMS (ESI+): m/z 404 (M + H)+, $R_t$: 1.65 min. |
| 50 | 7-(2,3-Difluoro-phenyl)-2-(2-quinolin-2-yl-ethyl)-2,3-dihydro-isoindol-1-one | $^1$H NMR (DMSO-$d_6$): δ 8.28 (d, J = 8.4 Hz, 1H), 7.92 (d, J = 8.0 Hz, 1H), 7.90 (d, J = 80 Hz, 1H), 7.71 (t, J = 7.2 Hz, 1H), 7.69 (d, J = 7.6 Hz, 2H), 7.54 (t, J = 6.8 Hz, 1H), 7.47 (d, J = 8.4 Hz, 1H), 7.35 (t, J = 3.2 Hz, 1H), 7.25 (t, J = 8.0 Hz, 1H), 7.17-7.13 (br, 1H), 4.53 (s, 2H), 3.95 (t, J = 7.2 Hz, 2H), 3.25 (t, J = 7.2 Hz, 2H); LCMS (ESI+): m/z 401 (M + H)+, $R_t$: 1.74 min. |
| 51 | 7-(2,5-Difluoro-phenyl)-2-(2-quinolin-2-yl-ethyl)-2,3- | $^1$H NMR (MeOD-$d_4$): δ 8.27 (d, J = 8.4 Hz, 1H), 7.91 (t, J = 9.6 Hz, 2H), 7.73 (d, J = 8.0 Hz, 1H), 7.64 (t, J = 7.2 Hz, 1H), 7.58 (d, J = 7.6 Hz, 2H), 7.50 (d, J = 8.8 Hz, |

| Ex. | IUPAC-Name | physico-chemical data |
|---|---|---|
|  | dihydro-isoindol-1-one | 1H), 7.36 (d, J = 8.4 Hz, 1H), 7.11 (t, J = 6.8 Hz, 2H), 6.99 (t, J = 3.6 Hz, 1H), 4.06 (t, J = 7.2 Hz, 2H), 3.35 (t, J = 7.2 Hz, 2H); LCMS (ESI+): m/z 401 (M + H)+, $R_t$: 1.74 min. |
| 52 | 7-(5-Fluoro-2-methoxy-phenyl)-2-(2-quinolin-2-yl-ethyl)-2,3-dihydro-isoindol-1-one | $^1$H NMR (DMSO-$d_6$): δ 8.588 (br, 1H), 8.08 (d, J = 8.4 Hz, 1H), 8.01 (d, J = 8.0 Hz, 1H), 7.86 (t, J = 7.2 Hz, 1H), 7.70 (t, J = 7.2 Hz, 1H), 7.57 (t, J = 6 Hz, 1H), 7.25 (d, J = 8.4 Hz, 1H), 7.13 (d, J = 6 Hz, 1H), 6.99 (d, J = 9.2 Hz, 1H), 6.86 (d, J = 9.2 Hz, 1H), 4.52 (s, 2H), 3.96 (t, J = 7.2 Hz, 2H), 3.36 (t, J = 7.2 Hz, 2H); LCMS (ESI+): m/z 413 (M + H)+, $R_t$: 1.74 min. |
| 53 | 7-(1H-Pyrazol-3-yl)-2-(2-quinolin-2-yl-ethyl)-2,3-dihydro-isoindol-1-one | $^1$H NMR (MeOD-$d_4$): δ 8.17 (d, J = 8.4 Hz, 1H), 7.85 (d, J = 10.8 Hz, 1H), 7.80 (d, J = 8.0 Hz, 1H), 7.79 (d, J = 7.2 Hz, 1H), 7.60 (t, J = 7.6 Hz, 1H), 7.54 (t, J = 7.6 Hz, 1H), 7.45 (br, 1H), 7.44 (s, 1H), 7.42 (s, 1H), 7.37 (d, J = 7.2 Hz, 1H), 6.78 (br, 1H), 4.45 (s, 2H), 4.03 (t, J = 7.2 Hz, 2H), 3.31 (t, J = 7.2 Hz, 2H); LCMS (ESI+): m/z 355 (M + H)+, $R_t$: 1.47 min. |
| 54 | 7-(6-Methoxy-pyridin-3-yl)-2-(2-quinolin-2-yl-ethyl)-2,3-dihydro-isoindol-1-one | $^1$H NMR (DMSO-$d_6$): δ 8.29 (d, J = 8.4 Hz, 1H), 8.21 (d, J = 2 Hz, 1H), 7.94 (d, J = 8.8 Hz, 1H), 7.90 (d, J = 4.4 Hz, 1H), 7.76 (d, J = 7.6 Hz, 1H), 7.70 (t, J = 8.4 Hz, 1H), 7.62 (t, J = 8.4 Hz, 1H), 7.58 (d, J = 8.4 Hz, 1H), 7.54 (t, J = 8.0 Hz, 1H), 7.52 (d, J = 8.4 Hz, 1H), 7.37 (d, J = 7.2 Hz, 1H), 6.81 (d, J = 8.4 Hz, 1H), 4.51 (s, 2H), 3.97 (t, J = 7.2 Hz, 2H), 3.89 (br, 3H), 3.27 (t, J = 7.2 Hz, 2H); LCMS (ESI+): m/z 396 (M + H)+, $R_t$: 1.55 min. |
| 55 | 7-(2-Fluoro-3-methoxy-phenyl)-2-(2-quinolin-2-yl-ethyl)-2,3-dihydro-isoindol-1-one | $^1$H NMR (DMSO-$d_6$): δ 8.57 (m, 1H), 8.08 (d, J = 8.4 Hz, 1H), 8.01 (d, J = 80 Hz, 1H), 7.86 (t, J = 4.8 Hz, 1H), 7.69 (m, 2H), 7.63 (d, J = 7.6 Hz, 1H), 7.63 (br, 1H), 7.31 (d, J = 8.4 Hz, 1H), 7.13 (t, J = 8.0 Hz, 1H), 7.07 (t, J = 7.2 Hz, 1H), 6.75 (t, J = 8.4 Hz, 1H), 4.55 (s, 2H), 3.96 (t, J = 7.2 Hz, 2H), 3.83 (br, 3H), 3.35 (t, J = 9.2 Hz, 2H); LCMS (ESI+): m/z 413 (M + H)+, $R_t$: 1.71 min. |
| 56 | 7-(2,3-Dihydro-benzofuran-5-yl)-2-(2-quinolin-2-yl-ethyl)-2,3-dihydro-isoindol-1-one | $^1$H NMR (DMSO-$d_6$): δ 8.28 (d, J = 8.4 Hz, 1H), 7.94 (d, J = 8.0 Hz, 1H), 7.90 (d, J = 8.4 Hz, 1H), 7.70 (t, J = 7.2 Hz, 1H), 7.57 (t, J = 7.6 Hz, 1H), 7.54 (t, J = 7.2 Hz, 1H), 7.48 (t, J = 8.4 Hz, 2H), 7.28 (d, J = 8.0 Hz, 1H), 7.24 (br, 1H), 7.14 (d, J = 7.2 Hz, 1H), 6.74 (d, J = 8.4 Hz, 1H), 4.49 (s, 2H), 4.55 (t, J = 7.2 Hz, 2H), 3.96 (t, J = 7.2 Hz, 2H), 3.24 (t, J = 9.2 Hz, 2H), 3.14 (t, J = 8.4 Hz, 2H); LCMS (ESI+): m/z 407 (M + H)+, $R_t$: 1.72 min. |
| 57 | 7-(2,3-Dimethoxy-phenyl)-2-(2-quinolin-2-yl-ethyl)-2,3-dihydro-isoindol-1-one | $^1$H NMR (DMSO-$d_6$): δ 8.26 (d, J = 8.4 Hz, 1H), 7.90 (t, J = 8.0 Hz, 2H), 7.70 (t, J = 8.0 Hz, 1H), 7.53 (br, 3H), 7.45 (d, J = 7.6 Hz, 1H), 7.18 (d, J = 7.6 Hz, 1H), 7.03 (d, J = 8.4 Hz, 1H), 6.99 (t, J = 8.4 Hz, 1H), 6.64 (d, J = 8.4 Hz, 1H), 4.55 (s, 2H), 3.92 (t, J = 7.2 Hz, 2H), 3.81 (br, 3H), 3.30 (br, 3H), 3.26 (t, J = 7.2 Hz, 2H); LCMS (ESI+): m/z 425 (M + H)+, $R_t$: 1.67 min. |
| 58 | 7-Pyrimidin-5-yl-2-(2-quinolin-2-yl-ethyl)-2,3-dihydro-isoindol-1-one | $^1$H NMR (DMSO-$d_6$): δ 9.13 (br, 1H), 8.78 (br, 1H), 8.62 (d, J = 8.4 Hz, 1H), 8.09 (d, J = 8.0 Hz, 1H), 7.99 (d, J = 8.0 Hz, 1H), 7.88 (t, J = 7.2 Hz, 1H), 7.72 (br, 4H), 7.50 (d, J = 7.6 Hz, 1H), 4.59 (s, 2H), 4.01 (t, J = 7.2 Hz, 2H), 3.39 (t, J = 7.2 Hz, 2H); LCMS (ESI+): m/z 367 (M + H)+, $R_t$: 1.38 min. |
| 59 | 7-(6-Morpholin-4-yl-pyridin-3-yl)-2-(2-quinolin-2-yl-ethyl)-2,3-dihydro-isoindol-1-one | $^1$H NMR (CDCl$_3$-d1): δ 8.73 (d, J = 8.4 Hz, 1H), 8.55 (d, J = 8.0 Hz, 1H), 8.38 (d, J = 2 Hz, 1H), 8.06 (d, J = 7.2 Hz, 1H), 8.04 (d, J = 7.6 Hz, 1H), 8.02 (d, J = 5.6 Hz, 1H), 7.84 (d, J = 7.6 Hz, 1H), 7.82 (d, J = 8.4 Hz, 1H), 7.61 (d, J = 8.0 Hz, 1H), 7.54 (d, J = 8.4 Hz, 1H), 7.34 (d, J = 7.2 Hz, 1H), 6.91 (d, J = 8.4 Hz, 1H), 4.60 (s, 2H), 4.172 (t, J = 7.2 Hz, 2H), 3.90 (br, 5H), 3.76 (br, 6H); LCMS (ESI+): m/z 451 (M + H)+, $R_t$: 1.36 min. |
| 60 | 7-(3-Methanesulfonyl-phenyl)-2-(2-quinolin-2-yl-ethyl)-2,3-dihydro-isoindol-1-one | $^1$H NMR (DMSO-$d_6$): δ 8.05 (d, J = 8.4 Hz, 1H), 7.37 (d, J = 8.0 Hz, 1H), 7.21 (br, 2H), 6.99 (br, 4H), 6.79 (d, J = 7.6 Hz, 1H), 6.75 (d, J = 7.6 Hz, 1H), 6.67 (s, 1H), 6.63 (d, J = 8.4 Hz, 1H), 6.53 (d, J = 8.0 Hz, 1H), H), 3.79 (s, 2H), 3.25 (t, J = 7.2 Hz, 2H), 2.718 (t, J = 7.2 Hz, 2H), 2.09 (br, 3H); LCMS (ESI+): m/z 443 (M + H)+, $R_t$: 1.56 min. |
| 61 | 7-(2-Methoxy-pyrimidin-5-yl)-2-(2-quinolin-2-yl-ethyl)- | $^1$H NMR (DMSO-$d_6$): δ 8.64 (s, 2H), 8.29 (d, J = 8.4 Hz, 1H), 7.93 (d, J = 8 Hz, 1H), 7.67 (br, 3H), 7.54 (t, J = 7.2 Hz, 1H), 7.45 (t, J = 7.6 Hz, 2H), 4.54 (s, 2H), |

| Ex. | IUPAC-Name | physico-chemical data |
|---|---|---|
|  | 2,3-dihydro-isoindol-1-one | 3.98 (t, J = 7.2 Hz, 4H), 3.27 (t, J = 7.2 Hz, 2H); LCMS (ESI+): m/z 397 (M + H)+, $R_t$: 1.5 min. |
| 62 | 7-Quinolin-5-yl-2-(2-quinolin-2-yl-ethyl)-2,3-dihydro-isoindol-1-one | $^1$H NMR (DMSO-d$_6$): δ 8.85 (d, J = 8.4 Hz, 1H), 8.26 (d, J = 8.0 Hz, 1H), 8.04 (d, J = 8.0 Hz, 1H), 7.94 (d, J = 7.2 Hz, 1H), 7.86 (d, J = 7.6 Hz, 1H), 7.76 (d, J = 6.8 Hz, 1H), 7.74 (d, J = 7.6 Hz, 1H), 7.70 (br, 3H), 7.68 (d, J = 8.0 Hz, 1H), 7.54 (t, J = 8.4 Hz, 1H), 7.42 (d, J = 7.2 Hz, 1H), 7.39 (d, J = 8.4 Hz, 1H), 7.37 (d, J = 8.4 Hz, 1H), 7.34 (d, J = 8.4 Hz, 1H), 4.67 (q, J = 7.2 Hz, 2H), 3.86 (t, J = 7.2 Hz, 2H), 3.20 (t, J = 7.2 Hz, 2H); LCMS (ESI+): m/z 416 (M + H)+, $R_t$: 1.36 min. |
| 63 | 7-(1H-Indol-4-yl)-2-(2-quinolin-2-yl-ethyl)-2,3-dihydro-isoindol-1-one | $^1$H NMR (DMSO-d$_6$): δ 11.09 (br, 1H), 8.28 (d, J = 8.4 Hz, 1H), 7.92 (t, J = 8.0 Hz, 2H), 7.71 (t, J = 8.0 Hz, 1H), 7.60 (t, J = 7.2 Hz, 1H), 7.56 (t, J = 7.6 Hz, 2H), 7.46 (d, J = 8.4 Hz, 1H), 7.42 (d, J = 7.6 Hz, 1H), 7.23 (t, J = 8.4 Hz, 1H), 7.05 (t, J = 8.0 Hz, 1H), 6.91 (d, J = 8.4 Hz, 1H), 6.02 (d, J = 7.2 Hz, 1H), 4.52 (s, 2H), 3.90 (t, J = 7.2 Hz, 2H), 3.24 (t, J = 7.2 Hz, 2H); LCMS (ESI+): m/z 404 (M + H)+, $R_t$: 1.65 min. |
| 64 | 7-(1H-Indol-6-yl)-2-(2-quinolin-2-yl-ethyl)-2,3-dihydro-isoindol-1-one | $^1$H NMR (DMSO-d$_6$): δ 11.11 (br, 1H), 8.29 (d, J = 8.4 Hz, 1H), 7.92 (t, J = 8.0 Hz, 2H), 7.71 (t, J = 8.0 Hz, 1H), 7.60 (d, J = 7.2 Hz, 1H), 7.56 (d, J = 7.6 Hz, 1H), 7.51 (br, 5H), 7.38 (d, J = 7.6 Hz, 2H), 7.07 (d, J = 8.4 Hz, 1H), 6.44 (br, 1H), 4.50 (s, 2H), 3.96 (t, J = 7.2 Hz, 2H), 3.27 (t, J = 7.2 Hz, 2H); LCMS (ESI+): m/z 404 (M + H)+, $R_t$: 1.72 min. |
| 65 | 7-(2-Methyl-pyridin-4-yl)-2-(2-quinolin-2-yl-ethyl)-2,3-dihydro-isoindol-1-one | $^1$H NMR (DMSO-d$_6$): δ 8.40 (d, J = 8.4 Hz, 1H), 8.29 (d, J = 8.0 Hz, 1H), 7.94 (d, J = 8.0 Hz, 1H), 7.87 (d, J = 7.2 Hz, 1H), 7.70 (t, J = 7.6 Hz, 1H), 7.66 (br, 2H), 7.55 (t, J = 8.4 Hz, 1H), 7.49 (t, J = 7.6 Hz, 1H), 7.38 (d, J = 8.4 Hz, 1H), 7.21 (br, 1H), 7.18 (d, J = 8.0 Hz, 1H), 4.55 (s, 2H), 3.97 (t, J = 7.2 Hz, 2H), 3.26 (t, J = 7.2 Hz, 2H), 2.46 (br, 3H); LCMS (ESI+): m/z 380 (M + H)+, $R_t$: 1.28 min. |
| 66 | 7-(2-Methoxy-pyridin-3-yl)-2-(2-quinolin-2-yl-ethyl)-2,3-dihydro-isoindol-1-one | $^1$H NMR (DMSO-d$_6$): δ 8.28 (d, J = 8.4 Hz, 1H), 8.16 (d, J = 80 Hz, 1H), 7.92 (d, J = 8.0 Hz, 2H), 7.71 (t, J = 7.2 Hz, 1H), 7.56 (br, 3H), 7.47 (d, J = 8.4 Hz, 2H), 7.28 (d, J = 7.6 Hz, 1H), 7.00 (d, J = 8.4 Hz, 1H), 4.49 (s, 2H), 3.93 (t, J = 7.2 Hz, 2H), 3.67 (br, 3H), 3.24 (t, J = 7.2 Hz, 2H); LCMS (ESI+): m/z 396 (M + H)+, $R_t$: 1.57 min. |
| 67 | 7-(3-Methoxymethyl-phenyl)-2-(2-quinolin-2-yl-ethyl)-2,3-dihydro-isoindol-1-one | $^1$H NMR (DMSO-d$_6$): δ 8.08 (d, J = 8.4 Hz, 1H), 7.78 (d, J = 8.0 Hz, 1H), 7.74 (d, J = 8.0 Hz, 1H), 7.56 (t, J = 7.2 Hz, 1H), 7.39 (t, J = 7.6 Hz, 2H), 7.31 (t, J = 7.6 Hz, 2H), 7.15 (br, 5H), 4.30 (s, 4H), 3.88 (t, J = 7.2 Hz, 2H), 3.23 (s, 3H), 3.167 (t, J = 7.2 Hz, 2H); LCMS (ESI+): m/z 409 (M + H)+, $R_t$: 1.70 min. |
| 68 | 7-Isoquinolin-4-yl-2-(2-quinolin-2-yl-ethyl)-2,3-dihydro-isoindol-1-one | $^1$H NMR (DMSO-d$_6$): δ 8.92 (d, J = 8.4 Hz, 1H), 8.50 (d, J = 8.0 Hz, 1H), 8.42 (br, 1H), 8.28 (d, J = 8.0 Hz, 1H), 8.11 (d, J = 8.4 Hz, 1H), 8.05 (t, J = 6.8 Hz 1H), 7.96-7.844 (br, 5H), 7.63 (d, J = 7.6 Hz, 1H), 7.54 (d, J = 8.4 Hz, 1H), 4.73 (d, J = 18 Hz, 1H), 4.58 (q, J = 7.6 Hz, 1H), 4.06 (q, J = 7.6 Hz, 1H), 3.63 (t, J = 7.2 Hz, 2H); LCMS (ESI+): m/z 416 (M + H)+, $R_t$: 1.35 min. |
| 69 | 7-(5-Methoxy-pyridin-3-yl)-2-(2-quinolin-2-yl-ethyl)-2,3-dihydro-isoindol-1-one | $^1$H NMR (DMSO-d$_6$): δ 8.28 (d, J = 8.4 Hz, 1H), 8.26 (d, J = 3.2 Hz, 1H), 8.19 (d, J = 1.2 Hz, 1H), 7.93 (d, J = 5.6 Hz, 1H), 7.88 (d, J = 8.4 Hz, 1H), 7.70 (d, J = 7.6 Hz, 1H), 7.65 (d, J = 6.4 Hz, 1H), 7.64 (s, 1H), 7.54 (t, J = 8.0 Hz, 1H), 7.48 (d, J = 8.4 Hz, 1H), 7.44 (d, J = 7.2 Hz, 1H), 7.40 (t, J = 2 Hz, 1H), 4.54 (s, 2H), 3.97 (t, J = 7.2 Hz, 2H), 3.80 (br, 3H), 3.27 (t, J = 7.2 Hz, 2H); LCMS (ESI+): m/z 396 (M + H)+, $R_t$: 1.34 min. |
| 70 | 7-(1-Methyl-1H-pyrazol-4-yl)-2-(2-quinolin-2-yl-ethyl)-2,3-dihydro-isoindol-1-one | $^1$H NMR (DMSO-d$_6$): δ 8.46 (br, 1H), 8.30 (d, J = 8.0 Hz, 1H), 7.98 (br, 1H), 7.94 (d, J = 1.6 Hz, 1H), 7.92 (d, J = 1.6 Hz, 1H), 7.72 (t, J = 6.4 Hz 1H), 7.59 (d, J = 7.6 Hz, 1H), 7.55 (d, J = 8.4 Hz, 1H), 7.51 (d, J = 8.0 Hz, 1H), 7.49 (d, J = 8.4 Hz, 1H), 7.38 (d, J = 7.2 Hz, 1H), 4.00 (t, J = 7.2 Hz, 2H), 3.86 (br, 3H), 3.28 (t, J = 7.2 Hz, 2H); LCMS (ESI+): m/z 369 (M + H)+, $R_t$: 1.46 min. |
| 71 | 7-Isoquinolin-5-yl-2-(2-quinolin-2-yl-ethyl)-2,3-dihydro-isoindol-1-one | $^1$H NMR (MeOD-d$_4$): δ 9.74 (br, 1H), 8.95 (d, J = 8.4 Hz, 1H), 8.45 (d, J = 8.0 Hz, 1H), 8.28 (d, J = 8.0 Hz, 1H), 8.25 (d, J = 7.2 Hz, 1H), 8.13 (d, J = 7.6 Hz, 1H), 8.09 (t, J = 8.4 Hz, 1H), 7.95-7.90 (br, 4H), 7.85-7.82 (br, 3H), 7.46 (t, J = 8.40 Hz, 1H), 4.10 (t, J = 7.2 Hz, |

| Ex. | IUPAC-Name | physico-chemical data |
|---|---|---|
| | | 2H), 3.63 (t, J = 7.2 Hz, 2H); LCMS (ESI+): m/z 416 (M + H)+, $R_t$: 1.35 min. |
| 72 | 7-Benzofuran-5-yl-2-(2-quinolin-2-yl-ethyl)-2,3-dihydro-isoindol-1-one | $^1$H NMR (DMSO-d$_6$): δ 8.95 (d, J = 8.4 Hz, 1H), 8.30 (d, J = 8.0 Hz, 1H), 8.11 (br, 1H), 7.95 (d, J = 8.0 Hz, 1H), 7.76 (d, J = 2 Hz, 1H), 7.66 (t, J = 7.6 Hz, 1H), 7.59 (d, J = 7.2 Hz, 1H), 7.48 (br, 1H), 7.41 (d, J = 8.4 Hz, 1H), 7.34 (d, J = 8.0 Hz, 1H), 7.12 (d, J = 8.4 Hz, 1H), 6.75 (br, 1H), 4.68 (s, 2H), 4.16 (t, J = 7.2 Hz, 2H), 3.61 (t, J = 7.2 Hz, 2H); LCMS (ESI+): m/z 405 (M + H)+, $R_t$: 1.76 min. |
| 73 | 7-(4-Methyl-thiophen-3-yl)-2-(2-quinolin-2-yl-ethyl)-2,3-dihydro-isoindol-1-one | $^1$H NMR (DMSO-d$_6$): δ 8.98 (d, J = 8.4 Hz, 1H), 8.28 (d, J = 8.0 Hz, 1H), 8.12 (br, 2H), 7.99 (d, J = 8.0 Hz, 1H), 7.97 (t, J = 7.2 Hz, 1H), 7.62 (d, J = 7.6 Hz, 2H), 7.23 (d, J = 7.2 Hz, 1H), 6.98 (d, J = 2.4 Hz, 1H), 6.88 (d, J = 2.4 Hz, 1H), 4.69 (s, 2H), 4.16 (t, J = 7.2 Hz, 2H), 3.63 (t, J = 7.2 Hz, 2H), 1.67 (br, 3H); LCMS (ESI+): m/z 385 (M + H)+, $R_t$: 1.73 min. |
| 74 | 7-(2-Methyl-2H-pyrazol-3-yl)-2-(2-quinolin-2-yl-ethyl)-2,3-dihydro-isoindol-1-one | $^1$H NMR (MeOD-d$_4$): δ 8.24 (d, J = 8.4 Hz, 1H), 7.86 (t, J = 8.0 Hz, 2H), 7.64 (t, J = 8.0 Hz, 2H), 7.53 (q, J = 7.2 Hz, 2H), 7.48 (d, J = 7.6 Hz, 1H), 7.42 (d, J = 6.8 Hz, 1H), 6.19 (d, J = 8.4 Hz, 1H), 4.58 (s, 2H), 4.06 (t, J = 7.2 Hz, 2H), 3.33 (t, J = 7.2 Hz, 2H), 3.24 (br, 3H); LCMS (ESI+): m/z 369 (M + H)+, $R_t$: 1.44 min. |
| 75 | 7-Quinolin-6-yl-2-(2-quinolin-2-yl-ethyl)-2,3-dihydro-isoindol-1-one | $^1$H NMR (DMSO-d$_6$): δ 8.91 (d, J = 8.4 Hz, 1H), 8.34 (d, J = 8.0 Hz, 1H), 8.29 (d, J = 8.0 Hz, 1H), 7.96-7.93 (br, 3H), 7.89 (d, J = 7.6 Hz, 1H), 7.78 (d, J = 8.4 Hz, 1H), 7.70 (t, J = 6.8 Hz, 1H), 7.67 (d, J = 8.4 Hz, 1H), 7.64 (d, J = 8.0 Hz, 1H), 7.56 (d, J = 8.4 Hz, 1H), 7.55 (d, J = 7.2 Hz, 1H), 7.48 (d, J = 9.2 Hz, 1H), 4.52 (s, 2H), 3.97 (t, J = 7.2 Hz, 2H), 3.75 (br, 3H), 3.27 (t, J = 7.2 Hz, 2H); LCMS (ESI+): m/z 416 (M + H)+, $R_t$: 1.37 min. |
| 76 | 7-(3-Fluoro-5-methoxy-phenyl)-2-(2-quinolin-2-yl-ethyl)-2,3-dihydro-isoindol-1-one | $^1$H NMR (DMSO-d$_6$): δ 8.28 (d, J = 8.4 Hz, 1H), 7.93 (d, J = 8.0 Hz, 1H), 7.89 (d, J = 8.0 Hz, 1H), 7.70 (t, J = 7.2 Hz, 2H), 7.55 (t, J = 7.6 Hz, 1H), 7.48 (d, 1H), 7.54 (t, J = 7.6 Hz, 1H), 7.48 (d, J = 8.4 Hz, 1H), 7.38 (d, J = 8.4 Hz, 1H), = 8.0 Hz, 1H), 6.83 (br, 3H), 4.52 (s, 2H), 3.94 (t, J = 7.2 Hz, 2H), 3.25 (t, J = 7.2 Hz, 2H); LCMS (ESI+): m/z 413 (M + H)+, $R_t$: 1.78 min. |
| 77 | 7-(5-Fluoro-pyridin-3-yl)-2-(2-quinolin-2-yl-ethyl)-2,3-dihydro-isoindol-1-one | $^1$H NMR (DMSO-d$_6$): δ 8.56 (d, J = 0.5 Hz, 1H), 8.48 (br, 1H), 8.29 (d, J = 8.0 Hz, 1H), 7.85 (t, J = 7.2 Hz, 1H), 7.76 (d, J = 7.6 Hz, 1H), 7.72 (d, J = 8.4 Hz, 1H), 7.68 (d, J = 7.2 Hz, 1H), 7.66 (br, 1H), 7.54 (d, J = 8.4 Hz, 1H), 7.49 (d, J = 8.0 Hz, 1H), 7.46 (t, J = 8.4 Hz, 1H), 4.55 (s, 2H), 3.98 (t, J = 7.2 Hz, 2H), 3.29 (t, J = 7.2 Hz, 2H); LCMS (ESI+): m/z 384 (M + H)+, $R_t$: 1.48 min. |
| 78 | 7-(1H-Pyrazol-4-yl)-2-(2-quinolin-2-yl-ethyl)-2,3-dihydro-isoindol-1-one | $^1$H NMR (DMSO-d$_6$): δ 12.89 (br, 1H), 8.30 (d, J = 8.4 Hz, 1H), 7.94 (br, 1H), 7.91 (br, 1H), 7.71 (t, J = 8.0 Hz, 1H), 7.62 (d, J = 7.2 Hz, 1H), 7.54-7.48 (m, 3H), 7.38 (d, J = 7.6 Hz, 1H), 4.00 (t, J = 7.2 Hz, 2H), 3.29 (t, J = 7.2 Hz, 2H); LCMS (ESI+): m/z 355 (M + H)+, $R_t$: 1.39 min. |
| 79 | 7-(5-Methanesulfonyl-pyridin-3-yl)-2-(2-quinolin-2-yl-ethyl)-2,3-dihydro-isoindol-1-one | $^1$H NMR (MeOD-d$_4$): δ 9.02 (br, 1H), 8.97 (d, J = 8.4 Hz, 1H), 8.81 (br, 1H), 8.32 (br, 1H), 8.31 (d, J = 8.0 Hz, 1H), 8.12 (d, J = 5.2 Hz, 1H), 7.98 (d, J = 8.4 Hz, 1H), 7.92 (t, J = 7.6 Hz, 1H), 7.76 (d, J = 7.6 Hz, 1H), 7.75 (d, J = 8.4 Hz, 1H), 7.55 (d, J = 8.0 Hz, 1H), 4.73 (s, 2H), 4.19 (t, J = 7.2 Hz, 2H), 3.64 (t, J = 7.2 Hz, 2H), 3.13 (br, 3H); LCMS (ESI+): m/z 444 (M + H)+, $R_t$: 1.44 min. |
| 80 | 7-(3-Morpholin-4-yl-phenyl)-2-(2-quinolin-2-yl-ethyl)-2,3-dihydro-isoindol-1-one | $^1$H NMR (DMSO-d$_6$): δ 8.28 (d, J = 8.4 Hz, 1H), 7.93 (d, J = 8.0 Hz, 1H), 7.88 (d, J = 8.0 Hz, 1H), 7.60-7.52 (br, 3H), 7.47 (d, J = 7.2 Hz, 1H), 7.34 (d, J = 7.6 Hz, 1H), 7.21 (d, J = 7.2 Hz, 1H), 6.95 (d, J = 8.4 Hz, 2H), 6.86 (d, J = 8.0 Hz, 1H), 4.55 (s, 2H), 3.96 (t, J = 7.2 Hz, 2H), 3.72 (br, 4H), 3.26 (t, J = 7.2 Hz, 2H), 3.061 (br, 4H); LCMS (ESI+): m/z 450 (M + H)+, $R_t$: 1.55 min. |
| 81 | {3-[3-Oxo-2-(2-quinolin-2-yl-ethyl)-2,3-dihydro-1H-isoindol-4-yl]-phenyl}-acetonitrile | $^1$H NMR (DMSO-d$_6$): δ 8.80 (d, J = 8.4 Hz, 1H), 8.14 (d, J = 8.0 Hz, 1H), 7.99-7.96 (m, 2H), 7.82 (t, J = 7.2 Hz, 2H), 7.53 (d, J = 7.6 Hz, 1H), 7.48 (d, J = 7.6 Hz, 1H), 7.24 (d, J = 8.4 Hz, 1H), 7.22 (t, J = 8.0 Hz, 3H), 7.05 (d, J = 8.4 Hz, 1H), 7.37 (d, J = 7.2 Hz, 1H), 4.55 (s, 2H), 4.03 (t, J = 7.2 Hz, 2H), 3.68 (br, 2H), |

| Ex. | IUPAC-Name | physico-chemical data |
|---|---|---|
| 82 | 2-(2-Quinolin-2-yl-ethyl)-7-thiazol-2-yl-2,3-dihydro-isoindol-1-one | 3.48 (t, J = 7.2 Hz, 2H); LCMS (ESI+): m/z 404 (M + H)+, R$_t$: 1.64 min. $^1$H NMR (MeOD-d$_4$): δ 9.03 (d, J = 8.4 Hz, 1H), 8.29 (d, J = 8.0 Hz, 1H), 8.21 (d, J = 8.0 Hz, 1H), 8.13 (d, J = 7.2 Hz, 1H), 8.09 (t, J = 12.0 Hz, 3H), 7.95 (d, J = 7.6 Hz, 1H), 7.91 (d, J = 4.8 Hz, 1H), 7.81 (d, J = 8.0 Hz, 2H), 7.43 (d, J = 8.41 Hz, 1H), 7.37 (d, J = 7.2 Hz, 1H), 4.80 (s, 2H), 4.26 (t, J = 7.2 Hz, 2H), 3.71 (t, J = 7.2 Hz, 2H); LCMS (ESI+): m/z 372 (M + H)+, R$_t$: 1.36 min. |
| 83 | 7-Pyrimidin-2-yl-2-(2-quinolin-2-yl-ethyl)-2,3-dihydro-isoindol-1-one | $^1$H NMR (MeOD-d$_4$): δ 8.86 (d, J = 8.8 Hz, 1H), 8.81 (d, J = 5.2 Hz, 2H), 8.16 (d, J = 7.2 Hz, 1H), 8.03 (d, J = 8.0 Hz, 1H), 7.99 (t, J = 7.6 Hz, 1H), 7.89 (t, J = 10.8 Hz, 2H), 7.82 (t, J = 8.4 Hz, 1H), 7.70 (d, J = 8.0 Hz, 2H), 7.50 (t, J = 4.8 Hz, 1H), 4.65 (s, 2H), 4.10 (t, J = 7.2 Hz, 2H), 3.55 (t, J = 7.2 Hz, 2H); LCMS (ESI+): m/z 367 (M + H)+, R$_t$: 1.32 min. |
| 84 | 7-(3H-Imidazol-4-yl)-2-(2-quinolin-2-yl-ethyl)-2,3-dihydro-isoindol-1-one | $^1$H NMR (MeOD-d$_4$): δ 8.98 (d, J = 8.4 Hz, 1H), 8.82 (br, 1H), 8.26 (d, J = 8.0 Hz, 1H), 8.20 (br, 1H), 8.19 (d, J = 8.0 Hz, 1H), 8.09 (t, J = 7.2 Hz, 1H), 7.77 (t, J = 7.6 Hz, 1H), 7.70 (d, J = 7.6 Hz, 1H), 4.80 (s, 2H), 4.30 (t, J = 7.2 Hz, 2H), 3.71 (t, J = 7.2 Hz, 2H); LCMS (ESI+): m/z 355 (M + H)+, R$_t$: 1.28 min. |
| 85 | 2-(2-Quinolin-2-yl-ethyl)-7-(5-trifluoromethyl-pyridin-2-yl)-2,3-dihydro-isoindol-1-one | $^1$H NMR (MeOD-d$_4$): δ 8.99 (d, J = 8.4 Hz, 1H), 8.84 (br, 1H), 8.30 (d, J = 8.0 Hz, 1H), 8.13 (d, J = 3.6 Hz, 2H), 7.98 (br, 3H), 7.75 (br, 2H), 7.63 (t, J = 7.2 Hz, 2H), 4.52 (s, 2H), 3.94 (t, J = 7.2 Hz, 2H), 3.25 (t, J = 7.2 Hz, 2H); LCMS (ESI+): m/z 434 (M + H)+, R$_t$: 1.69 min. |
| 86 | 7-(2-Methyl-pyridin-3-yl)-2-(2-quinolin-2-yl-ethyl)-2,3-dihydro-isoindol-1-one | $^1$H NMR (MeOD-d$_4$): δ 9.00 (d, J = 8.8 Hz, 1H), 8.66 (d, J = 8.0 Hz, 1H), 8.30 (d, J = 8.4 Hz, 1H), 8.19 (t, J = 8.0 Hz, 2H), 8.13 (t, J = 7.6 Hz, 1H), 8.01 (d, J = 8.8 Hz, 1H), 7.95 (t, J = 7.2 Hz, 1H), 7.81 (br, 3H), 7.41 (t, J = 4.8 Hz, 1H), 4.19 (q, J = 6.8 Hz, 2H), 3.65 (t, J = 6.8 Hz, 2H), 2.27 (br, 3H); LCMS (ESI+): m/z 380 (M + H)+, R$_t$: 1.26 min. |
| 87 | 7-(5-Methyl-pyridin-2-yl)-2-(2-quinolin-2-yl-ethyl)-2,3-dihydro-isoindol-1-one | $^1$H NMR (MeOD-d$_4$): δ 8.96 (d, J = 8.4 Hz, 1H), 8.65 (br, 1H), 8.45 (d, J = 8.0 Hz, 1H), 8.35 (d, J = 8.0 Hz, 1H), 8.25 (d, J = 8.4 Hz, 1H), 8.18 (d, J = 8.8 Hz, 1H), 8.12 (q, J = 4. Hz, 1H), 8.07 (t, J = 7.2 Hz, 1H), 8.03 (d, J = 8.4 Hz, 1H), 7.90 (br, 3H), 4.84 (s, 2H), 4.28 (t, J = 7.2 Hz, 2H), 3.70 (t, J = 7.2 Hz, 2H), 2.59 (br, 3H); LCMS (ESI+): m/z 380 (M + H)+, R$_t$: 1.31 min. |
| 88 | 7-(5-Fluoro-pyridin-2-yl)-2-(2-quinolin-2-yl-ethyl)-2,3-dihydro-isoindol-1-one | $^1$H NMR (MeOD-d$_4$): δ 8.78 (d, J = 8.4 Hz, 1H), 8.26 (br, 1H), 8.10 (d, J = 8.0 Hz, 1H), 7.93 (br, 1H), 7.79 (d, J = 8.4 Hz, 1H), 7.74 (t, J = 7.6 Hz, 1H), 7.53 (d, J = 7.6 Hz, 2H), 7.40 (d, J = 8.4 Hz, 1H), 7.30 (q, J = 8.0 Hz, 2H), 4.50 (s, 2H), 3.97 (t, J = 7.2 Hz, 2H), 3.43 (t, J = 7.2 Hz, 2H); LCMS (ESI+): m/z 384 (M + H)+, R$_t$: 1.48 min. |
| 89 | 7-(3-Methyl-pyridin-2-yl)-2-(2-quinolin-2-yl-ethyl)-2,3-dihydro-isoindol-1-one | $^1$H NMR (MeOD-d$_4$): δ 8.93 (d, J = 8.4 Hz, 1H), 8.63 (d, J = 6.8 Hz, 1H), 8.43 (d, J = 8.0 Hz, 1H), 8.25 (d, J = 7.2 Hz, 1H), 8.16 (d, J = 7.6 Hz, 1H), 8.10 (t, J = 7.6 Hz, 1H), 7.97-7.85 (br, 5H), 7.61 (d, J = 8.0 Hz, 1H), 4.80 (s, 2H), 4.16 (t, J = 7.2 Hz, 2H), 3.63 (t, J = 7.2 Hz, 2H), 2.11 (br, 3H); LCMS (ESI+): m/z 380 (M + H)+, R$_t$: 1.27 min. |
| 90 | 5-[3-Oxo-2-(2-quinolin-2-yl-ethyl)-2,3-dihydro-1H-isoindol-4-yl]-1,3-dihydro-indol-2-one | $^1$H NMR (MeOD-d$_4$): δ 9.00 (d, J = 8.4 Hz, 1H), 8.33 (d, J = 8.0 Hz, 1H), 8.15 (d, J = 8.0 Hz, 2H), 7.99 (t, J = 8.4 Hz, 2H), 7.64 (d, J = 7.6 Hz, 1H), 7.57 (d, J = 6.8 Hz, 1H), 7.35 (d, J = 8.4 Hz, 1H), 7.08 (d, J = 8.0 Hz, 1H), 7.02 (br, 1H), 6.77 (d, J = 8.4 Hz, 1H), 4.69 (s, 2H), 4.17 (t, J = 7.2 Hz, 2H), 3.62 (t, J = 7.2 Hz, 2H), 3.38 (br, 2H); LCMS (ESI+): m/z 420 (M + H)+, R$_t$: 1.48 min. |
| 91 | 7-(6-Methyl-pyridin-3-yl)-2-(2-quinolin-2-yl-ethyl)-2,3-dihydro-isoindol-1-one | $^1$H NMR (MeOD-d$_4$): δ 8.91 (d, J = 8.4 Hz, 1H), 8.80 (br, 1H), 8.41 (d, J = 8.4 Hz, 1H), 8.24 (d, J = 8.0 Hz, 1H), 8.14 (d, J = 7.2 Hz, 1H), 8.08 (t, J = 6.8 Hz, 1H), 7.95 (d, J = 7.6 Hz, 1H), 7.89 (t, J = 8.4 Hz, 1H), 7.84 (d, J = 8.0 Hz, 1H), 7.80 (d, J = 6.4 Hz, 2H), 7.56 (d, J = 7.2 Hz, 1H), 4.72 (s, 2H), 4.18 (t, J = 7.2 Hz, 2H), 3.62 (t, J = 7.2 Hz, 2H), 2.82 (br, 3H); LCMS (ESI+): m/z 380 (M + H)+, R$_t$: 1.28 min. |
| 92 | 7-(1H-Indol-7-yl)-2-(2-quinolin-2-yl-ethyl)-2,3-dihydro-isoindol-1-one | $^1$H NMR (MeOD-d$_4$): δ 10.55 (br, 1H), 8.55 (d, J = 12 Hz, 1H), 8.08 (d, J = 8.0 Hz, 1H), 8.00 (d, J = 8.0 Hz, 1H), 7.85 (t, J = 6.8 Hz, 1H), 7.70-7.60 (m, 5H), 7.51 (d, J = 7.6 Hz, 1H), 7.40 (d, J = 7.6 Hz, 1H), 7.17 (br, 1H), 6.93 (t, J = 8.4 Hz, 1H), 6.83 (d, J = 6.8 Hz, 1H), |

| Ex. | IUPAC-Name | physico-chemical data |
|---|---|---|
| | | 6.43 (br, 1H), 4.55 (s, 2H), 3.95 (t, J = 7.2 Hz, 2H), 3.35 (t, J = 7.2 Hz, 2H); LCMS (ESI+): m/z 404 (M + H)+, $R_t$: 1.73 min. |
| 93 | 7-(1H-Indazol-5-yl)-2-(2-quinolin-2-yl-ethyl)-2,3-dihydro-isoindol-1-one | 1H NMR (MeOD-d4): δ 8.96 (d, J = 8.4 Hz, 1H), 8.27 (d, J = 8.0 Hz, 1H), 8.11 (br, 2H), 7.96 (br, 3H), 7.67 (d, J = 7.2 Hz, 1H), 7.59 (t, J = 6.0 Hz, 2H), 7.41 (d, J = 7.6 Hz, 1H), 7.30 (d, J = 8.4 Hz, 1H), 7.21 (d, J = 8.0 Hz, 1H), 4.69 (s, 2H), 4.15 (t, J = 7.2 Hz, 2H), 3.62 (t, J = 7.2 Hz, 2H); LCMS (ESI+): m/z 405 (M + H)+, $R_t$: 1.53 min. |
| 94 | 7-(3-Methyl-3H-imidazol-4-yl)-2-(2-quinolin-2-yl-ethyl)-2,3-dihydro-isoindol-1-one | 1H NMR (MeOD-d4): δ 8.91 (br, 2H), 8.25 (d, J = 8.0 Hz, 1H), 8.15 (d, J = 8.0 Hz, 1H), 8.08 (t, J = 7.2 Hz, 1H), 7.96 (d, J = 7.6 Hz, 1H), 7.92-7.85 (br, 2H), 7.80 (t, J = 7.6 Hz, 1H), 7.51 (d, J = 8.4 Hz, 1H), 7.47 (br, 1H), 4.77 (s, 2H), 4.19 (t, J = 7.2 Hz, 2H), 3.62 (t, J = 7.2 Hz, 2H), 3.38 (br, 3H); LCMS (ESI+): m/z 369 (M + H)+, $R_t$: 1.23 min. |
| 95 | 7-(1-Methyl-1H-imidazol-2-yl)-2-(2-quinolin-2-yl-ethyl)-2,3-dihydro-isoindol-1-one | 1H NMR (MeOD-d4): δ 8.71 (d, J = 8.4 Hz, 1H), 8.14 (d, J = 8.0 Hz, 1H), 8.06 (d, J = 8.0 Hz, 1H), 7.99 (t, J = 7.2 Hz, 2H), 7.89 (t, J = 7.6 Hz, 1H), 7.83 (d, J = 7.6 Hz, 1H), 7.79 (t, J = 8.4 Hz, 1H), 7.71 (d, J = 8.0 Hz, 1H), 7.64 (br, 1H), 4.77 (s, 2H), 4.17 (t, J = 7.2 Hz, 2H), 3.55 (t, J = 7.2 Hz, 2H), 3.44 (br, 3H); LCMS (ESI+): m/z 369 (M + H)+, $R_t$: 1.20 min. |
| 96 | 6-[3-Oxo-2-(2-quinolin-2-yl-ethyl)-2,3-dihydro-1H-isoindol-4-yl]-1,3-dihydro-indol-2-one | 1H NMR (MeOD-d4): δ 8.99 (d, J = 8.4 Hz, 1H), 8.29 (d, J = 8.0 Hz, 1H), 8.13 (d, J = 3.6 Hz, 2H), 7.98 (t, J = 7.2 Hz, 1H), 7.94 (t, J = 4.0 Hz, 1H), 7.67 (d, J = 7.2 Hz, 1H), 7.60 (d, J = 8.4 Hz, 1H), 7.36 (d, J = 8.0 Hz, 1H), 7.10 (d, J = 8.4 Hz, 1H), 6.88 (br, 1H), 6.81 (d, J = 7.2 Hz, 1H), 4.68 (s, 2H), 4.17 (t, J = 7.2 Hz, 2H), 3.63 (t, J = 7.2 Hz, 2H), 3.53 (br, 2H); LCMS (ESI+): m/z 420 (M + H)+, $R_t$: 1.5 min. |
| 97 | 7-(1H-Indazol-6-yl)-2-(2-quinolin-2-yl-ethyl)-2,3-dihydro-isoindol-1-one | 1H NMR (MeOD-d4): δ 8.94 (d, J = 8.4 Hz, 1H), 8.24 (d, J = 8.0 Hz, 1H), 8.08 (d, J = 3.6 Hz, 2H), 7.96 (br, 1H), 7.94 (d, J = 7.2 Hz, 1H), 7.89 (q, J = 3.6 Hz, 1H), 7.69 (t, J = 7.6 Hz, 1H), 7.62 (d, J = 7.2 Hz, 1H), 7.53 (d, J = 8.0 Hz, 1H), 7.47 (br, 1H), 7.42 (d, J = 8.4 Hz, 1H), 6.931 (d, J = 7.2 Hz, 1H), 4.69 (s, 2H), 4.15 (t, J = 7.2 Hz, 2H), 3.61 (t, J = 7.2 Hz, 2H); LCMS (ESI+): m/z 405 (M + H)+, $R_t$: 1.54 min. |
| 98 | 2-(2-Quinolin-2-yl-ethyl)-7-(6-trifluoromethyl-pyridin-3-yl)-2,3-dihydro-isoindol-1-one | 1H NMR (MeOD-d4): δ 8.98 (d, J = 8.4 Hz, 1H), 8.62 (br, 1H), 8.29 (d, J = 8.0 Hz, 1H), 8.13 (d, J = 8.0 Hz, 2H), 7.99 (d, J = 7.2 Hz, 1H), 7.93 (d, J = 7.6 Hz, 1H), 7.73 (t, J = 7.6 Hz, 3H), 7.48 (d, J = 6.8 Hz, 1H), 4.73 (s, 2H), 4.17 (t, J = 7.2 Hz, 2H), 3.64 (t, J = 7.2 Hz, 2H); LCMS (ESI+): m/z 434 (M + H)+, $R_t$: 1.73 min. |

Ex. = EXAMPLE

Example 99

7-Morpholin-4-yl-2-(2-quinolin-2-yl-ethyl)-2,3-dihydro-isoindol-1-one

A 25 mL round-bottomed flask was charged with 7-bromo-2-(2-quinolin-2-yl-ethyl)-2,3-dihydro-isoindol-1-one from Example 5.4 (100 mg, 0.3 mmol), Pd(OAc)₂ (7 mg, 0.03 mmol), BINAP (37 mg, 0.06 mmol) in toluene (3 mL). The reaction mixture was sequentially treated with sodium t-butoxide (58 mg, 0.6 mmol) and morpholine (130 mg, 1.5 mmol). The reaction mixture was heated at 80° C. overnight. The solvent was removed under reduced pressure and the residue was purified by prep-TLC (PE/EA=1/2) to give the title compound (20 mg, 18%). LCMS (ESI+): m/z 374 (M+H)+, $R_t$: 1.93 min.; 1H NMR (DMSO-d6, 400 MHz) δ: 8.28 (d, J=8 Hz, 1H), 7.93 (t, J=8.4 Hz, 2H), 7.73 (m, 1H), 7.56 (t, J=7.6 Hz, 1H), 7.49 (d, J=8.4 Hz, 1H), 7.43 (t, J=7.6 Hz, 1H), 7.05 (d, J=7.6 Hz, 1H), 6.85 (d, J=8 Hz, 1H), 4.39 (s, 2H), 3.96 (t, J=7.2 Hz, 2H), 3.72 (t, J=4.4 Hz, 4H), 3.26 (t, J=7.2 Hz, 2H), 3.11 (t, J=4 Hz, 4H).

Compounds of Examples 100 to 110 were prepared analogously to the method described for Example 99.

Example 100

7-[4-(4-Methyl-piperazin-1-yl)-piperidin-1-yl]-2-(2-quinolin-2-yl-ethyl)-2,3-dihydro-isoindol-1-one trifluoroacetate ESI-MS: [M+Na+]=492.2, [M+H+]=470.3.

Example 101

7-(1S,4S)-2,5-Diaza-bicyclo[2.2.1]hept-2-yl-2-(2-quinolin-2-yl-ethyl)-2,3-dihydro-isoindol-1-one 1H NMR (DMSO-d6, 500 MHz): δ=9.08 (s br, 1 H), 8.77-8.56 (m, 2 H), 8.20-8.04 (m, 2 H), 7.91 (t, 1 H), 7.82-7.68 (m, 2 H), 7.37 (t, 1 H), 6.90 (d, 1 H), 6.69 (d, 1 H), 4.74 (s., 1 H), 4.44 (q, 2 H), 4.33 (s., 1H), 4.09-3.81 (m, 3 H), 3.40 (t, 2 H), 3.26 (s br., 1 H), 3.15 (m, 2 H), 1.97 (d., 1 H), 1.80 ppm (d., 1 H)

Example 102

7-piperazin-1-yl-2-(2-quinolin-2-yl-ethyl)-2,3-dihydro-isoindol-1-one $^1$H NMR (DMSO-d$_6$, 500 MHz): δ=8.92 (s br, 2 H), 8.63 (d, 1 H), 8.10 (d, 1 H), 8.05 (d, 1 H), 7.88 (t, 1 H), 7.76 (d, 1 H), 7.70 (t, 1 H), 7.46 (t, 1 H), 7.13 (d, 1 H), 6.90 (d, 1 H), 4.47 (s., 2 H), 3.99 (t, 2 H), 3.40 (t, 2H), 3.25-3.08 (m, 8 H)

Example 103

7-(3,8-Diaza-bicyclo[3.2.1]oct-8-yl)-2-(2-quinolin-2-yl-ethyl)-2,3-dihydro-isoindol-1-one ESI-MS: [M+Na$^+$]=421.20, 400.20, [M+H$^+$]=399.20.

Example 104

7-(1,1-Dioxo-1-thiomorpholin-4-yl)-2-(2-quinolin-2-yl-ethyl)-2,3-dihydro-isoindol-1-one ESI-MS: [M+Na$^+$]=444.10, [M+H$^+$]=422.10.

Example 105

7-[4-(1-Methyl-piperidin-4-yl)-piperazin-1-yl]-2-(2-quinolin-2-yl-ethyl)-2,3-dihydro-isoindol-1-one $^1$H NMR (DMSO-d$_6$, 500 MHz): δ=8.28 (d, 1 H), 7.88-8.60 (m, 2 H), 7.72 (t, 1H), 7.57 (t, 1 H), 7.49 (d, 1 H), 7.40 (t, 1 H), 7.00 (d, 1 H), 6.82 (d, 1 H), 4.39 (s br., 2 H), 3.93 (t, 2 H), 3.25 (t, 2 H), 3.10 (s br., 4 H), 2.80 (d, 2 H), 2.60 (s br., 4 H), 2.14 (s br., 4 H), 1.85 (t, 2 H), 1.72 (d., 2 H), 1.42 ppm (q, 2 H).

Example 106

7-(4-Pyridin-4-yl-piperazin-1-yl)-2-(2-quinolin-2-yl-ethyl)-2,3-dihydro-isoindol-1-one ESI-MS: [M+Na$^+$]=473.1, [M+H$^+$]=450.2.

Example 107

7-(4-Methyl-piperazin-1-yl)-2-(2-quinolin-2-yl-ethyl)-2,3-dihydro-isoindol-1-one ESI-MS: [M+Na$^+$]=409.1, [M+H$^+$]=387.1.

Example 108

7-(3-Phenyl-piperidin-1-yl)-2-(2-quinolin-2-yl-ethyl)-2,3-dihydro-isoindol-1-one ESI-MS: [M+Na$^+$]=470.2, [M+H$^+$]=448.2.

Example 109

7-(3-Phenoxy-piperidin-1-yl)-2-(2-quinolin-2-yl-ethyl)-2,3-dihydro-isoindol-1-one ESI-MS: [M+Na$^+$]=486.2, [M+H$^+$]=464.2.

Example 110

7-[1,4]Oxazepan-4-yl-2-(2-quinolin-2-yl-ethyl)-2,3-dihydro-isoindol-1-one hydrochloride ESI-MS: [M+Na$^+$]=410.1, [M+H$^+$]=388.1

Example 111

7-(7-Nitro-3,4-dihydroisoquinolin-2(1H)-yl)-2-(2-(quinolin-2-yl)ethyl)isoindolin-1-one The title compound was prepared in the same manner as the compound of Example 99 starting from 7-bromo-2-(2-quinolin-2-yl)-2,3-dihydro-isoindol-1-one from Example 5.4 and commercially available 7-nitro-1,2,3,4-tetrahydroisoquinoline hydrochloride (yield 25%). ESI-MS: [M+Na$^+$]=487.10, [M+H$^+$]=465.10

Example 112

7-(7-Amino-3,4-dihydroisoquinolin-2(1H)-yl)-2-(2-(quinolin-2-yl)ethyl)isoindolin-1-one 7-(7-Nitro-3,4-dihydroisoquinolin-2(1H)-yl)-2-(2-(quinolin-2-yl)ethyl)isoindolin-1-one from Example 111 (0.14 mmol, 66 mg) was added to tin chloride dihydrate (0.71 mmol, 160 mg) dissolved in concentrated HCl (37%, 2 mL) under vigorous stiffing. The mixture was further stirred for 2 h at 50° C. Upon cooling with an ice bath, the reaction mixture was basified with aq. NaOH and then extracted with ethyl acetate (3 times). The combined organic phases were washed once with sat. aq. NaCl, dried (Na$_2$SO$_4$), filtered and evaporated. The residue was purified on a SiOH Chromabond column, eluted with 0-2% methanol in CH$_2$Cl$_2$. Yield 34 mg (55%). ESI-MS [M+H$^+$]=435.20.

Example 113

4-Chloro-N-[2-[3-oxo-2-(2-quinolin-2-yl-ethyl)-2,3-dihydro-1H-isoindol-4-yl]-1,2,3,4-tetrahydro-isoquinolin-7-yl]-benzenesulfonamide 4-Chlorobenzene-1-sulfonyl chloride (0.03 mmol, 6 mg) was added to a cooled solution (4° C.) of 7-(7-amino-3,4-dihydroisoquinolin-2(1H)-yl)-2-(2-(quinolin-2-yl)ethyl)isoindolin-1-one from Example 112 (0.03 mmol, 11 mg) in pyridine (1 mL). The mixture was then stirred for 12 h at room temperature, poured into saturated aqueous NaHCO$_3$ and extracted twice with ethyl acetate. The combined organic phases were dried (Na$_2$SO$_4$), filtered and evaporated. The residue was purified on a SiOH Chromabond column, eluted with 0-2% methanol in CH$_2$Cl$_2$. Yield 5 mg (32%). ESI-MS: [M+Na$^{+]=}$632.20, [M+H$^+$]=610.20.

Example 114

4-Isopropyl-N-[2-[3-oxo-2-(2-quinolin-2-yl-ethyl)-2,3-dihydro-1H-isoindol-4-yl]-,2,3,4-tetrahydro-isoquinolin-7-yl]-benzenesulfonamide The title compound was prepared in the same manner as the compound of Example 113 but using 4-isopropylbenzene-1-sulfonyl chloride (0.03 mmol, 6 mg). Yield 2 mg (13%). ESI-MS: [M+Na]$^+$=639.20, [M+H$^+$]=617.30.

Example 115

2-[2-(6-Fluoro-quinolin-2-yl)-ethyl]-7-morpholin-4-yl-2,3-dihydro-isoindol-1-one trifluoroacetate The title compound was prepared in the same manner as the compound of Example 99 but using 2-(6-fluoro-quinolin-2-yl)-ethylamine from Example a5. ESI-MS: [M+Na$^+$]=414.1, [M+H$^+$]=392.1;

Example 116

2-[2-(6-Methoxy-quinolin-2-yl)-ethyl]-7-morpholin-4-yl-2,3-dihydro-isoindol-1-one hydrochloride The title compound was prepared in the same manner as the compound of Example 99 but using 2-(6-methoxy-quinolin-2-yl)-ethylamine from Example a4. ESI-MS: [M+Na]$^+$=426.1, [+H$^+$]=404.1;

Example 117

2-[2-(4-Chloro-quinolin-2-yl)-ethyl]-7-morpholin-4-yl-2,3-dihydro-isoindol-1-one trifluoroacetate The title compound was prepared in the same manner as the compound of Example 99 but using 2-(4-chloro-quinolin-2-yl)-ethylamine from Example a6. ESI-MS: [M+Na$^+$]=430.1, [M+H]$^+$=408.2;

Example 118

2-[2-(8-Chloro-quinolin-2-yl)-ethyl]-7-morpholin-4-yl-2,3-dihydro-isoindol-1-one The title compound was prepared in the same manner as the compound of Example 99 but using 2-(8-chloro-quinolin-2-yl)-ethylamine from Example a2. ESI-MS: [M+Na]$^+$=430.10, [+H$^+$]=408.10.

Example 119

4-Morpholin-4-yl-6-(2-quinolin-2-yl-ethyl)-6,7-dihydro-pyrrolo[3,4-b]pyridin-5-one 119.1 Ethyl 4-bromo-2-methylnicotinate Ethyl 2-methyl-4-oxo-1,4-dihydropyridine-3-carboxylate from Example 3.3 (8 g, 44 mmol) in 9 mL of POBr$_3$ was stirred at 100° C. overnight. The reaction mixture was poured into ice, adjusted to pH=7~8 with solid NaHCO$_3$, and then extracted with EtOAc (3 times). The organic phase was washed with water, dried (Na$_2$SO$_4$), filtered and evaporated to yield 3 g of ethyl 4-bromo-2-methylnicotinate (90% pure). ESI-MS: [M+H]$^+$=245.90, 244.90, 243.90.

119.2 Ethyl 4-bromo-2-(bromomethyl)nicotinate

N-Bromosuccinimide (2.46 mmol, 438 mg) and benzoyl peroxide (0.08 mmol, 20 mg) were added to a solution of ethyl 4-bromo-2-methylnicotinate (90% pure, 500 mg) in CCl$_4$ (15 mL) and stirred at reflux for 2 d. The solution was evaporated in vacuo to yield 597 mg of ethyl 4-bromo-2-(bromomethyl)nicotinate (56% pure).

119.3 4-Bromo-6-(2-(quinolin-2-yl)ethyl)-6,7-dihydro-5H-pyrrolo[3,4-b]pyridin-5-one K$_2$CO$_3$ (2.07 mmol, 286 mg) was added to a solution of ethyl 4-bromo-2-(bromomethyl)nicotinate (56% pure, 597 mg) in DMF (15 mL) and stirred for a few minutes. 2-(Quinolin-2-yl)ethylamine from Example a1 (1.04 mmol, 178 mg) was added and the mixture was further stirred at room temperature for 12 h. The suspension was filtrated and the filtrate evaporated in vacuo. Water was added and the solution basified with a 5% K$_2$CO$_3$ aqueous solution. The water phase was extracted with ethyl acetate (3 times); the organic phases were washed with water, dried (Na$_2$SO$_4$), filtered and evaporated. The residue was passed on a silicagel column eluted with ethyl acetate to yield 89 mg of 4-bromo-6-(2-(quinolin-2-yl)ethyl)-6,7-dihydro-5H-pyrrolo[3,4-b]pyridin-5-one. ESI-MS: [M+Na]$^+$=390.00, 371.00, 370.00, 369.05, [+H$^+$]=368.00.

119.4 4-Morpholin-4-yl-6-(2-quinolin-2-yl-ethyl)-6,7-dihydro-pyrrolo[3,4-b]pyridin-5-one The title compound was prepared in the same manner as the compound of Example 99 starting from 4-bromo-6-(2-(quinolin-2-yl)ethyl)-6,7-dihydro-5H-pyrrolo[3,4-b]pyridin-5-one. Yield 3 mg (12%). ESI-MS: [M+Na]$^+$=397.1, [+H$^+$]=375.1.

Example 120

7-Morpholino-2-(3-(pyrimidin-2-yl)phenethyl)isoindolin-1-one 120.1 7-Bromo-2-(3-(pyrimidin-2-yl)phenethyl)isoindolin-1-one A mixture of 2-(3-(pyrimidin-2-yl)phenyl)ethanamine from Example e1 (750 mg, 3.76 mmol), 2-bromo-6-bromomethyl-benzoic acid methyl ester from Example 5.3 (1209 mg, 4.14 mmol) and DIPEA (486 mg, 3.76 mmol) in isopropanol (15 mL) was stirred and refluxed overnight. The mixture was concentrated and the residue was purified by silica gel column (PE: EA=1:1) to give the title compound as a white solid (1.2 g, 80%). LCMS (ESI+): m/z 396 (M+H)$^+$, R$_t$: 0.87 min.

120.2 7-Morpholino-2-(3-(pyrimidin-2-yl)phenethyl)isoindolin-1-one

A mixture of the compound from example 120.1 (400 mg, 1.02 mmol), morpholine (442 mg, 5.07 mmol), PdCl$_2$(dppf) (74 mg, 0.10 mmol) and t-BuONa (195 mg, 2.03 mmol) in toluene (15 mL) was stirred at 80° C. under N$_2$ overnight. The mixture was concentrated and the residue was purified by Prep-HPLC to obtain the title compound as an off-white gel (60 mg, 14%). LCMS (ESI+): m/z 401 (M+H)$^+$, R$_t$: 1.76 min. $^1$H NMR (400 MHz, MeOD): δ 3.00 (t, J=7.2 Hz, 2H), 3.25 (m, 4H), 3.78-3.84 (m, 6H), 4.28 (s, 2H), 7.06-7.09 (m, 1H), 7.13-7.16 (m, 1H), 7.24 (t, J=4.8 Hz, 1H), 7.31 (d, J=5.2 Hz, 2H), 7.44 (t, J=7.8 Hz, 1H), 8.12-8.14 (m, 1H), 8.18 (s, 1H), 8.70 (d, J=4.8 Hz, 2H).

Example 121

7-(Pyridin-4-yl)-2-(3-(pyrimidin-2-yl)phenethyl)isoindolin-1-one

A mixture of the compound from Example 120.1 (100 mg, 0.25 mmol), pyridin-4-ylboronic acid (34 mg, 0.28 mmol), PdCl$_2$ (dppf) (19 mg, 0.03 mmol) and K$_2$CO$_3$ (105 mg, 0.76 mmol) in dioxane (12 mL) and H$_2$O (4 mL) was stirred at 100° C. under N$_2$ for 2 h. The mixture was concentrated and the residue was purified by Pre-HPLC to obtain the title compound as a white solid (50 mg, 51%). LCMS (ESI+): m/z 393 (M+H)$^+$, R$_t$: 1.94 min. $^1$H NMR (400 MHz, MeOD): δ 3.02 (t, J=7.2 Hz, 2H), 3.82 (t, J=7.2 Hz, 2H), 4.41 (s, 2H), 7.23 (t, J=4.8 Hz, 1H), 7.31-7.32 (m, 2H), 7.46-7.48 (m, 1H), 7.64-7.66 (m, 2H), 8.06 (d, J=6.4 Hz, 2H), 8.15-8.17 (m, 2H), 8.68 (d, J=4.8 Hz, 2H). 8.74 (d, J=6.4 Hz, 2H).

Example 122

(2-(2-Phenylpyrimidin-4-yl)ethyl)-7-(pyridin-4-yl)isoindolin-1-one 122.1 7-Bromo-2-(2-(2-phenylpyrimidin-4-yl)ethyl)isoindolin-1-one A mixture of the compound from Example f1 (100 mg, 0.50 mmol) and 2-bromo-6-bromomethyl-benzoic acid methyl ester from Example 5.3 (232 mg, 0.75 mmol) in THF (5 mL) was stirred at 70° C. overnight. The mixture was concentrated and the residue was purified by Prep-TLC (PE:EA=1:1) to give the title compound as a white solid (40 mg, 20%). LCMS (ESI+): m/z 394 (M+H)$^+$, R$_t$: 0.90 min.

122.2 (2-(2-Phenylpyrimidin-4-yl)ethyl)-7-(pyridin-4-yl)isoindolin-1-one

A mixture of the compound from Example 122.1 (40 mg, 0.10 mmol), pyridin-4-ylboronic acid (14 mg, 0.11 mmol), PdCl$_2$(dppf) (8 mg, 0.01 mmol) and K$_2$CO$_3$ (41 mg, 0.30 mmol) in dioxane (12 mL) and H$_2$O (4 mL) was stirred at 100° C. under N$_2$ for 2 h. The mixture was concentrated and the residue was purified by Prep-HPLC to obtain the title compound as a white solid (20 mg, 51%). LCMS (ESI+): m/z 393 (M+H)$^+$, R$_t$: 1.59 min.; $^1$H NMR (400 MHz, MeOD): δ 3.10 (t, J=6.2 Hz, 2H), 3.96 (t, J=6.8 Hz, 2H), 4.56 (s, 2H), 7.18-7.31 (m, 7H), 7.58 (d, J=4.8 Hz, 2H), 8.05 (d, J=7.2 Hz, 2H), 8.39 (s, 2H), 8.56 (d, J=4.8 Hz, 1H).

Example 123

Pyridine-3-sulfonic acid [3-oxo-2-(2-quinolin-2-yl-ethyl)-2,3-dihydro-1H-isoindol-4-yl]-amide 123.1 7-Nitro-2-(2-(quinolin-2-yl)ethyl)isoindolin-1-one Methyl 2-(bromomethyl)-6-nitrobenzoate (1.82 mmol, 500 mg) was added portionswise to a mixture of K$_2$CO$_3$ (4.56 mmol, 630 mg) and 2-(quinolin-2-yl)ethanamine dihydrochloride from Example a1 (3.04 mmol, 745 mg) in acetonitrile (50 mL). The suspension was then stirred 12 h at room temperature filtrated and the filtrate evaporated in vacuo. The residue was passed on a silicagel column eluted with ethyl acetate to yield 353 mg (58%) of the title compound.

123.2 7-Amino-2-(2-(quinolin-2-yl)ethyl)isoindolin-1-one

7-Nitro-2-(2-(quinolin-2-yl)ethyl)isoindolin-1-one from Example 123.1 (1.04 mmol, 345 mg) was hydrogenated on Pd/C (10%) in ethanol (50 mL) to give 122 mg (39%) of the title compound. ESI-MS: [2M+Na]$^+$=629.20, [M+Na]$^+$=326.10, 305.10, [M+H]$^+$=304.10.

123.3 Pyridine-3-sulfonic acid [3-oxo-2-(2-quinolin-2-yl-ethyl)-2,3-dihydro-1H-isoindol-4-yl]-amide Pyridine-3-sulfonyl chloride (0.05 mmol, 9 mg) was added dropwise to a solution of 7-amino-2-(2-(quinolin-2-yl)ethyl)isoindolin-1-one (0.05 mmol, 15 mg) in pyridine (1 mL) at 0° C. and the solution was further stirred 12 h at room temperature. A saturated aqueous solution of NaHCO$_3$ was added and the mixture was extracted with EtOAc (3 times). The combined organic phases were washed with water, dried and evaporated in vacuo. The residue was passed on a silicagel column eluted with EtOAc: 2M NH$_3$ in EtOH to give 4 mg (17%) of the title compound. $^1$H NMR (CDCl$_3$, 500 MHz): δ=9.92 (s br., 1 H), 9.07 (s, 1 H), 8.70 (d, 1 H), 8.09 (d, 1 H), 8.10 (d 1 H), 7.99 (d, 1 H), 7.80 (d, 1 H), 7.70 (t, 1 H), 7.59 (d, 1 H), 7.51 (t, 1 H), 7.41-7.29 (m, 3 H), 7.00 (d, 1 H), 4.29 (s, 2 H), 4.08 (t, 2 H), 3.32 (t, 2 H).

Example 124

7-[(Pyridin-2-ylmethyl)-amino]-2-(2-quinolin-2-yl-ethyl)-2,3-dihydro-isoindol-1-one 7-Amino-2-(2-(quinolin-2-yl)ethyl)isoindolin-1-one from Example 123.2 (0.07 mmol, 20 mg) and picolinaldehyde (0.07 mmol, 7 mg) were solved in methanol (1 mL) and stirred for 30 min. at room temperature. Zinc chloride (0.04 mmol, 5 mg) was added and the mixture was further stirred 30 min. Sodium cyanoborohydride (0.08 mmol, 5 mg) was finally added and the mixture was stirred 12 h at room temperature. A saturated aqueous solution of NaHCO$_3$ was added and the mixture was extracted with EtOAc (3 times). The joined organic phases were washed with water, dried and evaporated in vacuo. The residue was passed on a silicagel column eluted with EtOAc. Yield 20 mg (77%). ESI-MS: [M+H]$^+$=395.1.

Example 125

7-[(Pyridin-4-ylmethyl)-amino]-2-(2-quinolin-2-yl-ethyl)-2,3-dihydro-isoindol-1-one The title compound was prepared as described for Example 124 using isonicotinaldehyde (0.07 mmol, 7 mg). Yield 10 mg (39%). ESI-MS: [M+Na$^+$]=417.1, [M+H$^+$]=395.1.

Example 126

7-[(Pyridin-3-ylmethyl)-amino]-2-(2-quinolin-2-yl-ethyl)-2,3-dihydro-isoindol-1-one The title compound was prepared as described for Example 124 using nicotinaldehyde (0.07 mmol, 7 mg). Yield: 2 mg (7%). $^1$H NMR (CDCl$_3$, 500 MHz): δ=8.61 (s, 1 H), 8.50 (d, 1 H), 8.08 (d, 1 H), 8.05 (d 1 H), 7.78 (d, 1 H), 7.68 (t, 2 H), 7.48 (t, 1 H), 7.84 (d, 1 H), 7.30-7.11 (m, 3 H), 6.60 (d, 1 H), 6.40 (d, 1 H), 4.48 (d, 2 H), 4.25 (s, 2 H), 4.07 (t, 2 H), 3.36 (t, 2 H).

Example 127

7-(Pyridin-3-ylmethoxy)-2-(2-quinolin-2-yl-ethyl)-2,3-dihydro-isoindol-1-one 127.1 7-Methoxy-2-(2-quinolin-2-yl-ethyl)-2,3-dihydro-isoindol-1-one The title compound was prepared in analogy to the process described in Example 5.4 starting from 2-bromomethyl-6-methoxy-benzoic acid methyl ester (prepared in analogy to the method described for 2-bromomethyl-6-bromo-benzoic acid methyl ester) and 2-quinolin-2-yl-ethylamine from Example a1. ESI-MS: [2M+Na]$^+$=659.2, [M+H]$^+$=319.1

127.2 7-Hydroxy-2-(2-quinolin-2-yl-ethyl)-2,3-dihydro-isoindol-1-one

Demethylation of 7-methoxy-2-(2-quinolin-2-yl-ethyl)-2,3-dihydro-isoindol-1-one (0.43 mmol, 138 mg) with BBr$_3$ gave the title compound. Yield 71 mg (54%). ESI-MS: [2M+Na$^+$]=631.2, [M+Na$^+$]=327.0, [M+H$^+$]=305.1.

127.3 7-(Pyridin-3-ylmethoxy)-2-(2-quinolin-2-yl-ethyl)-2,3-dihydro-isoindol-1-one 3-(Bromomethyl)pyridine hydrobromide (0.07 mmol, 17 mg) was added portionswise to 7-hydroxy-2-(2-quinolin-2-yl-ethyl)-2,3-dihydro-isoindol-1-one (0.07 mmol, 20 mg) and cesium carbonate (0.33 mol, 107 mg) in DMF (15 mL). The reaction mixture was further stirred over 12 h at room temperature under an inert atmosphere of nitrogen. A saturated aqueous solution of $K_2CO_3$ was added and the mixture was extracted with EtOAc (3 times). The joined organic phases were washed with water, dried and evaporated in vacuo. The residue was passed on a silicagel column eluted first with EtOAc to elute the impurity and finally with $CH_2Cl_2$: MeOH 19:1. Yield 5 mg (19%). $^1$H NMR (DMSO-$d_6$, 500 MHz): δ=8.71 (s br., 1 H), 8.54 (s br., 1 H), 8.28 (d, 1 H), 7.97-7.88 (m, 3 H), 7.70 (t, 1 H), 7.53 (t, 1 H), 7.49 (d, 2 H), 7.41 (t, 1 H), 7.15-7.05 (m, 2 H), 5.27 (s br., 2 H), 4.43 (s br., 2 H), 3.96 (t, 2 H), 3.27 (t, 2 H).

Example 128

7-(Pyridin-4-ylmethoxy)-2-(2-quinolin-2-yl-ethyl)-2,3-dihydro-isoindol-1-one

The title compound was prepared in analogy to the process described in Example 127 using 4-(bromomethyl)pyridine hydrobromide (0.07 mmol, 17 mg). Yield 4 mg (15%). $^1$H NMR (DMSO-$d_6$, 500 MHz): δ=8.57 (d, 2 H), 8.28 (d, 1 H), 7.92 (d, 2 H), 7.70 (t, 1 H), 7.58-7.43 (m, 5 H), 7.10 (d, 1 H), 7.02 (d, 1 H), 5.29 (s, 2 H), 4.43 (s, 2 H), 3.99 (t, 2 H), 3.28 (t, 2 H).

Example 129

7-(Pyridin-2-ylmethoxy)-2-(2-quinolin-2-yl-ethyl)-2,3-dihydro-isoindol-1-one

The title compound was prepared in analogy to the process described in Example 127 using 2-(bromomethyl)pyridine hydrobromide (0.07 mmol, 17 mg). Yield 15 mg (57%). ESI-MS: [M+Na$^+$]=418.1, [M+H+]=396.1

Example 130

4-Morpholin-4-yl-2-(2-quinolin-2-yl-ethyl)-2,3-dihydro-isoindol-1-one; compound with trifluoroacetic acid 130.1 4-Bromo-2-(2-(quinolin-2-yl)ethyl)isoindolin-1-one The title compound was prepared in analogy to the process described in Example 119.3 starting from methyl 3-bromo-2-(bromomethyl)benzoate (1.62 mmol, 500 mg) and 2-(quinolin-2-yl)ethanamine from Example a1.
130.2 4-Morpholin-4-yl-2-(2-quinolin-2-yl-ethyl)-2,3-dihydro-isoindol-1-one; compound with trifluoro-acetic acid The title compound was prepared in analogy to the process described in Example 99 starting from the compound of Example 130.1 (0.08 mmol, 30 mg) and morpholine. Yield. 15 mg (37%).

Example 131

4-(1,1-Dioxo-1-thiomorpholin-4-yl)-2-(2-quinolin-2-yl-ethyl)-2,3-dihydro-isoindol-1-one The title compound was prepared in analogy to the process described in Example 99 starting from the compound of Example 130.1. Yield: 7 mg (15%). ESI-MS: [M+Na$^+$]=444.00, [M+H$^+$]=422.10.

The following compounds of the formula (I) described below were prepared using the standard operation procedures described above.

Example 132

7-[8-(4-Methyl-piperazine-1-sulfonyl)-3,4-dihydro-1H-isoquinolin-2-yl]-2-(2-quinolin-2-yl-ethyl)-2,3-dihydro-isoindol-1-one trifluoroacetate Example 133

7-[8-(Morpholine-4-sulfonyl)-3,4-dihydro-1H-isoquinolin-2-yl]-2-(2-quinolin-2-yl-ethyl)-2,3-dihydro-isoindol-1-one trifluoroacetate $^1$H NMR (DMSO-$d_6$, 500 MHz)=8.79 (d, 1 H), 8.18 (d, 1 H), 8.10 (d, 1 H), 7.97 (t, 1 H), 7.87 (d, 1 H), 7.78 (t, 1 H), 7.71 (d, 1 H), 7.45 (m, 3 H), 7.10 (d, 1 H), 6.86 (d, 1 H), 4.60 (s, 2 H), 4.50 (s, 2 H), 4.03 (m+H$_2$O), 3.61 (s, 4 H), 3.46 (t, 2 H), 3.32 (br. s., 2 H), 3.05 (br. s., 4 H), 2.83 (br. s., 2H)

Example 134

7-(2-Oxa-6-aza-spiro[3.4]oct-6-yl)-2-(2-quinolin-2-yl-ethyl)-2,3-dihydro-isoindol-1-one

ESI-MS: [M+H$^+$]=400.10.

Example 135

7-(1-oxo-thiomorpholin-4-yl)-2-(2-quinolin-2-yl-ethyl)-2,3-dihydro-isoindol-1-one

ESI-MS: [M+H$^+$]=406.10.

Example 136

7-(2-Oxa-6-aza-spiro[3.5]non-6-yl)-2-(2-quinolin-2-yl-ethyl)-2,3-dihydro-isoindol-1-one

ESI-MS: [M+H$^+$]=414.10.

Example 137

4-(1,1-Dioxo-thiomorpholin-4-yl)-6-(2-quinolin-2-yl-ethyl)-6,7-dihydro-pyrrolo[3,4-b]pyridin-5-one ESI-MS: [M+Na$^+$]=445.10, 424.10, [M+H$^+$]=423.10.

Example 138

4-(4-Methyl-piperazin-1-yl)-6-(2-quinolin-2-yl-ethyl)-6,7-dihydro-pyrrolo[3,4-b]pyridin-5-one ESI-MS: [M+Na$^+$]=410.10, 389.15, [M+H$^+$]=38.20.

Example 139

7-(3-Amino-azetidin-1-yl)-2-(2-quinolin-2-yl-ethyl)-2,3-dihydro-isoindol-1-one

ESI-MS: [M+H$^+$]=359.10.

Example 140

7-[4-(4-Methoxy-benzyloxy)-phenyl]-2-(2-quinolin-2-yl-ethyl)-2,3-dihydro-isoindol-1-one

ESI-MS: 502.20, [M+H$^+$]=501.20.

Example 141

4-piperazin-1-yl-2-(2-quinolin-2-yl-ethyl)-2,3-dihydro-isoindol-1-one

ESI-MS: [M+H$^+$]=373.15;

Example 142

7-(5,5-Difluoro-hexahydro-cyclopenta[c]pyrrol-2-yl)-2-(2-quinolin-2-yl-ethyl)-2,3-dihydro-isoindol-1-one

ESI-MS: [M+H$^+$]=434.20.

Example 143

7-(4,4-Difluoro-piperidin-1-yl)-2-(2-quinolin-2-yl-ethyl)-2,3-dihydro-isoindol-1-one

ESI-MS: [M+H$^+$]=408.10.

Example 144

4-(4-Methyl-piperazin-1-yl)-2-(2-quinolin-2-yl-ethyl)-2,3-dihydro-isoindol-1-one

ESI-MS: [M+H$^+$]=387.20.

Example 145

7-(Azetidin-3-ylamino)-2-(2-quinolin-2-yl-ethyl)-2,3-dihydro-isoindol-1-one

3-[3-oxo-2-(2-quinolin-2-yl-ethyl)-2,3-dihydro-1H-isoindol-4-ylamino]-1-carboxylic acid tert-butyl ester was prepared in the same manner as the compound of Example 99 starting from 7-bromo-2-(2-quinolin-2-yl-ethyl)-2,3-dihydro-isoindol-1-one from Example 5.4 and commercially available tert-butyl 3-aminoazetidine-1-carboxylate (yield: 63%). The protecting Boc group was subsequently cleaved using TFA (1 equivalent) by stirring 1 h at room temperature in dichloromethane (yield: 49%).

ESI-MS: [M+Na$^+$]=381.10, [M+H$^+$]=359.10.

Example 146

7-[4-(4-Isopropenyl-phenoxy)-phenyl]-2-(2-quinolin-2-yl-ethyl)-2,3-dihydro-isoindol-1-one

ESI-MS: 498.20, [M+H$^+$]=497.20.

Example 147

7-[(3S,4S)-4-(2-Fluoro-4-trifluoromethoxy-phenyl)-3-methyl-piperidin-1-yl]-2-(2-quinolin-2-yl-ethyl)-2,3-dihydro-isoindol-1-one trifluororacetate

ESI-MS: 565.20, [M+H$^+$]=564.20.

Example 148

7-[4-(2,6-Dimethyl-pyridin-3-yloxy)-3-fluoro-phenyl]-2-(2-quinolin-2-yl-ethyl)-2,3-dihydro-isoindol-1-one trifluoroacetate

ESI-MS: 505.20, [M+H$^+$]=504.20.

Example 149

7-(1-Pyridin-4-ylmethyl-1H-indol-5-yl)-2-(2-quinolin-2-yl-ethyl)-2,3-dihydro-isoindol-1-one trifluoroacetate

ESI-MS: 496.20, [M+H$^+$]=495.20.

Example 150

2-(2-Quinolin-2-yl-ethyl)-7-thiomorpholin-4-yl-2,3-dihydro-isoindol-1-one

ESI-MS: [M+Na$^+$]=412.10, 391.10, [M+H$^+$]=390.10.

Example 151

7-(8-Methyl-3,8-diaza-bicyclo[3.2.1]oct-3-yl)-2-(2-quinolin-2-yl-ethyl)-2,3-dihydro-isoindol-1-one

Example 152

7-(3-Methyl-3,8-diaza-bicyclo[3.2.1]oct-8-yl)-2-(2-quinolin-2-yl-ethyl)-2,3-dihydro-isoindol-1-one

ESI-MS: [M+H$^+$]=413.20.

Example 153

2-[2-(1-Methyl-1H-benzoimidazol-2-yl)-ethyl]-7-morpholin-4-yl-2,3-dihydro-isoindol-1-one

ESI-MS: [M+H$^+$]=377.20.

Example 154

7-(5-Methyl-hexahydro-pyrrolo[3,4-c]pyrrol-2-yl)-2-(2-quinolin-2-yl-ethyl)-2,3-dihydro-isoindol-1-one ESI-MS: [M+Na$^+$]=435.20, [M+H$^+$]=413.20.

Example 155

7-[3-Chloro-4-(4-hydroxy-4-methyl-cyclohexylamino)-phenyl]-2-(2-quinolin-2-yl-ethyl)-2,3-dihydro-isoindol-1-one hydrochloride

ESI-MS: 529.20, [M+H$^+$]=527.20, 526.20.

Example 156

4-(1H-Pyrazol-4-yl)-6-(2-quinolin-2-yl-ethyl)-6,7-dihydro-pyrrolo[3,4-b]pyridin-5-one ESI-MS: [M+Na$^+$]=378.10, 357.10, [M+H$^+$]=356.10.

Example 157

7-[4-(4-Ethyl-piperazin-1-yl)-piperidin-1-yl]-2-(2-quinolin-2-yl-ethyl)-2,3-dihydro-isoindol-1-one trifluoroacetate

ESI-MS: [M+H$^+$]=484.30.

Example 158

2-(2-Quinolin-2-yl-ethyl)-7-(3,4,5,6-tetrahydro-2H-[4,4']bipyridinyl-1-yl)-2,3-dihydro-isoindol-1-one trifluoroacetate

ESI-MS: [M+H$^+$]=449.20.

Example 159

7-(4-Pyridin-3-yl-piperazin-1-yl)-2-(2-quinolin-2-yl-ethyl)-2,3-dihydro-isoindol-1-one trifluoroacetate

ESI-MS: [M+H$^+$]=450.20.

Example 160

4-(4-Fluoro-phenyl)-6-(2-quinolin-2-yl-ethyl)-6,7-dihydro-pyrrolo[3,4-b]pyridin-5-one (di trifluoroacetate)

ESI-MS: 385.10, [M+H$^+$]=384.10.

Example 161

4-(4-Methoxy-phenyl)-6-(2-quinolin-2-yl-ethyl)-6,7-dihydro-pyrrolo[3,4-b]pyridin-5-one

ESI-MS: 397.10, [M+H$^+$]=396.10.

Example 162

4-(2-Methyl-2H-pyrazol-3-yl)-6-(2-quinolin-2-yl-ethyl)-6,7-dihydro-pyrrolo[3,4-b]pyridin-5-one hydrochloride ESI-MS: [M+Na$^+$]=392.15, 371.15, [M+H$^+$]=370.10.

Example 163

4-piperazin-1-yl-6-(2-quinolin-2-yl-ethyl)-6,7-dihydro-pyrrolo[3,4-b]pyridin-5-one $^1$H NMR (CDCl$_3$, 500 MHz)=8.29 (d, 1 H), 8.08 (d, 1 H), 8.02 (d, 1 H), 7.78 (d, 1H), 7.69 (t, 1 H), 7.50 (t, 1 H), 7.36 (d, 1 H), 6.60 (d, 1 H), 4.30 (s, 2 H), 4.11 (t, 2 H), 3.72 (q, 1 H), 3.48 (m sym., 4 H), 3.35 (t, 2 H), 3.07 (m sym., 4 H)

Example 165

4-(2-oxo-2,3-dihydro-1H-indol-6-yl)-6-(2-quinolin-2-yl-ethyl)-6,7-dihydro-pyrrolo[3,4-b]pyridin-5-one

ESI-MS: 422.10, [M+H$^+$]=421.10.

Example 166

4-Pyrimidin-5-yl-6-(2-quinolin-2-yl-ethyl)-6,7-dihydro-pyrrolo[3,4-b]pyridin-5-one $^1$H NMR (CDCl$_3$, 500 MHz) δ=9.28 (s, 1 H), 8.95 (s, 2 H), 8.79 (d, 1 H), 8.10 (d, 1 H), 7.96 (d, 1 H), 7.79 (d, 1 H), 7.68 (t, 1 H), 7.51 (t, 1 H), 7.36 (d, 1 H), 7.32 (m sym., 2 H), 4.55 (s, 2 H), 4.20 (t, 2 H), 3.40 (t, 2 H).

Example 167

7-[4-(4-Methyl-piperazin-1-ylmethyl)-phenyl]-2-(2-quinolin-2-yl-ethyl)-2,3-dihydro-isoindol-1-one trifluoroacetate ESI-MS: [M+Na$^+$]=499.20, [M+H$^+$]=477.20.

Example 168

7-(4-Morpholin-4-ylmethyl-phenyl)-2-(2-quinolin-2-yl-ethyl)-2,3-dihydro-isoindol-1-one trifluoroacetate ESI-MS: [M+Na$^+$]=486.20, [M+H$^+$]=464.20.

Example 169

7-(3-Methoxy-pyridin-4-yl)-2-(2-quinolin-2-yl-ethyl)-2,3-dihydro-isoindol-1-one trifluoroacetate

ESI-MS: [M+H]$^+$=396.15;

Example 170

7-(3-Chloro-pyridin-4-yl)-2-(2-quinolin-2-yl-ethyl)-2,3-dihydro-isoindol-1-one trifluoroacetate

ESI-MS: [M+H]$^+$=400.10.

Example 171

7-(2-Chloro-pyridin-4-yl)-2-(2-quinolin-2-yl-ethyl)-2,3-dihydro-isoindol-1-one trifluoroacetate

ESI-MS: [M+H]$^+$=400.10.

Example 172

7-(6-Methyl-pyridin-3-ylmethoxy)-2-(2-quinolin-2-yl-ethyl)-2,3-dihydro-isoindol-1-one

ESI-MS: 411.20, [M+H]$^+$=410.20.

Example 173

7-(3-Fluoro-pyridin-4-yl)-2-(2-quinolin-2-yl-ethyl)-2,3-dihydro-isoindol-1-one

ESI-MS: [M+H$^+$]=384.10.

Example 174

7-(3-Amino-4-methyl-piperidin-1-yl)-2-(2-quinolin-2-yl-ethyl)-2,3-dihydro-isoindol-1-one

ESI-MS: [M+H$^+$]=401.20.

Example 175

2-[2-(1H-Benzoimidazol-2-yl)-ethyl]-7-(1,1-dioxo-thiomorpholin-4-yl)-2,3-dihydro-isoindol-1-one ESI-MS: [M+Na$^+$]=433.10, [M+H$^+$]=411.10.

Example 176

7-[(1S,4S)-5-(4-Chloro-phenyl)-2,5-diaza-bicyclo[2.2.1]hept-2-yl]-2-(2-quinolin-2-yl-ethyl)-2,3-dihydro-isoindol-1-one trifluoroacetate $^1$H NMR (DMSO-d$_6$, 500 MHz)=8.76 (d, 1 H), 8.19 (d., 1 H), 8.11 (d, 1 H), 7.97 (t., 1 H), 7.88-7.76 (m, 2 H), 7.25 (t., 1 H), 7.13 (d, 2 H), 6.76 (d, 1 H), 6.59 (d, 1 H), 6.49 (d, 2 H), 4.78 (s., 1 H), 4.45 (br. s., 1 H), 4.39 (d, 2 H), 3.91 (m sym., 2 H), 3.88 (d, 1 H), 3.40 (m, 3 H), 3.00 (d, 1 H), 2.89 (d, 1 H), 1.90 (br. s., 2 H)

Example 177

7-(4-Methyl-piperazin-1-ylmethyl)-2-(2-quinolin-2-yl-ethyl)-2,3-dihydro-isoindol-1-one

ESI-MS: [M+H$^+$]=401.25;

Example 178

7-Morpholin-4-ylmethyl-2-(2-quinolin-2-yl-ethyl)-2,3-dihydro-isoindol-1-one

ESI-MS: [M+H$^+$]=388.20.

Example 179

7-(2-Methyl-pyridin-3-ylmethoxy)-2-(2-quinolin-2-yl-ethyl)-2,3-dihydro-isoindol-1-one ESI-MS: [M+Na$^+$]=432.20, 411.20, [M+H$^+$]=410.20.

Example 180

4-Methoxy-7-(1H-pyrazol-4-yl)-2-(2-quinolin-2-yl-ethyl)-2,3-dihydro-isoindol-1-one

ESI-MS: [M+H$^+$]=385.20.

Example 181

4-Pyridin-4-yl-2-(2-quinolin-2-yl-ethyl)-2,3-dihydro-isoindol-1-one

ESI-MS: [M+Na$^+$]=388.10, [M+H$^+$]=366.15;

Example 182

7-(2-Methoxy-pyridin-4-yl)-2-(2-quinolin-2-yl-ethyl)-2,3-dihydro-isoindol-1-one trifluoroacetate

ESI-MS: [M+H$^+$]=396.20.

Example 183

4-Methoxy-7-pyrimidin-5-yl-2-(2-quinolin-2-yl-ethyl)-2,3-dihydro-isoindol-1-one

ESI-MS: [M+H$^+$]=397.20.

Example 184

7-(1,1-Dioxothiomorpholin-4-yl)-2-[2-(1-methyl-1H-benzoimidazol-2-yl)-ethyl]-2,3-dihydro-isoindol-1-one trifluoroacetate ESI-MS: [M+Na$^+$]=447.15, [M+H$^+$]=425.20.

Example 185

4-Methoxy-7-pyridin-3-yl-2-(2-quinolin-2-yl-ethyl)-2,3-dihydro-isoindol-1-one trifluoroacetate $^1$H NMR (DMSO-d$_6$, 500 MHz)=8.90 (s, 1 H), 8.79 (d, 1 H), 8.70 (d, 1 H), 8.34 (d, 1 H), 8.13 (d, 1 H), 8.05 (d, 1 H), 7.91 (t, 1 H), 7.86 (t, 1 H), 7.79 (d, 1 H), 7.72 (t, 1 H), 7.55 (d, 1 H), 7.38 (d, 1 H), 4.54 (s, 2 H), 4.03 (t, 2 H), 3.96 (s, 3 H), 3.45 (t, 2 H).

Example 186

4-Methoxy-7-(4-methoxy-phenyl)-2-(2-quinolin-2-yl-ethyl)-2,3-dihydro-isoindol-1-one

ESI-MS: [M+H$^+$]=425.20.

Example 187

7-(4-Fluoro-phenyl)-4-methoxy-2-(2-quinolin-2-yl-ethyl)-2,3-dihydro-isoindol-1-one

ESI-MS: [M+H$^+$]=413.15;

Example 188

7-(4-Dimethylaminomethyl-phenyl)-2-(2-quinolin-2-yl-ethyl)-2,3-dihydro-isoindol-1-one (dihydrochloride)

ESI-MS: [M+Na$^+$]=444.25, 423.30, [M+H$^+$]=422.30.

Example 189

7-(1,1-Dioxo-thiomorpholin-4-yl)-4-methoxy-2-(2-quinolin-2-yl-ethyl)-2,3-dihydro-isoindol-1-one ESI-MS: [M+Na$^+$]=474.15, [M+H$^+$]=452.20.

Example 190

7-(1,1-Dioxo-tetrahydro-thiophen-3-ylamino)-2-(2-quinolin-2-yl-ethyl)-2,3-dihydro-isoindol-1-one ESI-MS: [M+Na$^+$]=444.15, [M+H$^+$]=422.15;

Example 191

7-(6-Fluoro-pyridin-3-ylmethoxy)-2-(2-quinolin-2-yl-ethyl)-2,3-dihydro-isoindol-1-one ESI-MS: [M+Na$^+$]=436.20, 415.20, [M+H$^+$]=414.20.

Example 192

7-(Hexahydro-pyrrolo[3,4-c]pyrrol-2-yl)-2-(2-quinolin-2-yl-ethyl)-2,3-dihydro-isoindol-1-one

ESI-MS: [M+H$^+$]=399.20.

Example 193

7-(4-Aminomethyl-phenyl)-2-(2-quinolin-2-yl-ethyl)-2,3-dihydro-isoindol-1-one

ESI-MS: [M+Na$^+$]=416.10, [M+H$^+$]=394.20.

Example 194

7-(4-Methylaminomethyl-phenyl)-2-(2-quinolin-2-yl-ethyl)-2,3-dihydro-isoindol-1-one ESI-MS: [M+Na$^+$]=430.20, [M+H$^+$]=408.30.

Example 195

2-[2-(1-Methyl-1H-benzoimidazol-2-yl)-ethyl]-7-pyridin-4-yl-2,3-dihydro-isoindol-1-one

ESI-MS: 370.10, [M+H$^+$]=369.10.

Example 196

2-[2-(1-Methyl-1H-benzoimidazol-2-yl)-ethyl]-7-pyridin-3-yl-2,3-dihydro-isoindol-1-one

ESI-MS: 370.10, [M+H$^+$]=369.10.

Example 197

2-[2-(1-Methyl-1H-benzoimidazol-2-yl)-ethyl]-7-pyrimidin-5-yl-2,3-dihydro-isoindol-1-one

ESI-MS: 371.15, [M+H$^+$]=370.10.

Example 198

4-Hydroxy-7-pyridin-4-yl-2-(2-quinolin-2-yl-ethyl)-2,3-dihydro-isoindol-1-one $^1$H NMR (DMSO-d$_6$, 500 MHz): δ=8.49 (d, 1 H), 8.28 (d, 1 H), 7.9 (m, 2 H), 7.55 (t, 1 H), 7.51 (t, 1 H), 7.48 (d, 1 H), 7.38 (d, 2 H), 7.24 (d, 1 H), 7.05 (d, 1 H), 4.38 (s, 1 H), 3.97 (t, 1 H), 3.27 (m+H$_2$O)

Example 199

4-Ethoxy-7-pyridin-4-yl-2-(2-quinolin-2-yl-ethyl)-2,3-dihydro-isoindol-1-one

ESI-MS: [M+H$^+$]=410.10.

Example 200

4-(1H-Pyrazol-3-yl)-2-(2-quinolin-2-yl-ethyl)-2,3-dihydro-isoindol-1-one

A Personal Chemistry Ermy's optimizer microwave was used. Each microwave tube was charged with 0.1 eq. of [1,1'-Bis(diphenylphosphino)-ferrocene]dichloro-palladium (II), complex with dichloromethane (7 mg). To the microwave tube, a solution of 4-bromo-2-(2-(quinolin-2-yl)ethyl)isoindolin-1-one from Example 130.1 (31 mg, 0.08 mmol) dissolved in dioxane (1.0 mL) was added, followed by the addition of 1H-pyrazol-3-ylboronic acid (11.2 mg, 0.1 mmol) dissolved in dioxane (0.35 mL). Then, 250 μL of 1M aqueous solution of Cs$_2$CO$_3$ was added and the resulting mixture was heated in the microwave for 1200 sec at 120° C. The reaction was filtered, checked by LC/MS and concentrated to dryness. The residues were dissolved in 1:1 DMSO/MeOH. Purification by reverse phase HPLC provided 4-(1H-pyrazol-3-yl)-2-(2-(quinolin-2-yl)ethyl)isoindolin-1-one (2.3 mg, 8%). $^1$H NMR (500 MHz, DMSO/D$_2$O) δ ppm 8.28 (d, J=8.54 Hz, 1 H) 8.01 (d, J=6.41 Hz, 1 H) 7.92 (t, J=8.09 Hz, 2 H) 7.84 (s, 1 H) 7.69-7.74 (m, 1 H) 7.50-7.62 (m, 4 H) 6.83 (s, 1 H) 4.80 (s, 2 H) 4.07 (t, J=7.17 Hz, 2 H) 3.34 (t, J=7.32 Hz, 2 H). MS (APCI) m/z 355 (M+H)$^+$; ESI-MS: 356.10, [M+H+]=355.10.

Example 201

4-Pyridin-3-yl-2-(2-quinolin-2-yl-ethyl)-2,3-dihydro-isoindol-1-one

Syntheses were performed using a Personal Chemistry Ermy's optimizer microwave. Each microwave tube was charged with 0.1 eq. of [1,1'-Bis(diphenylphosphino)-ferrocene]dichloropalladium(II), complex with dichloromethane (7 mg). To the microwave tube, a solution of 4-bromo-2-(2-(quinolin-2-yl)ethyl)isoindolin-1-one from Eample 130.1 (31 mg, 0.08 mmol) dissolved in dioxane (1.0 mL). was added, followed by pyridin-3-ylboronic acid (12.2 mg, 0.1 mmol) dissolved in dioxane (0.35 mL). Then, 250 uL of 1M aqueous solution of Cs$_2$CO$_3$ was added and the resulting mixture was heated in the microwave for 1200 sec at 120° C. The reaction was filtered, checked by LC/MS and concentrated to dryness. The residues were dissolved in 1:1 DMSO/MeOH. Purification by reverse phase HPLC provided 4-(pyridin-3-yl)-2-(2-(quinolin-2-yl)ethyl)isoindolin-1-one (14.6 mg, 47%). $^1$H NMR (500 MHz, DMSO/D$_2$O) δ ppm 8.80 (d, J=1.83 Hz, 1 H) 8.65 (dd, J=4.88, 1.53 Hz, 1H) 8.28 (d, J=8.55 Hz, 1 H) 8.00-8.06 (m, 1 H) 7.91 (dd, J=19.23, 8.24 Hz, 2 H) 7.70-7.76 (m, 3 H) 7.62-7.66 (m, 1 H) 7.49-7.59 (m, 3 H) 4.72 (s, 2 H) 4.03 (t, J=7.17 Hz, 2 H) 3.31 (t, J=7.32 Hz, 2 H); MS (APCI) m/z 366 (M+H)$^+$.

The following compounds of the formula (I) described below were prepared using the standard operation procedures described above.

Example 202

4-(2-Methyl-2H-pyrazol-3-yl)-2-(2-quinolin-2-yl-ethyl)-2,3-dihydro-isoindol-1-one trifluoroacetate ESI-MS: [M+Na$^+$]=391.10, 370.10, [M+H$^+$]=369.10.

Example 203

4-(4-Methoxy-phenyl)-2-(2-quinolin-2-yl-ethyl)-2,3-dihydro-isoindol-1-one trifluoroacetate

ESI-MS: 396.10, [M+H$^+$]=395.10.

Example 204

4-(3-Methoxy-propoxy)-7-pyridin-4-yl-2-(2-quinolin-2-yl-ethyl)-2,3-dihydro-isoindol-1-one

ESI-MS: 455.20, [M+H$^+$]=454.20.

Example 205

4-Isopropoxy-7-pyridin-4-yl-2-(2-quinolin-2-yl-ethyl)-2,3-dihydro-isoindol-1-one

ESI-MS: 425.20, [M+H$^+$]=424.20.

Example 206

7-(4-Pyrrolidin-1-yl-piperidin-1-yl)-2-(2-quinolin-2-yl-ethyl)-2,3-dihydro-isoindol-1-one trifluoroacetate

ESI-MS: [M+H$^+$]=441.25.

Example 207

7-[1,4']Bipiperidinyl-1'-yl-2-(2-quinolin-2-yl-ethyl)-2,3-dihydro-isoindol-1-one trifluoroacetate

ESI-MS: [M+H$^+$]=455.30.

Example 208

4-Pyrimidin-5-yl-2-(2-quinolin-2-yl-ethyl)-2,3-dihydro-isoindol-1-one

ESI-MS: [M+Na$^+$]=389.10, 368.10, [M+H$^+$]=367.10.

Example 209

7-(4-Methoxy-phenyl)-2-[2-(1-methyl-1H-benzoimidazol-2-yl)-ethyl]-2,3-dihydro-isoindol-1-one trifluoroacetate

ESI-MS: 399.20, [M+H$^+$]=398.20.

Example 210

4-Methoxy-7-(2-methyl-2H-pyrazol-3-yl)-2-(2-quinolin-2-yl-ethyl)-2,3-dihydro-isoindol-1-one

ESI-MS: 400.15, [M+H$^+$]=399.10.

Example 211

7-(4-Fluoro-phenyl)-2-[2-(1-methyl-1H-benzoimidazol-2-yl)-ethyl]-2,3-dihydro-isoindol-1-one trifluoroacetate

ESI-MS: 387.10, [M+H$^+$]=386.10.

Example 212

4-(4-Fluoro-phenyl)-2-(2-quinolin-2-yl-ethyl)-2,3-dihydro-isoindol-1-one trifluoroacetate ESI-MS: [M+Na$^+$]=405.10, 384.10, [M+H$^+$]=383.10.

Example 213

4-(2-Methyl-2H-pyrazol-3-yl)-6-(2-[1,2,4]triazolo[1,5-a]pyridin-2-yl-ethyl)-6,7-dihydro-pyrrolo[3,4-b]pyridin-5-one trifluoroacetate

ESI-MS: 361.10, [M+H$^+$]=360.10.

Example 214

6-[2-(1-Methyl-1H-benzoimidazol-2-yl)-ethyl]-4-(2-methyl-2H-pyrazol-3-yl)-6,7-dihydro-pyrrolo[3,4-b]pyridin-5-one

ESI-MS: 374.15, [M+H$^+$]=373.10.

Example 215

4-Pyrimidin-5-yl-6-(2-[1,2,4]triazolo[1,5-a]pyridin-2-yl-ethyl)-6,7-dihydro-pyrrolo[3,4-b]pyridin-5-one

ESI-MS: 359.10, [M+H$^+$]=358.10.

Example 216

6-[2-(1-Methyl-1H-benzoimidazol-2-yl)-ethyl]-4-morpholin-4-yl-6,7-dihydro-pyrrolo[3,4-b]pyridin-5-one

ESI-MS: 379.10, [M+H$^+$]=378.10.

Example 217

2-(2-Imidazo[1,2-a]pyridin-2-yl-ethyl)-4-methoxy-7-pyrimidin-5-yl-2,3-dihydro-isoindol-1-one trifluoroacetate

ESI-MS: [M+H$^+$]=386.10.

Example 218

2-(2-Imidazo[1,2-a]pyridin-2-yl-ethyl)-4-methoxy-7-pyridin-3-yl-2,3-dihydro-isoindol-1-one trifluoroacetate

ESI-MS: [M+H$^+$]=38510.

Example 219

7-(1S,5S)-3,6-Diaza-bicyclo[3.2.0]hept-3-yl-2-(2-quinolin-2-yl-ethyl)-2,3-dihydro-isoindol-1-one trifluoroacetate

ESI-MS: [M+H$^+$]=385.20.

Example 220

7-(3aR,7aS)-Octahydro-pyrrolo[3,2-c]pyridin-5-yl-2-(2-quinolin-2-yl-ethyl)-2,3-dihydro-isoindol-1-one trifluoroacetate

ESI-MS: [M+H$^+$]=413.20.

Example 221

2-[2-(5-Fluoro-1-methyl-1H-benzoimidazol-2-yl)-ethyl]-7-pyridin-4-yl-2,3-dihydro-isoindol-1-one trifluoroacetate

ESI-MS: [M+H$^+$]=387.10.

Example 222

2-[2-(1-Ethyl-1H-benzoimidazol-2-yl)-ethyl]-7-pyridin-4-yl-2,3-dihydro-isoindol-1-one trifluoroacetate

ESI-MS: [M+H$^+$]=383.10.

Example 223

2-(2-Benzothiazol-2-yl-ethyl)-7-pyridin-4-yl-2,3-dihydro-isoindol-1-one trifluoroacetate

ESI-MS: [M+H$^+$]=372.10.

Example 224

7-((R)-3-Amino-pyrrolidin-1-yl)-2-(2-quinolin-2-yl-ethyl)-2,3-dihydro-isoindol-1-one trifluoroacetate ESI-MS: [M+Na$^+$]=395.20, [M+H$^+$]=373.20.

Example 225

4-(1H-Pyrazol-4-yl)-2-(2-quinolin-2-yl-ethyl)-2,3-dihydro-isoindol-1-one $^1$H NMR (DMSO-d$_6$, 500 MHz)=13.20 (br. s., 1 H), 8.29 (d, 1 H), 8.22 (br. s., 1 H), 8.00 (br. s., 1 H), 7.93 (m, 2 H), 7.85 (m, 1 H), 7.72 (t, 1 H), 7.55 (t, 1 H), 7.50 (m, 3 H), 4.75 (s, 2 H), 4.05 (t, 2 H), 3.35 (m+H$_2$O)

Example 226

6-[2-(1-Methyl-1H-benzoimidazol-2-yl)-ethyl]-4-(4-methyl-piperazin-1-yl)-6,7-dihydro-pyrrolo[3,4-b]pyridin-5-one trifluoroacetate ESI-MS: [M+Na$^+$]=413.20, 392.20, [M+H$^+$]=391.20.

Example 227

4-Morpholin-4-yl-6-(2-[1,2,4]triazolo[1,5-a]pyridin-2-yl-ethyl)-6,7-dihydro-pyrrolo[3,4-b]pyridin-5-one

ESI-MS: 366.10, [M+H$^+$]=365.10.

Example 228

7-(2-Methyl-morpholin-4-yl)-2-(2-quinolin-2-yl-ethyl)-2,3-dihydro-isoindol-1-one trifluoroacetate ESI-MS: [M+Na$^+$]=410.10, 389.20, [M+H$^+$]=388.20.

Example 229

7-(2-Dimethylaminomethyl-morpholin-4-yl)-2-(2-quinolin-2-yl-ethyl)-2,3-dihydro-isoindol-1-one trifluoroacetate ESI-MS: [M+Na$^+$]=453.20, 432.20, [M+H$^+$]=431.20.

Example 230

7-Pyridin-4-yl-2-(2-[1,2,4]triazolo[1,5-a]pyridin-2-yl-ethyl)-2,3-dihydro-isoindol-1-one 230.1 7-Bromo-2-(2-[1,2,4]triazolo[1,5-a]pyridin-2-yl-ethyl)-2,3-dihydro-isoindol-1-one In a 20 mL microwave reaction vial, 2-bromo-6-bromomethylbenzoic acid methyl ester from Example 5.3 (3.1 g, 10 mmol), 2-[1,2,4]triazolo[1,5-a]pyridin-2-yl-ethylamine from Example g1) (1.6 g, 10 mmol) and DIPEA (1.3 g, 10 mmol) were dissolved in isopropanol (15 mL). The resulted mixture was heated on microwave at 100° C. for 1.5 h. The solvent was evaporated under reduced pressure. The residue was chromatographied on silica gel (solvent: CH$_2$Cl$_2$/CH$_3$OH (10:1; v/v). The title compound was obtained as a white solid (1.9 g, yield 51%). LC-MS: m/z=359 (M+H$^+$) R$_t$=1.60 min. $^1$H NMR (400 MHz, CDCl$_3$): δ=8.53-8.51 (m, 1H), 7.70-7.68 (m, 1H), 7.60-7.58 (m, 1H), 7.54-7.52 (m, 1H), 7.36-7.34 (m, 2H), 7.03-7.01 (m, 1H), 4.38 (s, 2H), 4.20-4.16 (t, J=6.8 Hz, 2H), 3.36-3.33 (t, J=6.8 Hz, 2H).

230.2 7-Pyridin-4-yl-2-(2-[1,2,4]triazolo[1,5-a]pyridin-2-yl-ethyl)-2,3-dihydro-isoindol-1-one A 5 mL microwave reaction vial was charged with the compound from Example 230.1 (96 mg, 0.27 mmol), pyridin-4-ylboronic acid (39.4 mg, 0.32 mmol) and Cs$_2$CO$_3$ (175 mg, 0.54 mmol) in DMF (3 mL). Pd(dppf)Cl$_2$ (4.4 mg, 5.4 μmol) was added to give a suspension. The mixture was purged with argon for 1 min. The resulting mixture was heated on microwave at 100° C. for 45 min. The reaction mixture was filtered through filter. The filtrate was purified by Prep-HPLC to give the title compound (40 mg, yield: 40.2%) as a white solid. LC-MS: m/z=356 (M+H$^+$); R$_t$=1.63 min.

$^1$H NMR (400 MHz, CDCl$_3$): δ=8.59-8.58 (m, 2H), 8.44-8.42 (m, 1H), 7.61-7.59 (m, 1H), 7.51-7.49 (m, 1H), 7.43-7.42 (m, 4H), 7.29-7.28 (m, 1H), 6.92-6.91 (m, 1H), 4.37 (s, 2H), 4.08-4.04 (t, J=7.2 Hz, 2H), 3.25-3.21 (t, J=7.2 Hz, 2H).

Example 231

7-Morpholin-4-yl-2-(2-[1,2,4]triazolo[1,5-a]pyridin-2-yl-ethyl)-2,3-dihydro-isoindol-1-one A 5 mL microwave reaction vial was charged with the compound from Example 230.1 (96 mg, 0.27 mmol), Cs$_2$CO$_3$ (175 mg, 0.54 mmol), Pd$_2$(dba)$_3$ (5 mg, 2 mol %) and X-PHOS (8 mg, 6 mol %). The solids were purged with argon for at least 5 min. A separate round bottom flask was charged with DMF (3 mL) and morpholine (73 mg, 0.54 mmol), degas with argon for at least 10 min. and then transferred to the microwave reaction vial under inert conditions. The resulting reaction mixture was heated on microwave at 100° C. for 1 h. The reaction mixture was filtered through filter. The filtrate was purified by Prep-HPLC to give the title compound (20 mg, yield: 19.6%) as a white solid. LC-MS: m/z=364 (M+H$^+$); R$_t$=1.65 min. $^1$H NMR (400 MHz, CDCl$_3$): δ=8.44-8.42 (m, 1H), 7.61-7.59 (m, 1H), 7.42-7.41 (m, 1H), 7.34-7.30 (m, 1H), 6.91-6.87 (m, 2H), 6.79-6.77 (m, 1H), 4.26 (s, 2H), 4.05-4.02 (t, J=6.8 Hz, 2H), 3.88-3.86 (m, 4H), 3.24-3.18 (m, 6H).

Example 232

7-(1,1-Dioxothiomorpholin-4-yl)-2-(2-[1,2,4]triazolo[1,5-a]pyridin-2-yl-ethyl)-2,3-dihydro-isoindol-1-one The title compound was prepared in analogy to the process described in example 231. LC-MS: m/z=412 (M+H$^+$); R$_t$=1.59 min. $^1$H NMR (400 MHz, CDCl$_3$): δ=8.54-8.52 (m, 1H), 7.72-7.70 (m, 1H), 7.57-7.55 (m, 1H), 7.45-7.41 (m, 1H), 7.06-7.02 (m, 2H), 6.90-6.88 (m, 1H), 4.38 (s, 2H), 4.16-4.12 (t, J=6.8 Hz, 2H), 3.74-3.73 (m, 4H), 3.35-3.31 (m, 6H)

Example 233

7-(4-Methyl-piperazin-1-yl)-2-(2-[1,2,4]triazolo[1,5-a]pyridin-2-yl-ethyl)-2,3-dihydro-isoindol-1-one The title compound was prepared in analogy to the process described in example 231. LC-MS: m/z=377 (M+H$^+$) R$_t$=1.53 min. $^1$H NMR (400 MHz, CDCl$_3$): δ=8.47 (s, 1H), 7.62 (s, 1H), 7.45 (s, 1H), 7.36-7.33 (m, 1H), 6.98-6.91 (m, 2H), 6.79-6.77 (m, 1H), 4.29 (s, 2H), 4.04 (s, 2H), 3.69-3.66 (m, 2H), 3.55-3.53 (m, 2H), 3.30-3.13 (m, 6H), 2.79 (s, 3H).

Example 234

7-(1,1-Dioxothiomorpholin-4-yl)-2-(2-imidazo[1,2-a]pyridin-2-yl-ethyl)-2,3-dihydro-isoindol-1-one A mixture of 7-bromo-2-(2-imidazo[1,2-a]pyridin-2-yl-ethyl)-2,3-dihydro-isoindol-1-one from Example 20.1 (100 mg, 0.281 mmol), thiomorpholine 1,1-dioxide (76 mg, 0.561 mmol), CS$_2$CO$_3$ (183 mg, 0.561 mmol), dicyclohexyl (2',4',6'-triisopropylbiphenyl-2-yl)phosphine (13.38 mg, 0.028 mmol) and Pd$_2$(dba)$_3$ (25.7 mg, 0.028 mmol) in DMF (2 mL) was heated to 100° C. for one hour in a microwave. The solvent was removed under reduced pressure, and the residue was purified by pre-HPLC to give the title compound (40 mg, 0.097 mmol, 34.7% yield) as white solid. LC-MS: m/z=411 (M+H$^+$) R$_t$=1.66 min. $^1$H NMR (400 MHz, CDCl$_3$): δ=8.06 (d, J=6.4 Hz, 1H), 7.54 (d, J=8.8 Hz, 1H), 7.46-7.40 (m, 2H), 7.15 (t, J=7.8 Hz, 1H), 7.05 (d, J=7.2 Hz, 1H), 6.91 (d, J=8.4 Hz, 1H), 6.79 (t, J=6.8 Hz, 1H), 4.32 (s, 2H), 4.03 (t, J=7.2 Hz, 2H), 3.76 (s, 4H), 3.36 (s, 4H), 3.19 (t, J=7.2 Hz, 2H).

Example 235

2-(2-Imidazo[1,2-a]pyridin-2-yl-ethyl)-7-pyridin-3-yl-2,3-dihydro-isoindol-1-one A mixture of 7-bromo-2-(2-imidazo[1,2-a]pyridin-2-yl-ethyl)-2,3-dihydro-isoindol-1-one from Example 20.1 (100 mg, 0.281 mmol), pyridin-3-ylboronic acid (51.8 mg, 0.421 mmol), Cs$_2$CO$_3$ (137 mg, 0.421 mmol) and Pd(dppf)Cl$_2$ (20.54 mg, 0.028 mmol) in DMF (2 mL) was heated in a Biotage microwave at about 100° C. for about 1 h. The mixture was purified by pre-HPLC to give the title compound (25.8 mg, 0.073 mmol, 25.9% yield) as a white solid. LC-MS: m/z=355 (M+H$^+$) R$_t$=1.70 min.
$^1$H NMR (400 MHz, DMSO-d$_6$): δ=8.67 (s, 1H), 8.66-8.56 (m, 1H), 8.47 (d, J=6.8 Hz 1H), 7.91-7.88 (m, 1H), 7.74 (s, 1H), 7.68-7.61 (m, 2H), 7.47-7.41 (m, 3H), 7.19-7.15 (m, 1H), 6.84-6.80 (m, 1H), 4.5 (s, 2H), 3.36 (s, 4H), 3.87 (t, J=7.4 Hz, 2H), 3.04 (t, J=7.2 Hz, 2H).

Example 236

7-(4-Fluoro-phenyl)-2-(2-imidazol[1,2-a]pyridin-2-yl-ethyl)-2,3-dihydro-isoindol-1-one The title compound was prepared in analogy to the process described in example 235. LC-MS: m/z=372 (M+H$^+$) R$_t$=1.979 min. $^1$H NMR (400 MHz, DMSO-d$_6$): δ=8.47 (d, J=6.4 Hz 1H), 7.74 (s, 1H), 7.63-7.45 (m, 5H), 7.36 (d, J=7.2 Hz 1H), 7.24-7.16 (m, 3H), 6.84 (t, J=7.2 Hz, 1H), 4.48 (s, 2H), 3.86 (t, J=7.4 Hz, 2H), 3.04 (t, J=7.2 Hz, 2H)

Example 237

2-(2-Imidazo[1,2-a]pyridin-2-yl-ethyl)-7-(4-methoxy-phenyl)-2,3-dihydro-isoindol-1-one The title compound was prepared in analogy to the process described in example 235. LC-MS: m/z=384 (M+H$^+$) R$_t$=1.95 min. $^1$H NMR (400 MHz, DMSO-d$_6$): δ=8.47 (d, J=6.8 Hz, 1H), 7.79 (s, 1H), 7.60-7.42 (m, 5H), 7.33-7.31 (m, 1H), 7.20-7.17 (m, 1H), 6.97-6.94 (m, 2H), 6.84-6.80 (m, 1H), 4.46 (s, 2H), 3.86-3.81 (m, 5H), 3.03 (t, J=7.2 Hz, 2H).

Example 238

2-(2-Imidazo[1,2-a]pyridin-2-yl-ethyl)-7-pyrimidin-5-yl-2,3-dihydro-isoindol-1-one The title compound was prepared in analogy to the process described in example 235. LC-MS: m/z=356 (M+H$^+$) R$_t$=1.61 min. $^1$H NMR (400 MHz, DMSO-d$_6$): δ=9.18 (s, 1H), 8.92 (s, 1H), 8.46 (d, J=7.2 Hz, 1H), 7.74-7.65 (m, 3H), 7.53-7.50 (m, 1H), 7.46-7.44 (m, 1H), 7.19-7.15 (m, 1H), 6.84-6.80 (m, 1H), 4.52 (s, 2H), 3.88 (t, J=7.6 Hz, 2H), 3.04 (t, J=7.2 Hz, 2H).

Example 239

2-(2-Imidazo[1,2-a]pyridin-2-yl-ethyl)-7-(2-methyl-2H-pyrazol-3-yl)-2,3-dihydro-isoindol-1-one The title compound was prepared in analogy to the process described in example 235. LC-MS: m/z=358 (M+H$^+$) R$_t$=1.70 min. $^1$H NMR (400 MHz, DMSO-d$_6$): δ=8.44 (d, J=6.8 Hz, 1H), 7.73 (s, 1H), 7.66-7.61 (m, 2H), 7.43 (d, J=8.0 Hz, 2H), 7.34 (d, J=8.0 Hz, 1H), 7.18-7.14 (m, 1H), 6.83-6.79 (m, 1H), 6.26 (d, J=1.6 Hz, 1H), 4.53 (s, 2H), 3.85 (t, J=7.0 Hz, 2H), 3.46 (s, 3H), 3.02 (t, J=7.0 Hz, 2H).

Example 240

2-(2-Imidazo[1,2-a]pyridin-2-yl-ethyl)-7-(2-methyl-pyridin-3-yl)-2,3-dihydro-isoindol-1-one The title compound was prepared in analogy to the process described in example 235. LC-MS: m/z=369 (M+H$^+$) R$_t$=1.73 min. $^1$H NMR (400 MHz, DMSO-d$_6$): δ=8.44-8.42 (m, 2H), 7.71 (s, 1H), 7.63-7.60 (m, 2H), 7.48-7.44 (m, 2H), 7.24-7.22 (m, 2H), 7.18-7.15 (m, 1H), 6.83-6.79 (m, 1H), 4.57-4.45 (m, 2H), 3.83 (t, J=7.2 Hz, 2H), 3.01 (t, J=7.2 Hz, 2H), 2.13 (s, 3H).

Example 241

6-[2-(2-Imidazo[1,2-a]pyridin-2-yl-ethyl)-3-oxo-2,3-dihydro-1H-isoindol-4-yl]-1,3-dihydro-indol-2-one A 5 mL microwave reaction vial was charged with 7-bromo-2-(2-imidazo[1,2-a]pyridin-2-yl-ethyl)-2,3-dihydro-isoindol-1-one from Example 20.1 (100 mg, 0.281 mmol), 6-(4,4,5,5-tetramethyl-1,3,2-dioxaborolan-2-yl)indolin-2-one (87 mg, 0.337 mmol) and aq. Na$_2$CO$_3$ (2 N, 0.5 mL) in dioxane (2 mL). Pd(PPh$_3$)$_4$ (3.24 mg, 2.81 µmol) was added. The resulting suspension was heated on microwave at 100° C. for 30 minutes. The solid was filtered. The filtrated was purified by Prep-HPLC to give the title compound (24.5 mg, 0.060 mmol, 21.37% yield). LC-MS: m/z=409 (M+H$^+$); R$_t$=1.74 min. $^1$H NMR (400 MHz, DMSO-d$_6$): δ=10.40 (s, 1H), 8.46 (d, J=6.4 Hz, 1H), 7.62-7.45 (m, 3H), 7.33-7.31 (m, 1H), 7.23-7.16 (m, 2H), 7.01-7.00 (m, 1H), 6.94 (s, 1H), 6.84-6.80 (m, 1H), 4.47 (s, 2H), 3.86 (t, J=6.8 Hz, 2H), 3.52 (s, 2H). 3.03 (t, J=7.2 Hz, 2H).

Example 242

2-(2-Imidazo[1,2-a]pyridin-2-yl-ethyl)-7-(1H-pyrazol-4-yl)-2,3-dihydro-isoindol-1-one The title compound was prepared in analogy to the process described in example 241. LC-MS: m/z=344 (M+H$^+$) R$_t$=1.64 min. $^1$H NMR (400 MHz, DMSO-d$_6$): δ=12.90 (s, 1H), 8.54 (s, 1H), 6.46 (d, J=6.8 Hz, 1H), 8.01 (s, 1H), 7.76 (s, 1H), 7.64 (d, J=7.2 Hz, 1H), 7.56-7.45 (m, 2H), 7.37 (d, J=7.6 Hz, 1H), 77.17 (t, J=8.4 Hz, 1H), 6.82 (t, J=7.2 Hz, 1H), 4.43 (s, 2H), 3.90-3.85 (m, 2H), 3.03 (t, J=7.4 Hz, 2H).

Example 243

2-(2-Imidazo[1,2-a]pyridin-2-yl-ethyl)-7-(1H-indazol-6-yl)-2,3-dihydro-isoindol-1-one The title compound was prepared in analogy to the process described in example 241. LC-MS: m/z=394 (M+H$^+$) R$_t$=1.79 min. $^1$H NMR (400 MHz, CDCl$_3$): δ=8.09 (s, 1H), 8.00 (d, J=6.8 Hz, 1H), 7.79 (d, J=8.8 Hz, 1H), 7.68 (s, 1H), 7.57-7.52 (m, 2H), 7.42-7.40 (m, 3H), 7.35 (d, J=8.4 Hz, 1H), 7.13 (t, J=7.8 Hz, 1H), 6.72 (t, J=6.6 Hz, 1H), 4.38 (s, 2H), 4.02 (t, J=7.0 Hz, 2H), 3.17 (t, J=7.0 Hz, 2H).

Example 244

7-(3H-Benzoimidazol-5-yl)-2-(2-imidazol[1,2-a]pyridin-2-yl-ethyl)-2,3-dihydro-isoindol-1-one The title compound was prepared in analogy to the process described in example 241. LC-MS: m/z=394 (M+H$^+$) R$_t$=1.67 min. $^1$H NMR (400 MHz, DMSO-d$_6$): δ=12.46 (s, 1H), 8.46 (d, J=7.2 Hz, 1H), 7.74 (s, 1H), 7.65-7.60 (m, 2H), 7.53-7.50 (m, 1H), 7.47-7.44 (m, 1H), 7.40-7.38 (m, 1H), 7.33-7.31 (m, 1H), 7.28-7.26 (m, 1H), 7.18-7.15 (m, 1H), 6.83-6.80 (m, 1H), 4.47 (s, 2H), 3.85 (t, J=7.2 Hz, 2H), 3.03 (t, J=7.2 Hz, 2H).

Example 245

5-[2-(2-Imidazo[1,2-a]pyridin-2-yl-ethyl)-3-oxo-2,3-dihydro-1H-isoindol-4-yl]-1,3-dihydro-benzoimidazol-2-one The title compound was prepared in analogy to the process described in example 241. LC-MS: m/z=410 (M+H$^+$) R$_t$=1.67 min. $^1$H NMR (400 MHz, CDCl$_3$): δ=10.71 (s, 1H), 10.05 (s, 1H), 8.09 (s, 1H), 7.62 (s, 1H), 7.47-7.42 (m, 2H), 7.41-7.35 (m, 2H), 7.26-7.23 (m, 1H), 7.00-6.98 (m, 3H), 6.77 (s, 1H), 6.49-6.48 (m, 1H), 4.39 (s, 2H), 4.12 (t, J=6.8 Hz, 2H), 3.27 (t, J=6.8 Hz, 2H).

The following compounds of the Examples 246 to 250 listed below were prepared in an analogous manner.

Example 246

4-(Pyridin-3-ylmethoxy)-2-(2-quinolin-2-yl-ethyl)-isoindole-1,3-dione $^1$H NMR (DMSO-d$_6$, 500 MHz): δ=8.71 (s, 1 H), 8.57 (d, 1 H), 8.27 (d, 1 H), 7.92 (d, 1 H), 7.88 (d, 1 H), 7.77 (m, 2 H), 7.67 (t, 1 H), 7.51-7.57 (m, 2 H), 7.46 (d, 2 H), 7.40 (d, 1 H), 5.38 (s, 2 H), 4.01 (t, 2 H), 3.24 (t, 2 H).

Example 247

4-(Pyridin-4-ylmethoxy)-2-(2-quinolin-2-yl-ethyl)-isoindole-1,3-dione

ESI-MS: [M+Na$^+$]=432.10, 411.10, [M+H$^+$]=410.10

Example 248

4-Methoxy-7-morpholin-4-yl-2-(2-quinolin-2-yl-ethyl)-2,3-dihydro-isoindol-1-one

ESI-MS: [M+H$^+$]=404.10.

Example 249

4-Pyridin-4-yl-2-(2-quinolin-2-yl-ethyl)-isoindole-1,3-dione dihydrochloride

ESI-MS: [M+Na$^+$]=402.10, 381.10, [M+H$^+$]=380.10

Example 250

4-(1,1-Dioxothiomorpholin-4-yl)-2-(2-quinolin-2-yl-ethyl)-isoindole-1,3-dione

ESI-MS: [M+Na$^+$]=458.10, 437.10, [M+H$^+$]=436.10

Example 251

7-(2-Methoxy-pyridin-4-yl)-2-(2-quinolin-2-yl-ethyl)-2,3-dihydro-isoindol-1-one

A Personal Chemistry Ermy's optimizer microwave was used. Each microwave tube was charged with 0.1 eq. of [1,1'-Bis(diphenylphosphino)-ferrocene]dichloro-palladium (II), complex with dichloromethane (7 mg). To the microwave tube, a solution of 7-bromo-2-(2-(quinolin-2-yl)ethyl)isoindolin-1-one from Example 5.4 (30 mg, 0.08 mmol) dissolved in dioxane (1.0 mL) was added, followed by 2-methoxypyridin-4-ylboronic acid (15.2 mg, 0.1 mmol) dissolved in dioxane (0.3 mL). Then, 250 µL of 1M aqueous solution of Cs$_2$CO$_3$ was added and the resulting mixture was heated in the microwave for 1200 sec at 120° C. The reaction was filtered, checked by LC/MS and concentrated to dryness. The residues were dissolved in 1:1 DMSO/MeOH. Purification by reverse phase HPLC gave 7-(2-methoxypyridin-4-yl)-2-(2-(quinolin-2-yl)ethyl)isoindolin-1-one (13 mg, 40%). $^1$H NMR (400 MHz, DMSO/D$_2$O) δ ppm 8.28 (d, J=8.54 Hz, 1 H) 8.11 (d, J=5.19 Hz, 1 H) 7.91 (dd, J=23.96, 8.39 Hz, 2 H) 7.63-7.75 (m, 3 H) 7.53-7.59 (m, 1 H) 7.48 (d, J=8.24 Hz, 1 H) 7.38 (dd, J=6.10, 2.44 Hz, 1H) 6.96 (dd, J=5.34, 1.37 Hz, 1 H) 6.80 (s, 1 H) 4.54 (s, 2 H) 3.97 (t, J=7.17 Hz, 2 H) 3.87 (s, 3 H) 3.28 (t, J=7.17 Hz, 2 H); MS (ESI) m/z 396 (M+H)$^+$.

The following compounds of the formula (I) described below were prepared using the standard operation procedures described above.

Example 252

7-(2-Ethyl-morpholin-4-yl)-2-(2-quinolin-2-yl-ethyl)-2,3-dihydro-isoindol-1-one trifluoroacetate ESI-MS: [M+Na$^+$]=424.10, 403.20, [M+H$^+$]=402.20

Example 253

2-[2-(1H-Imidazo[4,5-b]pyridin-2-yl)-ethyl]-7-pyridin-3-yl-2,3-dihydro-isoindol-1-one

ESI-MS: [M+H$^+$]=356.10

Example 254

2-[2-(1-Methyl-1H-benzoimidazol-2-yl)-ethyl]-7-(4-methyl-piperazin-1-yl)-2,3-dihydro-isoindol-1-one ESI-MS: [M+Na$^+$]=412.10, 391.20, [M+H$^+$]=390.20.

Example 255

6-(2-Imidazo[1,2-a]pyridin-2-yl-ethyl)-4-(2-methyl-2H-pyrazol-3-yl)-6,7-dihydro-pyrrolo[3,4-b]pyridin-5-one

ESI-MS: 360.10, [M+H$^+$]=359.10.

Example 256

6-(2-Imidazo[1,2-a]pyridin-2-yl-ethyl)-4-pyrimidin-5-yl-6,7-dihydro-pyrrolo[3,4-b]pyridin-5-one

ESI-MS: 358.10, [M+H$^+$]=357.10.

Example 257

4-(2-Oxa-6-aza-spiro[3.4]oct-6-yl)-6-(2-quinolin-2-yl-ethyl)-6,7-dihydro-pyrrolo[3,4-b]pyridin-5-one ESI-MS: [M+Na$^+$]=423.10, 402.20, [M+H$^+$]=401.15.

Example 258

4-(4,4-Difluoro-piperidin-1-yl)-6-(2-quinolin-2-yl-ethyl)-6,7-dihydro-pyrrolo[3,4-b]pyridin-5-one $^1$H NMR (CDCl$_3$, 500 MHz): δ=8.32 (d, 1 H), 8.08 (d, 1 H), 8.00 (d, 1 H), 7.79 (d, 1 H), 7.69 (t, 1 H), 7.51 (t, 1 H), 7.36 (d, 1 H), 6.61 (d, 1 H), 4.32 (s, 2 H), 4.13 (t, 2 H), 3.60 (br. s., 4 H), 3.36 (t, 2 H), 2.15-2.22 (m br, 4 H).

Example 259

7-(2,6-Dimethyl-morpholin-4-yl)-2-(2-quinolin-2-yl-ethyl)-2,3-dihydro-isoindol-1-one trifluoroacetate ESI-MS: [M+Na$^+$]=424.10, 403.20, [M+H$^+$]=402.20.

Example 260

6-(2-Quinolin-2-yl-ethyl)-4-(tetrahydro-furo[3,4-c]pyrrol-5-yl)-6,7-dihydro-pyrrolo[3,4-b]pyridin-5-one ESI-MS: [M+Na$^+$]=423.10, 402.20, [M+H$^+$]=401.20.

Example 261

4-Methoxy-7-(4-methyl-piperazin-1-yl)-2-(2-quinolin-2-yl-ethyl)-2,3-dihydro-isoindol-1-one di-trifluoroacetate ESI-MS: [M+Na$^+$]=439.15, 418.20, [M+H$^+$]=417.20.

Example 262

2-[2-(5-Fluoro-1-methyl-1H-benzoimidazol-2-yl)-ethyl]-7-morpholin-4-yl-2,3-dihydro-isoindol-1-one ESI-MS: [M+Na$^+$]=417.10, [M+H$^+$]=380.10

Example 263

2-(2-Benzothiazol-2-yl-ethyl)-7-morpholin-4-yl-2,3-dihydro-isoindol-1-one trifluoroacetate ESI-MS: [M+Na$^+$]=402.10, [M+H$^+$]=380.10

Example 264

2-(2-Imidazo[1,2-a]pyridin-2-yl-ethyl)-4-methoxy-7-morpholin-4-yl-2,3-dihydro-isoindol-1-one trifluoroacetate

ESI-MS: [M+H$^+$]=393.20.

Example 265

4-(3,6-Dihydro-2H-pyran-4-yl)-6-(2-quinolin-2-yl-ethyl)-6,7-dihydro-pyrrolo[3,4-b]pyridin-5-one ESI-MS: [M+Na$^+$]=394.10, 373.10, [M+H$^+$]=372.10.

Example 266

4-(4,5-Dihydro-furan-3-yl)-6-(2-quinolin-2-yl-ethyl)-6,7-dihydro-pyrrolo[3,4-b]pyridin-5-one

ESI-MS: 359.10, [M+H$^+$]=358.10.

Example 267

4-Methylsulfanylmethoxy-7-pyridin-4-yl-2-(2-quinolin-2-yl-ethyl)-2,3-dihydro-isoindol-1-one

ESI-MS: 443.10, [M+H$^+$]=442.10.

Example 268

4-Difluoromethoxy-7-pyridin-4-yl-2-(2-quinolin-2-yl-ethyl)-2,3-dihydro-isoindol-1-one $^1$H NMR (DMSO-d$_6$, 500 MHz): δ=8.56 (d, 2 H), 8.28 (d, 1 H), 7.93 (d, 1 H), 7.86 (d, 1 H), 7.70 (t, 1 H), 7.29-7.57 (m, 6 H), 4.60 (s, 1 H), 3.98 (t, 2 H), 3.58 (s, 1 H), 3.30 (t, 2 H), 2.28 (t, 1 H).

Example 269

4-Methoxy-7-[4-(1-methyl-piperidin-4-yl)-piperazin-1-yl]-2-(2-quinolin-2-yl-ethyl)-2,3-dihydro-isoindol-1-one di-trifluoroacetate ESI-MS: [M+Na]$^+$=522.20, 501.30, [M+H]$^+$=500.30.

Example 270

6-(2-Imidazo[1,2-a]pyridin-2-yl-ethyl)-4-morpholin-4-yl-6,7-dihydro-pyrrolo[3,4-b]pyridin-5-one di-trifluoroacetate

ESI-MS: 365.10, [M+H]$^+$=364.10.

Example 271

4-Pyridin-3-yl-2-(2-quinolin-2-yl-ethyl)-isoindole-1,3-dione

Example 272

4-Morpholin-4-yl-2-(2-quinolin-2-yl-ethyl)-isoindole-1,3-dione

ESI-MS: [M+Na]$^+$=410.10, 389.10, [M+H]$^+$=388.10.

Example 273

6-(2-Imidazo[1,2-a]pyridin-2-yl-ethyl)-4-(4-methyl-piperazin-1-yl)-6,7-dihydro-pyrrolo[3,4-b]pyridin-5-one $^1$H NMR (CDCl$_3$, 500 MHz): δ=8.28 (d, 1 H), 8.03 (d, 1 H), 7.52 (d, 1 H), 7.41 (s, 1 H), 7.14 (t, 1 H), 6.73 (t, 1 H), 6.61 (d, 1 H), 4.23 (s, 2 H), 4.02 (t, 2 H), 3.59 (br. s., 4 H), 3.15 (t, 2 H), 2.64 (br. s., 4 H), 2.37 (s, 4 H).

Example 274

7-(Oxetan-3-ylamino)-2-(2-quinolin-2-yl-ethyl)-2,3-dihydro-isoindol-1-one

ESI-MS: [M+Na]$^+$=382.10, 361.10, [+H]$^+$=360.10.

Example 275

4-(Oxetan-3-ylamino)-6-(2-quinolin-2-yl-ethyl)-6,7-dihydro-pyrrolo[3,4-b]pyridin-5-

$^1$H NMR (CDCl$_3$, 500 MHz): δ=8.20 (d, 1 H), 8.09 (d, 1 H), 8.02 (d, 1 H), 7.79 (d, 1 H), 7.69 (t, 1 H), 7.51 (t, 1 H), 7.36 (d, 1 H), 7.20 (m, 1 H), 6.19 (d, 1 H), 4.98 (t, 2 H), 4.64 (t, 2 H), 4.29 (s, 2 H), 4.12 (t, 2 H), 3.36 (t, 3 H).

Example 276

4-Methylaminomethoxy-7-pyridin-4-yl-2-(2-quinolin-2-yl-ethyl)-2,3-dihydro-isoindol-1-one $^1$H NMR (CDCl$_3$, 500 MHz): δ=8.63 (m, 3 H), 8.08 (d, 1 H), 7.99 (d, 1 H), 7.79 (d, 1 H), 7.69 (t, 1 H), 7.51 (t, 1 H), 7.41-7.29 (m, 3 H), 7.28 (d, 1 H), 5.07 (s, 2 H), 4.44 (d, 2 H), 4.11 (t, 2 H), 3.36 (t, 2 H), 2.61 (s, 3 H).

Example 277

7-(2-Ethyl-6-methyl-morpholin-4-yl)-2-(2-quinolin-2-yl-ethyl)-2,3-dihydro-isoindol-1-one ESI-MS: [M+Na]$^+$=438.20, 417.20, [M+H]$^+$=416.20.

Example 278

2-[2-(1-Ethyl-1H-benzoimidazol-2-yl)-ethyl]-7-morpholin-4-yl-2,3-dihydro-isoindol-1-one

ESI-MS: [M+H]$^+$=391.20.

Example 279

7-(Octahydro-[1,5]naphthyridin-1-yl)-2-(2-quinolin-2-yl-ethyl)-2,3-dihydro-isoindol-1-one trifluoroacetate

Example 280

4-Fluoro-2-(2-imidazo[1,2-a]pyridin-2-yl-ethyl)-7-pyridin-4-yl-2,3-dihydro-isoindol-1-one 280.1 4-Fluoro-2-(2-imidazo[1,2-a]pyridin-2-yl-ethyl)-7-iodo-2,3-dihydro-isoindol-1-one Et$_3$N (2.95 ml, 21.19 mmol) and 2-(imidazo[1,2-a]pyridin-2-yl)ethylamine from Example d1 (4.10 g, 25.4 mmol) were each added sequentially rapidly to a solution of ethyl 2-(bromomethyl)-3-fluoro-6-iodobenzoate from Example 16.3 (8.2 g, 21.19 mmol) in MeCN (5 mL). The reaction was heated in a microwave at about 100° C. for about 20 min. The solvent was removed and the resulting mixture was deposited onto silica gel and loaded onto a silica gel column and eluted with 50:1 CH$_2$Cl$_2$/MeOH.to give the title compound (3.2 g, 7.27 mmol, 34.3% yield). MS (ESI): m/z 422 (M+H)$^+$, R$_t$: 1.87 min. $^1$H-NMR (400 MHz, CDCl$_3$): δ 3.22 (t, J=7 Hz, 2H); 4.08 (t, J=6.8 Hz, 2H); 4.29 (s, 2H); 6.76 (t, J=6.8 Hz, 1H); 6.94 (t, J=8.4 Hz, 1H); 7.14-7.18 (m, 1H); 7.47 (s, 1H); 7.54 (d, J=8.8 Hz, 1H); 7.82-7.85 (m, 1H); 8.06 (d, J=6.8 Hz, 1H).

280.2 4-Fluoro-2-(2-imidazo[1,2-a]pyridin-2-yl-ethyl)-7-pyridin-4-yl-2,3-dihydro-isoindol-1-one K$_2$CO$_3$ (59.1 mg, 0.427 mmol) and bis(triphenylphosphin)palladium(II) chloride (10.00 mg, 0.014 mmol) were each added sequentially rapidly to a suspension of the compound from Example 280.1 (60 mg, 0.142 mmol) and pyridin-4-ylboronic acid (19.26 mg, 0.157 mmol) in DMF (1 mL)/water (0.200 mL). The reaction was heated in a microwave at about 120° C. for about 20 min. The mixture was purified via waters 2767 PHW003 (20-50% MeCN/water (NH$_4$OAc buffer) over 15 min.; Boston C18 10 um 21*250 mm column) to give the title compound (28.4 mg, 0.076 mmol, 53.5% yield).

MS (ESI): m/z 373 (M+H)$^+$, R$_t$: 1.74 min. $^1$H-NMR (400 MHz, CDCl$_3$): δ 3.18 (t, J=7.2 Hz, 2H); 4.03 (t, J=6.8 Hz, 2H); 4.44 (s, 2H); 6.73-6.77 (m, 1H); 7.13-7.17 (m, 1H); 7.24-7.28 (m, 1H); 7.34-7.37 (m, 1H); 7.42-7.45 (m, 3H); 7.52 (d, J=9.2 Hz, 1H); 8.04 (d, J=6.8 Hz, 1H); 8.67 (dd, J=4.4 Hz, 1H).

Example 281

5-[3-oxo-2-(2-quinolin-2-yl-ethyl)-2,3-dihydro-1H-isoindol-4-yl]-thiophene-2-carbonitrile A Personal Chemistry Ermy's optimizer microwave was used. Each microwave tube was charged with 0.1 eq. of

[1,1'-Bis(diphenylphosphino)-ferrocene]dichloro-palladium (II), complex with dichloromethane (7 mg). To the microwave tube, a solution of 7-bromo-2-(2-(quinolin-2-yl)ethyl) isoindolin-1-one from Example 5.4 (30 mg, 0.08 mmol) dissolved in dioxane (1.0 mL) was added, followed by 5-cyanothiophen-2-ylboronic acid (15.3 mg, 0.1 mmol) dissolved in dioxane (0.3 mL). Then, 250 µL of 1M aqueous solution of $Cs_2CO_3$ was added and the resulting mixture was heated in the microwave for 1200 sec at 120° C. The reaction was filtered, checked by LC/MS and concentrated to dryness. The residues were dissolved in 1:1 DMSO/MeOH. Purification by reverse phase HPLC provided 5-(3-oxo-2-(2-(quinolin-2-yl)ethyl)isoindolin-4-yl)thiophene-2-carbonitrile (2.7 mg, 8%). $^1$H NMR (400 MHz, DMSO-$d_6$/$D_2O$) δ ppm 8.23-8.31 (m, 1 H) 7.85-7.97 (m, 3 H) 7.42-7.77 (m, 7 H) 4.44-4.57 (m, 2 H) 4.00 (t, J=7.17 Hz, 2 H) 3.18-3.35 (m, 2 H). MS (ESI) m/z 396 (M+H)$^+$.

Example 282

7-[2-(4-Methyl-piperazin-1-yl)-pyrimidin-5-yl]-2-(2-quinolin-2-yl-ethyl)-2,3-dihydro-isoindol-1-one The title compound was prepared in analogy to the process described in Example 281 using 2-(4-methylpiperazin-1-yl)-5-(4,4,5,5-tetramethyl-1,3,2-dioxaborolan-2-yl) pyrimidine (30.4 mg, 0.1 mmol) dissolved in dioxane (0.3 mL) instead of 5-cyanothiophen-2-ylboronic acid (15.3 mg, 0.1 mmol) dissolved in dioxane (0.3 mL). Yield: 12.4 mg, 32%. $^1$H NMR (400 MHz, DMSO-$d_6$/$D_2O$) δ ppm 8.41 (s, 1 H) 8.29 (d, J=8.54 Hz, 1 H) 7.86-7.95 (m, 2 H) 7.69-7.75 (m, 1 H) 7.60-7.65 (m, 1 H) 7.52-7.58 (m, 3 H) 7.47-7.50 (m, 1 H) 7.38 (d, J=7.63 Hz, 1 H) 4.52 (s, 2 H) 3.98 (t, J=7.17 Hz, 2 H) 3.76-3.80 (m, 4 H) 3.28 (t, J=7.02 Hz, 2 H) 2.37-2.42 (m, 4 H) 2.21-2.24 (m, 3 H); MS (ESI) m/z 465 (M+H)$^+$.

Example 283

7-(2-Ethoxy-pyrimidin-5-yl)-2-(2-quinolin-2-yl-ethyl)-2,3-dihydro-isoindol-1-one The title compound was prepared in analogy to the process described in Example 281 using 2-ethoxypyrimidin-5-ylboronic acid (16.7 mg, 0.1 mmol) dissolved in dioxane (0.3 mL) instead of 5-cyanothiophen-2-ylboronic acid (15.3 mg, 0.1 mmol) dissolved in dioxane (0.3 mL). Yield: 10 mg, 29%. $^1$H NMR (400 MHz, DMSO/$D_2O$) δ ppm 8.59 (s, 2 H) 8.29 (d, J=8.54 Hz, 1 H) 7.83-7.96 (m, 2 H) 7.62-7.74 (m, 3 H) 7.53-7.58 (m, 1 H) 7.49 (d, J=8.54 Hz, 1 H) 7.42-7.46 (m, 1 H) 4.55 (s, 2 H) 4.37-4.44 (m, 2 H) 3.98 (t, J=7.17 Hz, 2 H) 3.28 (t, J=7.17 Hz, 2 H) 1.37 (t, J=7.02 Hz, 3 H); MS (ESI) m/z 411 (M+H)$^+$.

Example 284

7-(5-Pyrrolidin-1-ylmethyl-thiophen-2-yl)-2-(2-quinolin-2-yl-ethyl)-2,3-dihydro-isoindol-1-one The title compound was prepared in analogy to the process described in Example 281 using 1-((5-(4,4,5,5-tetramethyl-1,3,2-dioxaborolan-2-yl)thiophen-2-yl)methyl) pyrrolidine (29.3 mg, 0.1 mmol) dissolved in dioxane (0.3 mL) instead of 5-cyanothiophen-2-ylboronic acid (15.3 mg, 0.1 mmol) dissolved in dioxane (0.3 mL). Yield: 5.5 mg, 15%. $^1$H NMR (400 MHz, DMSO/$D_2O$) δ ppm 8.29 (d, J=8.24 Hz, 1 H) 7.93 (t, J=8.39 Hz, 2 H) 7.69-7.77 (m, 1 H) 7.55-7.60 (m, 2 H) 7.47-7.53 (m, 4 H) 6.92 (d, J=3.66 Hz, 1 H) 4.47-4.53 (m, 2 H) 4.00 (t, J=7.17 Hz, 2 H) 3.79 (s, 2 H) 3.29 (t, J=7.17 Hz, 2 H) 2.48 (t, 4 H) 1.64-1.89 (m, 4 H); MS (ESI) m/z 454 (M+H)$^+$.

Example 285

7-(2-Dimethylamino-pyrimidin-5-yl)-2-(2-quinolin-2-yl-ethyl)-2,3-dihydro-isoindol-1-one The title compound was prepared in analogy to the process described in Example 281 using 2-(dimethylamino) pyrimidin-5-ylboronic acid (16.7 mg, 0.1 mmol) dissolved in dioxane (0.3 mL) instead of 5-cyanothiophen-2-ylboronic acid (15.3 mg, 0.1 mmol) dissolved in dioxane (0.3 mL). Yield: 9.1 mg, 27%. $^1$H NMR (400 MHz, DMSO/$D_2O$) δ ppm 8.40 (s, 2 H) 8.29 (d, J=8.24 Hz, 1 H) 7.87-7.95 (m, 2 H) 7.69-7.75 (m, 1 H) 7.60-7.65 (m, 1 H) 7.56 (t, J=7.63 Hz, 2 H) 7.49 (d, J=8.54 Hz, 1 H) 7.37 (d, J=6.71 Hz, 1H) 4.51 (s, 2 H) 3.98 (t, J=7.17 Hz, 2 H) 3.28 (t, J=7.17 Hz, 2 H) 3.16 (s, 6 H); MS (ESI) m/z 410 (M+H)$^+$.

Example 286

7-(5-Piperidin-1-ylmethyl-thiophen-2-yl)-2-(2-quinolin-2-yl-ethyl)-2,3-dihydro-isoindol-1-one The title compound was prepared in analogy to the process described in Example 281 using 1-((5-(4,4,5,5-tetramethyl-1,3,2-dioxaborolan-2-yl)thiophen-2-yl)methyl) piperidine (30.7 mg, 0.1 mmol) dissolved in dioxane (0.3 mL) instead of 5-cyanothiophen-2-ylboronic acid (15.3 mg, 0.1 mmol) dissolved in dioxane (0.3 mL). Yield: 9.7 mg, 25%. $^1$H NMR (400 MHz, DMSO/$D_2O$) δ ppm 8.29 (d, J=8.24 Hz, 1 H) 7.93 (t, J=8.39 Hz, 2 H) 7.70-7.77 (m, 1 H) 7.47-7.59 (m, 6 H) 6.91 (d, J=3.36 Hz, 1H) 4.50 (s, 2 H) 4.00 (t, J=7.17 Hz, 2 H) 3.63 (s, 2 H) 3.29 (t, J=7.17 Hz, 2 H) 2.35-2.45 (m, 3 H) 1.83-2.04 (m, 2 H) 1.46-1.56 (m, 3 H) 1.35-1.44 (m, 2 H); MS (ESI) m/z 468 (M+H)$^+$.

Example 287

7-(3-Chlorothiophen-2-yl)-2-(2-quinolin-2-yl-ethyl)-2,3-dihydro-isoindol-1-one

The title compound was prepared in analogy to the process described in Example 281 using 3-chlorothiophen-2-ylboronic acid (16.2 mg, 0.1 mmol) dissolved in dioxane (0.3 mL) instead of 5-cyanothiophen-2-ylboronic acid (15.3 mg, 0.1 mmol) dissolved in dioxane (0.3 mL). Yield: 3.8 mg, 11%. $^1$H NMR (400 MHz, DMSO/$D_2O$) δ ppm 8.22-8.29 (m, 1 H) 7.88-7.95 (m, 2 H) 7.70-7.75 (m, 1 H) 7.64-7.68 (m, 1 H) 7.51-7.58 (m, 2 H) 7.51 (dd, J=7.02, 3.05 Hz, 1 H) 7.44-7.49 (m, 1 H) 7.36 (dd, J=5.65, 2.90 Hz, 1 H) 7.08 (d, J=5.19 Hz, 1 H) 4.46-4.56 (m, 2 H) 3.96 (t, J=7.17 Hz, 2 H) 3.18-3.29 (m, 2 H); MS (ESI) m/z 405 (M+H)$^+$.

Example 288

3-Methyl-5-[3-oxo-2-(2-quinolin-2-yl-ethyl)-2,3-dihydro-1H-isoindol-4-yl]-thiophene-2-carbonitrile The title compound was prepared in analogy to the process described in Example 281 using 5-cyano-4-methyl-thiophen-2-ylboronic acid (16.6 mg, 0.1 mmol) dissolved in dioxane (0.3 mL) instead of 5-cyanothiophen-2-ylboronic acid (15.3 mg, 0.1 mmol) dissolved in dioxane (0.3 mL).

Yield: 5.4 mg, 16%. $^1$H NMR (400 MHz, DMSO/D$_2$O) δ ppm 8.29 (d, J=8.55 Hz, 1 H) 7.92-7.95 (m, 1 H) 7.87 (d, J=8.54 Hz, 1 H) 7.70-7.74 (m, 1 H) 7.64-7.67 (m, 2 H) 7.53-7.59 (m, 2 H) 7.48-7.51 (m, 1 H) 7.45 (s, 1 H) 4.56 (s, 2 H) 4.00 (t, J=7.17 Hz, 2 H) 3.29 (t, J=7.17 Hz, 2 H) 2.39 (s, 3 H); MS (ESI) m/z 410 (M+H)$^+$.

Example 289

7-(2-Chlorothiophen-3-yl)-2-(2-quinolin-2-yl-ethyl)-2,3-dihydro-isoindol-1-one

The title compound was prepared in analogy to the process described in Example 281 but using 2-chlorothiophen-3-ylboronic acid (16.2 mg, 0.1 mmol) dissolved in dioxane (0.3 mL) instead of 5-cyanothiophen-2-ylboronic acid (15.3 mg, 0.1 mmol) dissolved in dioxane (0.3 mL). Yield: 5.6 mg, 17%. $^1$H NMR (400 MHz, DMSO/D$_2$O) δ ppm 8.28 (d, J=8.54 Hz, 1 H) 7.91 (dd, J=19.23, 7.93 Hz, 2 H) 7.69-7.75 (m, 1 H) 7.35-7.67 (m, 5 H) 7.29-7.34 (m, 1 H) 6.93 (d, J=5.80 Hz, 1 H) 4.53 (s, 2 H) 3.96 (t, J=7.17 Hz, 2 H) 3.27 (t, J=7.17 Hz, 2 H); MS (ESI) m/z 405 (M+H)$^+$.

Example 290

7-(2-Cyclopropyl-pyridin-4-yl)-2-(2-quinolin-2-yl-ethyl)-2,3-dihydro-isoindol-1-one The title compound was prepared in analogy to the process described in Example 281 but using 2-cyclopropylpyridin-4-ylboronic acid (16.2 mg, 0.1 mmol) dissolved in dioxane (0.3 mL) instead of 5-cyanothiophen-2-ylboronic acid (15.3 mg, 0.1 mmol) dissolved in dioxane (0.3 mL). Yield: 6.4 mg, 19%. $^1$H NMR (400 MHz, DMSO/D$_2$O) δ ppm 8.26-8.33 (m, 1 H) 7.90 (dd, J=30.36, 8.39 Hz, 2 H) 7.65-7.73 (m, 2 H) 7.47-7.58 (m, 4 H) 7.38 (dd, J=6.10, 2.14 Hz, 1 H) 7.18 (s, 1 H) 7.07-7.11 (m, 1 H) 4.56 (s, 2 H) 3.98 (t, J=7.02 Hz, 2 H) 3.28 (t, J=6.87 Hz, 2 H) 2.02 (s, 1 H) 0.88-1.01 (m, 4 H); MS (ESI) m/z 406 (M+H)$^+$.

Example 291

7-(3,6-Dimethoxy-pyridazin-4-yl)-2-(2-quinolin-2-yl-ethyl)-2,3-dihydro-isoindol-1-one The title compound was prepared in analogy to the process described in Example 281 but using 3,6-dimethoxypyridazin-4-ylboronic acid (18.3 mg, 0.1 mmol) dissolved in dioxane (0.3 mL) instead of 5-cyanothiophen-2-ylboronic acid (15.3 mg, 0.1 mmol) dissolved in dioxane (0.3 mL). Yield: 9.2 mg, 26%. $^1$H NMR (400 MHz, DMSO/D$_2$O) δ ppm 8.28 (d, J=7.94 Hz, 1 H) 7.86-7.96 (m, 2 H) 7.71-7.76 (m, 1 H) 7.61-7.67 (m, 2 H) 7.54-7.59 (m, 1 H) 7.47 (d, J=8.24 Hz, 1 H) 7.34 (dd, J=5.34, 3.20 Hz, 1 H) 6.98 (s, 1 H) 4.47-4.58 (m, 2 H) 3.90-4.05 (m, 5 H) 3.72 (s, 3 H) 3.22-3.34 (m, 2 H); MS (ESI) m/z 427 (M+H)$^+$.

The compounds of the Examples 292 to 294 can be prepared using the standard operation procedures described above Example 292

2-{2-[1-(2-Morpholin-4-yl-ethyl)-1H-benzoimidazol-2-yl]-ethyl}-7-pyridin-4-yl-2,3-dihydro-isoindol-1-one trifluoroacetate Example 293

2-{2-[1-(2-Dimethylamino-ethyl)-1H-benzoimidazol-2-yl]-ethyl}-7-pyridin-4-yl-2,3-dihydro-isoindol-1-one trifluoroacetate $^1$H NMR (DMSO-d$_6$, 500 MHz): δ=8.74 (d, 2 H), 7.97 (d, 1 H), 7.84-7.72 (m, 5 H), 7.53-7.59 (m, 3 H), 4.86 (t, 2 H), 4.73 (s, 2 H), 4.03-4.06 (m, 2 H), 3.61 (t, 2 H), 3.55 (br. s., 2 H), 2.94 (s, 6 H).

Example 294

2-{2-[1-(3-Dimethylamino-propyl)-1H-benzoimidazol-2-yl]-ethyl}-7-pyridin-4-yl-2,3-dihydro-isoindol-1-one trifluoroacetate $^1$H NMR (DMSO-d$_6$, 500 MHz): δ=9.92 (s br, 1 H), 8.68 (d, 2 H), 7.98 (d, 1 H), 7.82-7.74 (m, 3 H), 7.68 (d, 2 H), 7.62-7.50 (m, 3 H), 4.72 (s, 2 H), 4.54 (t, 2 H), 3.55 (t, 2 H), 3.22 (s br, 2 H), 2.75 (s, 6 H), 2.22 (m br, 2 H).

Example 295

4-Fluoro-2-(2-imidazo[1,2-a]pyridin-2-yl-ethyl)-7-morpholin-4-yl-2,3-dihydro-isoindol-1-one Dicyclohexyl(2',6'-dimethoxybiphenyl-2-yl)phosphine (146 mg, 0.356 mmol), Pd$_2$dba$_3$ (65.2 mg, 0.071 mmol) and K$_2$CO$_3$ (295 mg, 2.137 mmol) were each added sequentially rapidly to a solution of the compound from Example 280.1 (300 mg, 0.712 mmol) and morpholine (186 mg, 2.137 mmol) in DMF (3 mL). The reaction was heated in a microwave at about 140° C. for about 20 min. The mixture was purified via Gilson 281 (PHG008) (18-75% MeCN/Water (NH$_4$OAc buffer) over 15 min.; Waters X-bridge OBD C18 19*250 mm, 10 um) to give the title compound (15 mg, 0.039 mmol, 5.54% yield). MS (ESI): m/z 381 (M+H)$^+$, R$_t$: 1.77 min. $^1$H-NMR (400 MHz, CDCl$_3$-d): δ 3.17 (t, J=7.2 Hz, 2H); 3.22 (s, 4H); 3.95 (t, J=4.2 Hz, 4H); 4.01 (t, J=7.2 Hz, 2H); 4.32 (s, 2H); 6.75 (t, J=6.8 Hz, 1H); 6.84 (dd, J=8.6 Hz, 1H); 7.09 (t, J=8.4 Hz, 1H); 7.16 (t, J=8 Hz, 1H); 7.43 (s, 1H); 7.54 (d, J=9.2 Hz, 1H); 8.04 (d, J=6.8 Hz, 1H).

The compounds of the Examples 296 to 309 can be prepared using the standard operation procedures described above.

| Ex | IUPAC-Name | physico-chemical data |
|---|---|---|
| 296 | 1-Oxy-4-pyrimidin-5-yl-6-(2-quinolin-2-yl-ethyl)-6,7-dihydro-pyrrolo[3,4-b]pyridin-5-one | $^1$H NMR (CDCl$_3$, 500 MHz): δ = 9.24 (s, 1 H), 8.88 (s, 2 H), 8.37 (d, 1 H), 8.13 (d, 1 H), 8.01 (d, 1 H), 7.81 (d, 1 H), 7.69 (t, 1 H), 7.53 (t, 1 H), 7.33-7.37 (m, 2 H), 4.71 (s, 2 H), 4.20 (t, 2 H), 3.43 (t, 2 H) |

-continued

| Ex | IUPAC-Name | physico-chemical data |
|---|---|---|
| 297 | 6-(2-Quinolin-2-yl-ethyl)-4-(tetrahydro-pyran-4-yl)-6,7-dihydro-pyrrolo[3,4-b]pyridin-5-one | ESI-MS: 396.10, [M + Na$^+$] = 394.10, 375.10, [M + H$^+$] = 374.15, 373.10, 372.10 |
| 298 | 7-(2-Methoxymethyl-morpholin-4-yl)-2-(2-quinolin-2-yl-ethyl)-2,3-dihydro-isoindol-1-one | ESI-MS: [M + Na$^+$] = 440.10, 419.20, [M + H$^+$] = 418.20 |
| 299 | 4-Fluoromethoxy-7-pyridin-4-yl-2-(2-quinolin-2-yl-ethyl)-2,3-dihydro-isoindol-1-one | $^1$H NMR (CDCl$_3$, 500 MHz): δ = 8.64 (d, 2 H), 8.09 (d, 1 H), 7.99 (d, 1 H), 7.80 (d, 1 H), 7.69 (t, 1 H), 7.51 (t, 1 H), 7.41 (d, 2 H), 7.36 (d, 2 H), 7.29 (m, 1 H, incl. CHCl$_3$), 5.86 (s, 1 H), 5.75 (s, 1 H), 4.45 (s, 2 H), 4.12 (t, 2 H), 3.36 (t, 2 H) |
| 300 | 2-[2-(4-Fluoro-1-methyl-1H-benzoimidazol-2-yl)-ethyl]-7-pyridin-4-yl-2,3-dihydro-isoindol-1-one trifluoroacetate | ESI-MS: [M + H$^+$] = 387.10 |
| 301 | 2-[2-(1,5-Dimethyl-1H-benzoimidazol-2-yl)-ethyl]-7-pyridin-4-yl-2,3-dihydro-isoindol-1-one trifluoroacetate | ESI-MS: [M + H$^+$] = 383.10 |
| 302 | 2-[2-(1-Propyl-1H-benzoimidazol-2-yl)-ethyl]-7-pyridin-4-yl-2,3-dihydro-isoindol-1-one trifluoroacetate | ESI-MS: [M + H$^+$] = 397.20 |
| 303 | 2-[2-(1-Isopropyl-1H-benzoimidazol-2-yl)-ethyl]-7-pyridin-4-yl-2,3-dihydro-isoindol-1-one trifluoroacetate | ESI-MS: [M + H$^+$] = 397.20 |
| 304 | 2-[2-(1-Isopropyl-1H-benzoimidazol-2-yl)-ethyl]-7-morpholin-4-yl-2,3-dihydro-isoindol-1-one trifluoroacetate | |
| 305 | 7-Morpholin-4-yl-2-[2-(1-propyl-1H-benzoimidazol-2-yl)-ethyl]-2,3-dihydro-isoindol-1-one trifluoroacetate | ESI-MS: [M + Na$^+$] = 427.15, [M + H$^+$] = 405.20 |
| 306 | 2-[2-(1,5-Dimethyl-1H-benzoimidazol-2-yl)-ethyl]-7-morpholin-4-yl-2,3-dihydro-isoindol-1-one trifluoroacetate | ESI-MS: [M + H$^+$] = 391.20 |
| 307 | 2-[2-(4-Fluoro-1-methyl-1H-benzoimidazol-2-yl)-ethyl]-7-morpholin-4-yl-2,3-dihydro-isoindol-1-one trifluoroacetate | ESI-MS: [M + Na$^+$] = 417.10, [M + H$^+$] = 395.15 |
| 308 | 2-(2-Imidazo[1,2-a]pyridin-2-yl-ethyl)-4-morpholin-4-yl-2,3-dihydro-isoindol-1-one | ESI-MS: [M + H$^+$] = 363.10 |
| 309 | 6-(2-Quinolin-2-yl-ethyl)-4-(tetrahydro-furan-3-yl)-6,7-dihydro-pyrrolo[3,4-b]pyridin-5-one | |

Example 310

2-(2-Imidazo[1,2-a]pyridin-2-yl-ethyl)-7-morpholin-4-yl-2,3-dihydro-isoindol-1-one In a 5 mL microwave reaction vial, 7-bromo-2-(2-imidazo[1,2-a]pyridin-2-yl-ethyl)-2,3-dihydro-isoindol-1-one from Example 20.1 (100 mg, 0.281 mmol), Cs$_2$CO$_3$ (183 mg, 0.561 mmol), Pd$_2$(dba)$_3$ (25.7 mg, 0.028 mmol) and X-PHOS (13.38 mg, 0.028 mmol) were added. The solids were purged with argon for at least 5 min. A separate round bottom flask was charged with dioxane (3 mL) and morpholine (48 mg, 0.56 mmol), degas with argon for at least 10 min. and then the solvents were transferred to the microwave reaction vial under inert conditions. The resulted mixture was heated on microwave at 110° C. for 1 h. The reaction mixture was filtered. The filtrate was purified by Prep-HPLC to give the title compound (25 mg, yield: 24.6%) as a white solid. LC-MS: m/z 363 (M+H$^+$); R$_t$=1.71 min. $^1$H NMR (400 MHz, CDCl$_3$): δ 8.34 (d, J=6.8 Hz, 1H), 7.67 (s, 1H), 7.48-7.44 (m, 2H), 7.28 (t, J=8.8 Hz, 1H), 7.07 (d, J=7.2 Hz, 1H), 6.96 (d, J=8.0 Hz, 1H), 6.89 (t, J=6.4 Hz, 1H), 4.36 (s, 2H), 3.98 (t, J=7.2 Hz, 2H), 3.87-3.85 (m, 4H), 3.17-3.12 (m, 6H).

The compounds of the Examples 311 to 321 can be prepared using the standard operation procedures described above.

| Ex. | IUPAC-Name | physico-chemical data |
|---|---|---|
| 311 | 2-[2-(1H-Benzoimidazol-2-yl)-ethyl]-7-(4-fluoro-phenyl)-2,3-dihydro-isoindol-1-one trifluoroacetate | $^1$H NMR (DMSO-d6, 500 MHz): δ = 7.79-7.74 (m, 2 H), 7.63 (m, 2 H), 7.54-7.47 (m, 2 H), 7.33 (d, 1 H), 7.28 (t, 2 H), 7.04 (t, 2 H), 4.57 (s, 2 H), 3.99 (t, 2 H). |
| 312 | 2-[2-(1H-Benzoimidazol-2-yl)-ethyl]-7-pyrimidin-5-yl-2,3-dihydro-isoindol-1-one trifluoroacetate | ESI-MS: [M + H$^+$] = 356.10 |

| Ex. | IUPAC-Name | physico-chemical data |
|---|---|---|
| 313 | 2-[2-(1H-Benzoimidazol-2-yl)-ethyl]-7-(2-methyl-2H-pyrazol-3-yl)-2,3-dihydro-isoindol-1-one trifluoroacetate | ESI-MS: [M + H$^+$] = 358.10 |
| 314 | 2-(2-Imidazo[1,2-a]pyridin-2-yl-ethyl)-4-(1H-pyrazol-3-yl)-2,3-dihydro-isoindol-1-one trifluoroacetate | ESI-MS: [M + H$^+$] = 344.10 |
| 315 | 6-[2-(5,7-Dimethyl-[1,2,4]triazolo[1,5-a]pyrimidin-2-yl)-ethyl]-4-pyridin-4-yl-6,7-dihydro-pyrrolo[3,4-b]pyridin-5-one trifluoroacetate | $^1$H NMR (DMSO-d6, 500 MHz): δ = 8.85 (d, 1H), 8.76 (d, 2 H), 7.76 (d, 2 H), 7.57 (d, 1 H), 7.12 (s, 1 H), 4.68 (s, 2 H), 3.97 (t, 2 H), 3.21 (t, 2 H), 2.65 (s, 3 H), 2.56 (s, 3 H) |
| 316 | 2-(2-Imidazo[1,2-a]pyridin-2-yl-ethyl)-4-pyridin-4-yl-2,3-dihydro-isoindol-1-one | ESI-MS: [M + H$^+$] = 355.10 |
| 317 | 7-(3aS,8aR)-Octahydro-pyrrolo[3,4-c]azepin-2-yl-2-(2-quinolin-2-yl-ethyl)-2,3-dihydro-isoindol-1-one trifluoroacetate | ESI-MS: [M + H$^+$] = 427.20 |
| 318 | 7-(3aS,8aS)-Octahydro-pyrrolo[3,4-c]azepin-2-yl-2-(2-quinolin-2-yl-ethyl)-2,3-dihydro-isoindol-1-one trifluoroacetate | ESI-MS: [M + H$^+$] = 427.20 |
| 319 | 1-[5-Oxo-6-(2-quinolin-2-yl-ethyl)-6,7-dihydro-5H-pyrrolo[3,4-b]pyridin-4-yl]-piperidine-4-carboxylic acid ethyl ester | ESI-MS: [M + Na$^+$] = 467.20, 446.20, [M + H$^+$] = 445.20 |
| 320 | 4-[8-(Morpholine-4-sulfonyl)-3,4-dihydro-1H-isoquinolin-2-yl]-2-(2-quinolin-2-yl-ethyl)-2,3-dihydro-isoindol-1-one | ESI-MS: 571.20, 570.20, [M + H$^+$] = 569.20 |
| 321 | 4-[8-(4-Methyl-piperazine-1-sulfonyl)-3,4-dihydro-1H-isoquinolin-2-yl]-2-(2-quinolin-2-yl-ethyl)-2,3-dihydro-isoindol-1-one | ESI-MS: 584.20, 583.20, [M + H$^+$] = 582.20 |

Example 322

4-(3-Methyl-pyridin-4-yl)-6-(2-quinolin-2-yl-ethyl)-6,7-dihydro-pyrrolo[3,4-b]pyridin-5-one A Personal Chemistry Ermy's optimizer microwave was used. Each microwave tube was charged with 0.1 eq. of [1,1'-Bis(diphenylphosphino)-ferrocene]dichloro-palladium (II), complex with dichloromethane (7 mg). To the microwave tube, a solution of 4-bromo-6-(2-(quinolin-2-yl)ethyl)-6,7-dihydro-5H-pyrrolo[3,4-b]pyridin-5-one from Example 119.3 (31 mg, 0.08 mmol) dissolved in dioxane (1.0 mL) was added, followed by 3-methylpyridin-4-ylboronic acid (13.7 mg, 0.1 mmol) dissolved in dioxane (0.35 mL). Then, 250 µL of 1M aqueous solution of Cs$_2$CO$_3$ was added and the resulting mixture was heated in the microwave for 1200 sec at 120° C. The reaction was filtered, checked by LC/MS and concentrated to dryness. The residues were dissolved in 1:1 DMSO/MeOH. Purification by reverse phase HPLC provided the title compound (10.8 mg, 33%). $^1$H NMR (500 MHz, DMSO/D$_2$O) δ ppm 8.79 (d, J=5.19 Hz, 1 H) 8.42 (s, 1 H) 8.39 (d, J=4.88 Hz, 1 H) 8.27 (d, J=8.24 Hz, 1 H) 7.93 (d, J=7.32 Hz, 1 H) 7.81 (d, J=8.54 Hz, 1 H) 7.68-7.73 (m, 1 H) 7.54-7.58 (m, 1 H) 7.48 (d, J=8.54 Hz, 1 H) 7.30 (d, J=4.88 Hz, 1 H) 7.06 (d, J=4.88 Hz, 1 H) 4.65 (s, 2 H) 3.98 (t, J=6.87 Hz, 2 H) 3.29 (t, J=7.02 Hz, 2 H) 1.83 (s, 3 H); MS (ESI) m/z 381 (M+H)$^+$.

Example 323

4-(1H-Pyrazol-3-yl)-6-(2-quinolin-2-yl-ethyl)-6,7-dihydro-pyrrolo[3,4-b]pyridin-5-one The title compound was prepared in analogy to the process described in Example 322 but using 1H-pyrazol-3-ylboronic acid (11.2 mg, 0.1 mmol) dissolved in dioxane (0.35 mL) instead of 3-methylpyridin-4-ylboronic acid (13.7 mg, 0.1 mmol) dissolved in dioxane (0.35 mL). Yield: 6.6 mg, 22%. $^1$H NMR (500 MHz, DMSO/D$_2$O) δ ppm 8.73 (s, 1 H) 8.30 (d, J=8.24 Hz, 1 H) 7.94 (d, J=8.24 Hz, 3 H) 7.65-7.78 (m, 2 H) 7.55 (t, J=7.63 Hz, 2 H) 7.23 (s, 1 H) 4.49-4.77 (m, 2 H) 4.14 (s, 2 H) 3.38 (s, 2 H); MS (ESI) m/z 356 (M+H)$^+$.

Example 324

4-(3,6-dimethoxypyridazin-4-yl)-6-(2-(quinolin-2-yl)ethyl)-6,7-dihydro-5H-pyrrolo[3,4-b]pyridin-5-one The title compound was prepared in analogy to the process described in Example 322 but using 3,6-dimethoxy-pyridazin-4-ylboronic acid (18.3 mg, 0.1 mmol) dissolved in dioxane (0.35 mL) instead of 3-methylpyridin-4-ylboronic acid (13.7 mg, 0.1 mmol) dissolved in dioxane (0.35 mL). Yield: 3.2 mg, 7%. $^1$H NMR (500 MHz, DMSO/D$_2$O) δ ppm 8.80 (d, J=5.19 Hz, 1 H) 8.29 (d, J=8.54 Hz, 1 H) 7.93 (d, J=8.85 Hz, 1 H) 7.85 (d, J=8.85 Hz, 1 H) 7.69-7.76 (m, 1 H) 7.56 (t, J=7.48 Hz, 1 H) 7.45-7.51 (m, 2 H) 7.11 (s, 1 H) 4.62 (s, 2 H) 3.99 (s, 2 H) 3.98 (s, 3 H) 3.74 (s, 3 H) 3.29 (t, J=7.02 Hz, 2 H); MS (ESI) m/z 428 (M+H)$^+$.

Example 325

4-(2-Dimethylamino-pyrimidin-5-yl)-6-(2-quinolin-2-yl-ethyl)-6,7-dihydro-pyrrolo[3,4-b]pyridin-5-one The title compound was prepared in analogy to the process described in Example 322 but using 2-(dimethylamino)pyrimidin-5-ylboronic acid (16.7 mg, 0.1 mmol) dissolved in dioxane (0.35 mL) instead of 3-methylpyridin-4-ylboronic acid (13.7 mg, 0.1 mmol) dissolved in dioxane (0.35 mL). Yield: 3 mg, 8%. $^1$H NMR (500 MHz, DMSO/D$_2$O) δ ppm 8.68 (d, J=5.49 Hz, 1 H) 8.59 (s, 2 H) 8.29 (d, J=8.54 Hz, 1 H) 7.94 (d, J=7.93 Hz, 1 H) 7.85 (d, J=8.54 Hz, 1 H) 7.68-7.74 (m, 1 H) 7.53-7.58 (m, 1 H) 7.47-7.53 (m, 2 H) 4.56 (s, 2 H) 4.03 (t, J=7.02 Hz, 2 H) 3.31 (t, J=7.17 Hz, 2 H) 3.18 (s, 6 H); MS (ESI) m/z 411 (M+H)$^+$

Example 326

4-(2-Methyl-thiazol-5-yl)-6-(2-quinolin-2-yl-ethyl)-6,7-dihydro-pyrrolo[3,4-b]pyridin-5-one The title compound was prepared in analogy to the process described in Example 322 but using 2-methyl-5-(4,4,5,5-tetramethyl-1,3,2-dioxaborolan-2-yl)thiazole (22.5 mg, 0.1 mmol) dissolved in dioxane (0.35 mL) instead of 3-methylpyridin-4-ylboronic acid (13.7 mg, 0.1 mmol) dissolved in dioxane (0.35 mL). Yield: 4.4 mg, 13%. $^1$H NMR (500 MHz, DMSO/D$_2$O) δ ppm 8.67 (d, J=5.49 Hz, 1 H) 8.59 (s, 1 H) 8.30 (d, J=8.24 Hz, 1 H) 7.94 (d, J=7.63 Hz, 1 H) 7.87 (d, J=8.54 Hz, 1 H) 7.69-7.74 (m, 1 H) 7.63 (d, J=5.49 Hz, 1 H) 7.51-7.58 (m, 2 H) 4.57 (s, 2 H) 4.05 (t, J=7.17 Hz, 2 H) 3.33 (t, J=7.17 Hz, 2 H) 2.70 (s, 3 H); MS (ESI) m/z 387 (M+H)$^+$.

Example 327

4-(2-Ethoxy-pyrimidin-5-yl)-6-(2-quinolin-2-yl-ethyl)-6,7-dihydro-pyrrolo[3,4-b]pyridin-5-one The title compound was prepared in analogy to the process described in Example 322 but using 2-ethoxypyrimidin-5-ylboronic acid (16.8 mg, 0.1 mmol) dissolved in dioxane (0.35 mL) instead of 3-methylpyridin-4-ylboronic acid (13.7 mg, 0.1 mmol) dissolved in dioxane (0.35 mL). Yield: 2.7 mg, 8%. $^1$H NMR (500 MHz, DMSO/D$_2$O) δ ppm 8.75-8.79 (m, 3 H) 8.29 (d, J=8.24 Hz, 1 H) 7.94 (d, J=7.02 Hz, 1 H) 7.82 (d, J=8.54 Hz, 1 H) 7.68-7.73 (m, 1 H) 7.49-7.57 (m, 3 H) 4.61 (s, 2 H) 4.43 (q, J=7.02 Hz, 2 H) 4.03 (t, J=7.17 Hz, 2 H) 3.31 (t, J=7.17 Hz, 2 H) 1.37 (t, J=7.02 Hz, 3 H); MS (ESI) m/z 412 (M+H)$^+$.

Example 328

4-(2-Methoxy-pyridin-4-yl)-6-(2-quinolin-2-yl-ethyl)-6,7-dihydro-pyrrolo[3,4-b]pyridin-5-one The title compound was prepared in analogy to the process described in Example 322 but using 2-methoxypyridin-4-ylboronic acid (15.3 mg, 0.1 mmol) dissolved in dioxane (0.35 mL) instead of 3-methylpyridin-4-ylboronic acid (13.7 mg, 0.1 mmol) dissolved in dioxane (0.35 mL). Yield: 4.5 mg, 13%. $^1$H NMR (500 MHz, DMSO/D$_2$O) δ ppm 8.78 (d, J=5.19 Hz, 1 H) 8.29 (d, J=8.24 Hz, 1 H) 8.18-8.21 (m, 1 H) 7.94 (d, J=7.93 Hz, 1 H) 7.83 (d, J=8.54 Hz, 1 H) 7.67-7.75 (m, 1 H) 7.54-7.58 (m, 1 H) 7.47-7.52 (m, 2 H) 7.06 (dd, J=5.19, 1.53 Hz, 1 H) 6.94 (s, 1 H) 4.61 (s, 2 H) 4.01 (t, J=7.32 Hz, 2 H) 3.88 (s, 3 H) 3.31 (t, J=7.02 Hz, 2 H); MS (ESI) m/z 397 (M+H)$^+$.

Example 329

4-Pyridin-3-yl-6-(2-quinolin-2-yl-ethyl)-6,7-dihydro-pyrrolo[3,4-b]pyridin-5-one The title compound was prepared in analogy to the process described in Example 322 but using pyridin-3-ylboronic acid (12.2 mg, 0.1 mmol) dissolved in dioxane (0.35 mL) instead of 3-methylpyridin-4-ylboronic acid (13.7 mg, 0.1 mmol) dissolved in dioxane (0.35 mL). Yield: 8.7 mg, 28%. $^1$H NMR (500 MHz, DMSO/D$_2$O) δ ppm 8.78 (d, J=4.88 Hz, 1 H) 8.69 (d, J=1.53 Hz, 1 H) 8.62 (dd, J=4.88, 1.53 Hz, 1 H) 8.29 (d, J=8.24 Hz, 1 H) 7.91-7.97 (m, 2 H) 7.83 (d, J=8.54 Hz, 1 H) 7.68-7.74 (m, 1 H) 7.53-7.59 (m, 1 H) 7.50-7.53 (m, 2 H) 7.47 (dd, J=7.78, 4.73 Hz, 1 H) 4.62 (s, 2 H) 4.02 (t, J=7.17 Hz, 2 H) 3.31 (t, J=7.17 Hz, 2 H); MS (ESI) m/z 367 (M+H)$^+$.

Example 330

6-(2-Quinolin-2-yl-ethyl)-4-thiophen-3-yl-6,7-dihydro-pyrrolo[3,4-b]pyridin-5-one The title compound was prepared in analogy to the process described in Example 322 but using hiophen-3-ylboronic acid (12.8 mg, 0.1 mmol) dissolved in dioxane (0.35 mL) instead of 3-methylpyridin-4-ylboronic acid (13.7 mg, 0.1 mmol) dissolved in dioxane (0.35 mL). Yield: 1.9 mg, 6%. $^1$H NMR (500 MHz, DMSO/D$_2$O) δ ppm 8.67 (d, J=5.49 Hz, 1 H) 8.37 (dd, J=3.05, 1.22 Hz, 1 H) 8.30 (d, J=8.54 Hz, 1 H) 7.94 (d, J=7.63 Hz, 1 H) 7.87 (d, J=8.54 Hz, 1 H) 7.69-7.74 (m, 1 H) 7.50-7.66 (m, 5 H) 4.56 (s, 2 H) 4.05 (t, J=7.17 Hz, 2 H) 3.32 (t, J=7.17 Hz, 2 H); MS (ESI) m/z 371 (M+H)$^+$.

Example 331

4-Furan-3-yl-6-(2-quinolin-2-yl-ethyl)-6,7-dihydro-pyrrolo[3,4-b]pyridin-5-one

The title compound was prepared in analogy to the process described in Example 322 but using furan-3-ylboronic acid (11.1 mg, 0.1 mmol) dissolved in dioxane (0.35 mL) instead of 3-methylpyridin-4-ylboronic acid (13.7 mg, 0.1 mmol) dissolved in dioxane (0.35 mL). Yield: 3.6 mg, 12%. $^1$H NMR (500 MHz, DMSO/D$_2$O) δ ppm 8.88 (s, 1 H) 8.65 (d, J=5.49 Hz, 1 H) 8.30 (d, J=8.24 Hz, 1 H) 7.94 (d, J=8.24 Hz, 1 H) 7.89 (d, J=7.93 Hz, 1 H) 7.78 (t, J=1.68 Hz, 1 H) 7.70-7.74 (m, 1 H) 7.67 (d, J=5.19 Hz, 1H) 7.51-7.58 (m, 2 H) 7.22 (d, J=1.22 Hz, 1 H) 4.55 (s, 2 H) 4.06 (t, J=7.17 Hz, 2 H) 3.33 (t, J=7.17 Hz, 2 H); MS (ESI) m/z 356 (M+H)$^+$.

Example 332

4-(1,5-Dimethyl-1H-pyrazol-4-yl)-6-(2-quinolin-2-yl-ethyl)-6,7-dihydro-pyrrolo[3,4-b]pyridin-5-one The title compound was prepared in analogy to the process described in Example 322 but using 1,5-dimethyl-1H-pyrazol-4-ylboronic acid (13.9 mg, 0.1 mmol) dissolved in dioxane (0.35 mL) instead of 3-methylpyridin-4-ylboronic acid (13.7 mg, 0.1 mmol) dissolved in dioxane (0.35 mL). Yield: 9 mg, 28%. $^1$H NMR (500 MHz, DMSO/D$_2$O) δ ppm 8.62 (d, J=5.19 Hz, 1 H) 8.28 (d, J=8.54 Hz, 1 H) 7.93 (d, J=7.32 Hz, 1 H) 7.84 (d, J=8.24 Hz, 1 H) 7.69-7.73 (m, 1 H) 7.49-7.58 (m, 3 H) 7.28 (d, J=5.19 Hz, 1 H) 4.54 (s, 2 H) 4.02 (t, J=7.02 Hz, 2 H) 3.75 (s, 3 H) 3.30 (t, J=7.02 Hz, 2 H) 2.14 (s, 3 H); MS (ESI) m/z 384 (M+H)$^+$.

Example 333

4-(1-Ethyl-1H-pyrazol-4-yl)-6-(2-quinolin-2-yl-ethyl)-6,7-dihydro-pyrrolo[3,4-b]pyridin-5-one The title compound was prepared in analogy to the process described in Example 322 but using 1-ethyl-1H- pyrazol-4-ylboronic acid (13.9 mg, 0.1 mmol) dissolved in dioxane (0.35 mL) instead of 3-methylpyridin-4-ylboronic acid (13.7 mg, 0.1 mmol) dissolved in dioxane (0.35 mL). Yield: 1.1 mg, 3%. $^1$H NMR (500 MHz, DMSO/D$_2$O) δ ppm 8.82 (s, 1 H) 8.56 (d, J=5.49 Hz, 1 H) 8.28-8.33 (m, 2 H) 7.92 (dd, J=21.97, 8.24 Hz, 2 H) 7.70-7.74 (m, 1 H) 7.67 (d, J=5.19 Hz, 1 H) 7.51-7.58 (m, 2 H) 4.52 (s, 2 H) 4.17 (q, J=7.32 Hz, 2 H) 4.05 (t, J=7.17 Hz, 2 H) 3.32 (t, J=7.17 Hz, 2 H) 1.40 (t, J=7.32 Hz, 3 H); MS (ESI) m/z 384 (M+H)$^+$.

Example 334

4-(2,5-Dimethyl-2H-pyrazol-3-yl)-6-(2-quinolin-2-yl-ethyl)-6,7-dihydro-pyrrolo[3,4-b]pyridin-5-one The title compound was prepared in analogy to the process described in Example 322 but using 1,3-dimethyl-1H-pyrazol-5-ylboronic acid (13.9 mg, 0.1 mmol) dissolved in dioxane (0.35 mL) instead of 3-methylpyridin-4-ylboronic acid (13.7 mg, 0.1 mmol) dissolved in dioxane (0.35 mL). Yield: 3.9 mg, 12%. $^1$H NMR (500 MHz, DMSO/D$_2$O) δ ppm 8.76 (d, J=5.19 Hz, 1 H) 8.27 (d, J=8.54 Hz, 1 H) 7.93 (d, J=7.93 Hz, 1 H) 7.81 (d, J=8.54 Hz, 1 H) 7.67-7.71 (m, 1 H) 7.53-7.58 (m, 1 H) 7.50 (d, J=8.24 Hz, 1 H) 7.37 (d, J=5.19 Hz, 1 H) 6.15 (s, 1 H) 4.64 (s, 2 H) 4.02 (t, J=6.87 Hz, 2 H) 3.30 (t, J=7.02 Hz, 2 H) 3.27 (s, 3 H) 2.15 (s, 3 H); MS (ESI) m/z 384 (M+H)$^+$.

Example 335

4-(3,5-Dimethyl-isoxazol-4-yl)-6-(2-quinolin-2-yl-ethyl)-6,7-dihydro-pyrrolo[3,4-b]pyridin-5-one The title compound was prepared in analogy to the process described in Example 322 but using 3,5-dimethyl-isoxazol-4-ylboronic acid (14.1 mg, 0.1 mmol) dissolved in dioxane (0.35 mL) instead of 3-methylpyridin-4-ylboronic acid (13.7 mg, 0.1 mmol) dissolved in dioxane (0.35 mL). Yield: 3.6 mg, 11%. $^1$H NMR (500 MHz, DMSO/D$_2$O) δ ppm 8.75 (d, J=5.19 Hz, 1 H) 8.27 (d, J=8.54 Hz, 1 H) 7.92 (d, J=7.02 Hz, 1 H) 7.80 (d, J=8.54 Hz, 1 H) 7.67-7.72 (m, 1 H) 7.48-7.57 (m, 2 H) 7.37 (d, J=5.19 Hz, 1 H) 4.63 (d, J=4.88 Hz, 2 H) 3.97-4.06 (m, 2 H) 3.30 (t, J=6.87 Hz, 2 H) 2.10 (s, 3 H) 1.89 (s, 3 H); MS (ESI) m/z 385 (M+H)$^+$.

Example 336

4-(3-Methyl-thiophen-2-yl)-6-(2-quinolin-2-yl-ethyl)-6,7-dihydro-pyrrolo[3,4-b]pyridin-5-one The title compound was prepared in analogy to the process described in Example 322 but using 3-methylthiophen-2-ylboronic acid (14.2 mg, 0.1 mmol) dissolved in dioxane (0.35 mL) instead of 3-methylpyridin-4-ylboronic acid (13.7 mg, 0.1 mmol) dissolved in dioxane (0.35 mL). Yield: 10.2 mg, 37%. $^1$H NMR (500 MHz, DMSO/D$_2$O) δ ppm 8.70 (d, J=5.19 Hz, 1 H) 8.27 (d, J=8.24 Hz, 1 H) 7.92 (d, J=7.93 Hz, 1 H) 7.83 (d, J=8.54 Hz, 1 H) 7.68-7.73 (m, 1 H) 7.53-7.59 (m, 2 H) 7.50 (d, J=8.54 Hz, 1 H) 7.33 (d, J=4.88 Hz, 1 H) 6.96 (d, J=5.19 Hz, 1 H) 4.60 (s, 2 H) 4.01 (t, J=6.87 Hz, 2 H) 3.30 (t, J=7.02 Hz, 2 H) 1.86 (s, 3 H); MS (ESI) m/z 385 (M+H)$^+$.

Example 337

4-(1-Methyl-1H-pyrrol-3-yl)-6-(2-quinolin-2-yl-ethyl)-6,7-dihydro-pyrrolo[3,4-b]pyridin-5-one The title compound was prepared in analogy to the process described in Example 322 but using 1-methyl-3-(4,4,5,5-tetramethyl-1,3,2-dioxaborolan-2-yl)-1H-pyrrole (20.7 mg, 0.1 mmol) dissolved in dioxane (0.35 mL) instead of 3-methylpyridin-4-ylboronic acid (13.7 mg, 0.1 mmol) dissolved in dioxane (0.35 mL). Yield: 3.8 mg, 12%. $^1$H NMR (500 MHz, DMSO/D$_2$O) δ ppm 8.64 (d, J=5.19 Hz, 1 H) 8.28 (d, J=8.24 Hz, 1 H) 7.93 (d, J=7.93 Hz, 1 H) 7.84 (d, J=8.54 Hz, 1 H) 7.67-7.73 (m, 1 H) 7.52-7.58 (m, 1 H) 7.51 (d, J=8.54 Hz, 1 H) 7.30 (d, J=5.19 Hz, 1 H) 6.87-6.93 (m, 1 H) 6.28 (dd, J=3.66, 1.83 Hz, 1 H) 6.06-6.11 (m, 1 H) 4.57 (s, 2 H) 4.02 (t, J=7.02 Hz, 2 H) 3.30 (t, J=7.02 Hz, 2 H) 3.24-3.27 (m, 3 H); MS (ESI) m/z 369 (M+H)$^+$.

Example 338

4-Pyridazin-4-yl-6-(2-quinolin-2-yl-ethyl)-6,7-dihydro-pyrrolo[3,4-b]pyridin-5-one The title compound was prepared in analogy to the process described in Example 322 but using 4-(4,4,5,5-tetramethyl-1,3,2-dioxaborolan-2-yl)pyridazine (20.6 mg, 0.1 mmol) dissolved in dioxane (0.35 mL) instead of 3-methylpyridin-4-ylboronic acid (13.7 mg, 0.1 mmol) dissolved in dioxane (0.35 mL). Yield: 5 mg, 16%. $^1$H NMR (500 MHz, DMSO/D$_2$O) δ ppm 9.30-9.34 (m, 2 H) 8.87 (d, J=5.19 Hz, 1 H) 8.30 (d, J=8.54 Hz, 1 H) 7.94 (d, J=8.24 Hz, 1 H) 7.80-7.85 (m, 2 H) 7.69-7.73 (m, 1 H) 7.62 (d, J=5.19 Hz, 1 H) 7.56 (t, J=7.48 Hz, 1 H) 7.52 (d, J=8.24 Hz, 1 H) 4.66 (s, 2 H) 4.03 (t, J=7.17 Hz, 2 H) 3.32 (t, J=7.17 Hz, 2 H); MS (ESI) m/z 368 (M+H)$^+$.

Example 339

4-(2-Cyclopropyl-pyridin-4-yl)-6-(2-quinolin-2-yl-ethyl)-6,7-dihydro-pyrrolo[3,4-b]pyridin-5-one The title compound was prepared in analogy to the process described in Example 322 but using 2-cyclopropylpyridin-4-ylboronic acid (16.3 mg, 0.1 mmol) dissolved in dioxane (0.35 mL) instead of 3-methylpyridin-4-ylboronic acid (13.7 mg, 0.1 mmol) dissolved in dioxane (0.35 mL). Yield: 3.5 mg, 10%. $^1$H NMR (500 MHz, DMSO/D$_2$O) δ ppm 8.79 (d, J=5.19 Hz, 1 H) 8.40 (d, J=5.19 Hz, 1 H) 8.29 (d, J=8.54 Hz, 1 H) 7.94 (d, J=8.24 Hz, 1 H) 7.81 (d, J=8.54 Hz, 1 H) 7.68-7.73 (m, 1 H) 7.45-7.57 (m, 3 H) 7.28 (s, 1 H) 7.19 (dd, J=5.03, 1.68 Hz, 1 H) 4.63 (s, 2 H) 4.02 (t, J=7.02 Hz, 2 H) 3.30 (t, J=7.02 Hz, 2 H) 2.01-2.07 (m, 1 H) 0.88-1.01 (m, 4 H); MS (ESI) m/z 407 (M+H)$^+$.

Example 340

6-(2-Quinolin-2-yl-ethyl)-4-thiazol-4-yl-6,7-dihydro-pyrrolo[3,4-b]pyridin-5-one The title compound was prepared in analogy to the process described in Example 322 using thiazol-4-ylboronic acid (12.8 mg, 0.1 mmol) dissolved in dioxane (0.35 mL) instead of 3-methylpyridin-4-ylboronic acid (13.7 mg, 0.1 mmol) dissolved in dioxane (0.35 mL). Yield: 3 mg, 9%. $^1$H NMR (500 MHz, DMSO/D$_2$O) δ ppm 9.41 (d, J=1.83 Hz, 1 H) 9.21 (d, J=1.83 Hz, 1 H) 8.77 (d, J=5.19 Hz, 1 H) 8.30 (d, J=8.24 Hz, 1 H) 8.19 (d, J=5.49 Hz, 1 H) 7.94 (d, J=7.93 Hz, 1 H) 7.88 (d, J=8.24 Hz, 1 H) 7.70-7.74 (m, 1 H) 7.53-7.57 (m, 2 H) 4.60 (s, 2 H) 4.09 (t, J=7.17 Hz, 2 H) 3.35 (t, J=7.17 Hz, 2 H); MS (ESI) m/z 373 (M+H)$^+$.

Example 341

4-(2-Dimethylamino-pyrimidin-5-yl)-2-(2-quinolin-2-yl-ethyl)-2,3-dihydro-isoindol-1-one Syntheses were performed using a Personal Chemistry Ermy's optimizer microwave. Each microwave tube was charged with 0.1 eq. of [1,1'-Bis(diphenylphosphino)-ferrocene]dichloropalladium(II), complex with dichloromethane (7 mg). To the microwave tube, a solution of 4-bromo-2-(2-(quinolin-2-yl)ethyl)isoindolin-1-one from Example 130.1 (31 mg, 0.08 mmol) dissolved in dioxane (1.0 mL). was added, followed by 2-(dimethylamino)pyrimidin-5-ylboronic acid (16.7 mg, 0.1 mmol) dissolved in dioxane (0.35 mL). Then, 250 µL of 1M aqueous solution of $Cs_2CO_3$ was added and the resulting mixture was heated in the microwave for 1200 sec at 120° C. The reaction was filtered, checked by LC/MS and concentrated to dryness. The residues were dissolved in 1:1 DMSO/MeOH. Purification by reverse phase HPLC provided 4-(2-(dimethylamino)pyrimidin-5-yl)-2-(2-(quinolin-2-yl)ethyl)isoindolin-1-one (5 mg, 14%). $^1$H NMR (500 MHz, DMSO/$D_2$O) δ ppm 8.61 (s, 2 H) 8.28 (d, J=8.55 Hz, 1 H) 7.92 (dd, J=12.97, 8.09 Hz, 2 H) 7.49-7.75 (m, 6 H) 4.74 (s, 2 H) 4.02 (t, J=7.32 Hz, 2 H) 3.31 (t, J=7.32 Hz, 2 H) 3.20 (s, 6 H); MS (ESI) m/z 410 (M+H)$^+$. MS (APCI) m/z 410 (M+H)$^+$.

Example 342

4-(2-Methyl-thiazol-5-yl)-2-(2-quinolin-2-yl-ethyl)-2,3-dihydro-isoindol-1-one

The title compound was prepared in analogy to the process described in Example 341 but using 2-methyl-5-(4,4,5,5-tetramethyl-1,3,2-dioxaborolan-2-yl)thiazole (22.5 mg, 0.1 mmol) dissolved in dioxane (0.35 mL) instead of 2-(dimethylamino)pyrimidin-5-ylboronic acid (16.7 mg, 0.1 mmol) dissolved in dioxane (0.35 mL). Yield: 6.4 mg, 20%. $^1$H NMR (500 MHz, DMSO/$D_2$O) δ ppm 8.30 (d, J=8.54 Hz, 1 H) 8.01 (s, 1 H) 7.93 (dd, J=13.73, 7.93 Hz, 2 H) 7.81 (d, J=6.71 Hz, 1 H) 7.70-7.76 (m, 1 H) 7.63-7.66 (m, 1 H) 7.50-7.60 (m, 3 H) 4.71 (s, 2 H) 4.07 (t, J=7.17 Hz, 2 H) 3.34 (t, J=7.17 Hz, 2 H) 2.71 (s, 3 H); MS (APCI) m/z 386 (M+H)$^+$.

Example 343

4-(2-Ethoxy-pyrimidin-5-yl)-2-(2-quinolin-2-yl-ethyl)-2,3-dihydro-isoindol-1-one The title compound was prepared in analogy to the process described in Example 341 but using 2-ethoxypyrimidin-5-ylboronic acid (16.8 mg, 0.1 mmol) dissolved in dioxane (0.35 mL) instead of 2-(dimethylamino)pyrimidin-5-ylboronic acid (16.7 mg, 0.1 mmol) dissolved in dioxane (0.35 mL). Yield: 3.2 mg, 9%. $^1$H NMR (500 MHz, DMSO/$D_2$O) δ ppm 8.85 (s, 2 H) 8.28 (d, J=8.24 Hz, 1 H) 7.91 (dd, J=15.41, 8.09 Hz, 2 H) 7.69-7.76 (m, 3 H) 7.63 (t, J=7.48 Hz, 1 H) 7.54-7.59 (m, 1 H) 7.51 (d, J=8.24 Hz, 1 H) 4.76 (s, 2 H) 4.45 (q, J=7.02 Hz, 2 H) 4.02 (t, J=7.32 Hz, 2 H) 3.30 (t, J=7.32 Hz, 2 H) 1.39 (t, J=7.02 Hz, 3 H); MS (ESI) m/z 411 (M+H)$^+$. MS (APCI) m/z 411 (M+H)$^+$.

Example 344

4-(2-Methoxy-pyridin-4-yl)-2-(2-quinolin-2-yl-ethyl)-2,3-dihydro-isoindol-1-one

The title compound was prepared in analogy to the process described in Example 341 but using 2-methoxypyridin-4-ylboronic acid (15.2 mg, 0.1 mmol) dissolved in dioxane (0.35 mL) instead of 2-(dimethylamino)pyrimidin-5-ylboronic acid (16.7 mg, 0.1 mmol) dissolved in dioxane (0.35 mL). Yield: 8.8 mg, 26%. $^1$H NMR (500 MHz, DMSO/$D_2$O) δ ppm 8.24-8.31 (m, 2 H) 7.91 (dd, J=18.31, 7.93 Hz, 2 H) 7.70-7.77 (m, 3 H) 7.61-7.66 (m, 1 H) 7.56 (t, J=7.02 Hz, 1 H) 7.51 (d, J=8.54 Hz, 1 H) 7.19 (dd, J=5.49, 1.53 Hz, 1 H) 7.01 (s, 1 H) 4.72 (s, 2 H) 4.03 (t, J=7.17 Hz, 2 H) 3.92 (s, 3 H) 3.31 (t, J=7.32 Hz, 2 H); MS (ESI) m/z 396 (M+H)$^+$.

Example 345

2-(2-Quinolin-2-yl-ethyl)-4-thiophen-3-yl-2,3-dihydro-isoindol-1-one

The title compound was prepared in analogy to the process described in Example 341 but using thiophen-3-ylboronic acid (12.7 mg, 0.1 mmol) dissolved in dioxane (0.35 mL) instead of 2-(dimethylamino)pyrimidin-5-ylboronic acid (16.7 mg, 0.1 mmol) dissolved in dioxane (0.35 mL). Yield: 15 mg, 48%. $^1$H NMR (500 MHz, DMSO/$D_2$O) δ ppm 8.28 (s, 1 H) 7.41-7.98 (m, 11 H) 4.46-4.81 (m, 2 H) 3.97-4.27 (m, 2 H) 3.13-3.41 (m, 2 H); MS (ESI) m/z 371 (M+H)$^+$.

Example 346

4-Furan-3-yl-2-(2-quinolin-2-yl-ethyl)-2,3-dihydro-isoindol-1-one

The title compound was prepared in analogy to the process described in Example 341 but using furan-3-ylboronic acid (11.1 mg, 0.1 mmol) dissolved in dioxane (0.35 mL) instead of 2-(dimethylamino)pyrimidin-5-ylboronic acid (16.7 mg, 0.1 mmol) dissolved in dioxane (0.35 mL). Yield: 11.8 mg, 39%. $^1$H NMR (500 MHz, DMSO/$D_2$O) δ ppm 8.29 (d, J=8.54 Hz, 1 H) 8.13 (s, 1 H) 7.92 (dd, J=10.38, 8.54 Hz, 2 H) 7.81-7.86 (m, 2 H) 7.68-7.76 (m, 1 H) 7.50-7.59 (m, 4 H) 7.03 (s, 1 H) 4.71 (s, 2 H) 4.06 (t, J=7.32 Hz, 2 H) 3.36 (t, J=7.32 Hz, 2 H); MS (ESI) m/z 355 (M+H)$^+$.

Example 347

4-(1-Ethyl-1H-pyrazol-4-yl)-2-(2-quinolin-2-yl-ethyl)-2,3-dihydro-isoindol-1-one The title compound was prepared in analogy to the process described in Example 341 but using 1-ethyl-1H-pyrazol-4-ylboronic acid (13.9 mg, 0.1 mmol) dissolved in dioxane (0.35 mL) instead of 2-(dimethylamino)pyrimidin-5-ylboronic acid (16.7 mg, 0.1 mmol) dissolved in dioxane (0.35 mL). Yield: 4.8 mg, 15%. $^1$H NMR (500 MHz, DMSO/$D_2$O) δ ppm 8.30 (d, J=8.55 Hz, 1 H) 8.18 (s, 1 H) 7.89-7.97 (m, 3 H) 7.82 (dd, J=6.10, 2.44 Hz, 1 H) 7.69-7.76 (m, 1 H) 7.47-7.60 (m, 4 H) 4.71 (s, 2 H) 4.20 (q, J=7.12 Hz, 2 H) 4.07 (t, J=7.17 Hz, 2 H) 3.36 (t, J=7.32 Hz, 2 H) 1.43 (t, J=7.32 Hz, 3 H); MS (ESI) m/z 383 (M+H)$^+$.

Example 348

4-(2,5-Dimethyl-2H-pyrazol-3-yl)-2-(2-quinolin-2-yl-ethyl)-2,3-dihydro-isoindol-1-one The title compound was prepared in analogy to the process described in Example 341 but using 1,3-dimethyl- 1H-pyrazol-5-ylboronic acid (13.9 mg, 0.1 mmol) dissolved in dioxane (0.35 mL) instead of 2-(dimethylamino)pyrimidin-5-ylboronic acid (16.7 mg, 0.1 mmol) dissolved in dioxane (0.35 mL). Yield: 2.3 mg, 7%.

Example 349

4-(3,5-Dimethyl-isoxazol-4-yl)-2-(2-quinolin-2-yl-ethyl)-2,3-dihydro-isoindol-1-one The title compound was prepared in analogy to the process described in Example 341 but using 3,5-dimethyl-isoxazol-4-ylboronic acid (14.0 mg, 0.1 mmol) dissolved in dioxane (0.35 mL) instead of 2-(dimethylamino)pyrimidin-5-ylboronic acid (16.7 mg, 0.1 mmol) dissolved in dioxane (0.35 mL). Yield: 13.5 mg, 41%. $^1$H NMR (500 MHz, DMSO/D$_2$O) δ ppm 8.28 (d, J=8.54 Hz, 1 H) 7.93 (d, J=7.63 Hz, 1 H) 7.84 (d, J=8.24 Hz, 1 H) 7.68-7.75 (m, 2 H) 7.53-7.59 (m, 2 H) 7.45-7.51 (m, 2 H) 4.24 (s, 2 H) 4.01 (t, J=7.17 Hz, 2 H) 3.30 (t, J=7.02 Hz, 2 H) 2.16 (s, 3 H) 2.00 (s, 3 H); MS (APCI) m/z 384 (M+H)$^+$.

Example 350

4-(5-Methyl-pyrazin-2-yl)-2-(2-quinolin-2-yl-ethyl)-2,3-dihydro-isoindol-1-one

The title compound was prepared in analogy to the process described in Example 341 but using 2-methyl-5-(4,4,5,5-tetramethyl-1,3,2-dioxaborolan-2-yl)pyrazine (22.0 mg, 0.1 mmol) dissolved in dioxane (0.35 mL) instead of 2-(dimethylamino)pyrimidin-5-ylboronic acid (16.7 mg, 0.1 mmol) dissolved in dioxane (0.35 mL). Yield: 3.4 mg, 11%. $^1$H NMR (500 MHz, DMSO/D$_2$O) δ ppm 9.10 (d, J=1.22 Hz, 1 H) 8.58 (s, 1 H) 8.29 (d, J=8.24 Hz, 1 H) 8.21 (d, J=6.71 Hz, 1 H) 7.92 (dd, J=13.28, 8.09 Hz, 2 H) 7.70-7.78 (m, 1 H) 7.62-7.67 (m, 1 H) 7.54-7.61 (m, 2 H) 7.50-7.54 (m, 1 H) 4.87 (s, 2 H) 4.07 (t, J=7.17 Hz, 2 H) 3.33 (t, J=7.17 Hz, 2 H) 2.57 (s, 3 H); MS (APCI) m/z 381 (M+H)$^+$.

Example 351

4-(3-Methyl-thiophen-2-yl)-2-(2-quinolin-2-yl-ethyl)-2,3-dihydro-isoindol-1-one

The title compound was prepared in analogy to the process described in Example 341 but using 3-methylthiophen-2-ylboronic acid (14.1 mg, 0.1 mmol) dissolved in dioxane (0.35 mL) instead of 2-(dimethylamino)pyrimidin-5-ylboronic acid (16.7 mg, 0.1 mmol) dissolved in dioxane (0.35 mL). Yield: 16.3 mg, 50%. $^1$H NMR (500 MHz, DMSO/D$_2$O) δ ppm 8.28 (d, J=8.54 Hz, 1 H) 7.93 (d, J=7.63 Hz, 1 H) 7.86 (d, J=8.54 Hz, 1 H) 7.65-7.75 (m, 2 H) 7.48-7.60 (m, 5 H) 7.04 (d, J=4.88 Hz, 1 H) 4.41 (s, 2 H) 4.02 (t, J=7.02 Hz, 2 H) 3.30 (t, J=7.02 Hz, 2 H) 2.07 (s, 3 H); MS (ESI) m/z 385 (M+H)$^+$.

Example 352

4-(1-Methyl-1H-pyrrol-3-yl)-2-(2-quinolin-2-yl-ethyl)-2,3-dihydro-isoindol-1-one The title compound was prepared in analogy to the process described in Example 341 but using 1-methyl-3-(4,4,5,5-tetramethyl-1,3,2-dioxaborolan-2-yl)-1H-pyrrole (20.7 mg, 0.1 mmol) dissolved in dioxane (0.35 mL) instead of 2-(dimethylamino)pyrimidin-5-ylboronic acid (16.7 mg, 0.1 mmol) dissolved in dioxane (0.35 mL). Yield: 17 mg, 54%. $^1$H NMR (500 MHz, DMSO/D$_2$O) δ ppm 8.28 (d, J=8.54 Hz, 1 H) 7.91 (dd, J=19.07, 8.09 Hz, 2 H) 7.69-7.77 (m, 1 H) 7.48-7.62 (m, 5 H) 6.87-6.92 (m, 1 H) 6.23 (dd, J=3.51, 1.68 Hz, 1 H) 6.11-6.14 (m, 1 H) 4.51 (s, 2 H) 4.02 (t, J=7.17 Hz, 2 H) 3.55 (s, 3 H) 3.30 (t, J=7.17 Hz, 2 H); MS (APCI) m/z 368 (M+H)$^+$.

Example 353

4-Pyridazin-4-yl-2-(2-quinolin-2-yl-ethyl)-2,3-dihydro-isoindol-1-one

The title compound was prepared in analogy to the process described in Example 341 but using 4-(4,4,5,5-tetramethyl-1,3,2-dioxaborolan-2-yl)pyridazine (20.6 mg, 0.1 mmol) dissolved in dioxane (0.35 mL) instead of 2-(dimethylamino)pyrimidin-5-ylboronic acid (16.7 mg, 0.1 mmol) dissolved in dioxane (0.35 mL). Yield: 6.2 mg, 20%. $^1$H NMR (500 MHz, DMSO/D$_2$O) δ ppm 9.50-9.57 (m, 1 H) 9.32-9.37 (m, 1 H) 8.28 (d, J=8.24 Hz, 1 H) 7.86-7.98 (m, 4 H) 7.81 (d, J=6.71 Hz, 1 H) 7.68-7.75 (m, 2 H) 7.49-7.60 (m, 2 H) 4.85 (s, 2 H) 4.04 (t, J=7.32 Hz, 2 H) 3.31 (t, J=7.32 Hz, 2 H); MS (APCI) m/z 367 (M+H)$^+$.

Example 354

4-(2-Cyclopropyl-pyridin-4-yl)-2-(2-quinolin-2-yl-ethyl)-2,3-dihydro-isoindol-1-one The title compound was prepared in analogy to the process described in Example 341 but using 2-cyclopropylpyridin-4-ylboronic acid (16.2 mg, 0.1 mmol) dissolved in dioxane (0.35 mL) instead of 2-(dimethylamino)pyrimidin-5-ylboronic acid (16.7 mg, 0.1 mmol) dissolved in dioxane (0.35 mL). Yield: 14.2 mg, 41%. $^1$H NMR (500 MHz, DMSO/D$_2$O) δ ppm 8.44-8.53 (m, 1 H) 8.29 (d, J=8.54 Hz, 1 H) 7.92 (dd, J=17.09, 7.93 Hz, 2 H) 7.71-7.76 (m, 2 H) 7.61-7.70 (m, 2 H) 7.54-7.59 (m, 1 H) 7.50-7.53 (m, 1 H) 7.45 (s, 1 H) 7.31 (dd, J=5.19, 1.83 Hz, 1 H) 4.71 (s, 2 H) 4.04 (t, J=7.17 Hz, 2 H) 3.31 (t, J=7.32 Hz, 2 H) 2.11-2.24 (m, 1 H) 0.95-1.02 (m, 4 H); MS (ESI) m/z 406 (M+H)$^+$.

Example 355

2-(2-Quinolin-2-yl-ethyl)-4-thiazol-4-yl-2,3-dihydro-isoindol-1-one

The title compound was prepared in analogy to the process described in Example 341 but using thiazol-4-ylboronic acid (12.9 mg, 0.1 mmol) dissolved in dioxane (0.35 mL) instead of 2-(dimethylamino)pyrimidin-5-ylboronic acid (16.7 mg, 0.1 mmol) dissolved in dioxane (0.35 mL). Yield: 4.6 mg, 15%. $^1$H NMR (500 MHz, DMSO/D$_2$O) δ ppm 9.24 (d, J=1.83 Hz, 1 H) 8.29 (d, J=8.24 Hz, 1 H) 8.22 (d, J=1.83 Hz, 1 H) 8.18 (d, J=6.71 Hz, 1 H) 7.89-7.95 (m, 2 H) 7.70-7.75 (m, 1 H) 7.65-7.68 (m, 1 H) 7.50-7.62 (m, 3 H) 4.88 (s, 2 H) 4.08 (t, J=7.32 Hz, 2 H) 3.35 (t, J=7.32 Hz, 2 H); MS (ESI) m/z 372 (M+H)$^+$.

Example 356

4-(6-Methoxy-pyrazin-2-yl)-2-(2-quinolin-2-yl-ethyl)-2,3-dihydro-isoindol-1-one

The title compound was prepared in analogy to the process described in Example 341 but using 2-methoxy-6-

(4,4,5,5-tetramethyl-1,3,2-dioxaborolan-2-yl)pyrazine (23.6 mg, 0.1 mmol) dissolved in dioxane (0.35 mL) instead of 2-(dimethylamino)pyrimidin-5-ylboronic acid (16.7 mg, 0.1 mmol) dissolved in dioxane (0.35 mL). Yield: 3.5 mg, 10%.
$^1$H NMR (500 MHz, DMSO/D$_2$O) δ ppm 8.83 (s, 1 H) 8.23-8.31 (m, 3 H) 7.91 (dd, J=18.16, 7.78 Hz, 2 H) 7.79 (d, J=7.02 Hz, 1 H) 7.70-7.75 (m, 1 H) 7.66 (t, J=7.63 Hz, 1 H) 7.53-7.59 (m, 1 H) 7.51 (d, J=8.54 Hz, 1 H) 4.87 (s, 2 H) 4.06-4.14 (m, 2 H) 3.79 (s, 3 H) 3.33 (t, J=7.02 Hz, 2 H); MS (APCI) m/z 397 (M+H)$^+$.

The compounds of the Examples 357 to 377 can be prepared using the standard operation procedures described above.

| Ex. | IUPAC-Name | physico-chemical data |
|---|---|---|
| 357 | 4-(3-Phenyl-piperidin-1-yl)-2-(2-quinolin-2-yl-ethyl)-2,3-dihydro-isoindol-1-one trifluoroacetate | ESI-MS: 449.20, [M + H$^+$] = 448.20 |
| 358 | 6-(2-Imidazo[1,2-a]pyridin-2-yl-ethyl)-4-pyridin-3-yl-6,7-dihydro-pyrrolo[3,4-b]pyridin-5-one | ESI-MS: 357.10, [M + H$^+$] = 356.10 |
| 359 | 6-[2-(1-Methyl-1H-benzoimidazol-2-yl)-ethyl]-4-(oxetan-3-ylamino)-6,7-dihydro-pyrrolo[3,4-b]pyridin-5-one | ESI-MS: [M + H$^+$] = 364.10 |
| 360 | 6-(2-Imidazo[1,2-a]pyridin-2-yl-ethyl)-4-(oxetan-3-ylamino)-6,7-dihydro-pyrrolo[3,4-b]pyridin-5-one | ESI-MS: 351.10, [M + H$^+$] = 350.10 |
| 361 | 4-(3-Phenoxy-piperidin-1-yl)-2-(2-quinolin-2-yl-ethyl)-2,3-dihydro-isoindol-1-one | ESI-MS: 465.20, [M + H$^+$] = 464.20 |
| 362 | 2-(2-Imidazo[1,2-a]pyridin-2-yl-ethyl)-4-methoxy-7-(oxetan-3-ylamino)-2,3-dihydro-isoindol-1-one | ESI-MS: 380.10, [M + H$^+$] = 379.10 |
| 363 | 4-(4-Dimethylamino-piperidin-1-yl)-6-(2-quinolin-2-yl-ethyl)-6,7-dihydro-pyrrolo[3,4-b]pyridin-5-one hydrochloride | ESI-MS: 417.20, [M + H$^+$] = 416.20 |
| 364 | 6-[2-(1-Methyl-1H-benzoimidazol-2-yl)-ethyl]-4-pyrimidin-5-yl-6,7-dihydro-pyrrolo[3,4-b]pyridin-5-one | ESI-MS: 372.10, [M + H$^+$] = 371.10 |
| 365 | 6-(2-Imidazo[1,2-a]pyridin-2-yl-ethyl)-4-(1H-pyrazol-4-yl)-6,7-dihydro-pyrrolo[3,4-b]pyridin-5-one | ESI-MS: [M + H$^+$] = 345.10 |
| 366 | 1-[5-Oxo-6-(2-quinolin-2-yl-ethyl)-6,7-dihydro-5H-pyrrolo[3,4-b]pyridin-4-yl]-piperidine-4-carboxylic acid | ESI-MS: 418.10, [M + H$^+$] = 417.10 |
| 367 | 6-[2-(1-Methyl-1H-benzoimidazol-2-yl)-ethyl]-4-pyridin-4-yl-6,7-dihydro-pyrrolo[3,4-b]pyridin-5-one | ESI-MS: 371.10, [M + H$^+$] = 370.10 |
| 368 | 6-[2-(1-Methyl-1H-benzoimidazol-2-yl)-ethyl]-4-pyridin-3-yl-6,7-dihydro-pyrrolo[3,4-b]pyridin-5-one | ESI-MS: 371.10, [M + H$^+$] = 370.10 |
| 369 | 6-(2-Imidazo[1,2-a]pyridin-2-yl-ethyl)-4-pyridin-4-yl-6,7-dihydro-pyrrolo[3,4-b]pyridin-5-one | ESI-MS: 357.10, [M + H$^+$] = 356.10 |
| 370 | 4-Methoxy-2-[2-(1-methyl-1H-benzoimidazol-2-yl)-ethyl]-7-pyridin-4-yl-2,3-dihydro-isoindol-1-one | ESI-MS: 400.20, [M + H$^+$] = 399.20 |
| 371 | 4-Methoxy-2-[2-(1-methyl-1H-benzoimidazol-2-yl)-ethyl]-7-morpholin-4-yl-2,3-dihydro-isoindol-1-one | ESI-MS: [M + Na$^+$] = 429.20, 408.20, [M + H$^+$] = 407.20 |
| 372 | 2-(2-Imidazo[1,2-a]pyridin-2-yl-ethyl)-4-methoxy-7-(1H-pyrazol-4-yl)-2,3-dihydro-isoindol-1-one | $^1$H NMR (CDCl$_3$, 500 MHz): δ = 8.24 (s br, 2 H), 8.03 (d, 1 H), 7.58-7.50 (m, 2 H), 7.46 (s, 1 H), 7.14 (m sym, 1 H), 7.00 (d, 1 H), 6.73 (t, 1 H), 4.29 (s, 2 H), 4.13 (q, 1 H), 4.04 (t, 2 H), 3.88 (s, 3 H), 3.20 (t, 2 H) |
| 373 | 2-(2-Imidazo[1,2-a]pyridin-2-yl-ethyl)-4-methoxy-7-(2-methyl-2H-pyrazol-3-yl)-2,3-dihydro-isoindol-1-one | ESI-MS: 389.20, [M + H$^+$] = 388.20 |
| 374 | 2-(2-Imidazo[1,2-a]pyridin-2-yl-ethyl)-4-methoxy-7-pyridin-4-yl-2,3-dihydro-isoindol-1-one | ESI-MS: 386.20, [M + H$^+$] = 385.20 |
| 375 | 6-(2-Benzothiazol-2-yl-ethyl)-4-pyridin-4-yl-6,7-dihydro-pyrrolo[3,4-b]pyridin-5-one | ESI-MS: 374.10, [M + H$^+$] = 373.10 |
| 376 | 6-(2-Benzothiazol-2-yl-ethyl)-4-(oxetan-3-ylamino)-6,7-dihydro-pyrrolo[3,4-b]pyridin-5-one | ESI-MS: [M + Na$^+$] = 389.10, 368.10, [M + H$^+$] = 367.10 |
| 377 | 6-(2-Benzothiazol-2-yl-ethyl)-4-morpholin-4-yl-6,7-dihydro-pyrrolo[3,4-b]pyridin-5-one | ESI-MS: [M + Na$^+$] = 403.10, 382.10, [M + H$^+$] = 381.10 |

Example 378

4-Fluoro-2-(2-imidazo[1,2-a]pyridin-2-yl-ethyl)-7-pyridin-3-yl-2,3-dihydro-isoindol-1-one K$_2$CO$_3$ (98 mg, 0.712 mmol) and Pd(PPh$_3$)$_2$Cl$_2$ (16.66 mg, 0.024 mmol) were each added sequentially rapidly to a suspension of 4-fluoro-2-(2-(imidazo[1,2-a]pyridin-2-yl)ethyl)-7-iodoisoindolin-1-one from Example 280.1 (100.00 mg, 0.237 mmol) and pyridin-3-ylboronic acid (32.1 mg, 0.261 mmol) in DMF (5 ml)/water (1 ml). The reaction was heated in a Biotage microwave at about 120° C. for 20 min. The mixture was purified by Prep-HPLC to give the title compound (70 mg, 0.188 mmol, 79% yield) as white solid.

LC-MS: m/z 373 (M+H)R$_t$=1.74 min./3 min. $^1$H NMR (400 MHz, CDCl$_3$): δ=8.69 (d, J=2.0 Hz, 1H), 8.63 (m, 1H), 8.04 (d, J=6.8 Hz, 1H), 7.90-7.93 (m, 1H), 7.52 (d, J=9.2 Hz, 1H), 7.42 (s, 1H), 7.34-7.38 (m, 2H), 7.24-7.28 (m, 1H), 7.12 (t, J=8.4 Hz, 1H), 6.74 (t, J=6.8 Hz, 1H), 4.43 (s, 2H), 4.03 (t, J=7.0 Hz, 2H), 3.18 (t, J=7.2 Hz, 2H).

Example 379

4-Fluoro-7-(4-fluoro-phenyl)-2-(2-imidazol[1,2-a]pyridin-2-yl-ethyl)-2,3-dihydro-isoindol-1-one The title compound was prepared in analogy to the method described in Example 378. LC-MS: m/z 390 (M+H) RT=2.02 min./3 min. $^1$H NMR (400 MHz, CDCl$_3$): δ=8.03 (d, J=6.8 Hz, 1H), 7.52 (d, J=8.8 Hz, 1H), 7.46~7.5 (m, 2H), 7.41 (s, 1H), 7.29~7.3 (m, 1H), 7.11 (t, J=8.4 Hz, 1H), 7.09~7.15 (m, 3H), 6.74 (t, J=6.8 Hz, 1H), 4.40 (s, 2H), 4.02 (t, J=7.0 Hz, 2H), 3.17 (t, J=7.2 Hz, 2H).

Example 380

4-Fluoro-2-(2-imidazo[1,2-a]pyridin-2-yl-ethyl)-7-(4-methoxy-phenyl)-2,3-dihydro-isoindol-1-one The title compound was prepared in analogy to the method described in Example 378. LC-MS: m/z 402 (M+H); R$_t$=2.01 min./3 min. $^1$H NMR (400 MHz, CDCl$_3$): δ=8.02 (d, J=6.8 Hz, 1H), 7.52 (d, J=9.2 Hz, 1H), 7.46~7.47 (m, 2H), 7.41 (s, 1H), 7.30~7.33 (m, 2H), 7.27 (m, 1H), 7.11~7.21 (m, 2H), 6.96~6.98 (m, 2H), 6.73~6.75 (m, 1H), 4.44 (s, 2H), 4.02 (t, J=7.2 Hz, 2H), 3.86 (s, 3H), 3.17 (t, J=7.2 Hz, 2H).

Example 381

4-Fluoro-2-(2-imidazo[1,2-a]pyridin-2-yl-ethyl)-7-pyrimidin-5-yl-2,3-dihydro-isoindol-1-one The title compound was prepared in analogy to the method described in Example 378. LC-MS: m/z 374 (M+H); R$_t$=1.65 min./3 min. $^1$H NMR (400 MHz, CDCl$_3$): δ=9.23 (s, 1H), 8.88 (s, 2H), 8.05 (d, J=6.8 Hz, 1H), 7.52 (d, J=9.2 Hz, 1H), 7.41 (s, 1H), 7.31~7.35 (m, 2H), 7.15 (t, J=8.4 Hz, 1H), 6.51 (t, J=6.8 Hz, 1H), 4.46 (s, 2H), 4.04 (t, J=7.2 Hz, 2H), 3.19 (t, J=7.2 Hz, 2H).

Example 382

4-Fluoro-2-(2-imidazo[1,2-a]pyridin-2-yl-ethyl)-7-(2-methyl-2H-pyrazol-3-yl)-2,3-dihydro-isoindol-1-one The title compound was prepared in analogy to the method described in Example 378. LC-MS: m/z 376 (M+H) RT=1.88 min./3 min. $^1$H NMR (400 MHz, CDCl$_3$): δ=8.03 (d, J=6.8 Hz, 1H), 7.54 (d, J=1.6 Hz 1H), 7.50 (d, J=10 Hz, 1H), 7.45 (s, 1H), 7.31~7.34 (m, 2H), 7.24 (t, J=8.0 Hz, 1H), 7.12~7.14 (m, 1H), 6.72~6.76 (m, 1H), 6.28 (d, J=1.6 Hz 1H), 4.46 (s, 2H), 4.02 (t, J=7.0 Hz, 2H), 3.65 (s, 3H), 3.18 (t, J=7.2 Hz, 2H).

Example 383

4-Fluoro-2-(2-imidazo[1,2-a]pyridin-2-yl-ethyl)-7-(1H-pyrazol-4-yl)-2,3-dihydro-isoindol-1-one The title compound was prepared in analogy to the method described in Example 378. LC-MS: m/z 362 (M+H); R$_t$=1.69 min./3 min. $^1$H NMR (400 MHz, MeOD): δ=8.23 (d, J=6.8 Hz, 1H), 8.00 (brs, 2H), 7.58 (s, 1H), 7.49~7.52 (m, 1H), 7.35~7.37 (m, 1H), 7.17~7.21 (m, 2H), 6.74~6.78 (m, 1H), 4.36 (s, 2H), 3.89 (t, J=7.0 Hz, 2H), 3.06 (t, J=7.2 Hz, 2H).

The compounds of the Examples 384 to 555 can be prepared using the standard operation procedures described above.

| Ex. | IUPAC name | physico-chemical data |
|---|---|---|
| 384 | 4-[3-(Fluoromethyl)pyrrolidin-1-yl]-6-(2-imidazo[1,2-a]pyridin-2-ylethyl)-7H-pyrrolo[3,4-b]pyridin-5-one | ESI-MS: [M + Na+] = 402.20, [M + H+] = 380.2 |
| 385 | 6-[2-(1,3-Benzothiazol-2-yl)ethyl]-4-[3-(difluoromethyl)pyrrolidin-1-yl]-7H-pyrrolo[3,4-b]pyridin-5-one | ESI-MS: [M + Na+] = 437.10, [M + H+] = 415.10 |
| 386 | 4-[3-(Difluoromethyl)pyrrolidin-1-yl]-6-(2-imidazo[1,2-a]pyridin-2-ylethyl)-7H-pyrrolo[3,4-b]pyridin-5-one | ESI-MS: [M + Na+] = 420.10, [M + H+] = 398.10 |
| 387 | 6-[2-(1,3-Benzothiazol-2-yl)ethyl]-4-[3-(fluoromethyl)pyrrolidin-1-yl]-7H-pyrrolo[3,4-b]pyridin-5-one | ESI-MS: [M + Na+] = 419.00, [M + H+] = 397.10 |
| 388 | 4-(3-Methoxy-4-pyridyl)-2-[2-(2-quinolyl)ethyl]isoindolin-1-one | ESI-MS: [M + Na+] = 418.10, [M + H+] = 396.10 |
| 389 | 4-(3-Methoxy-4-pyridyl)-6-[2-(2-quinolyl)ethyl]-7H-pyrrolo[3,4-b]pyridin-5-one | ESI-MS: [M + K+] = 435.10, [M + Na+] = 419.05, [M + H+] = 397.10 |
| 390 | 6-[2-(1,3-Benzothiazol-2-yl)ethyl]-4-(1,1-dioxo-1,4-thiazinan-4-yl)-7H-pyrrolo[3,4-b]pyridin-5-one trifluoroacetate | ESI-MS: [M + K+] = 467.15, [M + Na+] = 451.10, [M + H+] = 429.05 |
| 391 | 6-[2-(Benzofuran-2-yl)ethyl]-4-(4-pyridyl)-7H-pyrrolo[3,4-b]pyridin-5-one | ESI-MS: [M + K+] = 394.10, [M + Na+] = 378.10, [M + H+] = 356.10 |
| 392 | 6-[2-(7-Methyl-2-quinolyl)ethyl]-4-morpholino-7H-pyrrolo[3,4-b]pyridin-5-one | ESI-MS: [M + Na+] = 411.10, [M + H+] = 389.15 |
| 393 | 6-[2-(Benzothiophen-2-yl)ethyl]-4-(4-pyridyl)-7H-pyrrolo[3,4-b]pyridin-5-one | ESI-MS: [M + K+] = 410.10, [M + Na+] = 394.1, [M + H+] = 372.10 |
| 394 | 6-[2-(7-Methyl-2-quinolyl)ethyl]-4-(4-pyridyl)-7H-pyrrolo[3,4-b]pyridin-5-one trifluoroacetate | ESI-MS: [M + K+] = 419.10, [M + H+] = 381.10 |

| Ex. | IUPAC name | physico-chemical data |
|---|---|---|
| 395 | 6-[2-(Benzothiophen-2-yl)ethyl]-4-morpholino-7H-pyrrolo[3,4-b]pyridin-5-one trifluoroacetate | ESI-MS: [M + K+] = 418.10, [M + Na+] = 402.10, [M + H+] = 380.10 |
| 396 | 2-[2-(1,3-Benzothiazol-2-yl)ethyl]-7-methoxy-4-(4-pyridyl)isoindolin-1-one | ESI-MS: [M + H+] = 402.10 |
| 397 | 6-[2-(Benzofuran-2-yl)ethyl]-4-morpholino-7H-pyrrolo[3,4-b]pyridin-5-one | ESI-MS: [M + H+] = 364.10 |
| 398 | 6-[2-(5-Isopropyl-2-pyridyl)ethyl]-4-(4-pyridyl)-7H-pyrrolo[3,4-b]pyridin-5-one | ESI-MS: [M + H+] = 359.20 |
| 399 | 2-[2-(1,3-Benzothiazol-2-yl)ethyl]-7-methoxy-4-(2-methylpyrazol-3-yl)isoindolin-1-one | ESI-MS: [M + K+] = 443.05, [M + Na+] = 427.10, [M + H+] = 405.10 |
| 400 | 2-[2-(1,3-Benzothiazol-2-yl)ethyl]-7-methoxy-4-(1H-pyrazol-3-yl)isoindolin-1-one | ESI-MS: [M + H+] = 391.10 |
| 401 | 6-[2-(5-Isopropyl-2-pyridyl)ethyl]-4-morpholino-7H-pyrrolo[3,4-b]pyridin-5-one | ESI-MS: [M + H+] = 367.20 |
| 402 | 6-[2-(6-Fluoro-1,3-benzothiazol-2-yl)ethyl]-4-(4-pyridyl)-7H-pyrrolo[3,4-b]pyridin-5-one | ESI-MS: [M + K+] = 429.00, [M + Na+] = 413.05, [M + H+] = 391.10 |
| 403 | 6-[2-(6-Chloro-1,3-benzothiazol-2-yl)ethyl]-4-(4-pyridyl)-7H-pyrrolo[3,4-b]pyridin-5-one | ESI-MS: [M + H+] = 407.10 |
| 404 | 6-[2-(6-Chloro-1,3-benzothiazol-2-yl)ethyl]-4-morpholino-7H-pyrrolo[3,4-b]pyridin-5-one | ESI-MS: [M + Na+] = 437.00, [M + H+] = 415.10 |
| 405 | 6-[2-(6-Fluoro-1,3-benzothiazol-2-yl)ethyl]-4-morpholino-7H-pyrrolo[3,4-b]pyridin-5-one | ESI-MS: [M + Na+] = 421.10, [M + H+] = 399.10 |
| 406 | 6-[2-(6-Methyl-2-quinolyl)ethyl]-4-(4-pyridyl)-7H-pyrrolo[3,4-b]pyridin-5-one | ESI-MS: [M + K+] = 419.05, [M + H+] = 381.10 |
| 407 | 6-[2-(4-Ethylthiazol-2-yl)ethyl]-4-(4-pyridyl)-7H-pyrrolo[3,4-b]pyridin-5-one | ESI-MS: [M + Na+] = 373.10, [M + H+] = 351.10 |
| 408 | 6-[2-(4,5-Dimethylthiazol-2-yl)ethyl]-4-(4-pyridyl)-7H-pyrrolo[3,4-b]pyridin-5-one | ESI-MS: [M + H+] = 351.10 |
| 409 | 6-[2-(3-Methyl-2-pyridyl)ethyl]-4-(4-pyridyl)-7H-pyrrolo[3,4-b]pyridin-5-one | ESI-MS: [M + H+] = 331.10 |
| 410 | 6-[2-(4-Methyl-2-pyridyl)ethyl]-4-(4-pyridyl)-7H-pyrrolo[3,4-b]pyridin-5-one | ESI-MS: [M + H+] = 331.10 |
| 411 | 4-Methoxy-2-[2-(1-methyl-1H-benzoimidazol-2-yl)-ethyl]-7-(oxetan-3-ylamino)-2,3-dihydro-isoindol-1-one | ESI-MS: [M + Na+] = 415.20, 394.20, [M + H+] = 393.20 |
| 412 | 4-(3-Fluoro-pyridin-4-yl)-6-(2-quinolin-2-yl-ethyl)-6,7-dihydro-pyrrolo[3,4-b]pyridin-5-one | ESI-MS: 386.10, [M + H+] = 385.10 |
| 413 | 6-(2-Imidazo[1,2-a]pyridin-2-yl-ethyl)-4-(1H-pyrazol-3-yl)-6,7-dihydro-pyrrolo[3,4-b]pyridin-5-one | ESI-MS: 346.10, [M + H+] = 345.10 |
| 414 | 4-Furan-3-yl-6-(2-imidazo[1,2-a]pyridin-2-yl-ethyl)-6,7-dihydro-pyrrolo[3,4-b]pyridin-5-one | ESI-MS: 346.10, [M + H+] = 345.10 |
| 415 | 6-[2-(1,5-Dimethyl-1H-benzoimidazol-2-yl)-ethyl]-4-morpholin-4-yl-6,7-dihydro-pyrrolo[3,4-b]pyridin-5-one | ESI-MS: 393.20, [M + H+] = 392.20 |
| 416 | 6-[2-(1,5-Dimethyl-1H-benzoimidazol-2-yl)-ethyl]-4-(oxetan-3-ylamino)-6,7-dihydro-pyrrolo[3,4-b]pyridin-5-one | ESI-MS: 379.20, [M + H+] = 378.20 |
| 417 | 6-[2-(1,3-Benzoxazol-2-yl)ethyl]-4-morpholino-7H-pyrrolo[3,4-b]pyridin-5-one | ESI-MS: [M + Na+] = 387.10, 366.10, [M + H+] = 365.10 |
| 418 | 6-[2-(1,3-Benzoxazol-2-yl)ethyl]-4-(4-pyridyl)-7H-pyrrolo[3,4-b]pyridin-5-one | ESI-MS: 358.10, [M + H+] = 357.10 |
| 419 | 6-[2-(1,3-Benzothiazol-2-yl)ethyl]-4-(4-methylpiperazin-1-yl)-7H-pyrrolo[3,4-b]pyridin-5-one | ESI-MS: [M + Na+] = 416.15, 395.15, [M + H+] = 394.15 |
| 420 | 6-[2-(1,3-Benzothiazol-2-yl)ethyl]-4-(2,3-dihydrofuran-4-yl)-7H-pyrrolo[3,4-b]pyridin-5-one trifluoroacetate | ESI-MS: 365.10, [M + H+] = 364.10 |
| 421 | 6-[2-(1,3-Benzothiazol-2-yl)ethyl]-4-(2-fluoro-4-pyridyl)-7H-pyrrolo[3,4-b]pyridin-5-one trifluoroacetate | ESI-MS: 392.10, [M + H+] = 391.10 |
| 422 | 6-[2-(1,3-Benzothiazol-2-yl)ethyl]-4-(3-furyl)-7H-pyrrolo[3,4-b]pyridin-5-one trifluoroacetate | ESI-MS: [M + Na+] = 384.19, 363.10, [M + H+] = 362.10 |
| 423 | 6-(2-Imidazo[2,1-b]thiazol-6-ylethyl)-4-(4-pyridyl)-7H-pyrrolo[3,4-b]pyridin-5-one trifluoroacetate | ESI-MS: 363.10, [M + H+] = 362.10 |

| Ex. | IUPAC name | physico-chemical data |
|---|---|---|
| 424 | 6-[2-(1,3-Benzothiazol-2-yl)ethyl]-4-(2-oxa-7-azaspiro[3.4]octan-7-yl)-7H-pyrrolo[3,4-b]pyridin-5-one | ESI-MS: [M + Na+] = 429.10, 408.15, [M + H+] = 407.10 |
| 425 | 6-(2-Imidazo[2,1-b]thiazol-6-ylethyl)-4-morpholino-7H-pyrrolo[3,4-b]pyridin-5-one | ESI-MS: 371.10, [M + H+] = 370.10 |
| 426 | 4-(1,3,3a,4,6,6a-Hexahydrofuro[3,4-c]pyrrol-5-yl)-6-[2-(1,3-benzothiazol-2-yl)ethyl]-7H-pyrrolo[3,4-b]pyridin-5-one | ESI-MS: [M + Na+] = 429.10, 408.15, [M + H+] = 407.10 |
| 427 | 6-[2-(1,3-Benzothiazol-2-yl)ethyl]-4-(4-piperidyloxy)-7H-pyrrolo[3,4-b]pyridin-5-one trifluoroacetate | ESI-MS: [M + Na+] = 417.10, 396.10, [M + H+] = 395.10 |
| 428 | 2-[2-(1,3-Benzothiazol-2-yl)ethyl]-4-(1H-pyrazol-3-yl)isoindolin-1-one | ESI-MS: [M + H+] = 361.10 |
| 429 | 6-[2-(1,3-Benzothiazol-2-yl)ethyl]-4-(1H-pyrazol-3-yl)-7H-pyrrolo[3,4-b]pyridin-5-one | ESI-MS: 363.10, [M + H+] = 362.10 |
| 430 | 6-[2-(1,3-Benzothiazol-2-yl)ethyl]-4-(3-pyridyl)-7H-pyrrolo[3,4-b]pyridin-5-one trifluoroacetate | ESI-MS: 374.10, [M + H+] = 373.10 |
| 431 | 2-[2-(1,3-Benzothiazol-2-yl)ethyl]-4-(4-pyridyl)isoindolin-1-one | ESI-MS: [M + H+] = 372.10 |
| 432 | 6-[2-(1,3-Benzothiazol-2-yl)ethyl]-4-(2-methylpyrazol-3-yl)-7H-pyrrolo[3,4-b]pyridin-5-one trifluoroacetate | ESI-MS: [M + Na+] = 398.10, 377.10, [M + H+] = 376.10 |
| 433 | 2-[2-(1,3-Benzothiazol-2-yl)ethyl]-4-morpholino-isoindolin-1-one | ESI-MS: [M + H+] = 380.10 |
| 434 | 4[3-(Difluoromethyl)pyrrolidin-1-yl]-6-[2-(2-quinolyl)ethyl]-7H-pyrrolo[3,4-b]pyridin-5-one | ESI-MS: [M + Na+] = 431.20, 410.20, [M + H+] = 409.20 |
| 435 | 4-[3-(Fluoromethyl)pyrrolidin-1-yl]-6-[2-(2-quinolyl)ethyl]-7H-pyrrolo[3,4-b]pyridin-5-one | ESI-MS: [M + Na+] = 413.20, 392.20, [M + H+] = 391.20 |
| 436 | 6-[2-(1,3-Benzothiazol-2-yl)ethyl]-4-thiazol-4-yl-7H-pyrrolo[3,4-b]pyridin-5-one | ESI-MS: 402.00, [M + Na+] = 401.00, 381.05, 380.05, [M + H+] = 379.00 |
| 437 | 4-Fluoro-7-(oxetan-3-ylamino)-2-[2-(2-quinolyl)ethyl]isoindolin-1-one | ESI-MS: 379.15, [M + H+] = 378.20 |
| 438 | 4-fluoro-7-(3-pyridyl)-2-[2-(2-quinolyl)ethyl]isoindolin-1-one | ESI-MS: 385.10, [M + H+] = 384.10 |
| 439 | 4-Fluoro-7-(2-methylpyrazol-3-yl)-2-[2-(2-quinolyl)ethyl]isoindolin-1-one | ESI-MS: 388.10, [M + H+] = 387.10 |
| 440 | 4-Fluoro-7-morpholino-2-[2-(2-quinolyl)ethyl]isoindolin-1-one | ESI-MS: [M + Na+] = 414.10, 393.20, [M + H+] = 392.20 |
| 441 | 4-Fluoro-7-(4-methoxyphenyl)-2-[2-(2-quinolyl)ethyl]isoindolin-1-one | ESI-MS: 414.15, [M + H+] = 413.20 |
| 442 | 4-Fluoro-7-(1H-pyrazol-4-yl)-2-[2-(2-quinolyl)ethyl]isoindolin-1-one trifluoroacetate | ESI-MS: 374.10, [M + H+] = 373.10 |
| 443 | 4-Fluoro-7-pyrimidin-5-yl-2-[2-(2-quinolyl)ethyl]isoindolin-1-one trifluoroacetate | ESI-MS: 386.10, [M + H+] = 385.10 |
| 444 | 4-Fluoro-7-(4-fluorophenyl)-2-[2-(2-quinolyl)ethyl]isoindolin-1-one | ESI-MS: [M + Na+] = 423.10, 402.10, [M + H+] = 401.10 |
| 445 | 6-[2-(1,3-Benzothiazol-2-yl)ethyl]-4-(2-methylpyrimidin-5-yl)-7H-pyrrolo[3,4-b]pyridin-5-one | ESI-MS: [M + Na+] = 410.10, 389.10, [M + H+] = 388.10 |
| 446 | 1-[5-oxo-6-[2-(2-quinolyl)ethyl]-7H-pyrrolo[3,4-b]pyridin-4-yl]azetidine-3-carboxylic acid | ESI-MS: 390.20, [M + H+] = 389.10 |
| 447 | 4-(oxetan-3-yloxy)-6-[2-(2-quinolyl)ethyl]-7H-pyrrolo[3,4-b]pyridin-5-one | ESI-MS: [M + H+] = 362.10 |
| 448 | 2-(2-Imidazo[1,2-a]pyridin-2-yl-ethyl)-7-methoxy-4-pyridin-4-yl-2,3-dihydro-isoindol-1-one trifluoroacetate | ESI-MS: [M + H+] = 385.10 |
| 449 | 2-[2-(1-Difluoromethyl-1H-benzoimidazol-2-yl)-ethyl]-7-morpholin-4-yl-2,3-dihydro-isoindol-1-one trifluoroacetate | ESI-MS: [M + Na+] = 435.10, [M + H+] = 413.10 |
| 450 | 2-[2-(1-Difluoromethyl-1H-benzoimidazol-2-yl)-ethyl]-7-pyridin-4-yl-2,3-dihydro-isoindol-1-one trifluoroacetate | ESI-MS: [M + H+] = 405.10 |
| 451 | 4-Pyridin-4-yl-6-(2-quinolin-2-yl-ethyl)-5,6-dihydro-pyrrolo[3,4-b]pyridin-7-one | ESI-MS: [M + H+] = 367.10 |
| 452 | 6-(2-Imidazo[1,2-a]pyridin-2-yl-ethyl)-4-pyridin-4-yl-5,6-dihydro-pyrrolo[3,4-b]pyridin-7-one | ESI-MS: [M + H+] = 356.10 |
| 453 | 6-(2-Quinolin-2-yl-ethyl)-6,7-dihydro-pyrrolo[3,4-b]pyridin-5-one trifluoroacetate | ESI-MS: [M + Na+] = 312.10, [M + H+] = 290.10 |

-continued

| Ex. | IUPAC name | physico-chemical data |
|---|---|---|
| 454 | 2-(2-Imidazo[1,2-a]pyridin-2-yl-ethyl)-7-methoxy-4-(1H-pyrazol-3-yl)-2,3-dihydro-isoindol-1-one | ESI-MS: [M + H+] = 374.10 |
| 455 | 2-[2-(1H-Imidazo[4,5-b]pyridin-2-yl)-ethyl]-7-pyridin-4-yl-2,3-dihydro-isoindol-1-one | ESI-MS: [M + Na+] = 378.10, [M + H+] = 356.10 |
| 456 | 2-(2-Imidazo[1,2-a]pyridin-2-yl-ethyl)-7-methoxy-4-pyridin-3-yl-2,3-dihydro-isoindol-1-one trifluoroacetate | ESI-MS: [M + H+] = 385.10 |
| 457 | 2-(2-Imidazo[1,2-a]pyridin-2-yl-ethyl)-7-methoxy-4-(4-methoxy-phenyl)-2,3-dihydro-isoindol-1-one trifluoroacetate | ESI-MS: [M + H+] = 414.20 |
| 458 | 4-(4-Methoxy-phenyl)-6-(2-quinolin-2-yl-ethyl)-5,6-dihydro-pyrrolo[3,4-b]pyridin-7-one trifluoroacetate | ESI-MS: [M + H+] = 396.20 |
| 459 | 4-(2-Methyl-2H-pyrazol-3-yl)-6-(2-quinolin-2-yl-ethyl)-5,6-dihydro-pyrrolo[3,4-b]pyridin-7-one trifluoroacetate | ESI-MS: [M + H+] = 370.10 |
| 460 | 6-(2-Imidazo[1,2-a]pyridin-2-yl-ethyl)-4-pyridin-3-yl-5,6-dihydro-pyrrolo[3,4-b]pyridin-7-one trifluoroacetate | ESI-MS: [M + H+] = 356.10 |
| 461 | 6-(2-Imidazo[1,2-a]pyridin-2-yl-ethyl)-4-(4-methoxy-phenyl)-5,6-dihydro-pyrrolo[3,4-b]pyridin-7-one trifluoroacetate | ESI-MS: [M + H+] = 385.10 |
| 462 | 6-(2-Imidazo[1,2-a]pyridin-2-yl-ethyl)-4-(2-methyl-2H-pyrazol-3-yl)-5,6-dihydro-pyrrolo[3,4-b]pyridin-7-one trifluoroacetate | ESI-MS: [M + H+] = 359.10 |
| 463 | 4-Pyridin-3-yl-6-(2-quinolin-2-yl-ethyl)-5,6-dihydro-pyrrolo[3,4-b]pyridin-7-one trifluoroacetate | ESI-MS: [M + H+] = 367.10 |
| 464 | 2-(2-Imidazo[1,2-a]pyridin-2-yl-ethyl)-7-methoxy-4-(2-methyl-2H-pyrazol-3-yl)-2,3-dihydro-isoindol-1-one trifluoroacetate | ESI-MS: [M + H+] = 388.20 |
| 465 | 4-(4-Pyridyl)-6-(2-quinoxalin-2-ylethyl)-7H-pyrrolo[3,4-b]pyridin-5-one | ESI-MS: [M + K+] = 406.10, [M + Na+] = 390.10, [M + H+] = 368.10 |
| 466 | 6-[2-(6-Methyl-2-pyridyl)ethyl]-4-morpholino-7H-pyrrolo[3,4-b]pyridin-5-one | ESI-MS: [M + Na+] = 361.10, [M + H+] = 339.20 |
| 467 | 4-Pyrimidin-5-yl-6-[2-(2-quinolyl)ethyl]-5H-pyrrolo[3,4-b]pyridin-7-one | ESI-MS: [M + H+] = 368.10 |
| 468 | 6-[2-(5-Methyl-2-pyridyl)ethyl]-4-morpholino-7H-pyrrolo[3,4-b]pyridin-5-one hydrochloride | ESI-MS: [M + Na+] = 361.20, [M + H+] = 339.20 |
| 469 | 6-[2-(1-Methylimidazol-2-yl)ethyl]-4-(4-pyridyl)-7H-pyrrolo[3,4-b]pyridin-5-one trifluoroacetate | ESI-MS: [M + H+] = 320.10 |
| 470 | 6-[2-(6-Methyl-2-pyridyl)ethyl]-4-(4-pyridyl)-7H-pyrrolo[3,4-b]pyridin-5-one trifluoroacetate | ESI-MS: [M + H+] = 331.15 |
| 471 | 4-(4-Pyridyl)-6-[2-(2-pyridyl)ethyl]-7H-pyrrolo[3,4-b]pyridin-5-one trifluoroacetate | ESI-MS: [M + H+] = 317.10 |
| 472 | 4-(4-Pyridyl)-6-(2-thieno[3,2-b]pyridin-5-ylethyl)-7H-pyrrolo[3,4-b]pyridin-5-one | ESI-MS: [M + H+] = 373.10 |
| 473 | 6-[2-(3,5-Dimethyl-2-pyridyl)ethyl]-4-(4-pyridyl)-7H-pyrrolo[3,4-b]pyridin-5-one | ESI-MS: [M + H+] = 345.15 |
| 474 | 6-[2-(5,6-Dimethyl-2-pyridyl)ethyl]-4-(4-pyridyl)-7H-pyrrolo[3,4-b]pyridin-5-one trifluoroacetate | ESI-MS: [M + H+] = 345.20 |
| 475 | 2-[2-[4-(3-Pyridyl)-5,7-dihydropyrrolo[3,4-b]pyridin-6-yl]ethyl]imidazo[1,2-a]pyridine trifluoroacetate | ESI-MS: [M + H+] = 342.20 |
| 476 | 6-[2-(5-Methyl-2-pyridyl)ethyl]-4-(3-pyridyl)-7H-pyrrolo[3,4-b]pyridin-5-one trifluoroacetate | ESI-MS: [2M + Na+] = 683.30, [M + H+] = 331.10 |
| 477 | 2-[2-[4-(2-Methylpyrazol-3-yl)-5,7-dihydropyrrolo[3,4-b]pyridin-6-yl]ethyl]imidazo[1,2-a]pyridine trifluoroacetate | ESI-MS: [M + H+] = 345.20 |
| 478 | 2-[2-[4-(4-Methoxyphenyl)-5,7-dihydropyrrolo[3,4-b]pyridin-6-yl]ethyl]imidazo[1,2-a]pyridine trifluoroacetate | ESI-MS: [M + H+] = 371.15 |
| 479 | 4-(1,1-Dioxo-1,4-thiazinan-4-yl)-6-[2-(5-methyl-2-pyridyl)ethyl]-7H-pyrrolo[3,4-b]pyridin-5-one trifluoroacetate | ESI-MS: [M + Na+] = 409.10, [M + H+] = 387.10 |
| 480 | 6-[2-(5-Methyl-2-pyridyl)ethyl]-4-pyrimidin-5-yl-7H-pyrrolo[3,4-b]pyridin-5-one trifluoroacetate | ESI-MS: [M + H+] = 332.10 |

-continued

| Ex. | IUPAC name | physico-chemical data |
|---|---|---|
| 481 | 6-[2-(5-Methyl-2-pyridyl)ethyl]-4-(4-pyridyl)-7H-pyrrolo[3,4-b]pyridin-5-one trifluoroacetate | ESI-MS: [M + K+] = 369.10, [M + H+] = 331.10 |
| 482 | 7-Morpholino-2-(2-quinoxalin-2-ylethyl)isoindolin-1-one | ESI-MS: [M + H+] = 375.10 |
| 483 | 6-[2-(6-Methoxy-2-pyridyl)ethyl]-4-morpholino-7H-pyrrolo[3,4-b]pyridin-5-one | ESI-MS: [M + H+] = 355.10 |
| 484 | 4-(4-Pyridyl)-6-[2-[4-(4-pyridyl)-2-quinolyl]ethyl]-7H-pyrrolo[3,4-b]pyridin-5-one | ESI-MS: [M + H+] = 444.20 |
| 485 | 4-(2,2,3,3,5,5,6,6-Octadeuteriomorpholin-4-yl)-6-[2-(2-quinolyl)ethyl]-7H-pyrrolo[3,4-b]pyridin-5-one | ESI-MS: [M + H+] = 383.20 |
| 486 | 4-Morpholino-6-[2-(5-phenyl-2-pyridyl)ethyl]-7H-pyrrolo[3,4-b]pyridin-5-one | ESI-MS: [M + H+] = 401.20 |
| 487 | 6-[2-(1-Methylimidazol-4-yl)ethyl]-4-(4-pyridyl)-7H-pyrrolo[3,4-b]pyridin-5-one trifluoroacetate | ESI-MS: [M + H+] = 320.10 |
| 488 | 6-[2-(5-Phenyl-2-pyridyl)ethyl]-4-(4-pyridyl)-7H-pyrrolo[3,4-b]pyridin-5-one trifluoroacetate | ESI-MS: [M + H+] = 393.20 |
| 489 | 6-[2-(3,5-Dimethyl-2-pyridyl)ethyl]-4-morpholino-7H-pyrrolo[3,4-b]pyridin-5-one | ESI-MS: [M + H+] = 353.20 |
| 490 | 6-[2-(5-Methyl-2-pyridyl)ethyl]-4-(oxetan-3-ylamino)-7H-pyrrolo[3,4-b]pyridin-5-one | ESI-MS: [M + H+] = 325.10 |
| 491 | 4-Morpholino-6-(2-thieno[3,2-b]pyridin-5-ylethyl)-7H-pyrrolo[3,4-b]pyridin-5-one | ESI-MS: [M + H+] = 381.10 |
| 492 | 6-[2-(6-Fluoroimidazo[1,2-a]pyridin-2-yl)ethyl]-4-morpholino-7H-pyrrolo[3,4-b]pyridin-5-one hydrochloride | ESI-MS: [M + H+] = 382.10 |
| 493 | 6-[2-(6-Fluoroimidazo[1,2-a]pyridin-2-yl)ethyl]-4-morpholino-7H-pyrrolo[3,4-b]pyridin-5-one trifluoroacetate | ESI-MS: [M + H+] = 382.10 |
| 494 | 6-[2-(6-Fluoroimidazo[1,2-a]pyridin-2-yl)ethyl]-4-(4-pyridyl)-7H-pyrrolo[3,4-b]pyridin-5-one trifluoroacetate | ESI-MS: [M + H+] = 374.10 |
| 495 | 4-Morpholino-6-(2-quinoxalin-2-ylethyl)-7H-pyrrolo[3,4-b]pyridin-5-one trifluoroacetate | ESI-MS: [M + H+] = 376.15 |
| 496 | 6-[2-(8-Methylimidazo[1,2-a]pyridin-2-yl)ethyl]-4-(4-pyridyl)-7H-pyrrolo[3,4-b]pyridin-5-one trifluoroacetate | ESI-MS: [M + H+] = 370.15 |
| 497 | 6-[2-(5-Fluoro-2-pyridyl)ethyl]-4-(4-pyridyl)-7H-pyrrolo[3,4-b]pyridin-5-one trifluoroacetate | ESI-MS: [M + H+] = 335.10 |
| 498 | 6-[2-(5-Fluoro-2-pyridyl)ethyl]-4-morpholino-7H-pyrrolo[3,4-b]pyridin-5-one trifluoroacetate | ESI-MS: [M + Na+] = 365.10, [M + H+] = 343.10 |
| 499 | 6-[2-(5-Ethyl-2-pyridyl)ethyl]-4-morpholino-7H-pyrrolo[3,4-b]pyridin-5-one trifluoroacetate | ESI-MS: [M + H+] = 353.2 |
| 500 | 4-Morpholino-6-[2-[5-(trifluoromethyl)-2-pyridyl]ethyl]-7H-pyrrolo[3,4-b]pyridin-5-one trifluoroacetate | ESI-MS: [M + Na+] = 415.10, [M + H+] = 393.10 |
| 501 | 6-[2-(5-Ethyl-2-pyridyl)ethyl]-4-(4-pyridyl)-7H-pyrrolo[3,4-b]pyridin-5-one trifluoroacetate | ESI-MS: [M + H+] = 345.20 |
| 502 | 6-[2-(5-Chloro-2-pyridyl)ethyl]-4-(4-pyridyl)-7H-pyrrolo[3,4-b]pyridin-5-one trifluoroacetate | ESI-MS: [M + H+] = 351.10 |
| 503 | 6-[2-(6-Methoxy-2-pyridyl)ethyl]-4-(3-pyridyl)-7H-pyrrolo[3,4-b]pyridin-5-one trifluoroacetate | ESI-MS: [M + Na+] = 369.10, [M + H+] = 347.10 |
| 504 | 6-[2-(5,6-Dimethyl-2-pyridyl)ethyl]-4-(oxetan-3-ylamino)-7H-pyrrolo[3,4-b]pyridin-5-one trifluoroacetate | ESI-MS: 357.10 (M + 18), [M + H+] = 339.10 |
| 505 | 6-[2-(5-Chloro-2-pyridyl)ethyl]-4-morpholino-7H-pyrrolo[3,4-b]pyridin-5-one | ESI-MS: [M + Na+] = 381.10, [M + H+] = 359.10 |
| 506 | 4-(4-Pyridyl)-6-[2-[5-(trifluoromethyl)-2-pyridyl]ethyl]-7H-pyrrolo[3,4-b]pyridin-5-one trifluoroacetate | ESI-MS: [M + H+] = 385.10 |
| 507 | 6-[2-(4,5-Dimethyl-2-pyridyl)ethyl]-4-(4-pyridyl)-7H-pyrrolo[3,4-b]pyridin-5-one trifluoroacetate | ESI-MS: [M + H+] = 345.10 |

-continued

| Ex. | IUPAC name | physico-chemical data |
|---|---|---|
| 508 | 4-Fluoro-2-(2-imidazo[1,2-a]pyridin-2-ylethyl)-7-(oxetan-3-ylamino)isoindolin-1-one trifluoroacetate | ESI-MS: [M + H+] = 367.10 |
| 509 | 6-[2-(6-Methoxy-2-pyridyl)ethyl]-4-(oxetan-3-ylamino)-7H-pyrrolo[3,4-b]pyridin-5-one | ESI-MS: [M + Na+] = 363.10, [M + H+] = 341.10 |
| 510 | 2,3,7,7-Tetradeuterio-6-[1,1-dideuterio-2-(3,4,5,6,7,8-hexadeuterio-2-quinolyl)ethyl]-4-(2,2,3,3,5,5,6,6-octadeuteriomorpholin-4-yl)pyrrolo[3,4-b]pyridin-5-one | ESI-MS: [M + H+] = 395.20 |
| 511 | 6-(2-Imidazo[1,2-a]pyridin-2-yl-1-methyl-ethyl)-4-morpholino-7H-pyrrolo[3,4-b]pyridin-5-one trifluoroacetate | ESI-MS: [M + H+] = 378.20 |
| 512 | 6-[2-(1,5-Naphthyridin-2-yl)ethyl]-4-(4-pyridyl)-7H-pyrrolo[3,4-b]pyridin-5-one | ESI-MS: [M + H+] = 368.10 |
| 513 | 2,3,7,7-Tetradeuterio-6-[2,2-dideuterio-2-(3,4,5,6,7,8-hexadeuterio-2-quinolyl)ethyl]-4-morpholino-pyrrolo[3,4-b]pyridin-5-one | ESI-MS: [M+] = 386.20 |
| 514 | 4-Morpholino-6-[2-(1,5-naphthyridin-2-yl)ethyl]-7H-pyrrolo[3,4-b]pyridin-5-one | ESI-MS: [M + Na+] = 398.10, [M + H+] = 376.10 |
| 515 | 6-[2-(3-Methoxy-2-pyridyl)ethyl]-4-[2-(3-methoxy-2-pyridyl)ethylamino]-7H-pyrrolo[3,4-b]pyridin-5-one | ESI-MS: [M + H+] = 420.20 |
| 516 | 6-[2-(4-Ethylthiazol-2-yl)ethyl]-4-morpholino-7H-pyrrolo[3,4-b]pyridin-5-one | ESI-MS: [M + H+] = 359.20 |
| 517 | 6-[2-(4-Cyclopropylthiazol-2-yl)ethyl]-4-(4-pyridyl)-7H-pyrrolo[3,4-b]pyridin-5-one | ESI-MS: [M + Na+] = 385.20, [M + H+] = 363.20 |
| 518 | 6-[2-(4-Cyclopropylthiazol-2-yl)ethyl]-4-morpholino-7H-pyrrolo[3,4-b]pyridin-5-one | ESI-MS: [M + H+] = 371.10 |
| 519 | 6-[2-(4,5-Dimethylthiazol-2-yl)ethyl]-4-morpholino-7H-pyrrolo[3,4-b]pyridin-5-one | ESI-MS: [M + Na+] = 381.10, [M + H+] = 359.10 |
| 520 | 6-[2-(4,5-Dimethyl-2-pyridyl)ethyl]-4-morpholino-7H-pyrrolo[3,4-b]pyridin-5-one | ESI-MS: [M + H+] = 353.10 |
| 521 | 6-[2-(4-Methyl-2-pyridyl)ethyl]-4-morpholino-7H-pyrrolo[3,4-b]pyridin-5-one | ESI-MS: [M + H+] = 339.10 |
| 522 | 6-[2-(3-Methyl-2-pyridyl)ethyl]-4-morpholino-7H-pyrrolo[3,4-b]pyridin-5-one | ESI-MS: [M + H+] = 339.20 |
| 523 | 6-(2-Imidazo[1,2-a]pyridin-2-ylethyl)-4-(3-thienyl)-7H-pyrrolo[3,4-b]pyridin-5-one | ESI-MS: [M + H+] = 361.10 |
| 524 | 6-(2-Imidazo[1,2-a]pyridin-2-ylethyl)-4-(2-methyl-3-furyl)-7H-pyrrolo[3,4-b]pyridin-5-one | ESI-MS: [M + H+] = 359.10 |
| 525 | 6-(2-Imidazo[1,2-a]pyridin-2-ylethyl)-4-(5-methyl-2-furyl)-7H-pyrrolo[3,4-b]pyridin-5-one | ESI-MS: [M + H+] = 359.10 |
| 526 | 6-[2-(6-Fluoroimidazo[1,2-a]pyridin-2-yl)ethyl]-4-(3-furyl)-7H-pyrrolo[3,4-b]pyridin-5-one | ESI-MS: [M + H+] = 363.10 |
| 527 | 6-[2-(1,3-Benzothiazol-2-yl)ethyl]-4-(4,4-difluoro-1-piperidyl)-7H-pyrrolo[3,4-b]pyridin-5-one trifluoroacetate | $^1$H NMR (METHANOL-d$_4$, 400 MHz): δ = 8.27 (d, H), 7.93 (d, 1 H), 7.87 (d, 1 H), 7.46-7.49 (m, 1 H), 7.37-7.42 (m, 1 H), 6.85 (d, 1 H), 4.40 (s, 2 H), 4.09 (t, 2 H), 3.48-3.58 (m, 6 H), 2.01-2.11 (m, 4 H) |
| 528 | 4-Methoxy-6-(2-quinolin-2-yl-ethyl)-6,7-dihydro-pyrrolo[3,4-b]pyridin-5-one | |
| 529 | 4-(2-Dimethylamino-ethoxy)-7-pyridin-4-yl-2-(2-quinolin-2-yl-ethyl)-2,3-dihydro-isoindol-1-one | $^1$H NMR (METHANOL-d$_4$, 400 MHz): δ = 8.65 (d, 2 H), 8.58 (d, 1 H), 8.08 (d, 1H), 7.99 (d, 1 H), 7.85-7.90 (m, 3 H), 7.71-7.75 (m, 2 H), 7.62 (d, 1 H), 7.43 (d, 1 H), 4.60-4.67 (m, 4 H), 4.14 (t, 2 H), 3.71-3.74 (t, 1 H), 3.51 (t, 2 H), 3.01-3.06 (m, 6 H) |
| 530 | 4-(4-Hydroxy-piperidin-1-yl)-6-(2-quinolin-2-yl-ethyl)-6,7-dihydro-pyrrolo[3,4-b]pyridin-5-one trifluoroacetate | $^1$H NMR (CHLOROFORM-d, 500 MHz): δ = 9.93-10.06 (m, 1 H), 8.79-8.90 (m, 1 H), 8.67 (d, 1 H), 8.56 (d, 1 H), 8.50 (d, 1 H), 8.03 (d, 1 H), 7.98 (t, 1 H), 7.73-7.86 (m, 2 H), 6.80 (d, 1 H), 5.00 (s. Br, 1 H), 4.57 (s, 2 H), 4.12 (t, 2 |

-continued

| Ex. | IUPAC name | physico-chemical data |
|---|---|---|
| | | H), 3.71 (t, 2 H), 3.41 (m br., 2 H), 3.25 (m br., 2 H), 2.29 (t, 3 H) |
| 531 | 1-[3-Oxo-2-(2-quinolin-2-yl-ethyl)-2,3-dihydro-1H-isoindol-4-ylmethyl]-azetidine-3-carboxylic acid methyl ester | $^1$H NMR (CHLOROFORM-d, 500 MHz): δ = 8.09 (d, 1 H), 8.00 (d, 1 H), 7.79 (d, 1 H), 7.69 (t, 1 H), 7.36-7.52 (m, 4 H), 4.32 (s, 2 H), 4.27 (s br., 1 H), 4.12 (t, 2 H), 3.72 (s, 2 H), 3.53-3.70 (m, 2 H), 3.50 (s br., 1 H), 3.37 (t, 3 H) |
| 532 | 4-(2-Fluoro-ethoxy)-7-pyridin-4-yl-2-(2-quinolin-2-yl-ethyl)-isoindole-1,3-dione | $^1$H NMR (CHLOROFORM-d, 400 MHz): δ = 8.60 (d, 2 H), 8.09 (d, 1 H), 7.90 (d br., 1 H), 7.79 (d, 1 H), 7.63 (t, 1 H), 7.46-7.57 (m, 2 H), 7.31 (t, 2 H), 7.21-7.28 (m, incl. CHCl$_3$), 4.89 (d, 1 H), 4.77 (d, 1 H), 4.53 (m sym., 1 H), 4.47 (m sym., 1 H), 4.14 (t, 2 H), 3.33 (t, 2 H) |
| 533 | 4-(2-Fluoro-ethoxy)-7-pyridin-4-yl-2-(2-quinolin-2-yl-ethyl)-2,3-dihydro-isoindol-1-one | $^1$H NMR (CHLOROFORM-d, 400 MHz): δ = 8.62 (d, 2 H), 8.09 (d, 1 H), 8.01 (d, 1 H), 7.79 (d, 1 H), 7.69 (t, 1 H), 7.50 (m, 1 H), 7.40 (d, 2 H), 7.30-7.40 (m, 2 H), 7.04 (d, 1 H), 4.84 (d, 1 H), 4.71 (d, 1 H), 4.46 (s, 2 H), 4.39 (d, 1 H), 4.32 (d, 1 H), 4.11 (t, 2 H), 3.37 (t, 2 H) |
| 534 | 4-(3-Fluoro-pyridin-4-yl)-6-(2-imidazo[1,2-a]pyridin-2-yl-ethyl)-6,7-dihydro-pyrrolo[3,4-b]pyridin-5-one | $^1$H NMR (CHLOROFORM-d, 500 MHz): δ = 8.77 (d, 1 H), 8.61 (s, 1 H), 8.54 (d, 1 H), 8.03 (d, 1 H), 7.54 (s, 1H), 7.52 (d, 1 H), 7.40-7.43 (m, 2 H), 7.33 (d, 1 H), 7.16 (t, 1 H), 6.75 (t, 1 H), 4.45 (s, 2 H), 4.08 (t, 2 H), 3.20 (t, 2 H) |
| 535 | 6-[2-(1,5-Dimethyl-1H-benzoimidazol-2-yl)-ethyl]-4-pyrimidin-5-yl-6,7-dihydro-pyrrolo[3,4-b]pyridin-5-one | $^1$H NMR (CHLOROFORM-d, 500 MHz): δ = 9.28 (s, 1 H), 8.96 (s, 2 H), 8.80 (d, 1 H), 7.46 (s, 1 H), 7.32 (d, 1 H), 7.18 (d, 1 H), 7.09 (d, 1 H), 4.69 (s, 2 H), 4.18 (t, 2 H), 3.72 (s, 3 H), 3.31 (t, 2 H), 2.46 (s, 3 H) |
| 536 | 6-[2-(1,5-Dimethyl-1H-benzoimidazol-2-yl)-ethyl]-4-pyridin-4-yl-6,7-dihydro-pyrrolo[3,4-b]pyridin-5-one | $^1$H NMR (CHLOROFORM-d, 500 MHz): δ = 8.76 (d, 1 H), 8.70 (d, 2 H), 7.46 (d, 3 H), 7.31 (d, 1 H), 7.18 (d, 1 H), 7.10 (d, 1 H), 4.66 (s, 2 H), 4.16 (t, 2 H), 3.73 (s, 3 H), 3.30 (t, 2 H), 2.46 (s, 3 H) |
| 537 | 2-(2-Imidazo[1,2-a]pyridin-2-ylethyl)-4-thiazol-4-yl-isoindolin-1-one | $^1$H NMR (CHLOROFORM-d, 400 MHz): δ = 8.87 (s, 1 H), 8.04 (d, 1 H), 7.96 (d, 1 H), 7.85 (d, 1 H), 7.50-7.58 (m, 4 H), 7.14 (t, 1 H), 6.73 (t, 1 H), 4.77 (s, 2 H), 4.12 (t, 2 H), 3.27 (t, 2 H) |
| 538 | 6-[2-(1,3-Benzothiazol-2-yl)ethyl]-4-(1H-pyrazol-4-yl)-7H-pyrrolo[3,4-b]pyridin-5-one trifluoroacetate | $^1$H NMR (DMSO-d$_6$, 500 MHz): δ = 8.70 (s, 2 H), 8.61 (d, 2 H), 8.06 (d, 1 H), 7.95 (d, 1 H), 7.77 (d, 1 H), 7.49 (t, 1 H), 7.41 (t, 1 H), 4.56 (s, 2 H), 4.06 (t, 2 H), 3.54 (t, 2 H) |
| 539 | 6-[2-(1,5-Dimethylbenzimidazol-2-yl)ethyl]-4-(3-pyridyl)-7H-pyrrolo[3,4-b]pyridin-5-one | $^1$H NMR (CHLOROFORM-d, 500 MHz): δ = 8.79 (d, 1 H), 8.74 (d, 1 H), 8.68 (dd, 1 H), 7.96 (dt, 1 H), 7.48 (s, 1 H), 7.40 (m sym., 1 H), 7.33 (d, 1 H), 7.18 (d, 1 H), 7.09 (d, 1 H), 4.64 (s, 2 H), 4.16 (t, 2 H), 3.72 (s, 3 H), 3.30 (t, 2 H), 2.46 (s, 3 H) |

-continued

| Ex. | IUPAC name | physico-chemical data |
|---|---|---|
| 540 | 6-[2-(1,5-Dimethylbenzimidazol-2-yl)ethyl]-4-(2-methylpyrazol-3-yl)-7H-pyrrolo[3,4-b]pyridin-5-one | $^1$H NMR (CHLOROFORM-d, 500 MHz): δ = 8.73 (d, 1 H), 7.55 (s, 1 H), 7.43 (s, 1 H), 7.24 (d, 1 H), 7.18 (d, 1 H), 7.09 (d, 1 H), 6.40 (s, 1 H), 4.67 (s, 2 H), 4.14 (t, 2 H), 3.75 (s, 3 H), 3.55 (s, 3 H), 3.31 (t, 2 H), 2.45 (s, 3 H) |
| 541 | 6-[2-(1,3-Benzothiazol-2-yl)ethyl]-4-(4-methoxyphenyl)-7H-pyrrolo[3,4-b]pyridin-5-one trifluoroacetate | $^1$H NMR (DMSO-$d_6$, 500 MHz): δ = 8.70 (d, 1 H), 8.06 (d, 1 H), 7.93 (d, 1 H), 7.61 (d, 2 H), 7.49 (t, 1 H), 7.39-7.45 (m, 2 H), 6.99 (d, 2 H), 4.59 (s, 2 H), 4.02 (t, 2 H), 3.82 (s, 3 H), 3.52 (t, 2 H) |
| 542 | 6-[2-(1,3-Benzothiazol-2-yl)ethyl]-4-(4-fluorophenyl)-7H-pyrrolo[3,4-b]pyridin-5-one trifluoroacetate | $^1$H NMR (DMSO-$d_6$, 500 MHz): δ = 8.75 (d, 1 H), 8.06 (d, 1 H), 7.92 (d, 1 H), 7.65-7.69 (m, 2 H), 7.46-7.50 (m, 2 H), 7.41 (t, 1 H), 4.62 (s, 2 H), 4.03 (t, 2 H), 3.52 (t, 2 H) |
| 543 | 6-[2-(1,3-Benzothiazol-2-yl)ethyl]-4-(3,6-dihydro-2H-pyran-4-yl)-7H-pyrrolo[3,4-b]pyridin-5-one | $^1$H NMR (CHLOROFORM-d, 400 MHz): δ = 8.74 (d, 1H), 7.96 (d, 1H), 7.86 (d, 1H), 7.48 (t, 1H), 7.39 (t, 1H), 7.20 (d, 1H), 6.12 (s, 1H), 4.60 (t, 2H), 4.54 (s, 2H), 4.19 (t, 2H), 3.54 (t, 2H), 2.93 (t, 2H), 1.78 (br. s, 2H) |
| 544 | 6-[2-(1,3-Benzothiazol-2-yl)ethyl]-4-pyrimidin-5-yl-7H-pyrrolo[3,4-b]pyridin-5-one | $^1$H NMR (CHLOROFORM-d, 400 MHz): δ = 9.29 (s, 1H), 9.01 (s, 2H), 8.80 (d, 1H), 7.95 (d, 1H), 7.84 (d, 1H), 7.47 (t, 1H), 7.33-7.38 (m, 2H), 4.55 (s, 2H), 4.20 (t, 2H), 3.54 (t, 2H) |
| 545 | 4-(Fluoromethoxy)-2-(2-imidazo[1,2-a]pyridin-2-ylethyl)-7-pyrimidin-5-yl-isoindoline-1,3-dione | $^1$H NMR (DMSO-$d_6$, 500 MHz): δ = 9.24 (s, 1 H), 8.98 (s, 2 H), 8.45 (d, 1 H), 7.92 (d, 1 H), 7.77 (s, 1 H), 7.74 (d, 1 H), 7.41 (d, 1 H), 7.16 (dd, 1 H), 6.83 (t, 1 H), 6.18 (s, 1 H), 6.07 (s, 1 H), 3.86 (t, 2 H), 2.99 (t, 2 H) |
| 546 | 4-(6-Fluoro-1,4-diazepan-1-yl)-6-[2-(2-quinolyl)ethyl]-7H-pyrrolo[3,4-b]pyridin-5-one | |
| 547 | 4-(4-Pyridyl)-6-[2-(4-quinolyl)ethyl]-7H-pyrrolo[3,4-b]pyridin-5-one trifluoroacetate | $^1$H NMR (METHANOL-$d_4$, 500 MHz): δ = 9.01 (d, 1 H), 8.88 (d, 1 H), 8.77 (d, 2 H), 8.61 (d, 1 H), 8.21 (d, 1 H), 8.11 (t, 1 H), 7.84-8.00 (m, 4 H), 7.58 (d, 1 H), 4.76 (s, 2 H), 4.11 (t, 2 H), 3.80 (t, 2 H) |
| 548 | 4-Morpholino-6-[2-(4-quinolyl)ethyl]-7H-pyrrolo[3,4-b]pyridin-5-one | $^1$H NMR (CHLOROFORM-d, 500 MHz): δ = 8.83 (d, 1H), 8.33 (d, 1H), 8.18-8.23 (m, 2H), 7.77 (t, 1H), 7.65 (t, 1H), 7.35 (d, 1H), 6.66 (d, 1H), 4.33 (s, 2H), 3.90-3.99 (m, 6H), 3.53-3.61 (m, 6H) |
| 549 | 2-(2-Imidazo[1,2-a]pyridin-2-yl-ethyl)-7-methoxy-4-pyrimidin-5-yl-2,3-dihydro-isoindol-1-one trifluoroacetate | $^1$H NMR (CHLOROFORM-d, 500 MHz): δ = 9.27 (s, 1 H), 8.94 (s, 1H), 8.45 (d, 1 H), 8.06 (s, 1 H), 7.96 (d, 1 H), 7.73 (t, 1 H), 7.55 (d, 1 H), 7.26-7.30 (m, 1 H), 7.06 (d, 1H), 4.62 (s, 2 H), 4.13 (t, 2 H), 3.97 (s, 3 H), 3.42 (m, 2H), 0.00 (s, 2 H) |
| 550 | 4-Morpholino-6-[2-(2-pyridyl)ethyl]-7H-pyrrolo[3,4-b]pyridin-5-one | $^1$H NMR (CHLOROFORM-d, 400 MHz): δ = 8.56 (d, 1 H), 8.32 (d, 1 H), 7.59 (td, 1 H), 7.20 (d, 1 H), 7.12-7.15 (m, 1 H), 6.61 (d, 1 H), 4.21 (s, 2 H), 4.00 (t, 3 H), |

-continued

| Ex. | IUPAC name | physico-chemical data |
|---|---|---|
| | | 3.89-3.93 (m, 3 H), 3.55 (dd, 4 H), 3.15 (t, 2H) |
| 551 | 6-[2-(5-Methyl-2-pyridyl)ethyl]-4-morpholino-7H-pyrrolo[3,4-b]pyridin-5-one | $^1$H NMR (CHLOROFORM-d, 400 MHz): δ = 8.37 (d, 1 H), 8.32 (d, 1 H), 7.39 (dd, 1 H), 7.09 (d, 1 H), 6.60 (d, 1 H), 4.19 (s, 2 H), 3.97 (t, 2H), 3.89-3.94 (m, 4 H), 3.53-3.57 (m, 4 H), 3.11 (t, 2 H), 2.30 (s, 3 H) |
| 552 | 6-[2-(7-Ethylimidazo[1,2-a]pyridin-2-yl)ethyl]-4-(4-pyridyl)-7H-pyrrolo[3,4-b]pyridin-5-one | $^1$H NMR (DMSO-$d_6$, 500 MHz): δ = 8.81 (br. s., 1 H), 8.67 (br. s., 2 H), 8.35 (br. s., 1 H), 7.66 (br. s., 1 H), 7.62 (br. s., 2 H), 7.52 (br. s., 1 H), 7.22 (br. s., 1 H), 6.73 (br. s., 1 H), 4.57 (br. s., 2 H), 3.88 (br. s., 2 H), 3.02 (br. s., 2 H), 2.62 (m, 2 H), 1.18-1.22 (m, 3 H) |
| 553 | 6-[2-(6-Methoxy-2-pyridyl)ethyl]-4-(4-pyridyl)-7H-pyrrolo[3,4-b]pyridin-5-one | $^1$H NMR (DMSO-$d_6$, 500 MHz): δ = 8.81 (d, 1H), 8.68 (d, 2 H), 7.58-7.62 (m, 3 H), 7.52 (d, 1 H), 6.89 (d, 1 H), 6.63 (d, 1 H), 4.55 (s, 2 H), 3.91 (t, 2 H), 3.72 (s, 3 H), 3.02 (t, 2 H) |
| 554 | 6-[2-(5,6-Dimethyl-2-pyridyl)ethyl]-4-morpholino-7H-pyrrolo[3,4-b]pyridin-5-one | $^1$H NMR (CHLOROFORM-d, 500 MHz): δ = 8.32 (d, 1 H), 7.30 (d, 1 H), 6.94 (d, 1 H), 6.61 (d, 1 H), 4.20 (s, 2 H), 3.96 (t, 2 H), 3.90-3.94 (m, 4 H), 3.55 (m, 4 H), 3.08 (t, 2 H), 2.46 (s, 3H), 2.24 (s, 3 H) |
| 555 | 6-[2-(7-Ethylimidazo[1,2-a]pyridin-2-yl)ethyl]-4-morpholino-7H-pyrrolo[3,4-b]pyridin-5-one | $^1$H NMR (CHLOROFORM-d, 400 MHz): δ = 8.31 (d, 1 H), 7.91 (d, 1 H), 7.32 (s, 2 H), 6.61 (t, 2 H), 4.24 (s, 2 H), 4.01 (t, 2H), 3.90-3.93 (m, 4 H), 3.54-3.57 (m, 4 H), 3.13 (t, 2 H), 2.68 (q, 2 H), 1.27 (t, 3 H) |

Example 556

7-Morpholino-2-(2-(thieno[3,2-b]pyridin-5-yl)ethyl)isoindolin-1-one

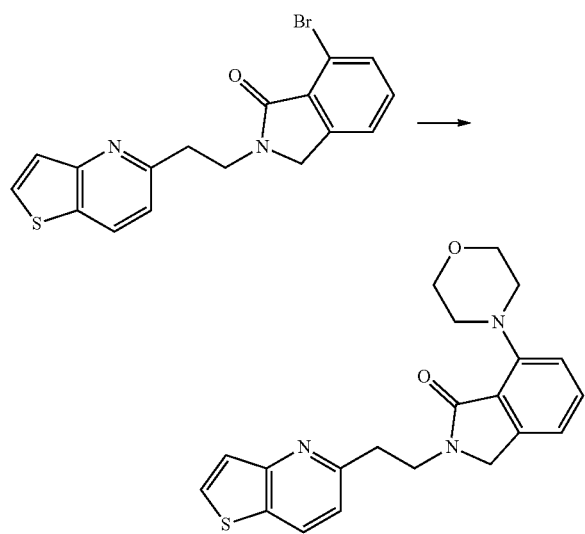

7-Bromo-2-(2-(thieno[3,2-b]pyridin-5-yl)ethyl)isoindolin-1-one (50 mg, 0.134 mmol) was dissolved in DMF (2 ml) in a 10 mL microwave reaction vial. The Pd$_2$(dba)$_3$ (24.53 mg, 0.027 mmol), Cs$_2$CO$_3$ (87 mg, 0.268 mmol), dicyclohexyl-(2',4',6'-triisopropylbiphenyl-2-yl)-phosphine (38.3 mg, 0.080 mmol) and morpholine (0.035 ml, 0.402 mmol) were each added sequentially rapidly to the solution. The suspension was heated in a Biotage microwave at about 110° C. for about 2 h. The resulting mixture was purified via Waters (0-40% MeCN/Water (NH$_4$OAc buffer) over 10 min. to give it as 7-morpholino-2-(2-(thieno[3,2-b]pyridin-5-yl)ethyl)isoindolin-1-one (4 mg, 10.54 μmol, 7.87% yield).

LC-MS: m/z 379.8 (M+H) RT=1.67 min./3 min.

$^1$H NMR (400 MHz, CDCl$_3$): δ=8.38 (d, J=8.4 Hz, 1H), 8.09 (d, J=5.6 Hz, 1H), 7.48 (d, J=4.8 Hz, 1H), 7.42 (t, J=7.6 Hz, 1H), 7.29 (d, J=8.4 Hz, 1H), 7.06 (d, J=7.6 Hz, 1H), 6.85 (d, J=8.4 Hz, 1H), 4.371, (s, 2H), 4.38 (t, J=7.2 Hz, 2H), 3.72 (t, J=4.4 Hz, 4H), 3.16 (t, J=7.2 Hz, 2H), 3.11 (t, J=4.2 Hz, 4H).

Example 557

7-(4-Fluorophenyl)-2-(2-(thieno[3,2-b]pyridin-5-yl)ethyl)isoindolin-1-one

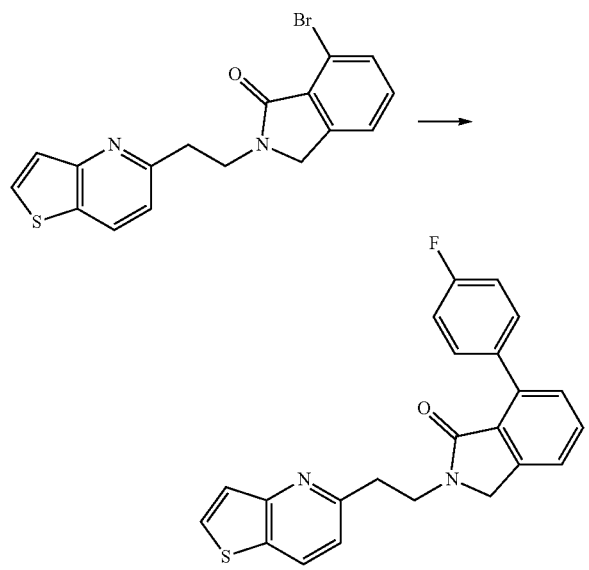

7-Bromo-2-(2-(thieno[3,2-b]pyridin-5-yl)ethyl)isoindolin-1-one (50 mg, 0.134 mmol) was dissolved in toluene (2 mL) and water (0.400 mL) in a 10 mL microwave reaction vial. Pd(PPh$_3$)$_2$Cl$_2$ (28.2 mg, 0.040 mmol) (SCRC), K$_2$CO$_3$ (55.5 mg, 0.404 mmol) and 4-fluorophenylboronic acid (22.5 mg, 0.161 mmol) were each added sequentially rapidly to the solution. The suspension was heated in a Biotage microwave at about 100° C. for about 1 h. The resulting mixture was purified via HPLC: Waters (0-40% MeCN/Water (NH$_4$OAc buffer) over 10 min.; 12 g Redi-Sep C-18 column). The following fractions were collected to give the title compound (23 mg, 0.059 mmol, 44.2% yield).

LC-MS: m/z 388.9 (M+H) RT=1.96 min./3 min.

$^1$H NMR (400 MHz, CDCl$_3$): δ=8.09 (d, J=8.4 Hz, 1H), 7.74 (d, J=5.2 Hz, 1H), 7.51-7.47 (m, 4H), 7.38 (s, 1H), 7.32 (d, J=7.2 Hz, 1H), 7.20 (d, J=8.4 Hz, 1H), 7.11 (d, J=8.8 Hz, 2H), 4.34, (s, 2H), 4.04 (t, J=7.4 Hz, 2H), 3.28 (t, J=7.4 Hz, 2H).

Examples 558-561

The compounds were obtained as the same scheme of example 558. The LCMS and $^1$H NMR data of them are listed behind.

| Ex. | IUPAC name | $^1$H NMR (CDCl$_3$/TMS, 400 MHz) δ; LCMS (ESI+) |
|---|---|---|
| 558 | 7-(4-Methoxyphenyl)-2-(2-thieno[3,2-b]pyridin-5-ylethyl)isoindolin-1-one | LC-MS: m/z 400.9 (M + H) RT = 1.91 min/3 min<br>$^1$H NMR (400 MHz, CDCl$_3$): δ = 8.09 (d, J = 8.4 Hz, 1H), 7.74 (d, J = 5.2 Hz, 1H), 7.50-7.47 (m, 4H), 7.34-7.33 (m, 2H), 7.206 (d, J = 8.4 Hz, 1H), 6.97 (d, J = 8.8 Hz, 1 H), 4.32 (s, 2H), 4.04 (t, J = 7.4 Hz, 2H), 3.85 (s, 3H), 3.29 (t, J = 7.4 Hz, 2H) |
| 559 | 7-Pyrimidin-5-yl-2-(2-thieno[3,2-b]pyridin-5-ylethyl)isoindolin-1-one | LC-MS: m/z 372.9 (M + H) RT = 1.60 min/3 min<br>$^1$H NMR (400 MHz, CDCl$_3$): δ = 9.22 (s, 1H), 8.88 (s, 2H), 8.11 (d, J = 8.4 Hz, 1H), 7.74 (d, J = 5.2 Hz, 1H), 7.62 (t, J = 7.6 Hz, 1H), 7.48 (t, J = 6.4 Hz, 2 H), 7.35 (d, J = 6.4 Hz, 1H), 7.21 (d, J = 8.0 Hz, 1H), 4.40 (s, 2H), 4.07 (t, J = 7.2 Hz, 2H), 3.30 (t, J = 7.2 Hz, 2H) |
| 560 | 7-(1H-Pyrazol-5-yl)-2-(2-thieno[3,2-b]pyridin-5-ylethyl)isoindolin-1-one | LC-MS: m/z 360.8 (M + H) RT = 1.75 min/3 min<br>$^1$H NMR (400 MHz, MeOD): δ = 8.31 (d, J = 8.0 Hz, 1H), 7.95 (t, J = 5.6 Hz, 2H), 7.63 (t, J = 7.8 Hz, 1H), 7.58 (s, 1H), 7.46-7.43 (m, 2H), 6.90 (d, J = 1.6 Hz, 1 H), 4.51 (s, 2H), 4.13 (t, J = 7.0 Hz, 2H), 3.37 (t, J = 7.0 Hz, 2H). |
| 561 | 7-(1H-Pyrazol-4-yl)-2-(2-thieno[3,2-b]pyridin-5-ylethyl)isoindolin-1-one | LC-MS: m/z 361.1 (M + H) RT = 1.48 min/3 min<br>$^1$H NMR (400 MHz, CDCl$_3$): δ = 12.93 (s, 1H), 8.50 (s, 1H), 8.38 (d, J = 8.4 Hz, 1H), 8.09 (d, J = 5.6 Hz, 1H), 8.05 (s, 1H), 7.61 (d, J = 7.6 Hz, 1 H), 7.53-7.49 (m, 2H), 7.37 (d, J = 7.2 Hz, 1H), 7.31 (d, J = 8.4 Hz, 1H), 4.43 (s, 2H), 3.94 (t, J = 7.2 Hz, 2H), 3.21 (t, J = 7.2 Hz, 2H) |

Biological Tests a) Measurement of PDE Activity

The recombinant PDE proteins are used in in vitro enzymatic reaction for measurement of PDE activity. These recombinant proteins, including PDE10A (human, rat and mouse PDE10) and isoforms of PDEs 1, 3, 4, and 5, were purchased from commercial vendor BPS Bioscience. The enzymatic activity of PDEs was determined by cAMP measurement kit from CisBio (IBA) using HTRF technology.

The PDE enzymatic reaction was carried out in assay buffer (20 mM Tris-HCl pH7.5, 10 mM MgCl$_2$, 0.1% bovine serum albumin) containing enzyme and substrate. The PDE enzymes concentration ranged from 10 pM-250 pM, depending on each enzyme's specific activity. The substrate cyclic nucleotide (cAMP or cGMP) concentration used in the assay was 20 nM for PDE10, and 100 nM for other PDEs. The inhibitory effect of compound was determined by incubating various concentration of inhibitor in the enzymatic assay. Typically, compound was serial diluted in DMSO then further diluted in assay buffer. Next, the compound at varying concentration was mixed with PDE enzyme. The reaction was initiated by addition of cyclic nucleotide substrate, and incubated for 60 minutes at 29 C. The reaction was stopped by addition of lysis buffer from assay kit. The cAMP-d2 and anti-cAMP cryptate in the lysis buffer detected the level of cAMP left from the PDE hydrolysis reaction. The PDE activity is reversely correlated with the amount of cAMP left in the reaction and can be converted to the percent activity of an uninhibited control (100%). Thus, IC$_{50}$ value of inhibitor can be obtained by plotting inhibitor concentration against PDE activity at that concentration. The results are shown in Table 1.

TABLE 1

| EXAMPLE | IC$_{50}$[1) |
|---|---|
| 1 | +++ |
| 2 | +++ |
| 3 | +++ |
| 4 | +++ |
| 5 | +++ |
| 6 | ++ |
| 7 | + |
| 8 | + |
| 9 | +++ |
| 10 | +++ |
| 11 | +++ |
| 12 | +++ |
| 13 | +++ |
| 14 | +++ |
| 15 | +++ |
| 16 | +++ |
| 17 | +++ |
| 18 | +++ |
| 19 | +++ |
| 20 | +++ |
| 21 | ++ |
| 22 | +++ |
| 23 | +++ |
| 25 | ++ |
| 27 | ++ |
| 29 | ++ |
| 30 | +++ |
| 31 | + |
| 32 | + |
| 33 | + |
| 34 | ++ |
| 43 | + |
| 45 | ++ |
| 46 | +++ |
| 50 | + |
| 51 | + |
| 53 | ++ |
| 54 | +++ |
| 56 | + |
| 58 | +++ |
| 61 | ++ |
| 64 | +++ |
| 65 | +++ |
| 70 | ++ |
| 72 | + |
| 73 | + |
| 74 | +++ |
| 75 | +++ |
| 77 | +++ |
| 78 | +++ |
| 82 | + |
| 84 | +++ |
| 86 | +++ |
| 88 | + |
| 91 | +++ |
| 93 | + |
| 94 | + |
| 96 | +++ |
| 97 | +++ |
| 98 | + |
| 99 | +++ |
| 101 | + |
| 102 | + |
| 103 | + |
| 104 | +++ |
| 105 | + |
| 106 | + |
| 107 | + |
| 110 | +++ |
| 115 | +++ |
| 116 | +++ |
| 117 | ++ |
| 119 | +++ |
| 120 | + |
| 121 | + |
| 125 | + |
| 126 | + |
| 127 | ++ |

TABLE 1-continued

| EXAMPLE | IC$_{50}$[1) |
|---|---|
| 130 | +++ |
| 131 | + |
| 134 | +++ |
| 135 | +++ |
| 137 | +++ |
| 138 | +++ |
| 141 | + |
| 143 | +++ |
| 145 | + |
| 150 | +++ |
| 153 | +++ |
| 156 | +++ |
| 160 | +++ |
| 161 | +++ |
| 162 | +++ |
| 163 | +++ |
| 165 | +++ |
| 166 | +++ |
| 169 | ++ |
| 170 | +++ |
| 171 | ++ |
| 173 | +++ |
| 175 | ++ |
| 179 | +++ |
| 180 | +++ |
| 181 | +++ |
| 182 | + |
| 183 | +++ |
| 184 | +++ |
| 185 | +++ |
| 186 | ++ |
| 187 | +++ |
| 188 | + |
| 189 | +++ |
| 190 | ++ |
| 193 | ++ |
| 194 | + |
| 195 | +++ |
| 196 | +++ |
| 197 | +++ |
| 200 | +++ |
| 201 | +++ |
| 202 | +++ |
| 203 | +++ |
| 204 | +++ |
| 205 | +++ |
| 208 | +++ |
| 210 | +++ |
| 211 | + |
| 212 | + |
| 214 | ++ |
| 215 | + |
| 216 | +++ |
| 217 | +++ |
| 218 | +++ |
| 221 | +++ |
| 222 | +++ |
| 223 | +++ |
| 225 | +++ |
| 227 | +++ |
| 230 | + |
| 234 | +++ |
| 235 | +++ |
| 236 | + |
| 238 | +++ |
| 239 | ++ |
| 240 | +++ |
| 241 | +++ |
| 242 | ++ |
| 243 | +++ |
| 244 | ++ |
| 245 | +++ |
| 246 | +++ |
| 247 | +++ |
| 248 | +++ |
| 250 | +++ |
| 251 | + |
| 253 | + |

TABLE 1-continued

| EXAMPLE | IC$_{50}$[1] |
|---|---|
| 255 | ++ |
| 256 | +++ |
| 257 | +++ |
| 258 | +++ |
| 260 | +++ |
| 261 | +++ |
| 262 | +++ |
| 263 | +++ |
| 264 | +++ |
| 265 | +++ |
| 266 | +++ |
| 267 | +++ |
| 268 | +++ |
| 270 | +++ |
| 271 | +++ |
| 274 | +++ |
| 275 | +++ |
| 276 | +++ |
| 278 | +++ |
| 279 | + |
| 280 | +++ |
| 281 | +++ |
| 292 | +++ |
| 293 | +++ |
| 294 | + |
| 295 | +++ |
| 296 | +++ |
| 297 | +++ |
| 299 | +++ |
| 300 | +++ |
| 301 | +++ |
| 302 | +++ |
| 303 | ++ |
| 304 | ++ |
| 305 | + |
| 306 | +++ |
| 307 | + |
| 308 | ++ |
| 309 | +++ |
| 310 | +++ |
| 312 | +++ |
| 313 | + |
| 314 | +++ |
| 316 | +++ |
| 317 | + |
| 319 | + |
| 321 | + |
| 322 | +++ |
| 323 | +++ |
| 326 | +++ |
| 329 | +++ |
| 330 | +++ |
| 331 | +++ |
| 332 | +++ |
| 333 | ++ |
| 334 | ++ |
| 335 | + |
| 336 | ++ |
| 337 | ++ |
| 338 | +++ |
| 341 | ++ |
| 342 | +++ |
| 343 | + |
| 344 | ++ |
| 345 | +++ |
| 346 | +++ |
| 347 | ++ |
| 348 | ++ |
| 349 | + |
| 350 | +++ |
| 351 | + |
| 352 | ++ |
| 353 | ++ |
| 354 | + |
| 355 | +++ |
| 356 | + |
| 363 | + |
| 364 | +++ |
| 365 | +++ |
| 366 | ++ |
| 367 | +++ |
| 368 | +++ |
| 369 | +++ |
| 370 | +++ |
| 371 | +++ |
| 372 | +++ |
| 373 | +++ |
| 374 | +++ |
| 375 | +++ |
| 376 | +++ |
| 377 | +++ |
| 378 | +++ |
| 379 | ++ |
| 380 | + |
| 381 | +++ |
| 382 | +++ |
| 383 | +++ |
| 384 | +++ |
| 385 | +++ |
| 386 | +++ |
| 387 | +++ |
| 388 | ++ |
| 389 | ++ |
| 390 | +++ |
| 392 | +++ |
| 394 | +++ |
| 396 | +++ |
| 397 | +++ |
| 397 | + |
| 398 | +++ |
| 399 | +++ |
| 400 | +++ |
| 401 | +++ |
| 402 | +++ |
| 403 | +++ |
| 405 | +++ |
| 406 | +++ |
| 407 | +++ |
| 409 | + |
| 409 | + |
| 411 | +++ |
| 412 | +++ |
| 413 | +++ |
| 414 | +++ |
| 415 | +++ |
| 416 | +++ |
| 417 | ++ |
| 418 | + |
| 421 | +++ |
| 422 | +++ |
| 423 | +++ |
| 424 | +++ |
| 425 | +++ |
| 426 | +++ |
| 428 | +++ |
| 429 | +++ |
| 430 | +++ |
| 431 | ++ |
| 432 | ++ |
| 434 | +++ |
| 435 | +++ |
| 436 | + |
| 437 | +++ |
| 438 | +++ |
| 439 | +++ |
| 440 | +++ |
| 441 | ++ |
| 442 | +++ |
| 443 | +++ |
| 444 | +++ |
| 445 | ++ |
| 446 | ++ |
| 447 | +++ |
| 448 | +++ |
| 449 | + |
| 450 | + |

TABLE 1-continued

| EXAMPLE | IC$_{50}$[1] |
|---|---|
| 451 | +++ |
| 452 | + |
| 454 | ++ |
| 456 | +++ |
| 457 | +++ |
| 458 | +++ |
| 459 | + |
| 461 | ++ |
| 463 | ++ |
| 464 | +++ |
| 465 | +++ |
| 466 | ++ |
| 467 | ++ |
| 472 | +++ |
| 473 | ++ |
| 474 | ++ |
| 479 | + |
| 481 | + |
| 482 | ++ |
| 483 | +++ |
| 484 | +++ |
| 485 | +++ |
| 486 | +++ |
| 488 | + |
| 489 | +++ |
| 491 | +++ |
| 493 | +++ |
| 494 | +++ |
| 495 | +++ |
| 496 | +++ |
| 499 | +++ |
| 501 | ++ |
| 503 | ++ |
| 505 | + |
| 507 | + |
| 510 | +++ |
| 512 | +++ |
| 513 | +++ |
| 514 | +++ |
| 516 | +++ |
| 517 | +++ |
| 518 | +++ |
| 519 | +++ |
| 520 | ++ |
| 521 | + |
| 522 | ++ |
| 523 | +++ |
| 524 | ++ |
| 526 | +++ |
| 527 | +++ |
| 528 | +++ |
| 529 | +++ |
| 530 | +++ |
| 531 | +++ |
| 532 | +++ |
| 533 | +++ |
| 534 | +++ |
| 535 | +++ |
| 536 | +++ |
| 537 | +++ |
| 538 | +++ |
| 539 | +++ |
| 540 | +++ |
| 541 | ++ |
| 542 | ++ |
| 544 | ++ |
| 545 | +++ |
| 549 | +++ |
| 550 | + |
| 551 | +++ |
| 552 | +++ |
| 553 | +++ |
| 554 | +++ |
| 555 | +++ |
| 556 | ++ |
| 559 | +++ |
| 560 | ++ |

[1] +++: IC$_{50}$ < 100 nM ++: 100 nM ≤ IC$_{50}$ ≤ 200 nM +: 200 nM < IC$_{50}$ < 500 nM b) Determination of the Microsomal Half-Life:

The metabolic stability of the compounds of the invention was determined in the following assay.

The test substances were incubated in a concentration of 0.5 μM as follows:

0.5 μM test substance are preincubated together with liver microsomes from different species (from rat, human or other species) (0.25 mg of microsomal protein/10 in 0.05 M potassium phosphate buffer of pH 7.4 in microtiter plates at 37° C. for 5 min. The reaction is started by adding NADPH (1 mg/mL). After 0, 5, 10, 15, 20 and 30 min., 50 μl aliquots are removed, and the reaction is immediately stopped and cooled with the same volume of acetonitrile. The samples are frozen until analyzed. The remaining concentration of undegraded test substance is determined by MSMS. The half-life (T½) is determined from the gradient of the signal of test substance/unit time plot, it being possible to calculate the half-life of the test substance, assuming first order kinetics, from the decrease in the concentration of the compound with time. The microsomal clearance (mCl) is calculated from mCl=ln 2/T½/(content of microsomal protein in mg/ml)×1000 [ml/min/mg] (modified from references: Di, The Society for Biomolecular Screening, 2003, 453-462; Obach, DMD, 1999 vol 27. N 11, 1350-1359). The results are shown in Table 2.

TABLE 2

| Ex. | Rat mCl[2] | Human mCl[2] |
|---|---|---|
| 2 | + | + |
| 3 | + | ++ |
| 4 | ○ | + |
| 7 | + | + |
| 8 | + | ○ |
| 9 | + | ++ |
| 10 | ++ | + |
| 11 | ++ | ++ |
| 12 | + | + |
| 14 | + | + |
| 15 | ○ | + |
| 19 | + | ○ |
| 20 | ++ | ++ |
| 54 | + | + |
| 58 | ++ | ○ |
| 86 | ○ | + |
| 91 | ++ | + |
| 96 | + | + |
| 98 | ++ | + |
| 99 | ++ | + |
| 100 | ++ | + |
| 101 | ○ | ++ |
| 102 | + | ++ |
| 103 | ++ | ++ |
| 104 | ++ | ++ |
| 106 | ++ | + |
| 107 | ++ | ++ |
| 110 | + | ○ |
| 115 | ++ | + |
| 116 | ++ | + |
| 119 | ++ | ++ |
| 120 | + | + |
| 121 | -- | + |
| 122 | + | ++ |
| 128 | + | ○ |
| 129 | ++ | + |

TABLE 2-continued

| Ex. | Rat mCl[2) | Human mCl[2) |
|---|---|---|
| 130 | ○ | + |
| 131 | ++ | ++ |
| 134 | + | ○ |
| 135 | ++ | ++ |
| 137 | ++ | ++ |
| 138 | ++ | ++ |
| 144 | + | ++ |
| 145 | ++ | ++ |
| 146 | + | ○ |
| 147 | + | ○ |
| 153 | ++ | ++ |
| 154 | −○ | ++ |
| 155 | + | ○ |
| 156 | + | ++ |
| 157 | ++ | ○ |
| 159 | + | ○ |
| 160 | ○ | + |
| 161 | ○ | + |
| 162 | ++ | ++ |
| 163 | ++ | ++ |
| 165 | ++ | ++ |
| 166 | ++ | ++ |
| 167 | + | ○ |
| 172 | + | + |
| 174 | + | ++ |
| 175 | ++ | ++ |
| 177 | ++ | ++ |
| 179 | + | ○ |
| 180 | ○ | + |
| 183 | + | + |
| 184 | ++ | + |
| 185 | + | ○ |
| 188 | + | + |
| 189 | + | + |
| 190 | + | + |
| 192 | ○ | ++ |
| 193 | ++ | ++ |
| 194 | + | + |
| 195 | + | ○ |
| 196 | ++ | ○ |
| 197 | ++ | + |
| 200 | ○ | + |
| 202 | ○ | + |
| 210 | ○ | + |
| 213 | ++ | ++ |
| 214 | ++ | ++ |
| 215 | ++ | ++ |
| 216 | ++ | ++ |
| 217 | ++ | ++ |
| 218 | ++ | ++ |
| 220 | ○ | + |
| 223 | ++ | ++ |
| 226 | ++ | ++ |
| 227 | ++ | ++ |
| 228 | + | ○ |
| 229 | ++ | ++ |
| 230 | ++ | ++ |
| 231 | ++ | ++ |
| 232 | ++ | ++ |
| 233 | ++ | ++ |
| 234 | ++ | ++ |
| 235 | ++ | + |
| 236 | + | + |
| 237 | + | + |
| 238 | ++ | + |
| 239 | ++ | ++ |
| 240 | + | ++ |
| 241 | ++ | ++ |
| 242 | + | ++ |
| 244 | ++ | ++ |
| 245 | ++ | ++ |
| 246 | ○ | + |
| 248 | ++ | ++ |
| 249 | ○ | + |
| 250 | ○ | + |
| 253 | ++ | ++ |
| 254 | ++ | ++ |
| 255 | ++ | ++ |

TABLE 2-continued

| Ex. | Rat mCl[2) | Human mCl[2) |
|---|---|---|
| 256 | ++ | ++ |
| 257 | + | + |
| 261 | ○ | ++ |
| 262 | ++ | + |
| 263 | ++ | + |
| 264 | ++ | ++ |
| 265 | + | + |
| 269 | ++ | ++ |
| 270 | ++ | ++ |
| 273 | ++ | ++ |
| 274 | + | + |
| 275 | ++ | ++ |
| 278 | + | + |
| 280 | + | + |
| 294 | ++ | + |
| 295 | ++ | ++ |
| 296 | ++ | ++ |
| 297 | + | + |
| 298 | + | + |
| 300 | + | ○ |
| 306 | ++ | + |
| 308 | ++ | ++ |
| 310 | ++ | ++ |
| 312 | ++ | ++ |
| 313 | ++ | ++ |
| 314 | ++ | ++ |
| 316 | + | ++ |
| 317 | ++ | + |
| 318 | ○ | + |
| 326 | + | + |
| 329 | + | + |
| 332 | ++ | ++ |
| 334 | ++ | ++ |
| 335 | ○ | + |
| 337 | ○ | + |
| 338 | ++ | ++ |
| 343 | ○ | + |
| 353 | + | ++ |
| 358 | ++ | ++ |
| 359 | ++ | ++ |
| 360 | ++ | ++ |
| 362 | ++ | ++ |
| 363 | ++ | ++ |
| 364 | ++ | ++ |
| 365 | + | ++ |
| 366 | ++ | ++ |
| 367 | ++ | ++ |
| 368 | ++ | ++ |
| 369 | ++ | ++ |
| 370 | ++ | ○ |
| 371 | ++ | ○ |
| 372 | ++ | ++ |
| 373 | ++ | ++ |
| 374 | ++ | ++ |
| 375 | ++ | ++ |
| 376 | ++ | ++ |
| 377 | ++ | ++ |
| 378 | ++ | + |
| 379 | ○ | + |
| 380 | ○ | + |
| 381 | ++ | + |
| 382 | ++ | ++ |
| 383 | ++ | ++ |
| 384 | + | ++ |
| 385 | + | + |
| 386 | + | ++ |
| 387 | ○ | + |
| 390 | + | ++ |
| 391 | ++ | ++ |
| 394 | ○ | ++ |
| 396 | + | ++ |
| 397 | + | −− |
| 398 | ○ | + |
| 399 | + | ++ |
| 400 | ○ | ++ |
| 401 | + | ++ |
| 402 | + | + |
| 403 | + | ++ |

TABLE 2-continued

| Ex. | Rat mCl²⁾ | Human mCl²⁾ |
|---|---|---|
| 405 | + | ○ |
| 408 | + | ++ |
| 409 | ++ | ++ |
| 411 | + | ○ |
| 413 | ++ | ++ |
| 414 | ++ | ++ |
| 415 | ++ | ++ |
| 416 | ++ | ++ |
| 417 | ++ | ++ |
| 418 | ++ | ++ |
| 421 | ++ | ○ |
| 422 | + | ++ |
| 424 | ++ | ++ |
| 425 | ++ | ○ |
| 426 | ++ | + |
| 428 | ○ | + |
| 429 | ++ | ++ |
| 430 | ++ | ++ |
| 431 | ○ | ++ |
| 432 | ++ | ++ |
| 436 | ++ | ++ |
| 445 | ++ | ++ |
| 446 | ++ | ++ |
| 447 | + | + |
| 448 | ++ | ++ |
| 449 | + | + |
| 450 | + | ○ |
| 451 | + | ++ |
| 452 | ++ | ++ |
| 454 | ++ | ++ |
| 456 | + | ++ |
| 457 | + | + |
| 459 | ++ | ++ |
| 461 | ○ | ++ |
| 463 | ++ | ++ |
| 464 | ++ | ++ |
| 465 | ++ | ++ |
| 466 | ○ | ++ |
| 467 | ++ | ++ |
| 472 | + | + |
| 473 | + | + |
| 474 | + | + |
| 479 | ++ | ++ |
| 481 | ++ | ++ |
| 482 | ++ | ++ |
| 483 | ++ | ++ |
| 485 | + | + |
| 486 | ○ | + |
| 488 | ○ | + |
| 489 | + | + |
| 491 | + | + |
| 493 | ++ | ++ |
| 494 | ++ | ++ |
| 495 | ++ | ++ |
| 496 | ++ | ++ |
| 501 | + | ++ |
| 503 | + | + |
| 505 | ++ | ++ |
| 507 | ○ | + |
| 510 | ○ | + |
| 512 | ++ | ++ |
| 513 | ○ | + |
| 514 | ++ | ++ |
| 516 | + | ++ |
| 518 | + | ++ |
| 519 | ○ | ++ |
| 520 | + | ++ |
| 521 | ++ | ++ |
| 522 | ++ | ++ |
| 524 | ○ | + |
| 526 | + | ++ |
| 528 | ++ | ++ |
| 529 | ++ | ++ |
| 530 | + | ++ |
| 531 | ++ | ++ |
| 534 | ++ | ++ |
| 535 | ++ | ++ |
| 536 | ++ | + |
| 537 | + | ++ |
| 538 | + | ++ |
| 539 | ++ | ++ |
| 540 | ++ | ++ |
| 541 | + | ++ |
| 542 | + | ++ |
| 544 | ++ | ++ |
| 545 | ++ | ++ |
| 549 | ++ | ++ |
| 550 | ++ | ++ |
| 551 | ++ | ++ |
| 552 | + | ++ |
| 553 | + | + |
| 554 | + | + |
| 555 | ++ | + |
| 556 | + | + |
| 559 | + | ○ |

Ex. Example
mCl mikrosomal clearance
²⁾++: 100 µl min⁻¹ mg⁻¹ +: 100-220 µl min⁻¹ mg⁻¹ ○ not avialable or >220 µl min⁻¹ mg⁻¹

We claim:

1. A compound of formula (I)

wherein
$X^1$ is N;
$X^2$ is N or C—$R^2$;
$X^3$ is N or C—$R^3$;
$X^4$ is N or C—$R^4$;
provided that 1 or 2 of the moieties $X^1$, $X^2$, $X^3$ or $X^4$ is N;
A is selected from the group consisting of O, S, S(=O), S(=O)$_2$, NR$^{5a}$ and CR$^5$R$^6$;
Het is
  i. monocyclic hetaryl having 1 or 2 nitrogen atoms and optionally a further heteroatom selected from the group consisting of O, S and N as ring members, which is unsubstituted or may carry 1, 2, 3 or 4 identical or different substituents $R^x$,
  ii. fused bicyclic hetaryl having 1 or 2 nitrogen atoms and optionally a further heteroatom selected from the group consisting of O, S and N as ring members, benzothienyl or benzofuryl, where bicyclic hetaryl, benzothienyl and benzofuryl are, independently of each other, unsubstituted or may carry 1, 2, 3 or 4 identical or different substituents $R^x$, or
  iii. phenyl, which carries a monocyclic hetaryl radical having 1 or 2 nitrogen atoms and optionally a further heteroatom selected from the group consisting of O, S and N as ring members, which in addition to monocyclic hetaryl, may carry 1, 2 or 3 identical or different substituents $R^x$,
where
  $R^x$ is selected from the group consisting of H, halogen, $C_1$-$C_4$-alkyl, $C_1$-$C_4$-alkoxy, $C_1$-$C_4$-fluoroalkyl, $C_1$-$C_4$-fluoroalkoxy, $C_3$-$C_6$-cycloalkyl, $C_1$-$C_4$-alkoxy-$C_1$-$C_4$-alkoxy, $C_1$-$C_4$-alkoxy-$C_1$-$C_4$-alkyl, OH, hydroxy-$C_1$-$C_4$-alkyl, O—$C_3$-$C_6$-cycloalkyl, benzyloxy, C(O)O—($C_1$-$C_4$-alkyl), O—(C$_1$-C$_4$-alkyl)-CO$_2$H, N(R$^{x1}$)(R$^{x2}$), C(O)N(R$^{x1}$)(R$^{x2}$), C$_1$-C$_4$-alkyl-N(R$^{x1}$)(R$^{x2}$), —NR$^{x3}$—C(O)—N(R$^{x1}$)(R$^{x2}$), NR$^{x3}$—C(O)O—(C$_1$-C$_4$-alkyl), —N(R$^{x3}$)—SO$_2$—R$^{x4}$, phenyl, CN, —SF$_5$, —OSF$_5$, —SO$_2$R$^{x4}$, —SR$^{x4}$ and trimethylsilyl, where R$^{x1}$, R$^{x2}$, R$^{x3}$ and R$^{x4}$, independently of each other are selected from the group consisting of hydrogen, C$_1$-C$_4$-alkyl, C$_1$-C$_4$-fluoroalkyl and C$_3$-C$_6$-cycloalkyl or R$^{x1}$ and R$^{x2}$ form together with the N atom to which they are attached a 3- to 7-membered, nitrogen heterocycle which may have 1, 2 or 3 further different or identical heteroatoms or heteroatom containing groups selected from the group consisting of O, N, S, SO and SO$_2$ as ring members and which may carry 1, 2, 3, 4, 5 or 6 C$_1$-C$_4$-alkyl substituents;

R$^4$ is Y-Cyc;

R$^2$, R$^3$ independently of each other, are selected from the group consisting of hydrogen, halogen, OH, C$_1$-C$_4$-alkyl, trimethylsilyl, C$_1$-C$_4$-alkoxy-C$_1$-C$_4$-alkyl, C$_1$-C$_4$-alkoxy-C$_1$-C$_4$-alkoxy, C$_2$-C$_4$-alkenyloxy, C$_1$-C$_4$-fluoroalkyl, C$_1$-C$_4$-fluoroalkoxy, cyclopropyl, optionally substituted by 1, 2 or 3 methyl groups, fluorinated cyclopropyl, CN, NR$^{x1}$R$^{x2}$ and the moiety Y-Cyc;

provided that one or two or the radicals R$^2$, R$^3$, R$^4$ are Y-Cyc;

R$^5$, R$^6$ independently of each other, are selected from the group consisting of hydrogen, OH, halogen, C$_1$-C$_4$-alkyl, trimethylsilyl, C$_1$-C$_4$-fluoroalkyl, C$_1$-C$_4$-fluoroalkoxy, C$_3$-C$_6$-cycloalkyl, optionally substituted by 1, 2 or 3 methyl groups, and fluorinated C$_3$-C$_6$-cycloalkyl or the radicals R$^5$, R$^6$ together with the carbon atom to which they are bound form a carbonyl group or a saturated 3- to 6-membered carbocycle or a saturated 3- to 6-membered heterocycle having 1 or 2 non-adjacent heteroatoms as ring members, where the carbocycle and the heterocycle are unsubstituted or may carry 1, 2, 3 or 4 substituents selected from the group consisting of fluorine and methyl;

R$^{5a}$ is selected from the group consisting of from C$_1$-C$_4$-alkyl, C$_1$-C$_4$-alkoxy, C$_1$-C$_4$-fluoroalkyl, C$_1$-C$_4$-fluoroalkoxy, C$_3$-C$_6$-cycloalkyl, optionally substituted by 1, 2 or 3 methyl groups, fluorinated C$_3$-C$_6$-cycloalkyl, phenyl, benzyl, 5- or 6-membered hetaryl having 1, 2 or 3 heteroatoms selected from the group consisting of O, S and N as ring members, and 5- or 6-membered hetarylmethyl having 1, 2 or 3 heteroatoms selected from the group consisting of O, S and N as ring members, where the rings in the last four mentioned radicals are unsubstituted or carry 1, 2, 3 or 4 substituents selected from the group consisting of fluorine, C$_1$-C$_4$-alkyl, C$_1$-C$_4$-fluoroalkyl, C$_1$-C$_4$-alkoxy and C$_1$-C$_4$-fluoroalkoxy;

R$^7$, R$^8$, R$^9$, R$^{10}$ independently of each other are selected from the group consisting of hydrogen, halogen, C$_1$-C$_4$-alkyl, trimethylsilyl, C$_1$-C$_4$-fluoroalkyl, C$_1$-C$_4$-fluoroalkoxy, and C$_3$-C$_6$-cycloalkyl, or the radicals together with the carbon atoms to which they are bound form a saturated 3- to 6-membered carbocycle or a saturated 3- to 6-membered heterocycle having 1 or 2 non-adjacent heteroatoms as ring members, where the carbocycle and the heterocycle are unsubstituted or may carry 1, 2, 3 or 4 substituents selected from the group consisting of fluorine and methyl or either the radicals R$^7$, R$^8$ or the radicals R$^9$, R$^{10}$ together with the carbon atom to which they are bound form a saturated 3- to 6-membered carbocycle or a saturated 3- to 6-membered heterocycle having 1 or 2 non-adjacent heteroatoms as ring members, where the carbocycle and the heterocycle are unsubstituted or may carry 1, 2, 3 or 4 substituents selected from the group consisting of fluorine and methyl;

Y is a chemical bond, CH$_2$, O, O—CH$_2$, NR$^y$, NR$^y$—CH$_2$, NR$^y$—S(O)$_2$, S, S(O), S(O)$_2$, 1,2-ethandiyl, 1,2-ethendiyl or 1,2-ethyndiyl, where R$^y$ is selected from the group consisting of hydrogen, C$_1$-C$_4$-alkyl, C$_1$-C$_4$-alkylcarbonyl, C$_1$-C$_4$-alkylsulfonyl, C$_1$-C$_4$-fluoroalkylsulfonyl;

Cyc is a radical selected from the group consisting of phenyl, naphthyl, 4- to 8-membered saturated or partially unsaturated monocarbocyclic radicals, 7- to 10-membered saturated or partially unsaturated bicarbocyclic radicals, 4- to 8-membered saturated or partially unsaturated heteromonocyclic radicals, saturated or partially unsaturated 7- to 10 membered heterobicyclic radicals, 5- or 6-membered monocyclic hetaryl, and 8- to 10 membered bicyclic hetaryl, where the saturated or partially unsaturated heteromonocyclic and heterobicyclic radicals have 1, 2, 3 or 4 heteroatoms or heteroatom containing groups as ring members, which are selected from group consisting of O, S, SO, SO$_2$ and N, and where the 5- or 6-membered monocyclic hetaryl and the 8- to 10-membered bicyclic hetaryl have 1, 2, 3 or 4 heteroatoms as ring members, which are selected from the group consisting of O, S and N, where phenyl, naphthyl, the saturated or partially unsaturated mono- and bicarbocyclic radicals, the heteromonocyclic and heterobicyclic radicals and the mono and bicyclic heteroaromatic radicals are unsubstituted or carry 1, 2, 3, 4 or 5 radicals R$^{C1}$ or one radical Y'—R$^{C2}$ and 0, 1, 2, 3 or 4 radicals R$^{C1}$; where R$^{C1}$ is selected from the group consisting of hydrogen, halogen, OH, CN, NO$_2$, C$_1$-C$_4$-alkyl, C$_1$-C$_4$-alkoxy, C$_1$-C$_4$-alkylsulfanyl, hydroxy-C$_1$-C$_4$-alkyl, C$_1$-C$_4$-alkoxy-C$_1$-C$_4$-alkyl, C$_1$-C$_4$-alkoxy-C$_1$-C$_4$-alkoxy, cyano-C$_1$-C$_4$-alkyl, C$_1$-C$_4$-fluoroalkyl, C$_1$-C$_4$-fluoroalkoxy, C$_1$-C$_4$-alkylsulfonyl, C(O)R$^a$, Z—C(O)OR$^b$, Z—C(O)NR$^c$R$^d$, S(O)$_2$NR$^c$R$^d$ and Z—NR$^e$R$^f$, where R$^a$ is selected from the group consisting of C$_1$-C$_4$-alkyl and C$_1$-C$_4$-fluoroalkyl, R$^b$ is selected from the group consisting of hydrogen, C$_1$-C$_4$-alkyl, C$_2$-C$_4$-alkenyl and C$_1$-C$_4$-fluoroalkyl, R$^c$, R$^d$ is selected from the group consisting of hydrogen, C$_1$-C$_4$-alkyl, C$_1$-C$_4$-fluoroalkyl, C$_1$-C$_4$-alkoxy and C$_1$-C$_4$-fluoroalkoxy, R$^e$, R$^f$ is selected from the group consisting of hydrogen, C$_1$-C$_4$-alkyl, C$_1$-C$_4$-fluoroalkyl, C$_1$-C$_4$-alkoxy and C$_1$-C$_4$-fluoroalkoxy, Z is a covalent bond or C$_1$-C$_4$-alkandiyl, or two radicals R$^{C1}$ which are bound at adjacent carbon atoms may form a fused 5- or 6-membered carbocyclic radical or a fused 5- or 6-membered heterocyclic radical having 1, 2 or 3 heteroatoms as ring members, which are selected from the group consisting of O, S and N;

or two radicals R$^{C1}$ which are bound at the same carbon atom may form a spiro 5- or 6-membered carbocyclic radical or a spiro 5- or 6-membered heterocyclic radical having 1 or 2 heteroatoms as ring members, which are selected from the group consisting of O, S and N, or two radicals R$^{C1}$ which are bound at the same carbon atom may form an oxygen atom,
where the fused and the spiro radicals are unsubstituted or carry 1, 2, 3 or 4 radicals R$^{C3}$;

Y' is a chemical bond, CH$_2$, O, O—CH$_2$, S(O)$_2$, NR$^{3"}$, NR$^{3"}$—CH$_2$ or NR$^{3"}$—S(O)$_2$, where R$^{3"}$ is selected from the group consisting of hydrogen, C$_1$-C$_4$-alkyl, C$_1$-C$_4$-alkylcarbonyl, C$_1$-C$_4$-alkylsulfonyl, C$_1$-C$_4$-fluoroalkylsulfonyl;

R$^{C2}$ is a carbocyclic or heterocyclic radical selected from the group consisting of 3- to 7-membered saturated or partially unsaturated monocarbocyclic radicals, 3- to 7-membered saturated or partially unsaturated heteromonocyclic radicals, having 1, 2 or 3 heteroatoms as ring members, which are selected from the group consisting of O, S and N, and 5- or 6-membered heteroaromatic radicals, having 1, 2 or 3 heteroatoms as ring members, which are selected from the group consisting of O, S and N, where the carbocyclic and the heterocyclic radical is unsubstituted or carries 1, 2, 3, 4 or 5 radicals R$^{C3}$;

R$^{C3}$ is selected from the group consisting of hydrogen, halogen, OH, CN, C$_1$-C$_4$-alkyl, C$_1$-C$_4$-alkoxy, hydroxy-C$_1$-C$_4$-alkyl, C$_1$-C$_4$-alkoxy-C$_1$-C$_4$-alkyl, cyano-C$_1$-C$_4$-alkyl, C$_1$-C$_4$-fluoroalkyl, C$_1$-C$_4$-fluoroalkoxy, C$_2$-C$_6$-alkenyl, C(O)R$^a$, Z—C(O)OR$^b$, Z—C(O)NR$^c$R$^d$, S(O)$_2$NR$^c$R$^d$ and Z—NR$^e$R$^f$, or two radicals R$^{C3}$ which are bound at the same atom may form an oxygen atom;

or an N-oxide, tautomer, hydrate or pharmaceutically acceptable salt thereof.

2. The compound of claim 1, where X$^2$ is C—R$^2$, X$^3$ is C—R$^3$ and X$^4$ is C—R$^4$.

3. The compound of claim 1, where R$^2$ and R$^3$, if present, have a meaning different from Y-Cyc.

4. The compound of claim 1, where X$^4$ is C—R$^4$.

5. The compound of claim 4, where X$^2$ is C—R$^2$ and X$^3$ is C—R$^3$.

6. The compound of claim 4 or 5, where R$^2$ and R$^3$, if present, are selected, independently of each other, from the group consisting of hydrogen, fluorine, C$_1$-C$_4$-alkyl, C$_1$-C$_2$-fluoroalkyl, C$_1$-C$_4$-alkoxy, C$_1$-C$_2$-fluoroalkoxy, cyclopropyl, optionally substituted by 1, 2 or 3 methyl groups, and fluorinated cyclopropyl.

7. The compound of claim 1, where A is CR$^5$R$^6$.

8. The compound of claim 7, where R$^5$ and R$^6$ are, independently of each other, selected from the group consisting of hydrogen, fluorine and methyl.

9. The compound of claim 1, which is of the formula (I-A)

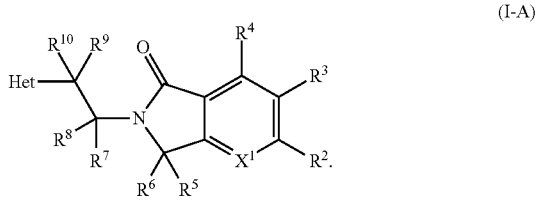

(I-A)

10. The compound of claim 1, where Het is selected from the group consisting of C-bound 6-membered monocyclic hetaryl, which has 1 or 2 nitrogen atoms as ring members, benzofuryl and C-bound, fused bicyclic hetaryl, which has 1 or 2 nitrogen atoms as ring members and optionally a further heteroatom selected from the group consisting of O, S and N as ring member;

where monocyclic hetaryl, benzofuryl and bicyclic hetaryl may be unsubstituted or may carry 1, 2, 3 or 4 substituents R$^x$.

11. The compound of claim 10, where Het has at least one imino-nitrogen as ring member, which located in the position adjacent to carbon atom bound to the group CR$^9$R$^{10}$.

12. The compound of claim 10, where Het is selected from the group consisting of 2-benzofuryl, 2-pyridyl, 3-pyridazinyl, 2-pyrimidinyl, 2-quinolinyl, 2-quinazolinyl, 2-quinoxalinyl, benzimidazol-2-yl, 1-methylbenzimidazol-2-yl, benzothiazolyl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl, where the aforementioned radicals may carry 1, 2 or 3 radicals selected from the group consisting of fluorine, chlorine, C$_1$-C$_4$-alkyl, fluoromethyl, difluoromethyl, trifluoromethyl, methoxy, fluoromethoxy, difluoromethoxy, trifluoromethoxy, cyclopropyl optionally substituted by 1, 2 or 3 methyl groups, and fluorinated cyclopropyl.

13. The compound of claim 1, where R$^7$ and R$^8$ are, independent of each other, selected from the group consisting of hydrogen and fluorine.

14. The compound of claim 1, which is of the formulae (I-Aa) or (I-Ab)

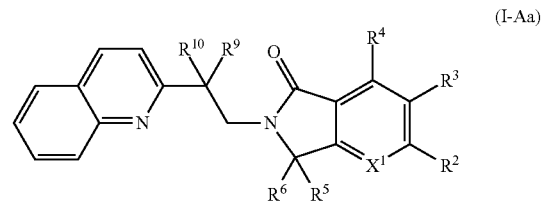

(I-Aa)

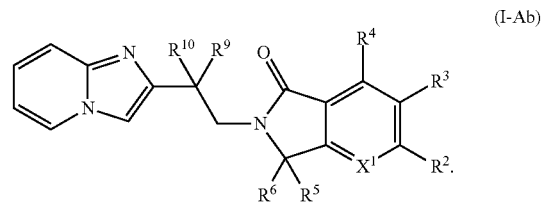

(I-Ab)

15. The compound of claim 14, where R$^5$ and R$^6$ are, independently of each other, selected from the group consisting of hydrogen, fluorine and methyl.

16. The compound of claim 1, which is of the formula (I-Ac)

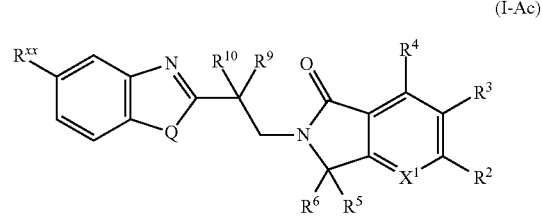

(I-Ac)

where Q is S or N—CH$_3$, R$^{xx}$ is hydrogen, fluorine or CH$_3$.

17. The compound of claim 1, which is of the formula (I-Ad)

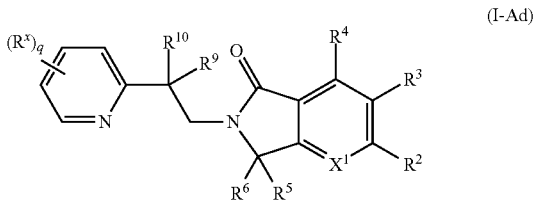

(I-Ad)

where q is 0 or 1 and $R^x$ is selected from the group consisting of $C_1$-$C_4$-alkyl, $C_1$-$C_4$-alkyl, $C_1$-$C_4$-alkoxy, $C_1$-$C_4$-fluoroalkyl, $C_1$-$C_4$-fluoroalkoxy, cyclopropyl, which is optionally substituted by 1, 2 or 3 methyl groups, and fluorinated cyclopropyl.

18. The compound of claim 1, where Y is selected from the group consisting of a chemical bond, O and NH.

19. The compound of claim 1, where Y is a chemical bond.

20. The compound of claim 1, where Cyc is a saturated 4-, 5-, 6-, 7- or 8-membered heteromonocycle or a saturated 7-, 8-, 9- or 10-membered heterobicycle, where the heteromonocycle and the heterobicycle have one nitrogen or oxygen atom as ring member and may have one further heteroatom or heteroatom group as ring member, which is selected from the group consisting of O, S, S(=O), S(=O)$_2$ and N, where the saturated heteromonocycle and the saturated heterobicycle are unsubstituted or carry 1, 2, 3, 4 or 5 radicals $R^{C1}$ or one radical Y'—$R^{C2}$ and 0, 1, 2, 3 or 4 radicals $R^{C1}$.

21. The compound of claim 1, where Y-Cyc is selected from the group consisting of 1-piperidinyl, 4,4-difluoro-1-piperidinyl, 4-piperidinyl, 1-methyl-4-piperidinyl, 1-piperazinyl, 4-methyl-1-piperazinyl, morpholin-4-yl, 2-oxa-6-azaspiro-[3,4]octyl, 2,5-diazabicyclo[2.2.1]heptan-2-yl, 3,8-diazabicyclo[3.2.1]octan-8-yl, thiomorpholin-4-yl, 1-oxothiomorpholin-4-yl, N-(oxetan-3-yl)amino, 1,1-dioxothiomorpholin-4-yl and oxetan-3-ylamino.

22. The compound of claim 1, where Cyc is phenyl or a 5- or 6 membered heteroaromatic radical, which has one heteroatom, selected from the group consisting of O, S and N as ring member and optionally one or two further heteroatoms as ring members, where phenyl and the 5- or 6 membered heteroaromatic radical are unsubstituted or either carry, independently of each other, 1, 2, 3, 4 or 5 radicals $R^{C1}$ or one radical Y'—$R^{C2}$ and 0, 1, 2, 3 or 4 radicals $R^{C1}$.

23. The compound of claim 22, where Y is a chemical bond and Cyc is selected from the group consisting of phenyl and 5- or 6-membered hetaryl selected from the group consisting of pyridyl, pyrimidinyl, furyl, thienyl, pyrrolyl, imidazolyl, pyrazolyl, oxazolyl and thiazolyl, where phenyl and hetaryl are unsubstituted or carry 1, 2 or 3 radicals $R^{C1}$ which are selected from the group consisting of fluorine, chlorine, CN, methyl, difluoromethyl, trifluoromethyl, methoxy and NH$_2$, or, if Cyc is phenyl, two radicals $R^{C1}$ which are bound to adjacent carbon atoms, together with the phenyl ring to which they are bound, form a bicyclic heterocyclic radical, which is selected from the group consisting of 5- or 6-indolyl, 5- or 6-benzimidazolyl, 5- or 6-benzopyrazolyl, 5- or 6-benzotriazolyl, 5- or 6-benzofuranyl, 2,3-dihydrobenzofuran-5-yl, 2,3-dihydrobenzofuran-6-yl, 1,3-dihydroindol-2-on-5-yl, 1,3-dihydroindol-2-on-6-yl, 5- or 6-quinolinyl, 5- or 6-isoquinolinyl, 5- or 6-quinazolinyl, 2-amino-5-quinazolinyl, and 2-amino-6-quinazolinyl.

24. The compound of claim 1, where $R^9$ and $R^{10}$ are, independent from each other, selected from the group consisting of hydrogen and fluorine.

25. The compound of claim 1, selected from the group consisting of
4-Pyridin-4-yl-6-(2-quinolin-2-yl-ethyl)-6,7-dihydro-pyrrolo[3,4-b]pyridin-5-one;
4-(1,1-Dioxo-thiomorpholin-4-yl)-6-(2-quinolin-2-yl-ethyl)-6,7-dihydro-pyrrolo[3,4-b]pyridin-5-one;
4-(4-Methyl-piperazin-1-yl)-6-(2-quinolin-2-yl-ethyl)-6,7-dihydro-pyrrolo[3,4-b]pyridin-5-one;
4-(1H-Pyrazol-4-yl)-6-(2-quinolin-2-yl-ethyl)-6,7-dihydro-pyrrolo[3,4-b]pyridin-5-one;
4-(4-Fluoro-phenyl)-6-(2-quinolin-2-yl-ethyl)-6,7-dihydro-pyrrolo[3,4-b]pyridin-5-one;
4-(4-Methoxy-phenyl)-6-(2-quinolin-2-yl-ethyl)-6,7-dihydro-pyrrolo[3,4-b]pyridin-5-one;
4-(2-Methyl-2H-pyrazol-3-yl)-6-(2-quinolin-2-yl-ethyl)-6,7-dihydro-pyrrolo[3,4-b]pyridin-5-one;
4-Piperazin-1-yl-6-(2-quinolin-2-yl-ethyl)-6,7-dihydro-pyrrolo[3,4-b]pyridin-5-one;
4-(2-Oxo-2,3-dihydro-1H-indol-6-yl)-6-(2-quinolin-2-yl-ethyl)-6,7-dihydro-pyrrolo[3,4-b]pyridin-5-one;
4-Pyrimidin-5-yl-6-(2-quinolin-2-yl-ethyl)-6,7-dihydro-pyrrolo[3,4-b]pyridin-5-one;
4-(2-Methyl-2H-pyrazol-3-yl)-6-(2-[1,2,4]triazolo[1,5-a]pyridin-2-yl-ethyl)-6,7-dihydro-pyrrolo[3,4-b]pyridin-5-one;
6-[2-(1-Methyl-1H-benzoimidazol-2-yl)-ethyl]-4-(2-methyl-2H-pyrazol-3-yl)-6,7-dihydro-pyrrolo[3,4-b]pyridin-5-one;
4-Pyrimidin-5-yl-6-(2-[1,2,4]triazolo[1,5-a]pyridin-2-yl-ethyl)-6,7-dihydro-pyrrolo[3,4-b]pyridin-5-one;
6-[2-(1-Methyl-1H-benzoimidazol-2-yl)-ethyl]-4-morpholin-4-yl-6,7-dihydro-pyrrolo[3,4-b]pyridin-5-one;
6-[2-(1-Methyl-1H-benzoimidazol-2-yl)-ethyl]-4-(4-methyl-piperazin-1-yl)-6,7-dihydro-pyrrolo[3,4-b]pyridin-5-one;
4-Morpholin-4-yl-6-(2-[1,2,4]triazolo[1,5-a]pyridin-2-yl-ethyl)-6,7-dihydro-pyrrolo[3,4-b]pyridin-5-one;
6-(2-Imidazo[1,2-a]pyridin-2-yl-ethyl)-4-(2-methyl-2H-pyrazol-3-yl)-6,7-dihydro-pyrrolo[3,4-b]pyridin-5-one;
6-(2-Imidazo[1,2-a]pyridin-2-yl-ethyl)-4-pyrimidin-5-yl-6,7-dihydro-pyrrolo[3,4-b]pyridin-5-one;
4-(2-Oxa-6-aza-spiro[3.4]oct-6-yl)-6-(2-quinolin-2-yl-ethyl)-6,7-dihydro-pyrrolo[3,4-b]pyridin-5-one;
4-(4,4-Difluoro-piperidin-1-yl)-6-(2-quinolin-2-yl-ethyl)-6,7-dihydro-pyrrolo[3,4-b]pyridin-5-one;
6-(2-Quinolin-2-yl-ethyl)-4-(tetrahydro-furo[3,4-c]pyrrol-5-yl)-6,7-dihydro-pyrrolo[3,4-b]pyridin-5-one;
4-(3,6-Dihydro-2H-pyran-4-yl)-6-(2-quinolin-2-yl-ethyl)-6,7-dihydro-pyrrolo[3,4-b]pyridin-5-one;
4-(4,5-Dihydro-furan-3-yl)-6-(2-quinolin-2-yl-ethyl)-6,7-dihydro-pyrrolo[3,4-b]pyridin-5-one;
6-(2-Imidazo[1,2-a]pyridin-2-yl-ethyl)-4-morpholin-4-yl-6,7-dihydro-pyrrolo[3,4-b]pyridin-5-one;
6-(2-Imidazo[1,2-a]pyridin-2-yl-ethyl)-4-(4-methyl-piperazin-1-yl)-6,7-dihydro-pyrrolo[3,4-b]pyridin-5-one;
1-Oxy-4-pyrimidin-5-yl-6-(2-quinolin-2-yl-ethyl)-6,7-dihydro-pyrrolo[3,4-b]pyridin-5-one;
6-(2-Quinolin-2-yl-ethyl)-4-(tetrahydro-pyran-4-yl)-6,7-dihydro-pyrrolo[3,4-b]pyridin-5-one;
6-(2-Quinolin-2-yl-ethyl)-4-(tetrahydro-furan-3-yl)-6,7-dihydro-pyrrolo[3,4-b]pyridin-5-one;

6-[2-(5,7-Dimethyl-[1,2,4]triazolo[1,5-a]pyrimidin-2-yl)-ethyl]-4-pyridin-4-yl-6,7-dihydro-pyrrolo[3,4-b]pyridin-5-one;

1-[5-Oxo-6-(2-quinolin-2-yl-ethyl)-6,7-dihydro-5H-pyrrolo[3,4-b]pyridin-4-yl]-piperidine-4-carboxylic acid ethyl ester;

4-(3-Methyl-pyridin-4-yl)-6-(2-quinolin-2-yl-ethyl)-6,7-dihydro-pyrrolo[3,4-b]pyridin-5-one;

4-(1H-Pyrazol-3-yl)-6-(2-quinolin-2-yl-ethyl)-6,7-dihydro-pyrrolo[3,4-b]pyridin-5-one;

4-(3,6-dimethoxypyridazin-4-yl)-6-(2-(quinolin-2-yl)ethyl)-6,7-dihydro-5H-pyrrolo[3,4-b]pyridin-5-one;

4-(2-Dimethylamino-pyrimidin-5-yl)-6-(2-quinolin-2-yl-ethyl)-6,7-dihydro-pyrrolo[3,4-b]pyridin-5-one;

4-(2-Methyl-thiazol-5-yl)-6-(2-quinolin-2-yl-ethyl)-6,7-dihydro-pyrrolo[3,4-b]pyridin-5-one;

4-(2-Ethoxy-pyrimidin-5-yl)-6-(2-quinolin-2-yl-ethyl)-6,7-dihydro-pyrrolo[3,4-b]pyridin-5-one;

4-(2-Methoxy-pyridin-4-yl)-6-(2-quinolin-2-yl-ethyl)-6,7-dihydro-pyrrolo[3,4-b]pyridin-5-one;

4-Pyridin-3-yl-6-(2-quinolin-2-yl-ethyl)-6,7-dihydro-pyrrolo[3,4-b]pyridin-5-one;

6-(2-Quinolin-2-yl-ethyl)-4-thiophen-3-yl-6,7-dihydro-pyrrolo[3,4-b]pyridin-5-one;

4-Furan-3-yl-6-(2-quinolin-2-yl-ethyl)-6,7-dihydro-pyrrolo[3,4-b]pyridin-5-one;

4-(1,5-Dimethyl-1H-pyrazol-4-yl)-6-(2-quinolin-2-yl-ethyl)-6,7-dihydro-pyrrolo[3,4-b]pyridin-5-one;

4-(1-Ethyl-1H-pyrazol-4-yl)-6-(2-quinolin-2-yl-ethyl)-6,7-dihydro-pyrrolo[3,4-b]pyridin-5-one;

4-(2,5-Dimethyl-2H-pyrazol-3-yl)-6-(2-quinolin-2-yl-ethyl)-6,7-dihydro-pyrrolo[3,4-b]pyridin-5-one;

4-(3,5-Dimethyl-isoxazol-4-yl)-6-(2-quinolin-2-yl-ethyl)-6,7-dihydro-pyrrolo[3,4-b]pyridin-5-one;

4-(3-Methyl-thiophen-2-yl)-6-(2-quinolin-2-yl-ethyl)-6,7-dihydro-pyrrolo[3,4-b]pyridin-5-one;

4-(1-Methyl-1H-pyrrol-3-yl)-6-(2-quinolin-2-yl-ethyl)-6,7-dihydro-pyrrolo[3,4-b]pyridin-5-one;

4-Pyridazin-4-yl-6-(2-quinolin-2-yl-ethyl)-6,7-dihydro-pyrrolo[3,4-b]pyridin-5-one;

4-(2-Cyclopropyl-pyridin-4-yl)-6-(2-quinolin-2-yl-ethyl)-6,7-dihydro-pyrrolo[3,4-b]pyridin-5-one;

6-(2-Quinolin-2-yl-ethyl)-4-thiazol-4-yl-6,7-dihydro-pyrrolo[3,4-b]pyridin-5-one;

6-(2-Imidazo[1,2-a]pyridin-2-yl-ethyl)-4-pyridin-3-yl-6,7-dihydro-pyrrolo[3,4-b]pyridin-5-one;

6-[2-(1-Methyl-1H-benzoimidazol-2-yl)-ethyl]-4-(oxetan-3-ylamino)-6,7-dihydro-pyrrolo[3,4-b]pyridin-5-one;

6-(2-Imidazo[1,2-a]pyridin-2-yl-ethyl)-4-(oxetan-3-ylamino)-6,7-dihydro-pyrrolo[3,4-b]pyridin-5-one;

4-(4-Dimethylamino-piperidin-1-yl)-6-(2-quinolin-2-yl-ethyl)-6,7-dihydro-pyrrolo[3,4-b]pyridin-5-one;

6-[2-(1-Methyl-1H-benzoimidazol-2-yl)-ethyl]-4-pyrimidin-5-yl-6,7-dihydro-pyrrolo[3,4-b]pyridin-5-one;

6-(2-Imidazo[1,2-a]pyridin-2-yl-ethyl)-4-(1H-pyrazol-4-yl)-6,7-dihydro-pyrrolo[3,4-b]pyridin-5-one;

1-[5-Oxo-6-(2-quinolin-2-yl-ethyl)-6,7-dihydro-5H-pyrrolo[3,4-b]pyridin-4-yl]-piperidine-4-carboxylic acid;

6-[2-(1-Methyl-1H-benzoimidazol-2-yl)-ethyl]-4-pyridin-4-yl-6,7-dihydro-pyrrolo[3,4-b]pyridin-5-one;

6-[2-(1-Methyl-1H-benzoimidazol-2-yl)-ethyl]-4-pyridin-3-yl-6,7-dihydro-pyrrolo[3,4-b]pyridin-5-one;

6-(2-Imidazo[1,2-a]pyridin-2-yl-ethyl)-4-pyridin-4-yl-6,7-dihydro-pyrrolo[3,4-b]pyridin-5-one;

6-(2-Benzothiazol-2-yl-ethyl)-4-pyridin-4-yl-6,7-dihydro-pyrrolo[3,4-b]pyridin-5-one; and 6-(2-Benzothiazol-2-yl-ethyl)-4-(oxetan-3-ylamino)-6,7-dihydro-pyrrolo[3,4-b]pyridin-5-one;

or an N-oxide, tautomer, hydrate or pharmaceutically acceptable salt thereof.

26. The compound of claim 1, where which is selected from the group consisting of 4-[3-(Fluoromethyl)pyrrolidin-1-yl]-6-(2-imidazo[1,2-a]pyridin-2-ylethyl)-7H-pyrrolo[3,4b]pyridin-5-one;

6-[2-(1,3-Benzothiazol-2-yl)ethyl]-4-[3-(difluoromethyl)pyrrolidin-1-yl]-7H-pyrrolo[3,4-b]pyridin-5-one;

4-[3-(Difluoromethyl)pyrrolidin-1-yl]-6-(2-imidazo[1,2-a]pyridin-2-ylethyl)-7H-pyrrolo[3,4-b]pyridin-5-one;

6-[2-(1,3-Benzothiazol-2-yl)ethyl]-4-[3-(fluoromethyl)pyrrolidin-1-yl]-7H-pyrrolo[3,4-b]pyridin-5-one;

4-(3-Methoxy-4-pyridyl)-6-[2-(2-quinolyl)ethyl]-7H-pyrrolo[3,4-b]pyridin-5-one;

6-[2-(1,3-Benzothiazol-2-yl)ethyl]-4-(1,1-dioxo-1,4-thiazinan-4-yl)-7H-pyrrolo[3,4-b]pyridin-5-one trifluoroacetate;

6-[2-(Benzofuran-2-yl)ethyl]-4-(4-pyridyl)-7H-pyrrolo[3,4-b]pyridin-5-one;

6-[2-(7-Methyl-2-quinolyl)ethyl]-4-morpholino-7H-pyrrolo[3,4-b]pyridin-5-one;

6-[2-(Benzothiophen-2-yl)ethyl]-4-(4-pyridyl)-7H-pyrrolo[3,4-b]pyridin-5-one;

6-[2-(7-Methyl-2-quinolyl)ethyl]-4-(4-pyridyl)-7H-pyrrolo[3,4-b]pyridin-5-one trifluoroacetate;

6-[2-(Benzothiophen-2-yl)ethyl]-4-morpholino-7H-pyrrolo[3,4-b]pyridin-5-one trifluoroacetate;

6-[2-(Benzofuran-2-yl)ethyl]-4-morpholino-7H-pyrrolo[3,4-b]pyridin-5-one;

6-[2-(5-Isopropyl-2-pyridyl)ethyl]-4-(4-pyridyl)-7H-pyrrolo[3,4-b]pyridin-5-one;

6-[2-(5-Isopropyl-2-pyridyl)ethyl]-4-morpholino-7H-pyrrolo[3,4-b]pyridin-5-one;

6-[2-(6-Fluoro-1,3-benzothiazol-2-yl)ethyl]-4-(4-pyridyl)-7H-pyrrolo[3,4-b]pyridin-5-one;

6-[2-(6-Chloro-1,3-benzothiazol-2-yl)ethyl]-4-(4-pyridyl)-7H-pyrrolo[3,4-b]pyridin-5-one;

6-[2-(6-Chloro-1,3-benzothiazol-2-yl)ethyl]-4-morpholino-7H-pyrrolo[3,4-b]pyridin-5-one;

6-[2-(6-Fluoro-1,3-benzothiazol-2-yl)ethyl]-4-morpholino-7H-pyrrolo[3,4-b]pyridin-5-one;

6-[2-(6-Methyl-2-quinolyl)ethyl]-4-(4-pyridyl)-7H-pyrrolo[3,4-b]pyridin-5-one;

6-[2-(4-Ethylthiazol-2-yl)ethyl]-4-(4-pyridyl)-7H-pyrrolo[3,4-b]pyridin-5-one;

6-[2-(4,5-Dimethylthiazol-2-yl)ethyl]-4-(4-pyridyl)-7H-pyrrolo[3,4-b]pyridin-5-one;

6-[2-(3-Methyl-2-pyridyl)ethyl]-4-(4-pyridyl)-7H-pyrrolo[3,4-b]pyridin-5-one;

6-[2-(4-Methyl-2-pyridyl)ethyl]-4-(4-pyridyl)-7H-pyrrolo[3,4-b]pyridin-5-one;

4-(3-Fluoro-pyridin-4-yl)-6-(2-quinolin-2-yl-ethyl)-6,7-dihydro-pyrrolo[3,4-b]pyridin-5-one;

6-(2-Imidazo[1,2-a]pyridin-2-yl-ethyl)-4-(1H-pyrazol-3-yl)-6,7-dihydro-pyrrolo[3,4-b]pyridin-5-one;

4-Furan-3-yl-6-(2-imidazo[1,2-a]pyridin-2-yl-ethyl)-6,7-dihydro-pyrrolo[3,4-b]pyridin-5-one;

6-[2-(1,5-Dimethyl-1H-benzoimidazol-2-yl)-ethyl]-4-morpholin-4-yl-6,7-dihydro-pyrrolo[3,4-b]pyridin-5-one;

6-[2-(1,5-Dimethyl-1H-benzoimidazol-2-yl)-ethyl]-4-(oxetan-3-ylamino)-6,7-dihydro-pyrrolo[3,4-b]pyridin-5-one;

6-[2-(1,3-Benzoxazol-2-yl)ethyl]-4-morpholino-7H-pyrrolo[3,4-b]pyridin-5-one;

6-[2-(1,3-Benzoxazol-2-yl)ethyl]-4-(4-pyridyl)-7H-pyrrolo[3,4-b]pyridin-5-one;
6-[2-(1,3-Benzothiazol-2-yl)ethyl]-4-(4-methylpiperazin-1-yl)-7H-pyrrolo[3,4-b]pyridin-5-one;
6-[2-(1,3-Benzothiazol-2-yl)ethyl]-4-(2,3-dihydrofuran-4-yl)-7H-pyrrolo[3,4-b]pyridin-5-one trifluoroacetate;
6-[2-(1,3-Benzothiazol-2-yl)ethyl]-4-(2-fluoro-4-pyridyl)-7H-pyrrolo[3,4-b]pyridin-5-one trifluoroacetate;
6-[2-(1,3-Benzothiazol-2-yl)ethyl]-4-(3-furyl)-7H-pyrrolo[3,4-b]pyridin-5-one trifluoroacetate;
6-(2-Imidazo[2,1-b]thiazol-6-ylethyl)-4-(4-pyridyl)-7H-pyrrolo[3,4-b]pyridin-5-one trifluoroacetate;
6-[2-(1,3-Benzothiazol-2-yl)ethyl]-4-(2-oxa-7-azaspiro[3.4]octan-7-yl)-7H-pyrrolo[3,4-b]pyridin-5-one;
6-(2-Imidazo[2,1-b]thiazol-6-ylethyl)-4-morpholino-7H-pyrrolo[3,4-b]pyridin-5-one;
4-(1,3,3a,4,6,6a-Hexahydrofuro[3,4-c]pyrrol-5-yl)-6-[2-(1,3-benzothiazol-2-yl)ethyl]-7H-pyrrolo[3,4-b]pyridin-5-one;
6-[2-(1,3-Benzothiazol-2-yl)ethyl]-4-(4-piperidyloxy)-7H-pyrrolo[3,4-b]pyridin-5-one trifluoroacetate;
6-[2-(1,3-Benzothiazol-2-yl)ethyl]-4-(1H-pyrazol-3-yl)-7H-pyrrolo[3,4-b]pyridin-5-one;
6-[2-(1,3-Benzothiazol-2-yl)ethyl]-4-(3-pyridyl)-7H-pyrrolo[3,4-b]pyridin-5-one trifluoroacetate;
6-[2-(1,3-Benzothiazol-2-yl)ethyl]-4-(2-methylpyrazol-3-yl)-7H-pyrrolo[3,4-b]pyridin-5-one trifluoroacetate;
4-[3-(Difluoromethyl)pyrrolidin-1-yl]-6-[2-(2-quinolyl)ethyl]-7H-pyrrolo[3,4-b]pyridin-5-one;
4-[3-(Fluoromethyl)pyrrolidin-1-yl]-6-[2-(2-quinolyl)ethyl]-7H-pyrrolo[3,4-b]pyridin-5-one;
6-[2-(1,3-Benzothiazol-2-yl)ethyl]-4-thiazol-4-yl-7H-pyrrolo[3,4-b]pyridin-5-one;
6-[2-(1,3-Benzothiazol-2-yl)ethyl]-4-(2-methylpyrimidin-5-yl)-7H-pyrrolo[3,4-b]pyridin-5-one;
1-[5-oxo-6-[2-(2-quinolyl)ethyl]-7H-pyrrolo[3,4-b]pyridin-4-yl]azetidine-3-carboxylic acid;
4-(oxetan-3-yloxy)-6-[2-(2-quinolyl)ethyl]-7H-pyrrolo[3,4-b]pyridin-5-one;
6-(2-Quinolin-2-yl-ethyl)-6,7-dihydro-pyrrolo[3,4-b]pyridin-5-one trifluoroacetate;
4-(4-Pyridyl)-6-(2-quinoxalin-2-ylethyl)-7H-pyrrolo[3,4-b]pyridin-5-one;
6-[2-(6-Methyl-2-pyridyl)ethyl]-4-morpholino-7H-pyrrolo[3,4-b]pyridin-5-one;
6-[2-(5-Methyl-2-pyridyl)ethyl]-4-morpholino-7H-pyrrolo[3,4-b]pyridin-5-one hydrochloride;
6-[2-(1-Methylimidazol-2-yl)ethyl]-4-(4-pyridyl)-7H-pyrrolo[3,4-b]pyridin-5-one trifluoroacetate;
6-[2-(6-Methyl-2-pyridyl)ethyl]-4-(4-pyridyl)-7H-pyrrolo[3,4-b]pyridin-5-one trifluoroacetate;
4-(4-Pyridyl)-6-[2-(2-pyridyl)ethyl]-7H-pyrrolo[3,4-b]pyridin-5-one trifluoroacetate;
4-(4-Pyridyl)-6-(2-thieno[3,2-b]pyridin-5-ylethyl)-7H-pyrrolo[3,4-b]pyridin-5-one;
6-[2-(3,5-Dimethyl-2-pyridyl)ethyl]-4-(4-pyridyl)-7H-pyrrolo[3,4-b]pyridin-5-one;
6-[2-(5,6-Dimethyl-2-pyridyl)ethyl]-4-(4-pyridyl)-7H-pyrrolo[3,4-b]pyridin-5-one trifluoroacetate;
6-[2-(5-Methyl-2-pyridyl)ethyl]-4-(3-pyridyl)-7H-pyrrolo[3,4-b]pyridin-5-one trifluoroacetate;
4-(1,1-Dioxo-1,4-thiazinan-4-yl)-6-[2-(5-methyl-2-pyridyl)ethyl]-7H-pyrrolo[3,4-b]pyridin-5-one trifluoroacetate;
6-[2-(5-Methyl-2-pyridyl)ethyl]-4-pyrimidin-5-yl-7H-pyrrolo[3,4-b]pyridin-5-one trifluoroacetate;
6-[2-(5-Methyl-2-pyridyl)ethyl]-4-(4-pyridyl)-7H-pyrrolo[3,4-b]pyridin-5-one trifluoroacetate;
4-(4-Pyridyl)-6-[2-[4-(4-pyridyl)-2-quinolyl]ethyl]-7H-pyrrolo[3,4-b]pyridin-5-one;
4-(2,2,3,3,5,5,6,6-Octadeuteriomorpholin-4-yl)-6-[2-(2-quinolyl)ethyl]-7H-pyrrolo[3,4-b]pyridin-5-one;
4-Morpholino-6-[2-(5-phenyl-2-pyridyl)ethyl]-7H-pyrrolo[3,4-b]pyridin-5-one;
6-[2-(1-Methylimidazol-4-yl)ethyl]-4-(4-pyridyl)-7H-pyrrolo[3,4-b]pyridin-5-one trifluoroacetate;
6-[2-(5-Phenyl-2-pyridyl)ethyl]-4-(4-pyridyl)-7H-pyrrolo[3,4-b]pyridin-5-one trifluoroacetate;
6-[2-(3,5-Dimethyl-2-pyridyl)ethyl]-4-morpholino-7H-pyrrolo[3,4-b]pyridin-5-one;
6-[2-(5-Methyl-2-pyridyl)ethyl]-4-(oxetan-3-ylamino)-7H-pyrrolo[3,4-b]pyridin-5-one;
4-Morpholino-6-(2-thieno[3,2-b]pyridin-5-ylethyl)-7H-pyrrolo[3,4-b]pyridin-5-one;
6-[2-(6-Fluoroimidazo[1,2-a]pyridin-2-yl)ethyl]-4-morpholino-7H-pyrrolo[3,4-b]pyridin-5-one hydrochloride;
6-[2-(6-Fluoroimidazo[1,2-a]pyridin-2-yl)ethyl]-4-morpholino-7H-pyrrolo[3,4-b]pyridin-5-one trifluoroacetate;
6-[2-(6-Fluoroimidazo[1,2-a]pyridin-2-yl)ethyl]-4-(4-pyridyl)-7H-pyrrolo[3,4-b]pyridin-5-one trifluoroacetate;
4-Morpholino-6-(2-quinoxalin-2-ylethyl)-7H-pyrrolo[3,4-b]pyridin-5-one trifluoroacetate;
6-[2-(8-Methylimidazo[1,2-a]pyridin-2-yl)ethyl]-4-(4-pyridyl)-7H-pyrrolo[3,4-b]pyridin-5-one trifluoroacetate;
6-[2-(5-Fluoro-2-pyridyl)ethyl]-4-(4-pyridyl)-7H-pyrrolo[3,4-b]pyridin-5-one trifluoroacetate;
6-[2-(5-Fluoro-2-pyridyl)ethyl]-4-morpholino-7H-pyrrolo[3,4-b]pyridin-5-one trifluoroacetate;
6-[2-(5-Ethyl-2-pyridyl)ethyl]-4-morpholino-7H-pyrrolo[3,4-b]pyridin-5-one trifluoroacetate;
4-Morpholino-6-[2-[5-(trifluoromethyl)-2-pyridyl]ethyl]-7H-pyrrolo[3,4-b]pyridin-5-one trifluoroacetate;
6-[2-(5-Ethyl-2-pyridyl)ethyl]-4-(4-pyridyl)-7H-pyrrolo[3,4-b]pyridin-5-one trifluoroacetate;
6-[2-(5-Chloro-2-pyridyl)ethyl]-4-(4-pyridyl)-7H-pyrrolo[3,4-b]pyridin-5-one trifluoroacetate;
6-[2-(6-Methoxy-2-pyridyl)ethyl]-4-(3-pyridyl)-7H-pyrrolo[3,4-b]pyridin-5-one trifluoroacetate;
6-[2-(5,6-Dimethyl-2-pyridyl)ethyl]-4-(oxetan-3-ylamino)-7H-pyrrolo[3,4-b]pyridin-5-one trifluoroacetate;
6-[2-(5-Chloro-2-pyridyl)ethyl]-4-morpholino-7H-pyrrolo[3,4-b]pyridin-5-one;
4-(4-Pyridyl)-6-[2-[5-(trifluoromethyl)-2-pyridyl]ethyl]-7H-pyrrolo[3,4-b]pyridin-5-one trifluoroacetate;
6-[2-(4,5-Dimethyl-2-pyridyl)ethyl]-4-(4-pyridyl)-7H-pyrrolo[3,4-b]pyridin-5-one trifluoroacetate;
6-[2-(6-Methoxy-2-pyridyl)ethyl]-4-(oxetan-3-ylamino)-7H-pyrrolo[3,4-b]pyridin-5-one;
2,3,7,7-Tetradeuterio-6-[1,1-dideuterio-2-(3,4,5,6,7,8-hexadeuterio-2-quinolyl)ethyl]-4-(2,2,3,3,5,5,6,6-octadeuteriomorpholin-4-yl)pyrrolo[3,4-b]pyridin-5-one;
6-(2-Imidazo[1,2-a]pyridin-2-yl-1-methyl-ethyl)-4-morpholino-7H-pyrrolo[3,4-b]pyridin-5-one trifluoroacetate;
6-[2-(1,5-Naphthyridin-2-yl)ethyl]-4-(4-pyridyl)-7H-pyrrolo[3,4-b]pyridin-5-one;

2,3,7,7-Tetradeuterio-6-[2,2-dideuterio-2-(3,4,5,6,7,8-hexadeuterio-2-quinolyl)ethyl]-4-morpholino-pyrrolo[3,4-b]pyridin-5-one;
4-Morpholino-6-[2-(1,5-naphthyridin-2-yl)ethyl]-7H-pyrrolo[3,4-b]pyridin-5-one;
6-[2-(3-Methoxy-2-pyridyl)ethyl]-4-[2-(3-methoxy-2-pyridyl)ethylamino]-7H-pyrrolo[3,4-b]pyridin-5-one;
6-[2-(4-Ethylthiazol-2-yl)ethyl]-4-morpholino-7H-pyrrolo[3,4-b]pyridin-5-one;
6-[2-(4-Cyclopropylthiazol-2-yl)ethyl]-4-(4-pyridyl)-7H-pyrrolo[3,4-b]pyridin-5-one;
6-[2-(4-Cyclopropylthiazol-2-yl)ethyl]-4-morpholino-7H-pyrrolo[3,4-b]pyridin-5-one;
6-[2-(4,5-Dimethylthiazol-2-yl)ethyl]-4-morpholino-7H-pyrrolo[3,4-b]pyridin-5-one;
6-[2-(4,5-Dimethyl-2-pyridyl)ethyl]-4-morpholino-7H-pyrrolo[3,4-b]pyridin-5-one;
6-[2-(4-Methyl-2-pyridyl)ethyl]-4-morpholino-7H-pyrrolo[3,4-b]pyridin-5-one;
6-[2-(3-Methyl-2-pyridyl)ethyl]-4-morpholino-7H-pyrrolo[3,4-b]pyridin-5-one;
6-(2-Imidazo[1,2-a]pyridin-2-ylethyl)-4-(3-thienyl)-7H-pyrrolo[3,4-b]pyridin-5-one;
6-(2-Imidazo[1,2-a]pyridin-2-ylethyl)-4-(2-methyl-3-furyl)-7H-pyrrolo[3,4-b]pyridin-5-one;
6-(2-Imidazo[1,2-a]pyridin-2-ylethyl)-4-(5-methyl-2-furyl)-7H-pyrrolo[3,4-b]pyridin-5-one;
6-[2-(6-Fluoroimidazo[1,2-a]pyridin-2-yl)ethyl]-4-(3-furyl)-7H-pyrrolo[3,4-b]pyridin-5-one;
6-[2-(1,3-Benzothiazol-2-yl)ethyl]-4-(4,4-difluoro-1-piperidyl)-7H-pyrrolo[3,4-b]pyridin-5-one trifluoroacetate;
4-Methoxy-6-(2-quinolin-2-yl-ethyl)-6,7-dihydro-pyrrolo[3,4-b]pyridin-5-one;
4-(4-Hydroxy-piperidin-1-yl)-6-(2-quinolin-2-yl-ethyl)-6,7-dihydro-pyrrolo[3,4-b]pyridin-5-one trifluoroacetate;
4-(3-Fluoro-pyridin-4-yl)-6-(2-imidazo[1,2-a]pyridin-2-yl-ethyl)-6,7-dihydro-pyrrolo[3,4-b]pyridin-5-one;
6-[2-(1,5-Dimethyl-1H-benzoimidazol-2-yl)-ethyl]-4-pyrimidin-5-yl-6,7-dihydro-pyrrolo[3,4-b]pyridin-5-one;
6-[2-(1,5-Dimethyl-1H-benzoimidazol-2-yl)-ethyl]-4-pyridin-4-yl-6,7-dihydro-pyrrolo[3,4-b]pyridin-5-one;
6-[2-(1,3-Benzothiazol-2-yl)ethyl]-4-(1H-pyrazol-4-yl)-7H-pyrrolo[3,4-b]pyridin-5-one trifluoroacetate;
6-[2-(1,5-Dimethylbenzimidazol-2-yl)ethyl]-4-(3-pyridyl)-7H-pyrrolo[3,4-b]pyridin-5-one;
6-[2-(1,5-Dimethylbenzimidazol-2-yl)ethyl]-4-(2-methylpyrazol-3-yl)-7H-pyrrolo[3,4-b]pyridin-5-one;
6-[2-(1,3-Benzothiazol-2-yl)ethyl]-4-(4-methoxyphenyl)-7H-pyrrolo[3,4-b]pyridin-5-one trifluoroacetate;
6-[2-(1,3-Benzothiazol-2-yl)ethyl]-4-(4-fluorophenyl)-7H-pyrrolo[3,4-b]pyridin-5-one trifluoroacetate;
6-[2-(1,3-Benzothiazol-2-yl)ethyl]-4-(3,6-dihydro-2H-pyran-4-yl)-7H-pyrrolo[3,4-b]pyridin-5-one;
6-[2-(1,3-Benzothiazol-2-yl)ethyl]-4-pyrimidin-5-yl-7H-pyrrolo[3,4-b]pyridin-5-one;
4-(6-Fluoro-1,4-diazepan-1-yl)-6-[2-(2-quinolyl)ethyl]-7H-pyrrolo[3,4-b]pyridin-5-one;
4-(4-Pyridyl)-6-[2-(4-quinolyl)ethyl]-7H-pyrrolo[3,4-b]pyridin-5-one trifluoroacetate;
4-Morpholino-6-[2-(4-quinolyl)ethyl]-7H-pyrrolo[3,4-b]pyridin-5-one;
4-Morpholino-6-[2-(2-pyridyl)ethyl]-7H-pyrrolo[3,4-b]pyridin-5-one;
6-[2-(5-Methyl-2-pyridyl)ethyl]-4-morpholino-7H-pyrrolo[3,4-b]pyridin-5-one;
6-[2-(7-Ethylimidazo[1,2-a]pyridin-2-yl)ethyl]-4-(4-pyridyl)-7H-pyrrolo[3,4-b]pyridin-5-one;
6-[2-(6-Methoxy-2-pyridyl)ethyl]-4-(4-pyridyl)-7H-pyrrolo[3,4-b]pyridin-5-one;
6-[2-(5,6-Dimethyl-2-pyridyl)ethyl]-4-morpholino-7H-pyrrolo[3,4-b]pyridin-5-one; and
6-[2-(7-Ethylimidazo[1,2-a]pyridin-2-yl)ethyl]-4-morpholino-7H-pyrrolo[3,4-b]pyridin-5-one;
or an N-oxide, tautomer or pharmaceutically acceptable salt thereof.

27. A pharmaceutical composition comprising at least one compound of claim 1 or an N-oxide, tautomer or pharmaceutically acceptable salt thereof and at least one excipient.

28. The compound of claim 1 which is 4-morpholin-4-yl-6-(2-quinolin-2-yl-ethyl)-6,7-dihydro-pyrrolo[3,4-b]pyridin-5-one or an N-oxide, tautomer or pharmaceutically acceptable salt thereof.

29. The compound of claim 1 which is 4-(oxetan-3-ylamino)-6-(2-quinolin-2-yl-ethyl)-6,7-dihydro-pyrrolo[3,4-b]pyridin-5-one or an N-oxide, tautomer or pharmaceutically acceptable salt thereof.

30. The compound of claim 1 which is 6-(2-benzothiazol-2-yl-ethyl)-4-morpholin-4-yl-6,7-dihydro-pyrrolo[3,4-b]pyridin-5-one or an N-oxide, tautomer or pharmaceutically acceptable salt thereof.

31. The compound of claim 1 which is 6-[2-(6-methoxy-2-pyridyl)ethyl]-4-morpholino-7H-pyrrolo[3,4-b]pyridin-5-one or an N-oxide, tautomer or pharmaceutically acceptable salt thereof.

32. The compound of claim 1, where $X^1$ is N; $X^2$ is C—$R^2$; $X^3$ is C—$R^3$; and $X^4$ is C—$R^4$.

33. A method for treating a neurological and psychiatric disorder which can be treated by inhibition of phosphodiesterase type 10A, said method comprising administering an effective amount of at least one compound of claim 1 or a N-oxide, tautomer or pharmaceutically acceptable salt thereof to a subject in need thereof, wherein the neurological or psychiatric disorder is selected from the group consisting of schizophrenia, cognitive dysfunction associated with schizophrenia, bipolar disorder; depression, cognitive dysfunction associated with Alzheimer's disease, diet-induced obesity, Huntington's disease, and anxiety.

* * * * *